United States Patent
Chen et al.

(10) Patent No.: US 8,314,111 B2
(45) Date of Patent: *Nov. 20, 2012

(54) FUSED BICYCLIC MOTOR INHIBITORS

(75) Inventors: Xin Chen, Commack, NY (US); Heather Coate, San Diego, CA (US); Andrew Philip Crew, N. Babylon, NY (US); Han-Qing Dong, Syosset, NY (US); Ayako Honda, Quincy, MA (US); Mark Joseph Mulvihill, Melville, NY (US); Paula A. R. Tavares, Kew Gardens, NY (US); Jing Wang, Syosset, NY (US); Douglas S. Werner, Holtsville, NY (US); Kam W. Siu, Farmingdale, NY (US); Bijoy Panicker, Holbrook, NY (US); Apoorba Bharadwaj, Jamestown, NC (US); Lee D. Arnold, Mt. Sinai, NY (US); Meizhong Jin, Dix Hills, NY (US); Brian Volk, Sayville, NY (US); Quinghua Weng, West Islip, NY (US); James David Beard, New York, NY (US)

(73) Assignee: OSI Pharmaceuticals, LLC, Farmingdale, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/106,954

(22) Filed: May 13, 2011

(65) Prior Publication Data

US 2011/0218183 A1 Sep. 8, 2011

Related U.S. Application Data

(62) Division of application No. 12/622,545, filed on Nov. 20, 2009, now Pat. No. 7,943,767, and a division of application No. 13/085,722, filed on Apr. 13, 2011, which is a division of application No. 12/622,545, which is a division of application No. 11/599,663, filed on Nov. 15, 2006, now Pat. No. 7,700,594.

(60) Provisional application No. 60/854,247, filed on Oct. 25, 2006, provisional application No. 60/737,581, filed on Nov. 17, 2005.

(51) Int. Cl.
  *C07D 487/04* (2006.01)
  *C07D 403/04* (2006.01)
  *C07D 403/14* (2006.01)
  *A61K 31/519* (2006.01)
  *A61P 19/02* (2006.01)

(52) U.S. Cl. .................... 514/262.1; 544/256
(58) Field of Classification Search ............. 544/256; 514/262.1
See application file for complete search history.

(56) References Cited

U.S. PATENT DOCUMENTS

| | | | |
|---|---|---|---|
| 5,869,485 A | 2/1999 | Missbach | |
| 6,001,839 A | 12/1999 | Calderwood et al. | |
| 7,923,555 B2 * | 4/2011 | Chen et al. ............ | 544/256 |
| 2002/0156081 A1 | 10/2002 | Hirst et al. | |
| 2003/0073218 A1 | 4/2003 | Shokat | |
| 2003/0187001 A1 | 10/2003 | Calderwood et al. | |
| 2005/0004142 A1 | 1/2005 | Adams et al. | |
| 2005/0130994 A1 | 6/2005 | Chen et al. | |
| 2006/0019957 A1 | 1/2006 | Crew et al. | |
| 2006/0084654 A1 | 4/2006 | Beck et al. | |
| 2006/0235031 A1 | 10/2006 | Arnold et al. | |
| 2007/0112005 A1 | 5/2007 | Chen et al. | |
| 2007/0149521 A1 | 6/2007 | Crew et al. | |
| 2007/0167383 A1 | 7/2007 | Roberts et al. | |
| 2007/0203143 A1 | 8/2007 | Sheppard et al. | |
| 2007/0254883 A1 | 11/2007 | Crew et al. | |
| 2007/0280928 A1 | 12/2007 | Buck et al. | |
| 2007/0293516 A1 | 12/2007 | Knight et al. | |
| 2008/0032960 A1 | 2/2008 | Knight et al. | |
| 2009/0099174 A1 | 4/2009 | Smith | |
| 2009/0124638 A1 | 5/2009 | Shokat et al. | |
| 2009/0163468 A1 | 6/2009 | Chen et al. | |
| 2009/0263397 A1 | 10/2009 | Buck et al. | |
| 2009/0274698 A1 | 11/2009 | Bhagwat et al. | |
| 2010/0099679 A1 | 4/2010 | Chen et al. | |
| 2011/0015197 A1 | 1/2011 | Castelhano et al. | |

FOREIGN PATENT DOCUMENTS

| | | |
|---|---|---|
| WO | 0119829 | 3/2001 |
| WO | 2005037836 | 4/2005 |
| WO | 2005044835 | 5/2005 |
| WO | 2005047289 | 5/2005 |
| WO | 2005097800 | 10/2005 |
| WO | 2006012422 | 2/2006 |
| WO | 2006068760 | 6/2006 |
| WO | 2007061737 | 5/2007 |
| WO | 2007064993 | 6/2007 |
| WO | 2007114926 | 10/2007 |
| WO | 2007115620 | 10/2007 |
| WO | 2007126841 | 11/2007 |
| WO | 2011005909 | 7/2010 |
| WO | 2011014726 | 7/2010 |

OTHER PUBLICATIONS

U.S. Appl. No. 13/085,722 Apr. 13, 2011 Chen.

(Continued)

*Primary Examiner* — Venkataraman Balasubramanian

(57) ABSTRACT

Compounds represented by Formula (I)

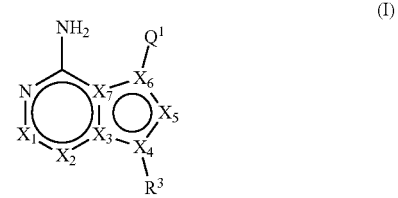

or a pharmaceutically acceptable salt thereof, are inhibitors of mTOR and useful in the treatment of cancer.

2 Claims, No Drawings

OTHER PUBLICATIONS

U.S. Appl. No. 61/311,832 Mar. 9, 2010 Barr.
Bergstrom, D. et al. (1981) Journal of Organic Chemistry 46(7):1423-1431.
Bergstrom, D. et al. (1991) Journal of Organic Chemistry 56(19):5598-5602.
Bishop, A. et al. (1999) Journal of the American Chemical Society 121(4):627-631.
Buzko, O. et al. (2002) Journal of Computer-Aided Design 16(2):113-127.
Hubbard, R.D. et al. (2007) Bioorganic & Medicinal Chemistry Letters 17(19):5406-5409.
Kinkade, C.W. et al. (2008) Journal of Clinical Investigation 118(9):3051-3064.
Legrier, M. et al. (2007) Cancer Research 67(23):11300-11308.
Papadimitrakopoulou, V. and Adjei, A.A. (2006) Journal of Thoracic Oncology 1(7): 749-751.
Prousek, J. (1984) Collection of Czechoslovak Chemical Communications 49(8):1788-1794.
Raslan, M.A. et al. (2000) Heteroatom Chemistry 11(2):94-201.
Seela, F. et al. (2000) Helvetica Chimica Acta 83(5):910-927.
Schram, K. et al. (1974) Journal of Carbohydrates, Nucleosides, Nucleotides 1(1):39-54.
Database Beilstein—Beilstein Institute for Organic Chemistry, Frankfurt-Main, DE XP002449941. Database accession Nos. 4560199, 4563868, 4573145, 4589920 (BRNs). Abstract (This document included in 10052 ISR attached to Bergstrom 1423. Bergstrom ref cited for OS-10052, but not Database Beilstein) 1981.
Database Beilstein—Beilstein Institute for Organic Chemistry, Frankfurt-Main, DE XP002449942. Database accession Nos. 759552, 7598012, 7598776, 7599702, 7601233, 7604323, 8071040, 8075363, 8077883, 8082219, 8086506, 8088093, 8572470, 8574862, 8581421, 8596325 (BRNs). abstract (This document included in 10052 ISR attached to Seela 910. Bergstrom ref cited for OS-10052, but not Database Beilstein) 1996-2000.
International Preliminary Report on Patentability in PCT/US2006/044461(May 20, 2008).
International Preliminary Report on Patentability in PCT/US2009/037505 (Sep. 21, 2010).
International Search Report in PCT/US2006/044461 (Nov. 9, 2007).
International Search Report in PCT/US2007/002027 (Sep. 9, 2007).
International Search Report in PCT/US2009/037505 (Aug. 6, 2009).
International Search Report in PCT/US2010/041278 (Mar. 24, 2011).
Written Opinion of the International Search Authority in PCT/US2006/044461(May 17, 2008).
Written Opinion of the International Search Authority in PCT/US2007/002027 (May 7, 2008).

* cited by examiner

FUSED BICYCLIC MOTOR INHIBITORS

This application claims the benefit of U.S. Patent Application Nos. 60/737,581 filed Nov. 17, 2005, and 60/854,247 filed Oct. 25, 2006.

BACKGROUND OF THE INVENTION

The present invention is directed to bicyclic compounds that are inhibitors of mammalian Target Of Rapamycin (mTOR) kinase (also known as FRAP, RAFT, RAPT, SEP). In particular, the present invention is directed to fused bicyclic compounds that are mTOR inhibitors useful in the treatment of cancer.

International Patent Publication WO 2001 019828 describes the preparation of heteroaromatic amines as protein kinase inhibitors. International Patent Publication WO 2005/047289 describes pyrrolopyrimidine compounds useful in treatment of cancer. Bergstrom et al., *J. Org. Chem.*, 56:5598-5602(1991) describes Palladium-Mediated Synthesis of C-5 Pyrimidine Nucleoside Thioethers from Disulfides and Mercurinucleosides.

It has been shown that high levels of dysregulated mTOR activity are associated with variety of human cancers and several hamartoma syndromes, including tuberous sclerosis complex, the PTEN-related hamartoma syndromes and Peutz-Jeghers syndrome. Although rapamycin analogues are in clinical development for cancer as mTOR kinase inhibitor, the clinical out come with CCI-779 is just modest in breast and renal cancer patients. This is probably because rapamycin partially inhibits mTOR function through raptor-mTOR complex (mTORC1). It has been also found that ⅔ of the breast cancer and ½ of renal cancer patients are resistant to rapamycin therapy. With a recent discovery of rictor-mTOR complex (mTORC2) which is involved in phosphorylation of AKT (S473) that is important in regulation of cell survival and modulation of PKCα that plays a major role in regulation of actin cytoskeletal organization in a rapamycin-independent manner, and inhibition of these activities of mTOR is probably important for broader antitumor activity and better efficacy. Therefore, it is desirable to develop novel compounds that are direct inhibitors of mTOR kinase, which would inhibit mTORC1 and mTORC2.

Rapamycin, a macrolide antibiotic has been shown to specifically inhibit mTOR kinase activity in vitro and in vivo in several studies. Although precise mechanism by which rapamycin inhibits mTOR function is not well understood, it is known that rapamycin first binds to FKBP12 (FK506 binding protein) and then binds to FRB domain of mTOR and thus inhibit mTOR activity by inducing conformational changes, which inhibits substrate binding. Rapamycin has been widely used as a specific mTOR inhibitor in preclinical studies to demonstrate role of mTOR in signal transduction and cancer. But rapamycin was not developed as a cancer therapy because of stability and solubility problems even though significant antitumor activity was observed in the NCI screening programme. However, synthesis of rapamycin analogues with superior solubility and stability properties has led to run the clinical trails with CCI-779, RAD001 and AP23573. The most advanced rapamycin analogue, CCI-779 has shown modest anti-tumor activity in Phase II breast renal carcinoma and mantle cell lymphoma clinical trials.

The Tor genes were originally identified in yeast as the targets of the drug rapamycin. The structurally and functionally conserved mammalian counter part of yeast TOR, mTOR was later discovered. mTOR is a member of the phosphoinositide kinase-related kinase (PIKK) family, but rather than phosphorylating phosphoinositides, phosphorylates proteins on serine or threonine residues. Genetic studies have shown that mTOR is essential for cell growth and development in fruit flies, nematodes and mammals, and the disruption of the genes encoding mTOR results in lethality in all species. Several studies have demonstrated that mTOR has a central role in controlling cell growth, proliferation and metabolism. mTOR regulates a wide range of cellular functions, including translation, transcription, mRNA turnover, protein stability, actin cytoskeletal organization and autophagy. There are two mTOR complexes in mammalian cells. mTOR complex I (mTORC1) is a raptor-mTOR complex, which mainly regulates cell growth in a rapamycin-sensitive manner whereas mTOR complex II (mTORC2) is a rictor-mTOR complex, which regulates cytoskeletal organization in a rapamycin-insensitive manner.

The best-characterized function of mTOR in mammalian cells is regulation of translation. Ribosomal S6 kinase (S6K) and eukaryotic initiation factor 4E binding protein 1 (4E-BP1), the most extensively studied substrates of mTOR, are key regulators of protein translation. S6K is the major ribosomal protein kinase in mammalian cells. Phosphorylation of S6 protein by S6K selectively increases the translation of mRNAs containing a tract of pyrimidines motif; these mRNAs often encode ribosomal proteins and other translational regulators. Thus, S6K enhances overall translation capacity of cells. 4E-BP1, another well-characterized mTOR target, acts as a translational repressor by binding and inhibiting the eukaryotic translation initiation factor 4E (eIF4E), which recognizes the 5' end cap of eukaryotic mRNAs. Phosphorylation of 4E-BP1 by mTOR results in a dissociation of 4E-BP1 from eIF4E, thereby relieving the inhibition of 4E-BP1 on eIF4E-dependent translation initiation. eIF4E overexpression enhances cell growth and transforms cells by increasing the translation of a subset of key growth-promoting proteins, including cyclin D1, c-Myc and VEGF. Therefore, mTOR-dependent regulation of both 4E-BP1 and S6K might be one mechanism by which mTOR positively regulates cell growth. mTOR integrates two of the most important extracellular and intracellular signals involved in the regulation of cell growth: growth factors and nutrients. Growth factor, such as insulin or IGF1 and nutrients, such as amino acids or glucose, enhance mTOR function, as evidenced by an increased phosphorylation of S6K and 4E-BP1. Rapamycin or dominant negative mTOR inhibits these effects, indicating that mTOR integrates the regulation of signals from growth factors and nutrients.

Signalling pathways that are upstream and downstream of mTOR are often deregulated in variety of cancers, including breast, lung, kidney, prostate, blood, liver, ovarian, thyroid, GI tract and lymphoma. Oncogenes including overexpressed receptor tyrosine kinases and constitutively activated mutant receptors activate PI3K-mediated signaling pathways. Additional alterations of the PI3K-mTOR pathway in human cancers include amplification of the p110 catalytic subunit of PI3K, loss of PTEN phosphatase function, amplification of AKT2, mutations in TSC1 or TSC2, and overexpression or amplification of eIF4E or S6K1. Mutation or loss of heterozygosity in TSC1 and TSC2 most often give rise to Tuberous Sclerosis (TSC) syndrome. TSC is rarely associated with malignant tumors, although patients with TSC are at risk for malignant renal cancer of clear-cell histology. Although inactivation of TSC might not lead to malignancy per se, deregulation of this pathway seems crucial for angiogenesis in developing malignancies. TSC2 regulates VEGF production through mTOR-dependent and -independent manner.

With the recent discovery of rapamycin independent function of mTOR (by mTOR2) in phosphorylation AKT (at S473) that is important in regulation of cell survival and modulation of PKCα, which plays a major role in regulation of actin cytoskeletal organization, it is believed that inhibition of mTOR function by rapamycin is partial. Therefore, discovery of a direct mTOR kinase inhibitor, which would completely inhibit the function of both mTORC1 and mTORC2, is required for broader anti-tumor activity and better efficacy. Here we describe the discovery of direct mTOR kinase inhibitors, which can be used in the treatment of variety of cancers—including breast, lung, kidney, prostate, blood, liver, ovarian, thyroid, GI tract and lymphoma—and other indications such as rheumatoid arthritis, hamartoma syndromes, transplant rejection, IBD, multiple sclerosis and immunosuppression.

Recent success of Tarceva™, an EGFR kinase inhibitor for the treatment of NSCLC and prior success with Gleevec™ for the treatment of CML indicate that it is possible to develop selective kinase inhibitors for the effective treatment of cancers. Although there are several anti-cancer agents including kinase inhibitors, there is still continuing need for improved anti-cancer drugs, and it would be desirable to develop new compounds with better selectivity, potency or with reduced toxicity or side effects.

Thus, it is desirable to develop compounds that exhibit mTOR inhibition in order to treat cancer patients. Further, such compounds may be active in other kinases such as, for example, PI3K, Src, KDR, to add efficacy in breast, non-small cell lung cancer (NSCLC), renal cell carcinoma, mantle cell lymphoma, endometrial cancers, or other hamartoma syndromes.

SUMMARY OF THE INVENTION

Compounds represented by Formula (I)

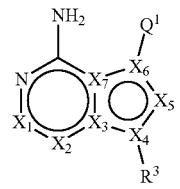

(I)

or a pharmaceutically acceptable salt thereof, are inhibitors of mTOR and useful in the treatment of cancer.

DETAILED DESCRIPTION OF THE INVENTION

The compounds of the present invention are represented by Formula (I)

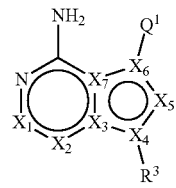

(I)

or a pharmaceutically acceptable salt thereof, wherein:
$X_1$, and $X_2$ are each independently N or C-$(E^1)_{aa}$;
$X_5$ is N, C-$E^1)_{aa}$, or N-$(E^1)_{aa}$;
$X_3$, $X_4$, $X_6$, and $X_7$ are each independently N or C;
wherein at least one of $X_3$, $X_4$, $X_5$, $X_6$, and $X_7$ is independently N or N-$(E^1)_{aa}$;
$R^3$ is $C_{0-10}$alkyl, cyclo$C_{3-10}$alkyl, aminomethylcyclo$C_{3-10}$alkyl, bicyclo$C_{5-10}$alkyl, aryl, heteroaryl, aralkyl, heteroaralkyl, heterocyclyl or heterobicyclo$C_{5-10}$alkyl any of which is optionally substituted by one or more independent $G^{11}$ substituents;
$Q^1$ is -A$(R^1)_m$B$(W)_n$ or —B$(G^{11})_n$A$(Y)_m$;
A and B are respectively, 5 and 6 membered aromatic or heteroaromatic rings, fused together to form a 9-membered heteroaromatic system excluding 5-benzo[b]furyl and 3-indolyl; and excluding 2-indolyl, 2-benzoxazole, 2-benzothiazole, 2-benzimidazolyl, 4-aminopyrrolopyrimidin-5-yl, 4-aminopyrrolopyrimidin-6-yl, and 7-deaza-7-adenosinyl derivatives when $X_1$ and $X_5$ are CH, $X_3$, $X_6$ and $X_7$ are C, and $X_2$ and $X_4$ are N;
or $Q^1$ is -A$(R^1)_m$A$(Y)_m$, wherein each A is the same or different 5-membered aromatic or heteroaromatic ring, and the two are fused together to form an 8-membered heteroaromatic system;
$R^1$ is independently, hydrogen, —N($C_{0-8}$alkyl)($C_{0-8}$alkyl), hydroxyl, halogen, oxo, aryl(optionally substituted with 1 or more $R^{31}$ groups), hetaryl(optionally substituted with 1 or more $R^{31}$ groups), $C_{1-6}$alkyl, —$C_{0-8}$alkyl$C_{3-8}$cycloalkyl, —$C_{0-8}$alkyl-NR$^{311}$S(O)$_{0-2}$NR$^{321}$R$^{331}$, —$C_{0-8}$alkyl-S(O)$_{0-2}$NR$^{311}$R$^{321}$, —$C_{0-8}$alkyl-NR$^{311}$COR$^{321}$, —$C_{0-8}$alkyl-NR$^{311}$CO$_2$R$^{321}$, —$C_{0-8}$alkyl-NR$^{311}$CONR$^{321}$R$^{331}$, —$C_{0-8}$alkyl-CONR$^{311}$R$^{321}$, —$C_{0-8}$alkyl-CON(R$^{311}$)S(O)$_{0-2}$R$^{321}$, —$C_{0-8}$alkyl-CO$_2$R$^{311}$, —$C_{0-8}$alkyl-S(O)$_{0-2}$R$^{311}$, —$C_{0-8}$alkyl-O—$C_{1-8}$alkyl, —$C_{0-8}$alkyl-O—$C_{0-8}$alkyl$C_{3-8}$cycloalkyl, $C_{0-8}$alkyl-O—$C_{0-8}$alkylheterocyclyl, —$C_{0-8}$alkyl-O—$C_{0-8}$alkylaryl, —$C_{0-8}$alkylaryl, —$C_{0-8}$alkylhetaryl, —$C_{0-8}$alkylheterocyclyl, —$C_{0-8}$alkyl-O—$C_{0-8}$alkylhetaryl, —$C_{0-8}$alkyl-S—$C_{0-8}$alkyl, —$C_{0-8}$alkyl-S—$C_{0-8}$alkyl$C_{3-8}$cycloalkyl, —$C_{0-8}$alkyl-S—$C_{0-8}$alkylheterocyclyl, —$C_{0-8}$alkyl-S—$C_{0-8}$alkylaryl, —$C_{0-8}$alkyl-S—$C_{0-8}$alkylhetaryl, —$C_{0-8}$alkyl-N(R$^{311}$)—$C_{0-8}$alkyl, —$C_{0-8}$alkyl-N(R$^{311}$)—$C_{0-8}$alkyl$C_{3-8}$cycloalkyl, —$C_{0-8}$alkyl-N(R$^{311}$)—$C_{0-8}$alkylheterocyclyl, —$C_{0-8}$alkyl-N(R$^{311}$)—$C_{0-8}$alkylaryl, —$C_{0-8}$alkyl-N(R$^{311}$)—$C_{0-8}$alkylhetaryl, —CO$C_{0-8}$alkyl-NR$^{311}$R$^{321}$, —$C_{2-8}$alkenyl, —$C_{2-8}$alkynyl, NO$_2$, CN, CF$_3$, OCF$_3$, OCHF$_2$; provided that $Q^1$ is not N-methyl-2-indolyl, N-(phenylsulfonyl)-2-indolyl, or N-tert-butoxycarbonyl W is independently, hydrogen, —N($C_{0-8}$alkyl)($C_{0-8}$alkyl), hydroxyl, halogen, oxo, aryl (optionally substituted with 1 or more $R^{31}$ groups), hetaryl (optionally substituted with 1 or more $R^{31}$ groups), $C_{1-6}$alkyl, —$C_{0-8}$alkyl$C_{3-8}$cycloalkyl, —$C_{0-8}$alkyl-NR$^{312}$S(O)$_{0-2}$R$^{322}$, —$C_{0-8}$alkyl-NR$^{311}$S(O)$_{0-2}$NR$^{321}$R$^{331}$, —$C_{0-8}$alkyl-NR$^{311}$CO$_2$R$^{321}$, —$C_{0-8}$alkyl-CON(R$^{311}$)S(O)$_{0-2}$R$^{321}$, —$C_{0-8}$alkyl-S(O)$_{0-2}$NR$^{312}$R$^{322}$, $C_{0-8}$alkyl-NR$^{312}$COR$^{322}$, —$C_{0-8}$alkyl-NR$^{312}$CONR$^{322}$R$^{332}$, —$C_{0-8}$alkyl-CONR$^{312}$R$^{322}$, —$C_{0-8}$alkyl-CO$_2$R$^{312}$, —$C_{0-8}$alkylS(O)$_{0-2}$R$^{312}$, —$C_{0-8}$alkyl-O—$C_{1-8}$alkyl, —$C_{0-8}$alkyl-O—$C_{0-8}$alkylcyclyl, —$C_{0-8}$alkyl-O—$C_{0-8}$alkylheterocycloalkyl, —$C_{0-8}$alkyl-O—$C_{0-8}$alkylaryl, -Oaryl, —$C_{0-8}$alkyl-O—$C_{0-8}$alkylhetaryl, —$C_{0-8}$alkylaryl, —$C_{0-8}$alkylhetaryl, —$C_{0-8}$alkylheterocyclyl, —$C_{0-8}$alkyl-S—$C_{0-8}$alkyl, —$C_{0-8}$alkyl-S—$C_{0-8}$alkyl$C_{3-8}$cycloalkyl, —$C_{0-8}$alkyl-S—$C_{0-8}$alkylheterocycloalkyl, —$C_{0-8}$alkyl-S—$C_{0-8}$alkylaryl, —$C_{0-8}$alkyl-S—$C_{0-8}$alkylhetaryl, —$C_{0-8}$alkyl-N(R$^{312}$)—$C_{0-8}$alkyl, —$C_{0-8}$alkyl-N(R$^{312}$)—$C_{0-8}$alkyl$C_{3-8}$cycloalkyl, —$C_{0-8}$alkyl-N(R$^{312}$)—$C_{0-8}$alkylheterocycloalkyl, —$C_{0-8}$alkyl-N(R$^{312}$)—$C_{0-8}$alkylaryl, —$C_{0-8}$alkyl-N(R$^{312}$)—$C_{0-8}$alkylhetaryl, —$C_{0-8}$alkyl-NR$^{312}$R$^{322}$, —$C_{2-8}$alkenyl, —$C_{2-8}$alkynyl, NO$_2$, CN, CF$_3$, OCF$_3$, OCHF$_2$; provided that $Q^1$ is not 4-benzyloxy-2-indolyl;

Y is independently, hydrogen, —N($C_{0-8}$alkyl)($C_{0-8}$alkyl), hydroxyl, halogen, oxo, aryl(optionally substituted with 1 or more $R^{31}$ groups), hetaryl(optionally substituted with 1 or more $R^{31}$ groups), $C_{0-6}$alkyl, —$C_{0-8}$alkyl$C_{3-8}$cycloalkyl, —$C_{0-8}$alkyl-$NR^{311}S(O)_{0-2}R^{321}$, —$C_{0-8}$alkyl-$NR^{311}S(O)_{0-2}$ $NR^{321}R^{331}$, —$C_{0-8}$alkyl-$NR^{311}CO_2R^{321}$, —$C_{0-8}$alkyl-CON ($R^{311}$)$S(O)_{0-2}R^{321}$, —$C_{0-8}$alkyl-$S(O)_{0-2}NR^{311}R^{321}$, —$C_{0-8}$ alkyl-$NR^{311}COR^{321}$, —$C_{0-8}$alkyl-$NR^{311}CONR^{321}R^{3311}$, —$C_{0-8}$alkyl-$CONR^{311}R^{321}$, —$C_{0-8}$alkyl-$CO_2R^{311}$, —$C_{0-8}$ alkyl$S(O)_{0-2}R^{311}$, —$C_{0-8}$alkyl-O—$C_{1-8}$alkyl, —$C_{0-8}$alkyl-O—$C_{0-8}$alkyl$C_{3-8}$cycloalkyl, —$C_{0-8}$alkyl-O—$C_{0-8}$alkylheterocycloalkyl, —$C_{0-8}$alkyl-O—$C_{0-8}$alkylaryl, —$C_{0-8}$alkyl-O—$C_{0-8}$alkylhetaryl, —$C_{0-8}$alkylaryl, —$C_{0-8}$alkylhetaryl, —$C_{0-8}$alkylheterocyclyl, —$C_{0-8}$alkyl-S—$C_{0-8}$alkyl, —$C_{0-8}$alkyl-S—$C_{0-8}$alkyl$C_{3-8}$cycloalkyl, —$C_{0-8}$alkyl-S—$C_{0-8}$alkylheterocycloalkyl, —$C_{0-8}$alkyl-S—$C_{0-8}$alkylaryl, —$C_{0-8}$alkyl-S—$C_{0-8}$alkylhetaryl, —$C_{0-8}$alkyl-N($R^{311}$)—$C_{0-8}$alkyl, —$C_{0-8}$alkyl-N($R^{311}$)—$C_{0-8}$alkyl$C_{3-8}$cycloalkyl, —$C_{0-8}$alkyl-N($R^{311}$)—$C_{0-8}$alkylheterocycloalkyl, —$C_{0-8}$alkyl-N ($R^{311}$)—$C_{0-8}$alkylaryl, —$C_{0-8}$alkyl-N($R^{311}$)—$C_{0-8}$alkylhetaryl, —$C_{0-8}$alkyl-$NR^{311}R^{321}$, —$C_{2-8}$alkenyl, —$C_{2-8}$alkynyl, $NO_2$, CN, $CF_3$, $OCF_3$, $OCHF_2$; provided that $Q^1$ is not 2-carboxy-5-benzo[b]thiophenyl;

$G^{11}$ is halo, oxo, —$CF_3$, —$OCF_3$, —$OR^{312}$, —$NR^{312}R^{322}$, —$C(O)R^{312}$, —$C(O)C_{3-8}$cycloalkyl, —$CO_2C_{3-8}$cycloalkyl, —$CO_2R^{312}$, —$C(=O)NR^{312}R^{322}$, —$NO_2$, —CN, —$S(O)_{0-2}$ $R^{312}$, —$SO_2NR^{312}R^{322}$, $NR^{312}(C=O)R^{322}$, $NR^{312}C(=O)$ $OR^{322}$, $NR^{312}C(=O)NR^{322}R^{332}$, $NR^{312}S(O)_{0-2}R^{322}$, —$C(=S)OR^{312}$, —$C(=O)SR^{312}$, —$NR^{312}C(=NR^{322})$ $NR^{332}R^{341}$, —$NR^{312}C(=NR^{322})OR^{332}$, —$NR^{312}C(=NR^{322})SR^{332}$, —$OC(=O)OR^{312}$, —$OC(=O)NR^{312}R^{322}$, —$OC(=O)SR^{312}$, —$SC(=O)OR^{312}$, —$SC(=O)$ $NR^{312}R^{322}$, —$P(O)OR^{312}OR^{322}$, $C_{1-10}$alkylidene, $C_{0-10}$alkyl, $C_{2-10}$alkenyl, $C_{2-10}$alkynyl, —$C_{1-10}$alkoxy-$C_{1-10}$alkyl, —$C_{1-10}$alkoxy$C_{2-10}$alkenyl, —$C_{1-10}$alkoxy$C_{2-10}$ alkynyl, —$C_{1-10}$alkylthio$C_{1-10}$alkyl, —$C_{1-10}$alkylthio$C_{2-10}$ alkenyl, —$C_{1-10}$alkylthio$C_{2-10}$alkynyl, cyclo$C_{3-8}$alkyl, cyclo$C_{3-8}$alkenyl, -cyclo$C_{3-8}$alkyl$C_{1-10}$alkyl, -cyclo$C_{3-8}$alkenyl$C_{1-10}$alkyl, -cyclo$C_{3-8}$alkyl$C_{2-10}$alkenyl, cyclo$C_{3-8}$alkenyl$C_{2-10}$alkenyl, -cyclo$C_{3-8}$alkyl$C_{2-10}$alkynyl, cyclo$C_{3-8}$alkenyl$C_{2-10}$alkynyl, -heterocyclyl-$C_{0-10}$alkyl, heterocyclyl-$C_{2-10}$alkenyl, or -heterocyclyl-$C_{2-10}$alkynyl, any of which is optionally substituted with one or more independent halo, oxo, —$CF_3$, —$OCF_3$, —$OR^{313}$, —$NR^{313}R^{323}$, —$C(O)R^{313}$, —$CO_2R^{313}$, —$C(=O)NR^{313}R^{323}$, —$NO_2$, —CN, —$S(O)_{0-2}$ $R^{313}$, —$SO_2NR^{313}R^{323}$, —$NR^{313}C(=O)R^{323}$, —$NR^{313}C(=O)OR^{323}$, —$NR^{313}C(=O)NR^{323}R^{333}$, —$NR^{313}S(O)_{0-2}$ $R^{323}$, —$C(=S)OR^{313}$, —$C(=O)SR^{313}$, —$NR^{313}C(=NR^{323})NR^{333}R^{342}$, —$NR^{313}C(=NR^{323})OR^{333}$, —$NR^{313}C(=NR^{323})SR^{333}$, —$OC(=O)OR^{333}$, —$OC(=O)$ $NR^{313}R^{323}$, —$OC(=O)SR^{313}$, —$SC(=O)OR^{313}$, —$P(O)$ $OR^{313}OR^{323}$ or —$SC(=O)NR^{313}R^{323}$ substituents;

or $G^{11}$ is aryl-$C_{0-10}$alkyl, aryl-$C_{2-10}$alkenyl, aryl-$C_{2-10}$ alkynyl, hetaryl-$C_{0-10}$alkyl, hetaryl-$C_{2-10}$alkenyl, or hetaryl-$C_{2-10}$alkynyl, where the attachment point is from either the left or right as written, where any of which is optionally substituted with one or more independent halo, —$CF_3$, —$OCF_3$, —$OR^{313}$, —$NR^{313}R^{323}$, —$C(O)R^{313}$, —$CO_2R^{313}$, —$C(=O)NR^{313}R^{323}$, —$NO_2$, —CN, —$S(O)_{0-2}$ $R^{313}$, —$SO_2NR^{313}R^{323}$, —$NR^{313}C(=O)R^{323}$, —$NR^{313}C(=O)$ $OR^{323}$, —$NR^{313}C(=O)NR^{323}R^{333}$, —$NR^{313}S(O)_{0-2}$ $R^{323}$, —$C(=S)OR^{313}$, —$C(=O)SR^{313}$, —$NR^{323}C(=NR^{313})$ $NR^{333}R^{342}$, —$NR^{313}C(=NR^{323})OR^{333}$, —$NR^{313}C(=NR^{323})SR^{333}$, —$OC(=O)OR^{313}$, —$OC(=O)$ $NR^{313}R^{323}$, —$OC(=O)SR^{313}$, —$SC(=O)OR^{313}$, —$P(O)$ $OR^{313}OR^{323}$, or —$SC(=O)NR^{313}R^{323}$ substituents; provided that $G^{11}$ is not N—$CH_2CO_2H$ when $R^3$ is 4-piperidinyl;

$R^{31}$, $R^{32}$, $R^{33}$, $R^{311}$, $R^{321}$, $R^{331}R^{312}R^{322}$, $R^{332}$, $R^{341}$, $R^{313}$, $R^{323}$, $R^{333}$, and $R^{342}$, in each instance, is independently $C_{0-8}$alkyl optionally substituted with an aryl, heterocyclyl or hetaryl substituent, or $C_{0-8}$alkyl optionally substituted with 1-6 independent halo, —$CON(C_{0-8}$alkyl$)$ $(C_{0-8}$alkyl$)$, —$CO(C_{0-8}$alkyl$)$, —$OC_{0-8}$alkyl, -Oaryl, -Ohetaryl, -Oheterocyclyl, —$S(O)_{0-2}$aryl, —$S(O)_{0-2}$ hetaryl, —$S(O)_{0-2}$heterocyclyl, —$S(O)_{0-2}C_{0-8}$alkyl, —$N(C_{0-8}$alkyl$)(C_{0-8}$alkyl$)$, —$N(C_{0-8}$alkyl$)CON(C_{0-8}$ alkyl$)(C_{0-8}$alkyl$)$, —$N(C_{0-8}$alkyl$)CO(C_{1-8}$alkyl$)$, —$N(C_{0-8}$alkyl$)CO(C_{3-8}$cycloalkyl$)$, —$N(C_{0-8}$alkyl$)$ $CO_2(C_{1-8}$alkyl$)$, —$S(O)_{1-2}N(C_{0-8}$alkyl$)(C_{0-8}$alkyl$)$, —$NR^{11}S(O)_{1-2}(C_{0-8}$alkyl$)$, —$CON(C_{3-8}$cycloalkyl$)$ $(C_{3-8}$cycloalkyl$)$, —$CON(C_{0-8}$alkyl$)(C_{3-8}$cycloalkyl$)$, —$N(C_{3-8}$cycloalkyl$)CON(C_{0-8}$alkyl$)(C_{0-8}$alkyl$)$, —$N(C_{3-8}$cycloalkyl$)CON(C_{3-8}$cycloalkyl$)(C_{0-8}$alkyl$)$, —$N(C_{0-8}$alkyl$)CON(C_{3-8}$cycloalkyl$)(C_{0-8}$alkyl$)$, —$N(C_{0-8}$alkyl$)CO_2(C_{3-8}$cycloalkyl$)$, —$N(C_{3-8}$cycloalkyl$)CO_2(C_{3-8}$cycloalkyl$)$, $S(O)_{1-2}N(C_{0-8}$alkyl$)$ $(C_{3-8}$cycloalkyl$)$-$NR^{11}S(O)_{1-2}(C_{3-8}$cycloalkyl$)$, $C_{2-8}$alkenyl, $C_{2-8}$alkynyl, CN, $CF_3$, OH, or optionally substituted aryl substituents; such that each of the above aryl, heterocyclyl, hetaryl, alkyl or cycloalkyl groups may be optionally, independently substituted with —$N(C_{0-8}$alkyl$)(C_{0-8}$alkyl$)$, hydroxyl, halogen, oxo, aryl, hetaryl, $C_{0-6}$alkyl, $C_{0-8}$alkylcyclyl, —$C_{0-8}$alkyl-N $(C_{0-8}$alkyl$)$-$S(O)_{0-2}$—($C_{0-8}$alkyl$)$, $C_{0-8}$alkyl-$S(O)_{0-2}$— $N(C_{0-8}$alkyl$)(C_{0-8}$alkyl$)$, —$C_{0-8}$alkyl-$N(C_{0-8}$alkyl$)CO$ $(C_{0-8}$alkyl$)$, —$C_{0-8}$alkyl-$N(C_{0-8}$alkyl$)CO$—$N(C_{0-8}$ alkyl$)(C_{0-8}$alkyl$)$, $C_{0-8}$alkyl-CO—$N(C_{0-8}$alkyl$)(C_{0-8}$ alkyl$)$, —$C_{1-8}$alkyl-$CO_2$—$(C_{0-8}$alkyl$)$, —$C_{0-8}$alkyl-$S(O)_{0-2}$—$(C_{0-8}$alkyl$)$, —$C_{0-8}$alkyl-O—$C_{1-8}$alkyl, —$C_{0-8}$alkyl-O—$C_{0-8}$alkylcyclyl, —$C_{0-8}$alkyl-O—$C_{0-8}$alkylheterocyclyl, —$C_{0-8}$alkyl-O—$C_{0-8}$alkylaryl, —$C_{0-8}$alkyl-O—$C_{0-8}$alkylhetaryl, —$C_{0-8}$alkyl-S—$C_{0-8}$alkyl, —$C_{0-8}$alkyl-S—$C_{0-8}$alkylcyclyl, —$C_{0-8}$alkyl-S—$C_{0-8}$alkylheterocyclyl, —$C_{0-8}$alkyl-S—$C_{0-8}$alkylaryl, —$C_{0-8}$alkyl-S—$C_{0-8}$alkylhetaryl, —$C_{0-8}$alkyl-N($C_{0-8}$alkyl)-$C_{0-8}$alkyl, —$C_{0-8}$alkyl-N($C_{0-8}$alkyl)-$C_{0-8}$alkylcyclyl, $C_{0-8}$alkyl-N($C_{0-8}$alkyl)-$C_{0-8}$alkylheterocyclyl, —$C_{0-8}$alkyl-N($C_{0-8}$alkyl)-$C_{0-8}$alkylaryl, —$C_{0-8}$alkyl-N($C_{0-8}$alkyl)-$C_{0-8}$alkylhetaryl, $C_{2-8}$alkenyl, $C_{2-8}$alkynyl, $NO_2$, CN, $CF_3$, $OCF_3$, $OCHF_2$, —$C_{0-8}$alkyl$C_{3-8}$cycloalkyl,
—$C_{0-8}$alkyl-O—$C_{0-8}$alkyl,
—$C_{0-8}$alkyl-N($C_{0-8}$alkyl)($C_{0-8}$alkyl),
—$C_{0-8}$alkyl-$S(O)_{0-2}$—$C_{0-8}$alkyl, or
heterocyclyl optionally substituted with 14 independent $C_{0-8}$alkyl, cyclyl, or substituted cyclyl substituents;

$E^1$ in each instance is independently halo, —$CF_3$, —$OCF_3$, —$OR^2$, —$NR^{31}R^{32}$, —$C(=O)R^{31}$, —$CO_2R^{31}$, —$CONR^{31}R^{32}$, —$NO_2$, —CN, —$S(O)_{0-2}R^{31}$, —$S(O)_{0-2}$ $NR^{31}R^{32}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)$ $OR^{31}$, —$C(=O)SR^{31}$, —$NR^{31}C(=NR^{32})NR^{33}R^{31}$, —$NR^{31}C(=NR^{32})OR^{33}$, —$NR^{31}C(=NR^{31})SR^{31}$, —$OC(=O)OR^{31}$, —$OC(=O)NR^{31}R^{32}$, —$OC(=O)SR^{31}$, —$SC(=O)OR^{31}$, —$SC(=O)N^{31}R^{32}$, $C_{0-10}$alkyl, $C_{2-10}$alkenyl, $C_{2-10}$alkynyl, —$C_{1-10}$alkoxy$C_{1-10}$alkyl, —$C_{1-10}$alkoxy$C_{2-10}$ alkenyl, —$C_{1-10}$alkoxy$C_{2-10}$alkynyl, —$C_{1-10}$alkylthio$C_{1-10}$ alkyl, —$C_{1-10}$alkylthio$C_{2-10}$alkenyl, $C_{1-10}$alkylthio$C_{2-10}$ alkynyl, cyclo$C_{3-8}$alkyl, cyclo$C_{3-8}$alkenyl, -cyclo$C_{3-8}$ alkyl$C_{1-10}$alkyl, -cyclo$C_{3-8}$alkenyl$C_{1-10}$alkyl, -cyclo$C_{3-8}$ alkylC$_{2-10}$alkenyl, -cycloC$_{3-8}$alkenylC$_{2-10}$alkenyl, -cyclo-C$_{3-8}$alkylC$_{2-10}$alkynyl, -cycloC$_{3-8}$alkenylC$_{2-10}$alkynyl, -heterocyclyl-C$_{0-10}$alkyl, -heterocyclyl-C$_{2-10}$alkenyl, or -heterocyclyl-C$_{2-10}$alkynyl, any of which is optionally substituted with one or more independent halo, oxo, —CF$_3$, —OCF$_3$, —OR$^{31}$, —NR$^{31}$R$^{32}$, —C(=O)R$^{31}$, CO$_2$R$^{31}$, —C(=O)NR$^{31}$R$^{32}$, —NO$_2$, —CN, —S(=O)$_{0-2}$R$^{31}$, —SO$_2$NR$^{31}$, —NR$^{31}$C(=O)R$^{32}$, —NR$^{31}$C(=O)OR$^{31}$, —NR$^{31}$C(=O)NR$^{32}$R$^{33}$, —NR$^{31}$S(O)$_{0-2}$R$^{31}$, —C(=S)OR$^{31}$, —C(O)SR$^{31}$, —NR$^{31}$C(=NR$^{32}$)NR$^{33}$R$^{31}$, —NR$^{31}$C(=NR$^{32}$)OR$^{33}$, —NR$^{31}$C(=NR$^{32}$)SR$^{33}$, —OC(=O)OR$^{31}$, —OC(=O)NR$^{31}$R$^{32}$, —OC(=O)SR$^{31}$, —SC(=O)OR$^{31}$, or —SC(=O)NR$^{31}$R$^{32}$ substituents;

or E$^1$ in each instance is independently aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, where the attachment point is from either the left or right as written, where any of which is optionally substituted with one or more independent halo, —CF$_3$, —OCF$_3$, —R$^{31}$, —NR$^{31}$R$^{32}$, —C(O)R$^{31}$, CO$_2$R$^{31}$, —C(=O)NR$^{31}$R$^{32}$, —NO$_2$, —CN, —S(O)$_{0-2}$R$^{31}$, —S(O)$_{0-2}$NR$^{31}$R$^{32}$, —NR$^{31}$C(=O)R$^{32}$, —NR$^{31}$C(=O)R$^{32}$, —NR$^{31}$C(=O)NR$^{32}$R$^{33}$, —N$^{31}$S(O)$_{0-2}$R$^{32}$, —C(=S)OR$^{31}$, —C(=C)SR$^{31}$, —NR$^{31}$C(=NR$^{32}$)NR$^{33}$R$^{31}$, —NR$^{31}$C(=N$^{32}$)OR$^{33}$, —NR$^{31}$C(=NR$^{32}$)SR$^{33}$, —OC(=O)OR$^{31}$, —OC(=O)NR$^{31}$R$^{32}$, —OC(=O)SR$^{31}$, —SC(=O)OR$^{31}$, or —SC(=O)NR$^{31}$R$^{32}$ substituents;

in the cases of —NR$^{31}$NR$^{32}$, —NR$^{311}$R$^{321}$, —NR$^{312}$R$^{322}$, —NR$^{332}$R$^{341}$, —NR$^{313}$R$^{323}$, and —NR$^{323}$R$^{333}$, the respective R$^{31}$ and R$^{32}$, R$^{311}$ and R$^{321}$, R$^{312}$ and R$^{322}$, R$^{331}$ and R$^{341}$, R$^{313}$ and R$^{323}$, and R$^{323}$ and R$^{333}$ are optionally taken together with the nitrogen atom to which they are attached to form a 3-10 membered saturated or unsaturated ring; wherein said ring in each instance independently is optionally substituted by one or more independent —N(C$_{0-8}$alkyl)(C$_{0-8}$alkyl), hydroxyl, halogen, oxo, aryl, hetaryl, C$_{0-6}$alkyl, —C$_{0-8}$alkylC$_{3-8}$cycloalkyl, —C$_{0-8}$alkyl-N(C$_{0-8}$alkyl)S(O)$_{0-2}$C$_{0-8}$alkyl, —C$_{0-8}$alkyl-N(C$_{0-8}$alkyl)S(O)$_{0-2}$N(C$_{0-8}$alkyl)(C$_{0-8}$alkyl), —C$_{0-8}$alkyl-N(C$_{0-8}$alkyl)CO$_2$(C$_{0-8}$alkyl), —C$_{0-8}$alkyl-CON((C$_{0-8}$alkyl))S(O)$_{0-2}$(C$_{0-8}$alkyl), —C$_{0-8}$alkyl-S(O)$_{0-2}$N(C$_{0-8}$alkyl)(C$_{0-8}$alkyl), —C$_{0-8}$alkyl-N(C$_{0-8}$alkyl)CO(C$_{0-8}$alkyl), —C$_{0-8}$alkyl-N(C$_{0-8}$alkyl)CON(C$_{0-8}$alkyl)(C$_{0-8}$alkyl), —C$_{0-8}$alkyl-CON(C$_{0-8}$alkyl)(C$_{0-8}$alkyl), —C$_{0-8}$alkyl-CO$_2$(C$_{0-8}$alkyl), —C$_{0-8}$alkylS(O)$_{0-2}$(C$_{0-8}$alkyl), —C$_{0-8}$alkyl-O—C$_{0-8}$-alkyl, —C$_{0-8}$alkyl-O—C$_{0-8}$alkylcyclyl, —C$_{0-8}$alkyl-O—C$_{0-8}$alkylheterocycloalkyl, —C$_{0-8}$alkyl-O—C$_{0-8}$alkylaryl, -Oaryl, —C$_{0-8}$alkyl-O—C$_{0-8}$alkylhetaryl, —C$_{0-8}$alkyl-S—C$_{0-8}$alkyl, —C$_{0-8}$alkyl-S—C$_{0-8}$alkylC$_{3-8}$cycloalkyl, —C$_{0-8}$alkyl-S—C$_{0-8}$alkylheterocycloalkyl, —C$_{0-8}$alkyl-S—C$_{0-8}$alkylaryl, —C$_{0-8}$alkyl-S—C$_{0-8}$alkylhetaryl, —C$_{0-8}$alkyl-N(C$_{0-8}$alkyl)-C$_{0-8}$alkyl, —C$_{0-8}$alkyl-N(C$_{0-8}$alkyl)-C$_{0-8}$alkylC$_{3-8}$cycloalkyl, —C$_{0-8}$alkyl-N(C$_{0-8}$alkyl)-C$_{0-8}$alkylheterocycloalkyl, —C$_{0-8}$alkyl-N(C$_{0-8}$alkyl)-C$_{0-8}$alkylaryl, —C$_{0-8}$alkyl-N(C$_{0-8}$alkyl)-C$_{0-8}$alkylhetaryl, —C$_{0-8}$alkyl-N(C$_{0-8}$alkyl)(C$_{0-8}$alkyl), C$_{2-8}$alkenyl, C$_{2-8}$alkynyl, NO$_2$, CN, CF$_3$, OCF$_3$, or OCHF$_2$ substituents; wherein said ring in each instance independently optionally includes one or more heteroatoms other than the nitrogen;

m is 0, 1, 2, or 3;
n is 0, 1, 2, 3, or 4;
aa is 0 or 1; and
provided that Formula I is not
trans-4-[8-amino-1-(7-chloro-4-hydroxy-1H-indol-2-yl) imidazo[1,5-α]pyrazin-3-yl]cyclohexanecarboxylic acid,
cis-3-[8-amino-1-(7-chloro-1H-indol-2-yl)imidazo[1,5-α] pyrazin-3-yl]cyclobutanecarboxylic acid,
trans-4-{8-amino-1-[7-(3-isopropylphenyl-1H-indol-2-yl] imidazo[1,5-α]pyrazin-3-yl}cyclohexanecarboxylic acid or
trans-4-{8-amino-1-[7-(2,5-dichloro)phenyl-1H-indol-2-yl] imidazo[1,5-α]pyrazin-3-yl}cyclohexanecarboxylic acid.

According to an aspect of the present invention, the compounds are represented by Formula I, or a pharmaceutically acceptable salt thereof, wherein X$_1$ and X$_2$ are CH; X$_3$ and X$_5$ are N; and X$_4$, X$_6$ and X$_7$ are C; and the other variables are as described above for Formula I.

In an embodiment of this aspect of the present invention, the compounds are represented by Formula I, or a pharmaceutically acceptable salt thereof, wherein X$_1$ and X$_2$ are CH; X$_3$ and X$_5$ are N; and X$_4$, X$_6$ and X$_7$ are C; Q$^1$ is -A(R$^1$)$_m$B(W)$_n$; and the other variables are as described above for Formula I.

In another embodiment of this aspect of the present invention, the compounds are represented by Formula I, or a pharmaceutically acceptable salt thereof, wherein X$_1$ and X$_2$ are CH; X$_3$ and X$_5$ are N; and X$_4$, X$_6$ and X$_7$ are C; Q$^1$ is —B(G$^{11}$)$_n$A(Y)$_m$; and the other variables are as described above for Formula I.

In yet another embodiment of this aspect of the present invention, the compounds are represented by Formula I, or a pharmaceutically acceptable salt thereof, wherein X$_1$ and X$_2$ are CH; X$_3$ and X$_5$ are N; and X$_4$, X$_6$ and X$_7$ are C; Q$^1$ is optionally substituted indolyl; and the other variables are as described above for Formula I.

In still another embodiment of this aspect of the present invention, the compounds are represented by Formula I, or a pharmaceutically acceptable salt thereof, wherein X$_1$ and X$_2$ are CH; X$_3$ and X$_5$ are N; and X$_4$, X$_6$ and X$_7$ are C; Q$^1$ is optionally substituted benzothienyl; and the other variables are as described above for Formula I.

In an embodiment of this aspect of the present invention, the compounds are represented by Formula I, or a pharmaceutically acceptable salt thereof, wherein X$_1$ and X$_2$ are CH; X$_3$ and X$_5$ are N; and X$_4$, X$_6$ and X$_7$ are C; Q$^1$ is optionally substituted benzimidazolyl; and the other variables are as described above for Formula I.

In another embodiment of this aspect of the present invention, the compounds are represented by Formula I, or a pharmaceutically acceptable salt thereof, wherein X$_1$ and X$_2$ are CH; X$_3$ and X$_5$ are N; and X$_4$, X$_6$ and X$_7$ are C; Q$^1$ is optionally substituted benzoxazolyl; and the other variables are as described above for Formula I.

According to a second aspect of the present invention, the compounds are represented by Formula I, or a pharmaceutically acceptable salt thereof, wherein X$_1$ is CH; X$_2$, X$_3$ and X$_5$ are N; and X$_4$, X$_6$ and X$_7$ are C; and the other variables are as described above for Formula I.

In an embodiment of the second aspect of the present invention, the compounds are represented by Formula I, or a pharmaceutically acceptable salt thereof, wherein X$_1$ is CH; X$_2$, X$_3$ and X$_5$ are N; and X$_4$, X$_6$ and X$_7$ are C; Q$^1$ is -A(R$^1$)$_m$B(W)$_n$; and the other variables are as described above for Formula I.

In another embodiment of the second aspect of the present invention, the compounds are represented by Formula I, or a pharmaceutically acceptable salt thereof, wherein X$_1$ is CH; X$_2$, X$_3$ and X$_5$ are N; and X$_4$, X$_6$ and X$_7$ are C; Q$^1$ is —B(G$^{11}$)$_n$A(Y)$_m$; and the other variables are as described above for Formula I.

In yet another embodiment of the second aspect of the present invention, the compounds are represented by Formula I, or a pharmaceutically acceptable salt thereof, wherein X$_1$ is CH; X$_2$, X$_3$ and X$_5$ are N; and X$_4$, X$_6$ and X$_7$ are C; Q$^1$ is optionally substituted indolyl; and the other variables are as described above for Formula I.

In still another embodiment of the second aspect of the present invention, the compounds are represented by Formula I, or a pharmaceutically acceptable salt thereof, wherein $X_1$ is CH; $X_2$, $X_3$ and $X_5$ are N; and $X_4$, $X_6$ and $X_7$ are C; $Q^1$ is optionally substituted benzimidazolyl; and the other variables are as described above far Formula I.

In another embodiment of the second aspect of the present invention, the compounds are represented by Formula I, or a pharmaceutically acceptable salt thereof, wherein $X_1$ is CH; $X_2$, $X_3$ and $X_5$ are N; and $X_4$, $X_4$ and $X_7$ are C; $Q^1$ is optionally substituted benzoxazolyl; and the other variables are as described above for Formula I.

In yet still another embodiment of the second aspect of the present invention, the compounds are represented by Formula I, or a pharmaceutically acceptable salt thereof, wherein $X_1$ is CH; $X_2$, $X_3$ and $X_5$ are N; and $X_4$, $X_6$ and $X_7$ are C; $Q^1$ is optionally substituted benzothienyl; and the other variables are as described above for Formula I.

The compounds of the present invention include:

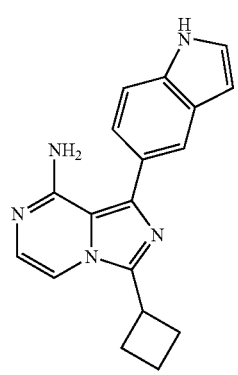

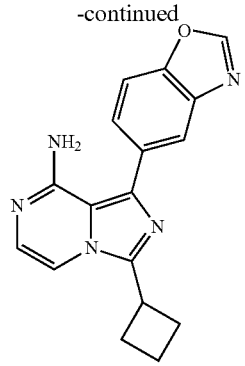

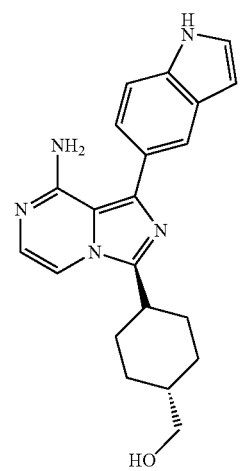

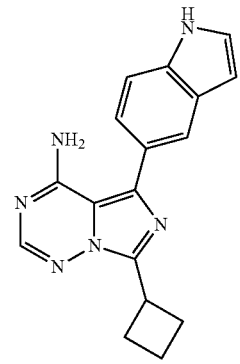

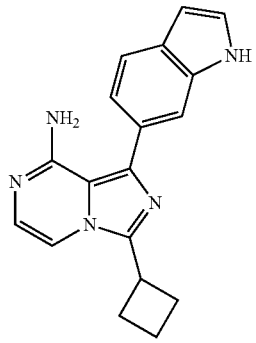

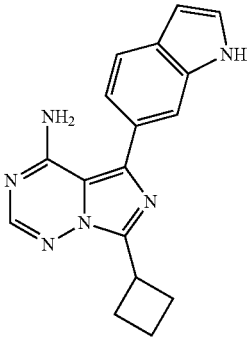

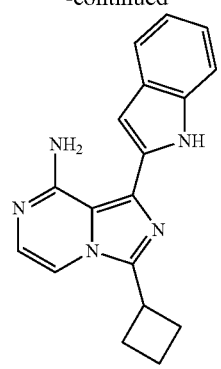
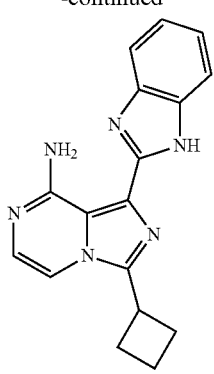
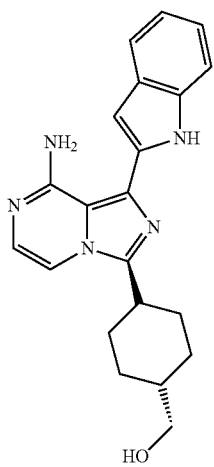
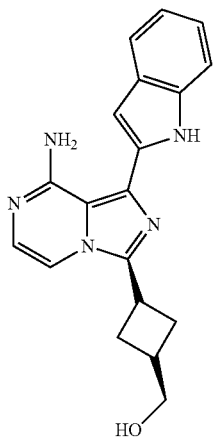
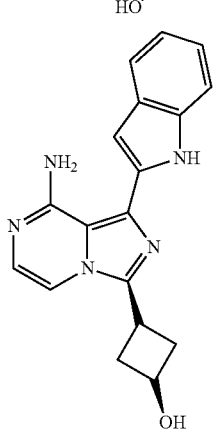

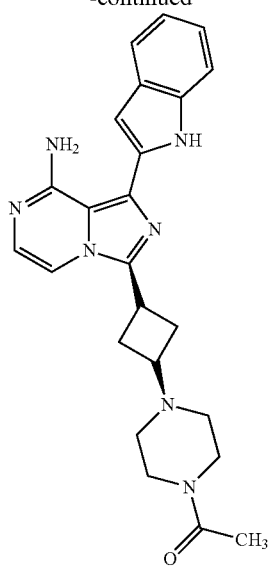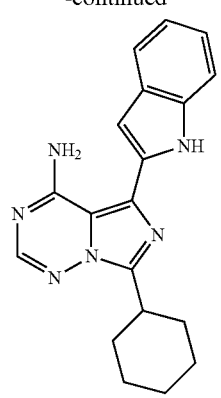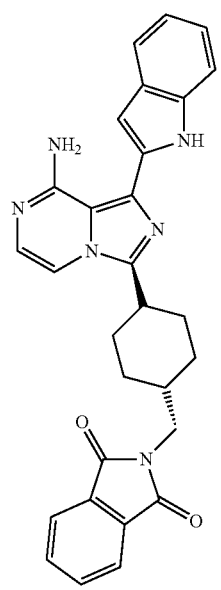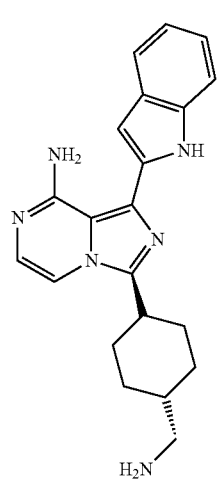

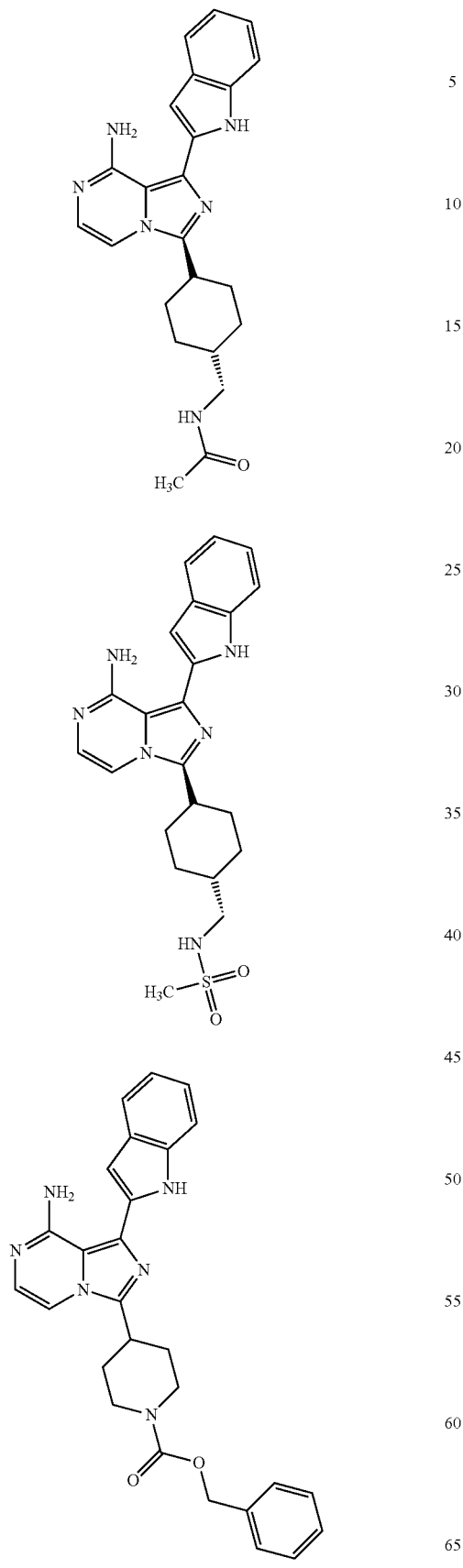
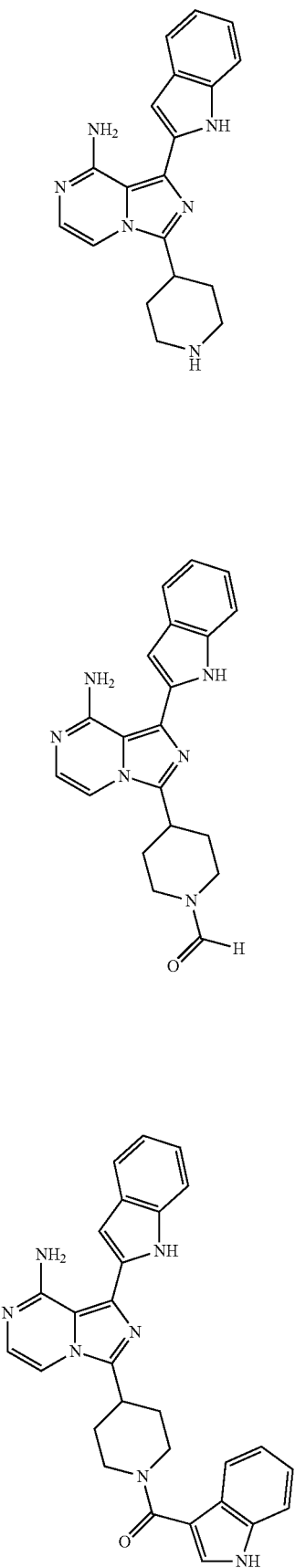

17
-continued
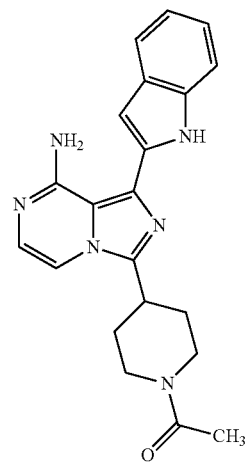
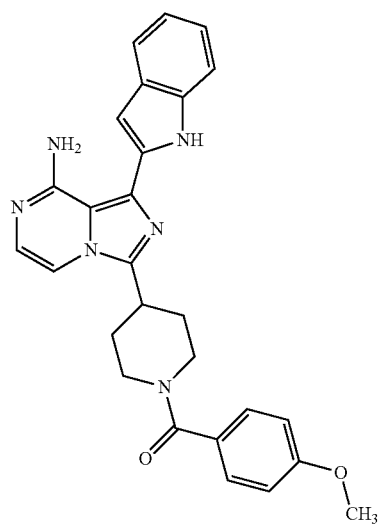
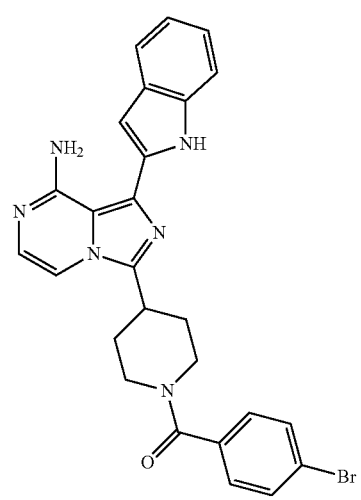
18
-continued
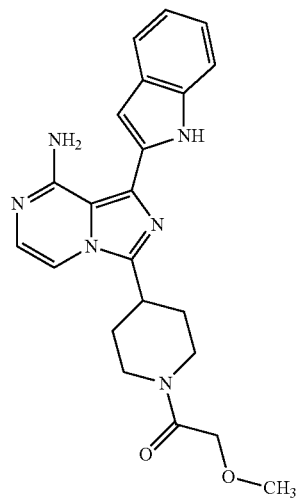
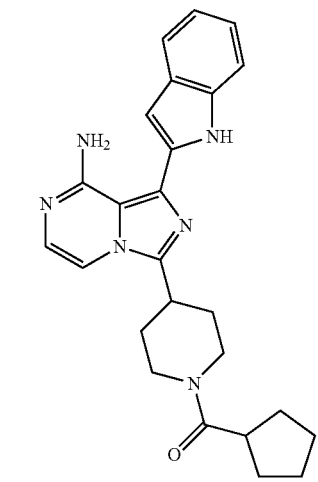

-continued
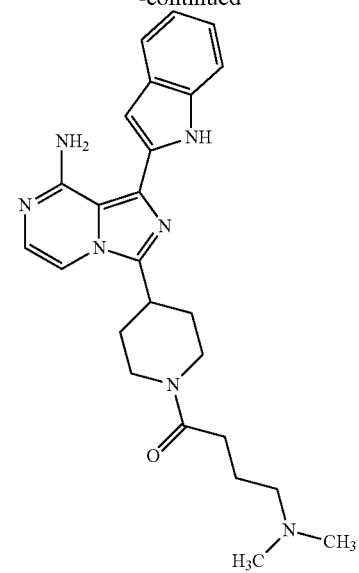
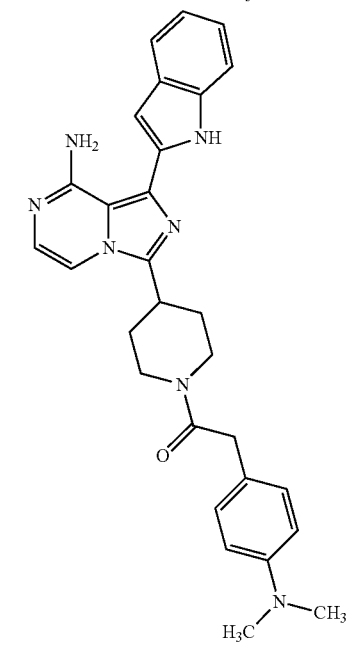
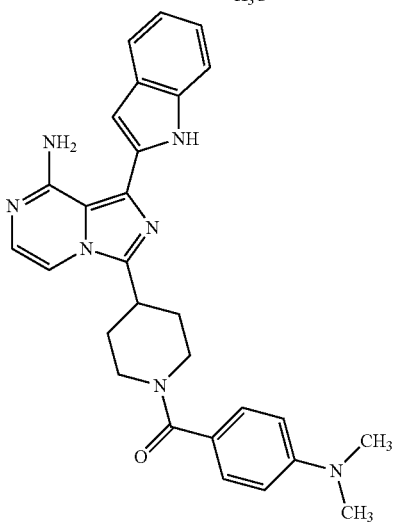
-continued
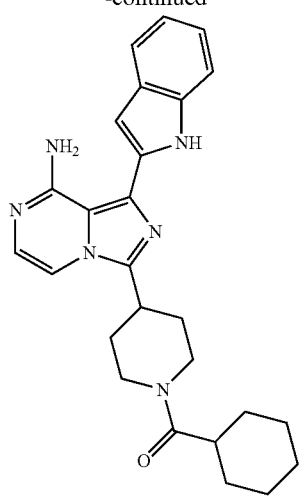
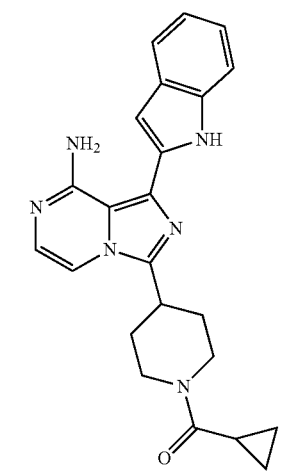
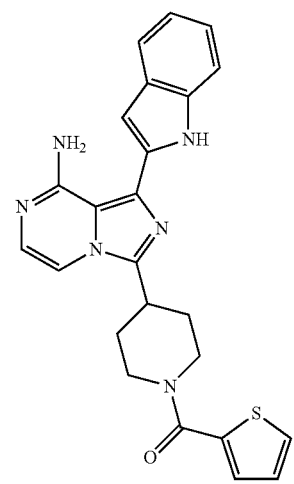

21
-continued
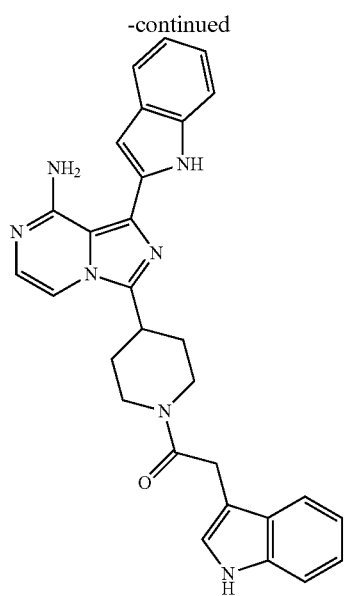
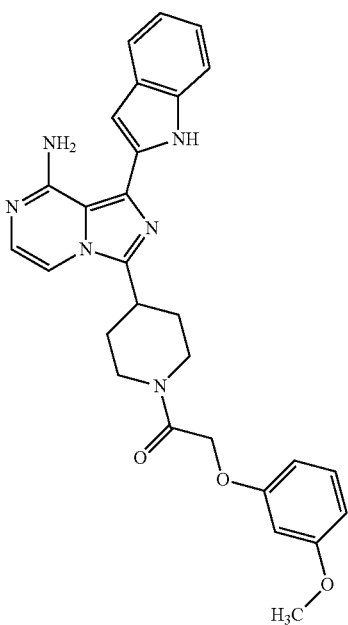
22
-continued
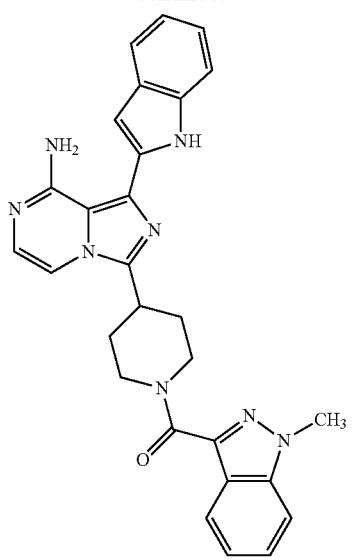
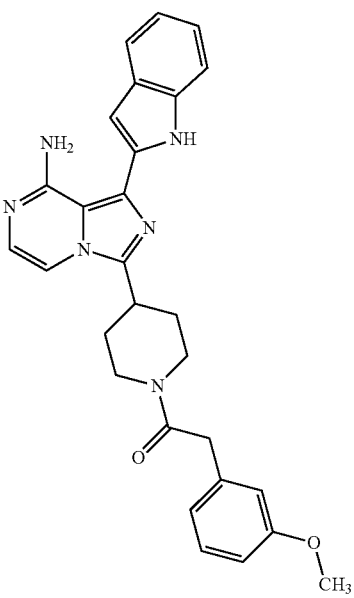
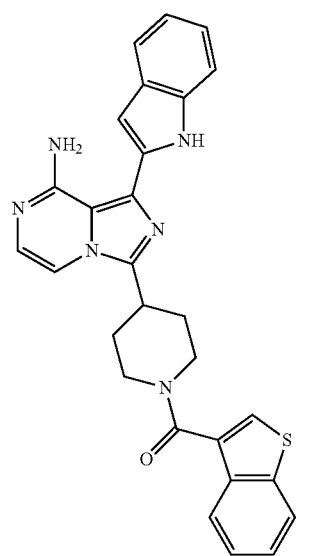

-continued
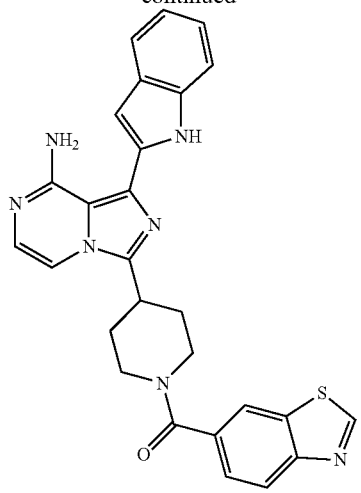
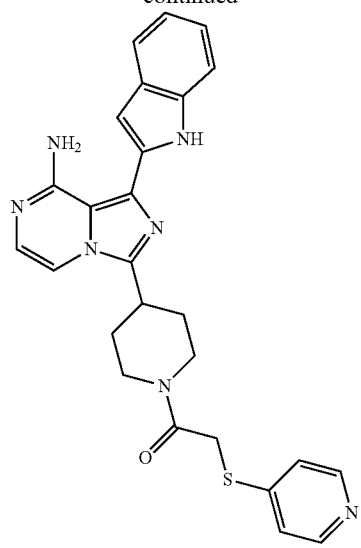
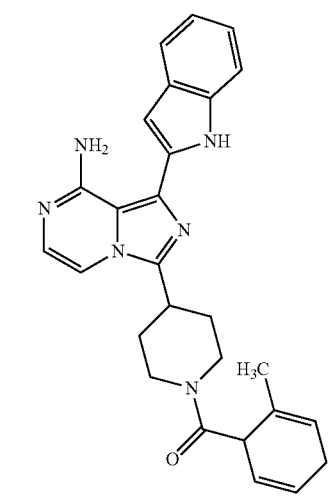
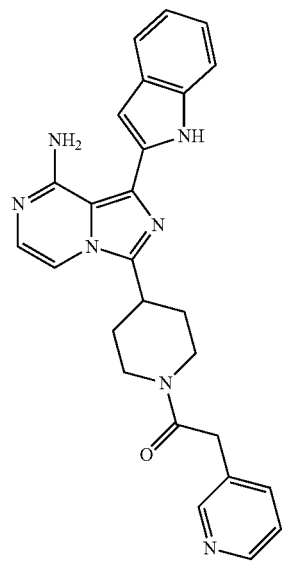
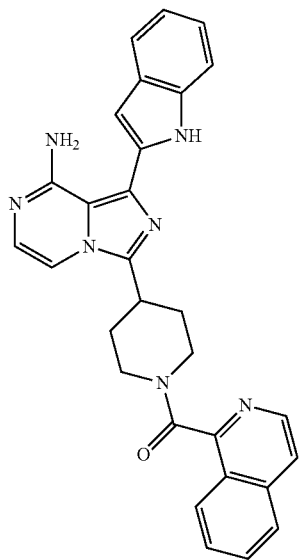
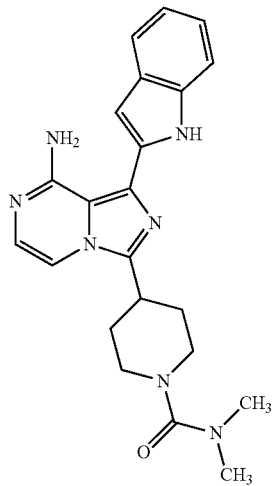

-continued
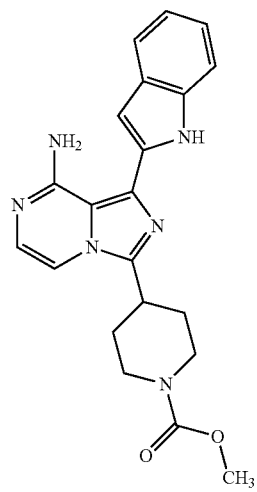
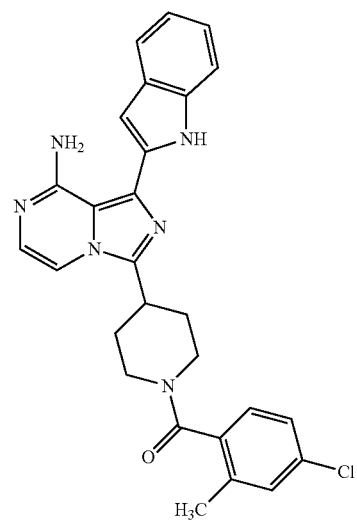
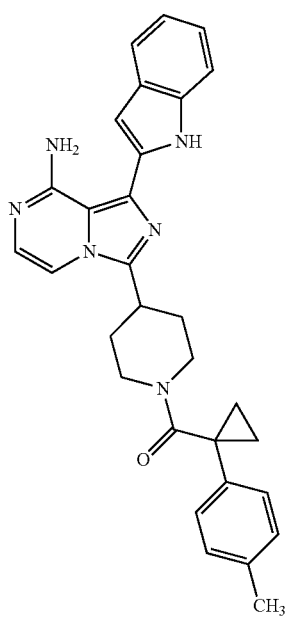
-continued
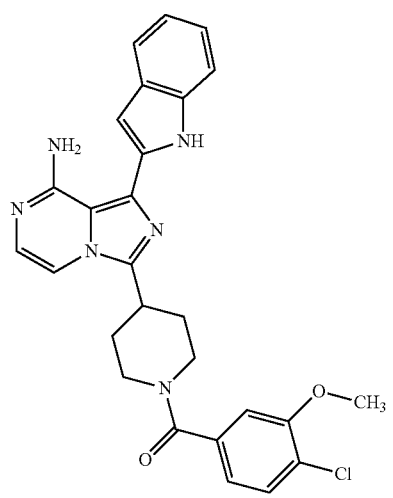
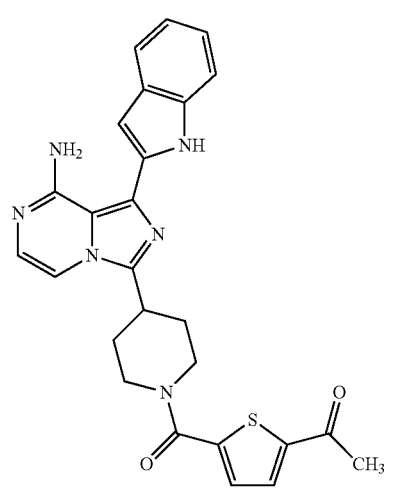
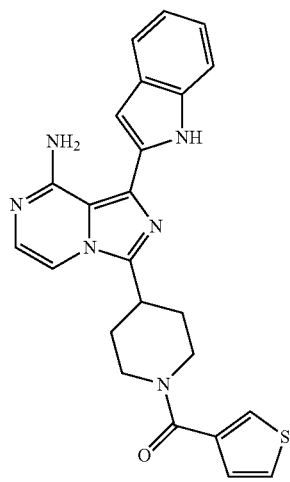

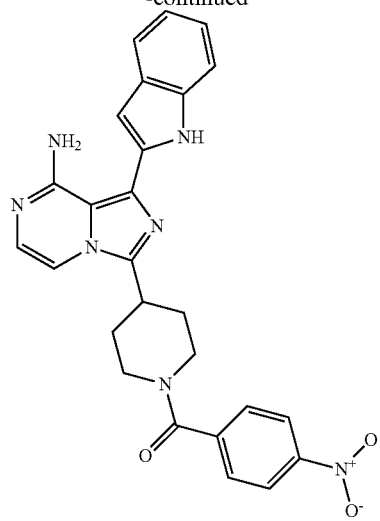
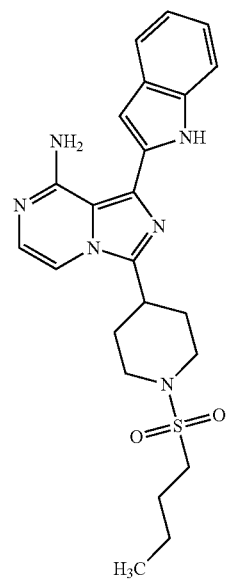
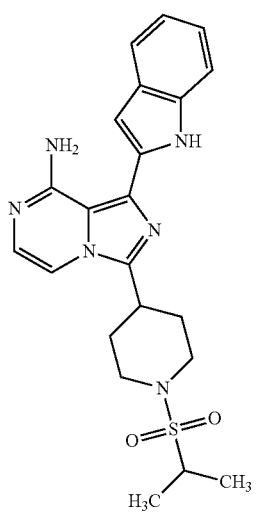
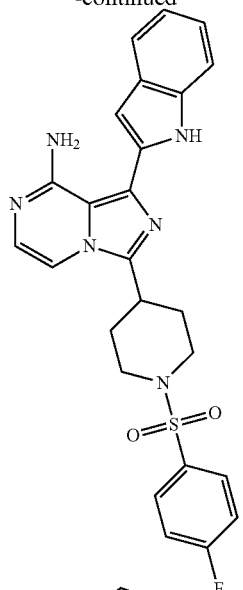
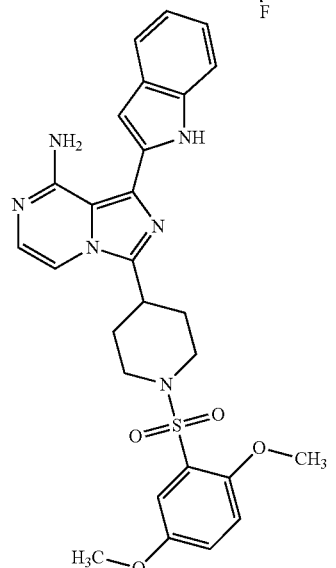
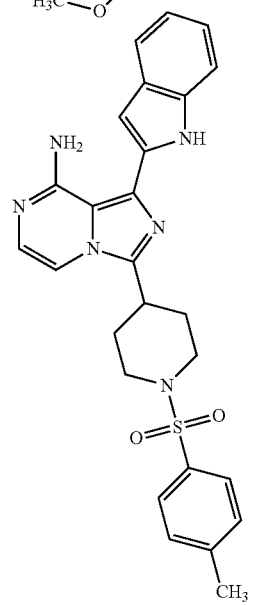

29
-continued
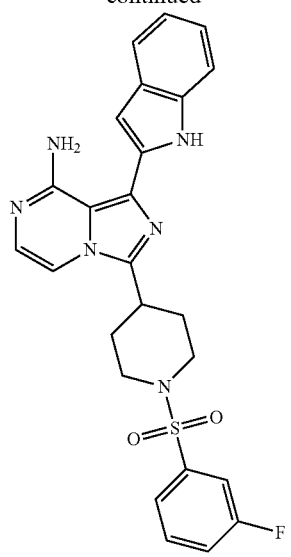
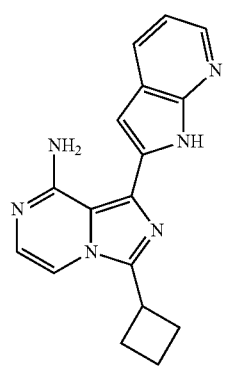
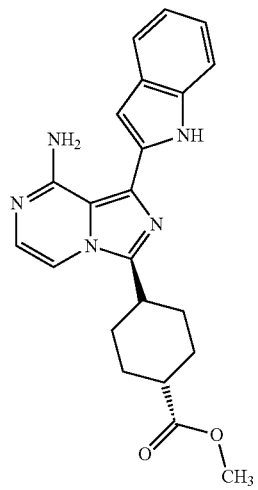
30
-continued
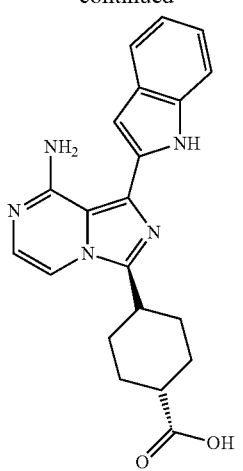
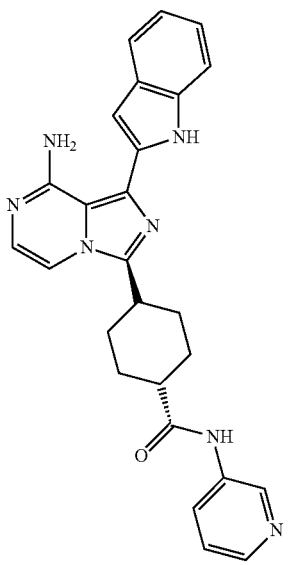
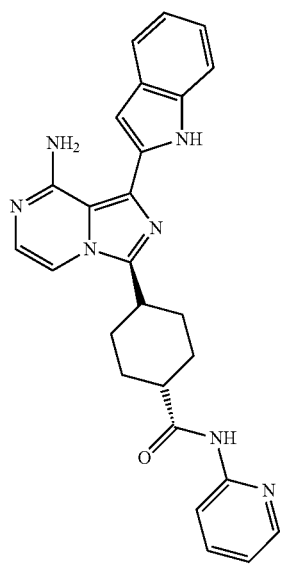

31
-continued
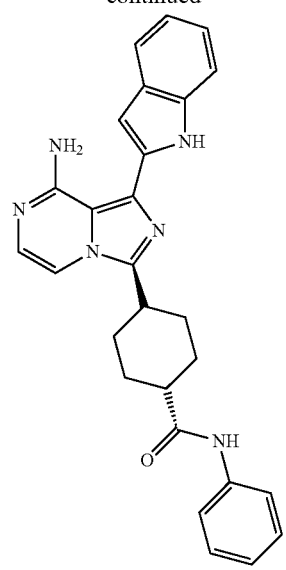
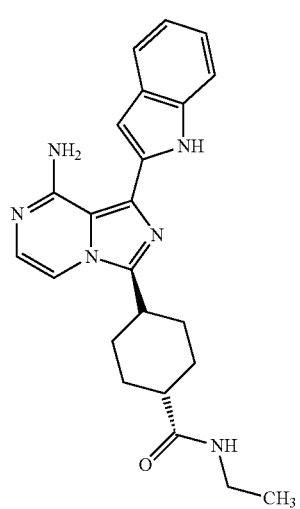
32
-continued
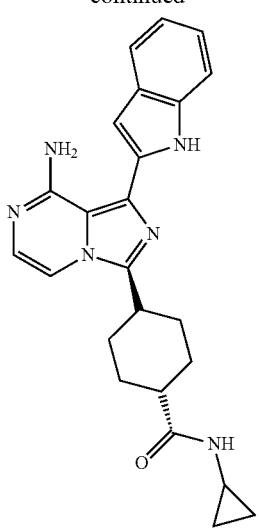
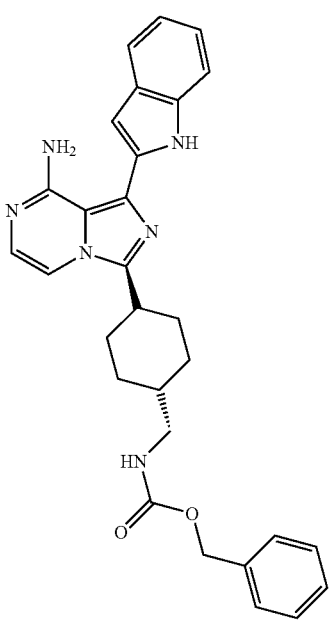
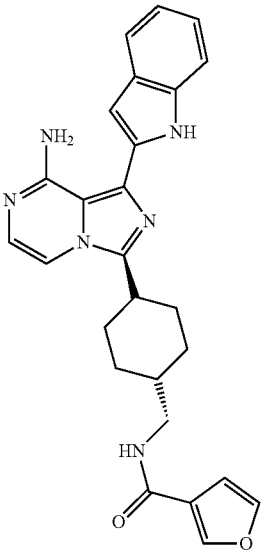

33
-continued
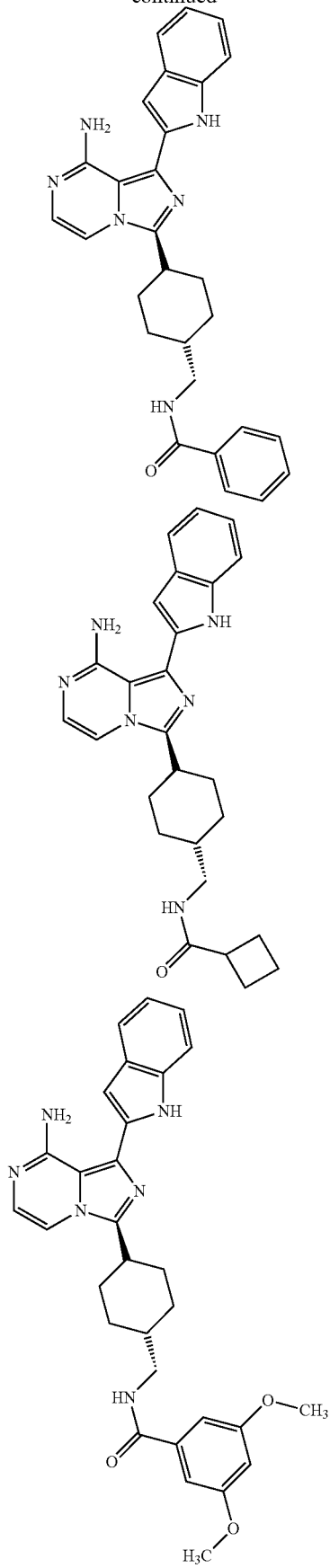
34
-continued
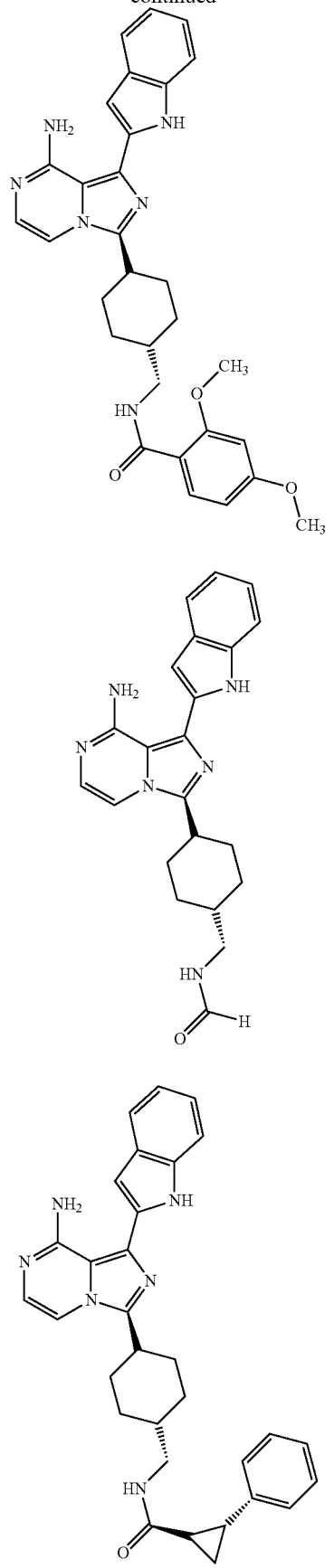

35
-continued
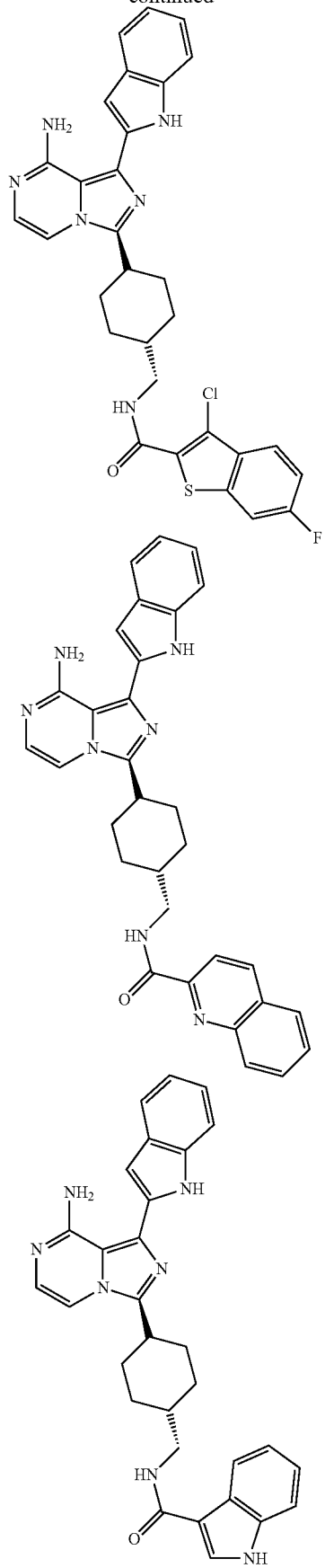
36
-continued
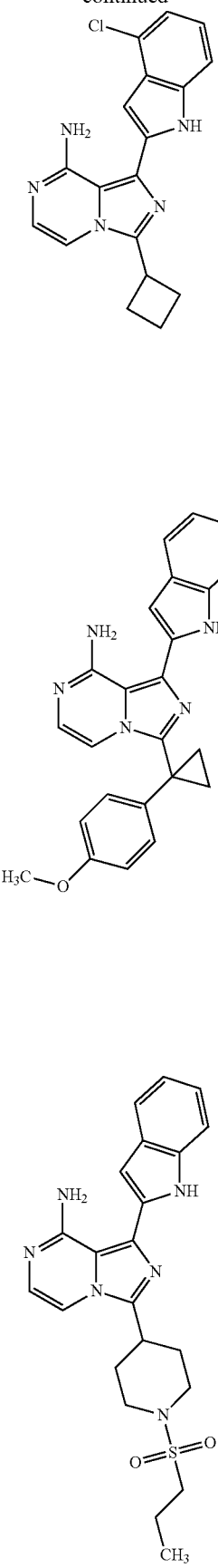

37
-continued
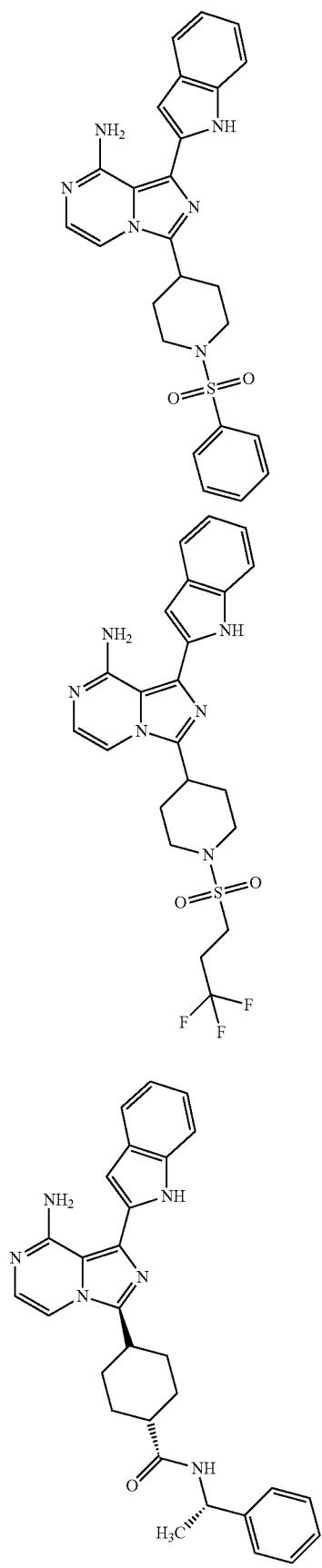
38
-continued

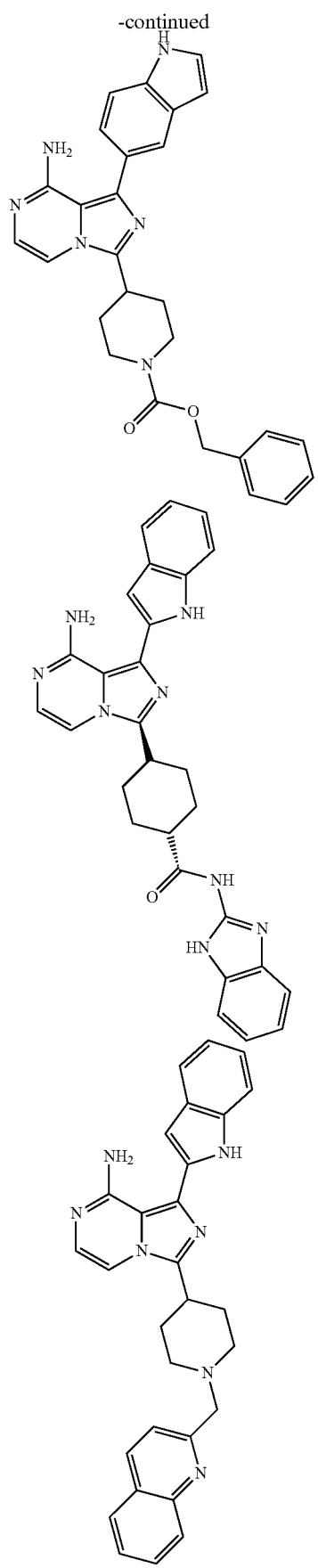
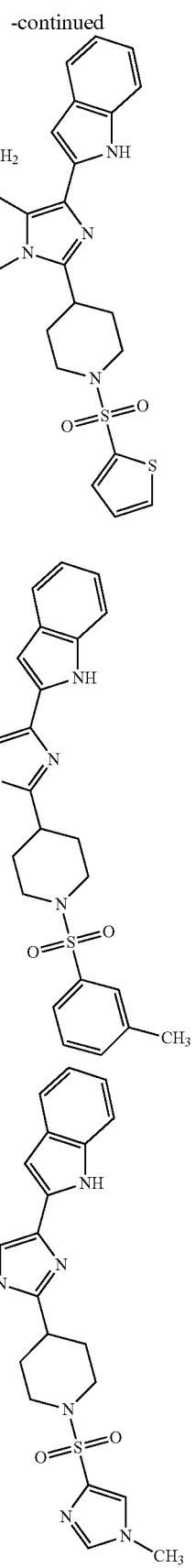
or a pharmaceutically acceptable salt thereof.

The present invention includes a composition comprising a compound according to Formula I, or a pharmaceutically acceptable salt thereof, and a pharmaceutically acceptable carrier.

The present invention includes a composition comprising a compound according to Formula I, or a pharmaceutically acceptable salt thereof; and an anti-neoplastic, anti-tumor, anti-angiogenic, or chemotherapeutic agent.

The present invention includes a method of treatment of hyperproliferative disorder comprising a step of administering an effective amount of a compound according to Formula I, or a pharmaceutically acceptable salt thereof.

The present invention includes a method of treatment of hyperproliferative disorder comprising a step of administering an effective amount of a compound according to Formula I, or a pharmaceutically acceptable salt thereof, wherein the hyperproliferative disorder is breast cancer, lung cancer, non-small cell lung cancer, kidney cancer, renal cell carcinoma, prostate cancer, cancer of the blood, liver cancer, ovarian cancer, thyroid cancer, endometrial cancer, cancer of the GI tract, lymphoma, renal cell carcinoma, mantle cell lymphoma, or endometrial cancer.

The present invention includes a method of treatment of rheumatoid arthritis, hamartoma syndromes, transplant rejection, IBD, multiple sclerosis or immunosuppression diseases comprising a step of administering an effective amount of the compound according to Formula I, or a pharmaceutically acceptable salt thereof.

The present invention includes intermediates useful in making the compounds of the invention. Such intermediates include compounds represented by

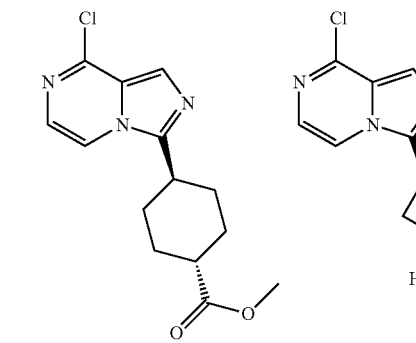

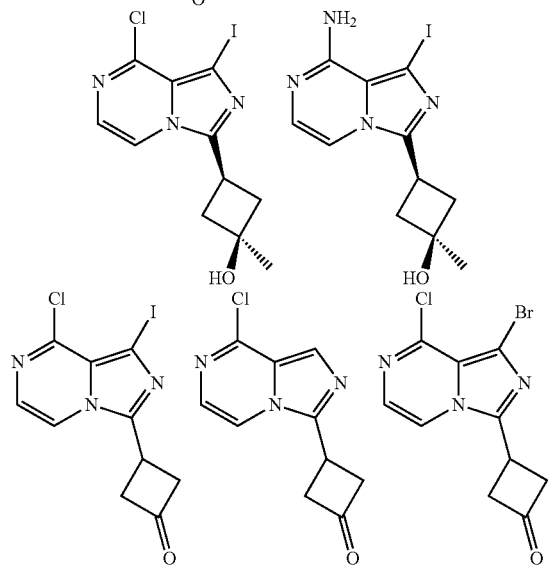

-continued

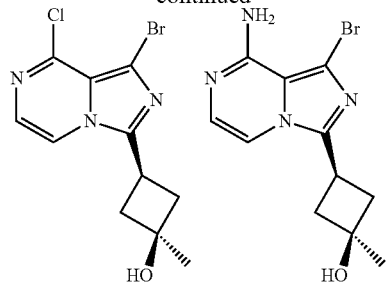

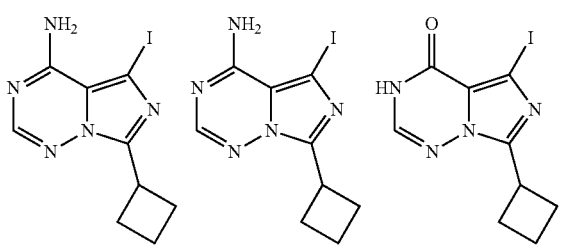

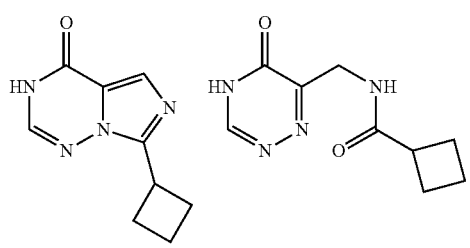

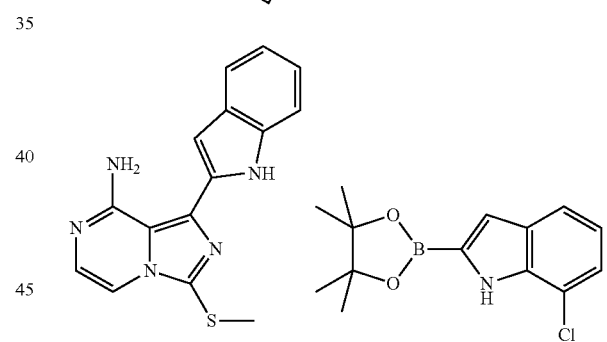

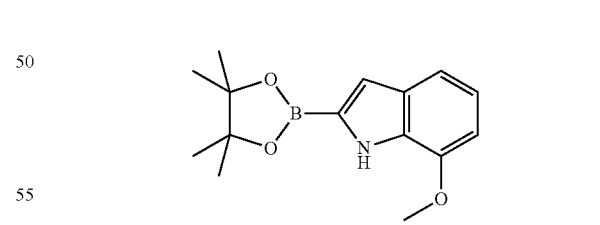

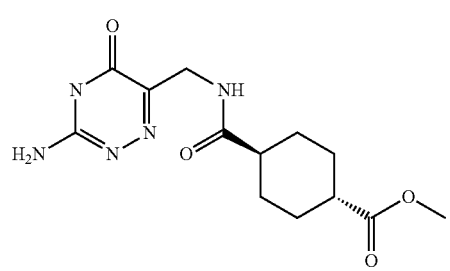

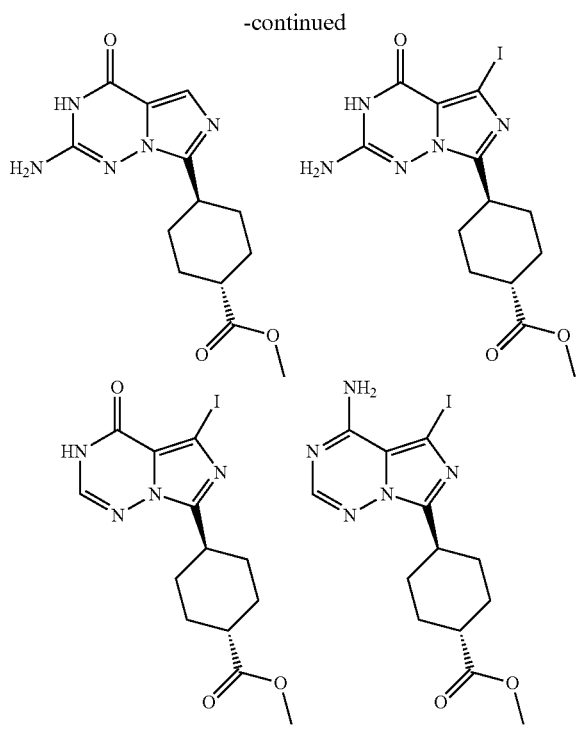

or a pharmaceutically acceptable salt thereof.

In all of the above circumstances forbidden or unstable valences, N—S, N-halogen bonds are excluded.

As used herein, unless stated otherwise, "alkyl" as well as other groups having the prefix "alk" such as, for example, alkoxy, alkanyl, alkenyl, alkynyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains having at least one unsaturated carbon-carbon bond.

As used herein, "$C_{0-4}$alkyl" for example is used to mean an alkyl having 0-4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group.

The terms "cycloalkyl", "carbocyclic ring", "cyclic", or "cyclyl" mean 3-10 membered mono or polycyclic aromatic, partially aromatic or non-aromatic ring carbocycles containing no heteroatoms, and include mono-, bi-, and tricyclic saturated carbocycles, as well as fused and bridged systems. Such fused ring systems can include one ring that is partially or fully unsaturated, such as a benzene ring, to form fused ring systems, such as benzofused carbocycles. Cycloalkyl includes such fused ring systems as spirofused ring systems. Examples of cycloalkyl and carbocyclic rings include $C_{3-8}$cycloalkyl such as cyclopropyl, cyclobutyl, cyclopentyl, cyclohexyl, and decahydronaphthalene, adamantane, indanyl, 1,2,3,4-tetrahydronaphthalene and the like.

The term "halogen" includes fluorine, chlorine, bromine, and iodine atoms.

The term "carbamoyl" unless specifically described otherwise means —C(O)—NH— or —NH—C(O)—.

The term "aryl" is well known to chemists. The preferred aryl groups are phenyl and naphthyl.

The term "hetaryl" is well known to chemists. The term includes 5- or 6-membered heteroaryl rings containing 14 heteroatoms chosen from oxygen, sulfur, and nitrogen in which oxygen and sulfur are not next to each other. Examples of such heteroaryl rings are furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The term "hetaryl" includes hetaryl rings with fused carbocyclic ring systems that are partially or fully unsaturated, such as a benzene ring, to form a benzofused hetaryl. For example, benzimidazole, benzoxazole, benzothiazole, benzofuran, quinoline, isoquinoline, quinoxaline, and the like.

Unless otherwise stated, the terms "heterocyclic ring", "heterocycle", "heterocyclic", and "heterocyclyl" are equivalent, and is defined as for cyclic but also contains one or more atoms chosen independently from N, O, and S (and the N and S oxides), provided such derivatives exhibit appropriate and stable valencies. The terms include 448-membered saturated rings containing one or two heteroatoms chosen from oxygen, sulfur, and nitrogen. Examples of heterocyclic rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, azepane, azocane, [1,3]dioxane, oxazolidine, piperazine, homopiperazine, morpholine, thiomorpholine, and the like. Other examples of heterocyclic rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocyclic rings. The term "heterocyclic" also includes fused ring systems, including het-het fused systems, and can include a carbocyclic ring that is partially or fully unsaturated, such as a benzene ring, to form benzofused heterocycles. For example, 3,4-dihydro-1,4-benzodioxine, tetrahydroquinoline, tetrahydroisoquinoline, isoindoline and the like.

Compounds described herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art the products of such procedures can be a mixture of stereoisomers.

The invention also encompasses a pharmaceutical composition that is comprised of a compound of Formula I in combination with a pharmaceutically acceptable carrier.

Preferably the composition is comprised of a pharmaceutically acceptable carrier and a therapeutically effective amount of a compound of Formula I as described above (or a pharmaceutically acceptable salt thereof.

Moreover, within this preferred embodiment, the invention encompasses a pharmaceutical composition for the treatment of disease by inhibition of mTor, comprising a pharmaceutically acceptable carrier and a non-toxic therapeutically effective amount of compound of formula I as described above (or a pharmaceutically acceptable salt thereof).

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric tartaric, p-toluenesulfonic acid and the like. Particularly preferred are citric, hydrobromic, hydrochloric, maleic, phosphoric, sulfuric and tartaric acids.

The pharmaceutical compositions of the present invention comprise a compound represented by formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration. e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material, which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fingi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical sue such as, for example, an aerosol, cream, ointment lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. He suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and compositions of the present invention are useful in the treatment of cancers of the breast, lung, kidney, prostate, blood, liver, ovarian, thyroid, GI tract and lymphoma The compounds and compositions are useful against cancers including non-small cell lung cancer (NSCLC), renal cell carcinoma, mantle cell lymphoma, and endometrial cancers. Further, the compounds and compositions are useful in treating other indications such as rheumatoid arthritis, hamartoma syndromes, transplant rejection, irritable bowel disease (IBD), multiple sclerosis and immunosuppression.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, cancers of the breast, lung, kidney, prostate, blood, liver, ovarian, thyroid, GI tract and lymphoma may be effectively treated by the administration of from about 0.01 to 50 mg of the compound per kilogram of body weight per day, or alternatively about 0.5 mg to about 3.5 g per patient per day.

Dosage levels on the order of from about 0.01 mg/g to about 150 mg/kg of body weight per day are useful in the treatment of non-small cell lung cancer (NSCLC), renal cell carcinoma, mantle cell lymphoma, and endometrial cancers, or alternatively about 0.5 mg to about 7 g per patient per day. They may be treated by the administration of from about 0.01 to 50 mg of the compound per kilogram of body weight per day, or alternatively about 0.5 mg to about 3.5 g per patient per day.

Dosage levels on the order of from about 0.01 mg/kg to about 150 mg/kg of body weight per day are useful in the treatment of rheumatoid arthritis, hamartoma syndromes, transplant rejection, irritable bowel disease (IBD), multiple sclerosis and immunosuppression, or alternatively about 0.5 mg to about 7 g per patient per day. They may be treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

Biochemical Assay for Inhibition of mTOR Activity:

The ability of compounds to inhibit the mTOR kinase activity was determined in an in vitro immunoprecipitation (P) kinase assay using recombinant 4E-BP1 as a substrate. The assay determines the ability of compounds to inhibit phosphorylation of 4E-BP1 a well-known physiological substrate of mTOR. The immunocapture mTOR complex from HeLa cells is incubated with various concentrations of compounds and His-tag 4E-BP1 in kinase assay buffer prior to addition of ATP to start the reaction at RT. The reaction is stopped after 30 mins and the phosphorylated His-tag 4E-BP1 is captured on a Nickel-chelate plate overnight at 4° C. The phosphothreonine content of 4E-BP1 is then measured using phospho-4E-BP1 (T37/46) primary antibody and corresponding anti rabbit IgG IS conjugated, secondary antibody. The secondary antibody has a reporter enzyme (eg. horseradish peroxidase, HP) covalently attached, such that binding of primary antibody to phosphorylated 4E-BP1 can be determined quantitatively which is equal to the amount secondary antibody bound to it. The amount of secondary antibody can be determined by incubation with an appropriate HRP substrate.

The Stock Reagents Used are as Follows:

Cell Lysis Buffer:
40 mM HEPES, pH 7.5 containing 120 mM NaCl, 1 mM EDTA, 10 mM sodium pyrophosphate, 10 mM β-glycerophosphate, 50 mM sodium fluoride, 1.5 mM sodium vanadate and 0.3% CHAPS.

Complete Mini EDTA-Free Protease Inhibitors (Roche, Catalog #11 836 170 001)

HeLa Cell Pellets (Paragon Bioservices)

Protein G Coated Plates for Immunoprecipitation (Pierce, Catalog #15131)

mTOR (aka FRAP) N-19 Antibody (Santa Cruz Biotechnology, Catalog #sc-1549)

IP Wash Buffer:
50 mM HEPES, pH 7.5 containing 150 mM NaCl

Kinase Buffer:
20 mM HEPES, pH 7.5 containing 10 mM MgCl2, 4 mM MnCl2, 10 mM b mercaptoethanol and 200 uM sodium vanadate. Make fresh for assay.

Recombinant 4E-BP1 (aka PHAS I) (Calbiochem, Catalog #516675)
Dilute 4E-BP1 stock (1 mg/mL) 120 times in kinase assay buffer to obtain a concentration of 0.25 ug/well in 30 uL ATP Solution
Prepare 330 uM ATP stock In kinase buffer Ni-Chelate Plate (Pierce, Catalog #15242)

Antibody Dilution Buffer:
TBST containing 5% skin milk
Phospho-4E-BP1 (T37/46) Antibody:
1:1000 dilution of phospho-4E-BP1 (T37/46) antibody (Cell Signaling Technology, catalog #9459) in antibody dilution buffer
Donkey Anti Rabbit IgG, HRP Conjugated
1:10,000 dilution of anti rabbit IgG HRP conjugated (GE Healthcare, Catalog# NA934) in antibody dilution buffer
HRP Substrate:
Chemiluminescent reagents (Pierce, catalog# 37074)
Assay Protocol:

HeLa cell lysate was prepared in bulk by homogenizing 25 g of cell pellet in 60 mL of cell lysis buffer and then, centrifuged at 12,000 rpm for 30 min. The clear supernatant was transferred to fresh tube, aliquoted, quickly frozen and stored at −80° C. until use.

Protein G coated 96-well plate is washed once with lysis buffer and 50 µL of diluted mTOR antibody is added to each well, and incubated at RT for 30-60 min. Then, 50 µg of HeLa cell lysate was added to each well in 50 µL of lysis buffer and incubated at 4° C. in a cold room on a shaker for 2-3 h. Lysate was removed and the plate was washed with 100 µL of complete lysis buffer for 3 times. The plate was further washed 2 times with 100 µL of high salt wash buffer. Diluted 4E-BP1 (substrate) is added to each well in 30 µL. The compounds were added in various concentrations in 5 µL to each well. The drug concentrations varied from 30 µM to 0.1 µM. The final DMSO concentration was 1%. Only DMSO was added to positive control wells. For negative control wells, no ATP solution was added but instead 15 µL of kinase buffer was added, the reaction was started by addition of ATP in 15 µL to a final concentration of 100 µM to rest of the wells except negative control wells. The reaction was carried out for 30 min at RT. Then, 45 µL of the reaction mixture was transferred to Ni-chelate plate and incubated overnight at 4° C. The plate was washed once with antibody dilution buffer and 50 µL of diluted phospho-4E-BP1 antibody was added to each well, and incubated at RT for 1 h. Then, the plate was washed 4 times with TBST and 50 uL of diluted anti-rabbit secondary antibody was added to each plate, and incubated at RT for 1 h. The plate was washed 4 times with 100 µL of TBST. To each well, 50 µL, of Pierce Femto chemiluminescent reagent was added and the chemiluminescence was measured using victor machine.

Comparison of the assay signals obtained in the presence of compound with those of positive and negative controls, allows the degree of inhibition of phospho-4E-BP1 phosphorylation to be determined over a range of compound concentrations. These inhibition values were fitted to a sigmoidal dose-response inhibition curve to determine the $IC_{50}$ values (i.e. the concentration of the compound that inhibits phosphorylation of 4E-BP1 by 50%).

mTOR Cell-Based Mechanistic Assay to Measure the Inhibition of Phosphorylation of 4E-BP1 (T37/46)

MDA-MB-231 cells were plated in 96 well plates at $2 \times 10^4$ cells/well in 90 ul of complete growth medium and incubated at 37° C. O/N in a $CO_2$ incubator. Cells were treated with various compounds in a dose response manner for 3 h at 37° C. in a $CO_2$ incubator before making cell lysates to measure inhibition of phosphorylation of 4E-BP1 at T37/46. Cell lysates were transferred to a 96-well plate coated with 4E-BP1 antibodies to capture phospho-4E-BP1 (T37/46) and incubated O/N at 4° C. The amount of phospho-4E-BP1 in each well is further measured by incubating the wells with anti-rabbit phospho-4E-BP1 (T37146) antibodies and a corresponding goat anti-rabbit IgG conjugated to HRP. Amount of HRP present in each well is measured by a chemiluminescence method, which corresponds to amount of phospho-4E-BP in each well. $IC_{50}$ values were determined using a 6-point dose response curve.

Biochemical Assay for Inhibition of IGF-1R Activity:

IGF-1R inhibition was shown in a tyrosine kinase assay using purified GST fusion protein containing the cytoplasmic kinase domain of human IGF-1R expressed in Sf9 cells. This assay is carried out in a final volume of 90 µL containing 1-100 nM (depending on the specific activity) in an Immulon-4 96-well plate (Thermo Labsystems) pre-coated with 1 Swell of substrate poly-glu-tyr (4:1 ratio) in kinase buffer (50 mM Hepes, pH 7.4, 125 mM NaCl, 24 mM $MgCl_2$, mM $MnCl_2$, 1% glycerol, 200 µM $Na_3VO_4$, and 2 mM DTT). The enzymatic reaction was initiated by addition of ATP at a final concentration of 100 µM. After incubation at room temperature for 30 minutes, the plates were washed with 2 mM Imidazole buffered saline with 0.02% Tween-20. Then the plate was incubated with anti-phosphotyrosine mouse monoclonal antibody pY-20 conjugated with horse radish peroxidase (HRP) (Calbiochem) at 167 ng/mL diluted in phosphate buffered saline (PBS) containing 3% bovine serum albumin (BSA), 0.5% Tween-20 and 200 µM $Na_3VO_4$ for 2 hours at room temperature. Following 3× 250 µL washes, the bound anti-phosphotyrosine antibody was detected by incubation with 100 µl/well ABTS (Kirkegaard & Perry Labs, Inc.) for 30 minutes at room temperature. The reaction was stopped by the addition of 100 µl/well 1% SDS, and the phosphotyrosine dependent signal was measured by a plate reader at 4051490 nm.

The EXAMPLES of this invention demonstrated at least one of the following:

I) Inhibited phosphorylation of 4E-BP1 by immunocaptured human mTOR as determined in the Biochemical Assay for Inhibition of mTOR Activity with $IC_{50}$ values between 0.001 µM and 11.00 µM. It is advantageous that the $IC_{50}$ values be less than 1.00 µM and more advantageous that the $IC_{50}$ values be below 0.1 µM. Even more advantageous, the $IC_{50}$ values be less than 0.01 µM.

II) Inhibited the phosphorylation of 4E-BP1 (T37/46) in the mTOR Cell-based Mechanistic Assay with $IC_{50}$ values below 40 µM.

III) Inhibition of IGF-1R in the Biochemical Assay for Inhibition of IGF-1R Activity with $IC_{50}$ values less than 15 µM.

EXPERIMENTAL

The following schemes, intermediates and examples serve to demonstrate how to synthesize compounds of this invention, but in no way limit the invention. Additionally, the following abbreviations are used: Me for methyl, Et for ethyl, iPr or iPr for isopropyl, n-Bu for n-butyl, t-Bu for tert-butyl, Ac for acetyl, Ph for phenyl, 4Cl-Ph or (4Cl)Ph for 4-chlorophenyl, 4Me-Ph or (4Me)Ph for 4-methylphenyl, p-CH3O) Ph for p-methoxyphenyl, (p-NO2)Ph for p-nitrophenyl, 4Br-Ph or (4Br)Ph for 4-bromophenyl, 2-CF3-Ph or (2CF3)Ph for 2-trifluoromethylphenyl, DMAP for 4-(dimethylamino)pyridine, DCC for 1,3-dicyclohexylcarbodiimide, EDC for 1-(3-dimethylaminopropyl)-3-ethylcarbodiimide hydrochloride, HOBt for 1-hydroxybenzotriazole, HOAt for 1-hydroxy-7-azabenzotriazole, TMP for tetramethylpiperidine, n-BuLi for n-butyllithium, CDI for 1,1'-carbonyldiimidazole, DEAD for diethyl azodicarboxylate, PS-PPh3 for polystyrene triphenylphosphine, DIEA for diisopropylethylamine, DIAD for diisopropyl azodicarboxylate, DBAD for di-tert-butyl azodicarboxylate, HPFC for high performance flash chromatography, rt or RT for room temperature, min for minute, h for hour, Bn for benzyl, and LAH for lithium aluminum hydride.

Accordingly, the following are compounds that are useful as intermediates in the formation of mTOR inhibiting EXAMPLES.

The compounds of Formula I of this invention and the intermediates used in the synthesis of the compounds of this invention were prepared according to the following methods. Method A was used when preparing compounds of Formula I-AA

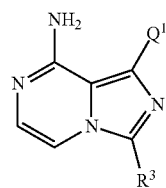

as shown below in Scheme 1:
Method A:

Scheme 1

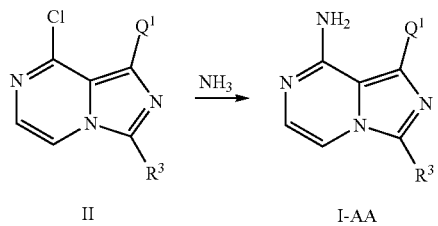

where $Q^1$ and $R^3$ are as defined previously for compound of Formula I.

In a typical preparation of compounds of Formula I-AA, compound of Formula II was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvents were isopropanol and a mixture of THF and isopropanol. The above process was carried out at temperatures between about −78° C. and about 120° C. Preferably, the reaction was carried out between 80° C. and about 120° C. The above process to produce compounds of the present invention was preferably carried in a sealed reaction vessel such as but not limited to a thick walled glass reaction vessel or a stainless steel Parr bomb. An excess amount of the reactant ammonia, was preferably used.

The compounds of Formula II of Scheme 1 were prepared as shown below in Scheme 2.

Scheme 2

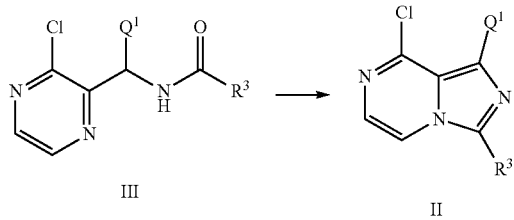

where $Q^1$ and $R^3$ are as defined previously for compound of Formula I.

In a typical preparation of a compound of Formula II, an intermediate of Formula III was treated with $POCl_3$ or the isolated "Vilsmeier salt" [CAS# 33842-02-3] in a suitable solvent at a suitable reaction temperature. Suitable solvents for use in the above process included, but were not limited to, ethers such as tetrahydrofuran (THF), glyme, and the like; acetonitrile; and chlorinated solvents such as methylene chloride ($CH_2Cl_2$) or chloroform ($CHCl_3$). If desired, mixtures of these solvents were used or no solvent was used. The preferred solvents included methylene chloride and acetonitrile. The above process was carried out at temperatures between about −78° C. and about 120° C. Preferably, the reaction was carried out between 20° C. and about 95° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula III of Scheme 2 were prepared as shown below in Scheme 3:

Scheme 3

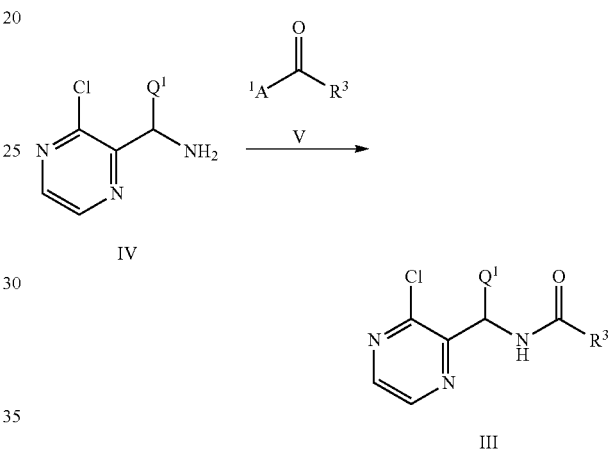

where $Q^1$ and $R^1$ are as defined previously for compound of Formula I and $A^1$=OH, alkoxy, or a leaving group such as a halogen or imidazole.

In a typical preparation, of a compound of Formula III, a compound of Formula IV and compound of Formula V were reacted under suitable amide coupling conditions. Suitable conditions include but are not limited to treating compounds of Formula IV and V (when $A^1$=OH) with coupling reagents such as DCC or EDC in conjunction with DMAP, HOAt, HOAt and the like. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvents were methylene chloride and DMF. The above process was carried out at temperatures between about 0° C. and about 80° C. Preferably, the reaction was carried out at about rt. The above process to produce compounds of the present invention was preferably carried out at about atmospheric pressure although higher or lower pressures were used if desired. Substantially equimolar amounts of reactants were preferably used although higher or lower amounts were used if desired. Alternatively, compounds of Formula IV and V (where $A^1$=F, Cl, Br, I) were reacted with bases such as triethylamine or ethyldiisopropylamine and the like in conjunction with DMAP and the like. Suitable solvents for use in this process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially equimolar amounts of compounds of Formula IV and V (where $A^1$=F, Cl, Br, I) and base and substoichiometric amounts of DMAP were preferably used although higher or lower amounts were used if desired. Additionally, other suitable reaction conditions for the conversion of a compound of Formula IV to a compound of Formula III can be found in Larock, R. C. Comprehensive Organic Transformations, 2nd ed.; Wiley and Sons: New York, 1999, pp 1941-1949.

The compounds of Formula IV of Scheme 3 were prepared as shown below in Scheme 4:

Scheme 4

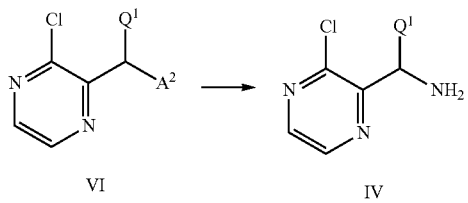

VI          IV where $Q^1$ is as defined previously for compound of Formula I and $A^2$=phthalimido or $N_3$.

In a typical preparation, of a compound of Formula IV, a compound of Formula VI is reacted under suitable reaction conditions in a suitable solvent. When $A^2$=phthalimido, suitable conditions include treatment of compound of Formula VI with hydrazine in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride; alcoholic solvents such as methanol and ethanol. If desired, mixtures of these solvents may be used, however the preferred solvent was ethanol. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired. In the transformation of compound of Formula VI to IV, if $A^2$=$N_3$, then one skilled in the art would recognize that typical azide reduction conditions could be employed, including but not limited to $PPh_3$ and water or hydrogenation in the presence of a metal catalyst such as palladium.

The compounds of Formula VI of Scheme 4 were prepared as shown below in Scheme 5.

Scheme 5

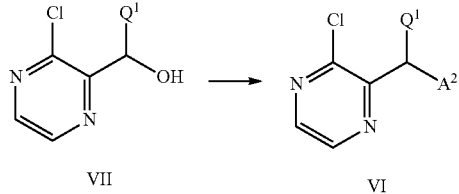

VII          VI where $Q^1$ is as defined previously for compound of Formula I and $A^2$=phthalimido or $N_3$.

In a typical preparation of a compound of Formula VI (when $A^2$=phthalimido), a compound of Formula VII was reacted with a phthalimide under typical Mitsunobu conditions in a suitable solvent in the presence of suitable reactants. Suitable solvents for use in the above process included, but were not limited to, ethers such as tetrahydrofuran (THF), glyme, and the like; dimethylformamide (MD), dimethyl sulfoxide (DMSO); acetonitrile ($CH_3CN$); chlorinated solvents such as methylene chloride ($CH_2Cl_2$) or chloroform ($CHCl_3$). If desired, mixtures of these solvents were used, however, the preferred solvent was THF. Suitable reactants for use in the above process included, but were not limited to, triphenylphosphine and the like, and an azodicarboxylate DIAD, DEAD, DBAD). The preferred reactants were triphenylphosphine or resin-bound triphenylphosphine (PS-$PPh_3$), and DIAD. The above process may be carried out at temperatures between about −78° C. and about 10° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired. Generally, one equivalent or a slight excess, 1.1 equivalents, of triphenylphosphine, DIAD and phthalimide was used per equivalent of compound of Formula VII. Additionally, compound of Formula VII can be reacted with $Ts_2O$, $Ms_2O$, $Tf_2O$, TsCl, MsCl, or $SOCl_2$ in which the hydroxy group is converted to a leaving group such as its respective tosylate, mesylate, triflate, or halogen such as chloro and subsequently reacted with an amine equivalent such as $NH(Boc)_2$, phthalimide, potassium phthalimide, or sodium azide. Conversion of the amine equivalents by known methods such as by treating under acidic conditions (NH $(Boc)_2$), with hydrazine (phthalimide) as shown in Scheme 4, or with triphenylphosphine/water (azide) will afford the desired amine as shown in Scheme 4.

The compounds of Formula VII of Scheme 5 were prepared from aldehydes $Q^1$-CHO and a 2-chloropyrazine VIII as shown below in Scheme 6:

Scheme 6

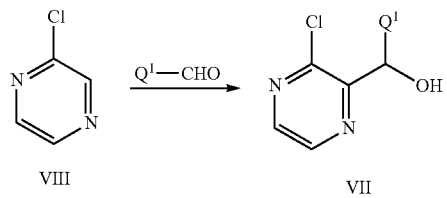

VIII          VII where $Q^1$ is as defined previously for compound of Formula I.

In a typical preparation, of a compound of Formula VI, a compound of Formula VIII was reacted under suitable reaction conditions in a suitable solvent with a compound of Formula $Q^1$-CHO. Suitable conditions included but were not limited to treating compounds of Formula VIII with a base such as lithium tetramethylpiperidide (Li-TMP) followed by treating with compounds of Formula $Q^1$-CHO. Lithium tetramethylpiperidide may be prepared by reacting tetramethylpiperidine with n-butyllithium at −78° C. and warming up to 0° C. Suitable solvents for use in the above process included, but were not limited to, ethers such as tetrahydrofuran (THF), glyme, and the like. Polar solvents such as hexamethylphosphoramide (HMPA), 1,3-dimethyl-3,4,5,6-tetrahydro-2(1H)-pyrimidinone DMPU), and the like may be added if necessary. If desired, mixtures of these solvents were used, however, the preferred solvent was THF. The above process may be carried out at temperatures between about −80° C. and about 20° C. Preferably, the reaction was carried out at −78° C. to 0° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula I of this invention and the intermediates used in the synthesis of the compounds of this invention were also prepared according to the following methods. Method AA was used when preparing compounds of Formula I-AA from compound of Formula I-AAA as shown below in Scheme 7:

Method AA:

Scheme 7

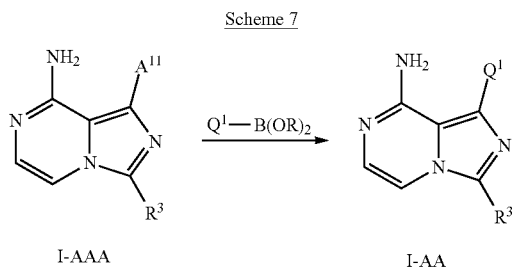

I-AAA        I-AA where $Q^1$ and $R^3$ are as defined previously for compound of Formula I, $A^{11}$=halogen such as Cl, Br, or I and $B(OR)_2$= suitable boronic acid/ester.

In a typical preparation of compounds of Formula I-AA, compound of Formula I-AAA was reacted with a suitable boronic acid/ester ($Q^1$-$B(OR)_2$) in a suitable solvent via typical Suzuki coupling procedures. Suitable solvents for use in the above process included, but were not limited to, ethers such as tetrahydrofuran (THF), glyme, dioxane, dimethoxyethane, and the like; dimethylformamide (DMF); dimethyl sulfoxide DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was dimethoxyethane/water. The above process was carried out at temperatures between about −78° C. and about 120° C. Preferably, the reaction was carried out between 60° C. and about 100° C. The above process to produce compounds of the present invention was preferably carried out at about atmospheric pressure although higher or lower pressures were used if desired. Substantially equimolar amounts of reactants were preferably used although higher or lower amounts were used if desired.

One skilled in the art will appreciate that alternative methods may be applicable for preparing compounds of Formula I-AA from I-AAA. For example, compound of Formula I-AAA could be reacted with a suitable organotin reagent $Q^1$-$SnBu_3$ or the like in a suitable solvent via typical Stille coupling procedures.

The compounds of Formula I-AAA of Scheme 7 were prepared as shown below in Scheme 8.

Scheme 8

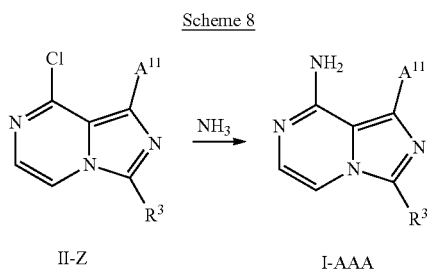

II-Z        I-AAA where $R^3$ is as defined previously for compound of Formula I and $A^{11}$=halogen such as Cl, Br, or I.

In a typical preparation of compounds of Formula I-AAA, compound of Formula II-Z was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvents were isopropanol and a mixture of THF and isopropanol. The above process was carried out at temperatures between about −78° C. and about 120° C. Preferably, the reaction was carried out between 80° C. and about 120° C. The above process to produce compounds of the present invention was preferably carried in a sealed reaction vessel such as but not limited to a thick walled glass reaction vessel or a stainless steel Parr bomb. An excess amount of the reactant, ammonia, was preferably used.

The compounds of Formula II-Z of Scheme 8 were prepared as shown below in Scheme 9.

Scheme 9

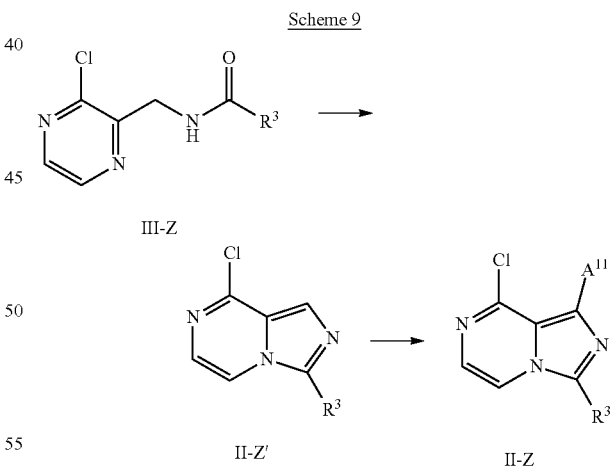

III-Z

II-Z'        II-Z where $R^3$ is as defined previously for compound of Formula I and $A^{11}$=halogen such as Cl, Br, or I.

In a typical preparation of a compound of Formula II-Z, intermediate III-Z was converted to compound of Formula II-Z'. Intermediate of Formula III-Z was treated with $POCl_3$ in a suitable solvent at a suitable reaction temperature. Suitable solvents for use in the above process included, but were not limited to, ethers such as tetrahydrofuran (THY), glyme, and the like; acetonitrile; and chlorinated solvents such as methylene chloride ($CH_2Cl_2$) or chloroform ($CHCl_3$). If desired, mixtures of these solvents were used. The preferred solvents included methylene chloride and acetonitrile. The above process was carried out at temperatures between about −78° C. and about 120° C. Preferably, the reaction was carried out between 20° C. and about 95° C. The above process to produce compounds of the present invention was preferably carried out at about atmospheric pressure although higher or lower pressures were used if desired. Substantially equimolar amounts of reactants were preferably used although higher or lower amounts were used if desired. In the conversion of compound of Formula III-Z to II-Z', suitable halogenating agent were used, but were not limited to, $Br_2$, $I_2$, $Cl_2$, N-chlorosuccinimide, N-bromosuccinimide, or N-iodosuccinimide. The preferred halogenating agent was N-iodosuccinimide. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was DMF. The above process was carried out at temperatures between about −78° C. and about 120° C. Preferably, the reaction was carried out between 40° C. and about 75° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula III-Z of Scheme 9 were prepared as shown below in Scheme 10:

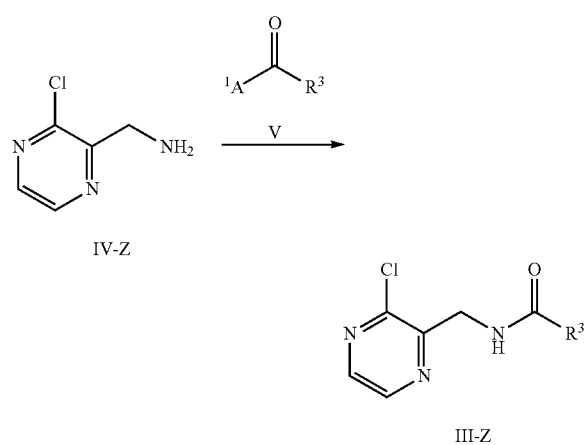

III-Z where $R^3$ is as defined previously for compound of Formula I and $A^1$=OH, alkoxy, or a leaving group such as chloro or imidazole.

In a typical preparation, of a compound of Formula III-Z a compound of Formula IV-Z and compound of Formula V were reacted under suitable amide coupling conditions. Suitable conditions include but are not limited to treating compounds of Formula IV-Z and V (when $A^1$=OH) with coupling reagents such as DCC or EDC in conjunction with DMAP, HOBt, HOAt and the like. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired. Additionally, if compound of Formula IV-Z was a salt or bis-salt, a suitable base was required and included, but was not limited to, diisopropylethylamine or triethylamine. Alternatively, compounds of Formula IV-Z and V (where $A^1$=F, Cl, Br, I) were reacted with bases such as triethylamine or ethyldiisopropylamine and the like in conjunction with DMAP and the like. Suitable solvents for use in this process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially equimolar amounts of compounds of Formula IV-Z and V (where $A^1$=F, Cl, Br, I) and base and substoichiometric amounts of DMAP were preferably used although higher or lower amounts were used if desired. Additionally, other suitable reaction conditions for the conversion of an amine (compound of Formula IV-Z) to an amide (compound of Formula III-Z) can be found in Larock, R. C. Comprehensive Organic Transformations, 2nd ed.; Wiley and Sons: New York, 1999, pp 1941-1949.

The compounds of Formula IV-Z of Scheme 10 were prepared as shown below in Scheme 11:

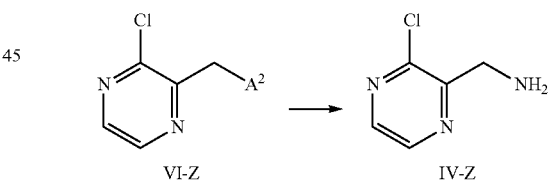

where $A^2$ is phthalimido or $N_3$.

In a typical preparation, of a compound of Formula IV-Z, a compound of Formula VI-Z is reacted under suitable reaction conditions in a suitable solvent. When $A^2$=phthalimido, suitable conditions include treatment of compound of Formula VI-Z with hydrazine in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride; alcoholic solvents such as methanol and ethanol. If desired, mixtures of these solvents may be used, however the preferred solvent was ethanol. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula VI-Z of Scheme 11 were prepared as shown below in Scheme 12:

Scheme 12

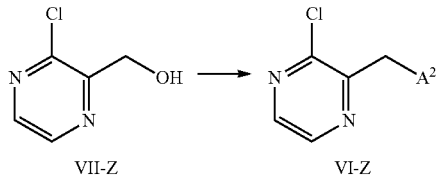

VII-Z                   VI-Z where $A^2$=phthalimido or $N_3$.

In a typical preparation of a compound of Formula VI-Z (when $A^2$=phthalimido), a compound of Formula VII-Z was reacted with a phthalimide under typical Mitsunobu conditions in a suitable solvent in the presence of suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); chlorinated solvents such as methylene chloride ($CH_2Cl_2$) or chloroform ($CHCl_3$). If desired, mixtures of these solvents were used, however, the preferred solvent was THF. Suitable reactants for use in the above process included, but were not limited to, triphenylphosphine and the like, and an azodicarboxylate (DIAD, DEAD, DBAD). The preferred reactants were triphenylphosphine or resin-bound triphenylphosphine (PS-$PPh_3$) and DIAD. The above process may be carried out at temperatures between about −78° C. and about 100° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired. Generally, 1.0 or 1.1 equivalents of triphenylphosphine, DIAD and phthalimide was used per equivalent of compound of Formula VII-Z. Additionally, compound of Formula VII-Z can be reacted with $Ts_2O$, $Ms_2O$, $Tf_2O$, TsCl, MsCl, or $SOCl_2$ in which the hydroxy group is converted to a leaving group such as its respective tosylate, mesylate, triflate, or halogen such as chloro and subsequently reacted with an amine equivalent such as $NH(Boc)_2$, phthalimide, potassium phthalimide or sodium azide. Conversion of the amine equivalents by known methods such as by treating under acidic conditions (NH$(Boc)_2$), with hydrazine phthalimide) as shown in Scheme 4, or with triphenylphosphine/water (azide) will afford the desired amine as shown in Scheme 4.

The compounds of Formula VI-Z of Scheme 12 were prepared from 2-chloropyrazine VIII as shown below in Scheme 13:

Scheme 13

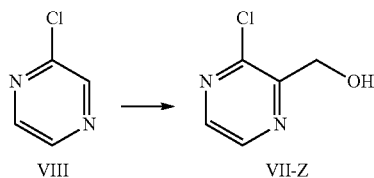

VIII                    VII-Z

In a typical preparation, of a compound of Formula VII-Z, a compound of Formula VIII was reacted under suitable reaction conditions in a suitable solvent. Suitable reaction conditions included, but were not limited to, treating compounds of Formula VIII with a base such as lithium tetramethylpiperidide (Li-TMP) followed by treatment with a reagent containing a carbonyl equivalent followed by treatment with a suitable reducing agent. Lithium tetramethylpiperidide may be prepared by reacting tetramethylpiperidine with n-butyllithium at −78° C. and warming up to 0° C. Suitable solvents for use in the above process included, but were not limited to, ethers such as tetrahydrofuran (THF), glyme, and the like. Polar solvents such as hexamethylphosphoramide (HMPA), 1,3-dimethyl-3,4,5,6-tetrahydro-2(1H)-pyrimidinone (DMPU), and the like may be added if necessary. If desired, mixtures of these solvents were used, however, the preferred solvent was THF. Suitable carbonyl equivalent reagents include, but are not limited to, formamides such as DMF or suitable chloroformate such as methyl or ethyl chloroformate. After addition of the suitable carbonyl equivalent reagent, the reaction if charged with a polar protic solvent such as, but not limited to, methanol or ethanol followed by treatment with a suitable reducing agent such as sodium borohydride. The above process may be carried out at temperatures between about −80° C. and about 20° C. Preferably, the reaction was carried out at −78° C. to 0° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula X-Z ($Q^1$-CHO) of Scheme 6 were prepared as shown below in Scheme 14:

Scheme 14

IX-Z            X-Z where Q1 is as defined previously for compound of Formula I.

In a typical preparation, of a compound of Formula X-Z ($Q^1$-HO), a compound of Formula IX-Z ($Q^1$-$CH_3$) was reacted with a suitable oxidizing agent under suitable reaction conditions. Suitable oxidizing agents included, but were not limited to, selenium dioxide. Suitable reaction conditions for use in the above process included, but were not limited to, heating a mixture of selenium dioxide and compounds of Formula IX-Z ($Q^1$-$CH_3$) neat or in a suitable solvent such as, but not limited to, chlorobenzene or sulpholane. The above process may be carried out at temperatures between about 120° C. and about 180° C. Preferably, the reaction was carried out at 150° C. to 165° C. The above process to produce compounds of the present invention was preferably carried out at about atmospheric pressure although higher or lower pressures were used if desired. Preferably, 1-1.5 eq. selenium dioxide were used although higher or lower amounts were used if desired. Alternatively, a compound of Formula IX-Z ($Q^1$-$CH_3$) was reacted first with a halogenating agent and a radical initiator under suitable reaction conditions in a suitable solvent to give a compound of Formula $Q^1$-$CH_2$Hal (wherein Hal=Cl or Br) that was then further reacted with DMSO and a base under suitable reaction conditions to give a compound of Formula X-Z ($Q^1$-CHO). Suitable halogenating agents included, but were not limited to, bromine, N-bromosuccinimide, and chlorine. Preferably, N-bromosuccinimide was used. Suitable radical initiators included, but were not limited to, 2,2'-azobisisobutyronitrile (AIBN) and UV light. Preferably, AIBN was used. Preferably, carbon tetrachloride was used as solvent for the halogenation step, although other halogenated solvents may be added. The halogenation may be carried out at temperatures between about 60° C. and about 10° C. Preferably, the reaction was carried out at about 80° C. Suitable bases included, but were not limited to, sodium hydrogencarbonate, sodium dihydrogenphosphate, disodium hydrogenphosphate, and collidine. Preferably, sodium hydrogencarbonate was used. DMSO was preferably used as solvent although other solvents may be added. The second step may be carried out at temperatures between about 40° C. and about 140° C. Preferably, the reaction was carried out at about 90° C. Additionally, other suitable reaction conditions for the conversion of $Q^1$-$CH_3$ to $Q^1$-CHO can be found in Larock, R. C. Comprehensive Organic Transformations, 2nd ed.; Wiley and Sons: New York, 1999, pp 1205-1207 and 1222-1224.

The compounds of Formula XIV-Z ($Q^1$-B(OR)$_2$) of Scheme 7 were prepared as shown below in Scheme 15:

Scheme 15

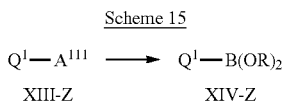

XIII-Z  XIV-Z where $Q^1$ is as defined previously for compound of Formula I, $A^{111}$=OTf or halogen such as Cl, Br, or I and B(OR)$_2$=suitable boronic acid/ester.

In a typical preparation, of a compound of Formula XIV-Z ($Q^1$-B(OR)$_2$), a compound of Formula XIII-Z ($Q^1$-$A^{111}$) was reacted with a suitable metal catalyst and a suitable boronating agent under suitable reaction conditions. Suitable metal catalyst agents included, but were not limited to, Pd(OAc)$_2$ in the presence of 1,3-bis(2,6-diisopropylphenyl)imidazolium chloride. Suitable boronating agents included, but were not limited to, bis(pinacolato)diboron. Suitable reaction conditions for use in the above process included, but were not limited to, heating a mixture of Pd(OAc)$_2$, 1,3-bis(2,6-diisopropylphenyl)imidazolium chloride, KOAc, and bis(pinacol)borane in a suitable solvent such as, but not limited to, THF. The above process may be carried out at temperatures between about 20° C. and about 100° C. Preferably, the reaction was carried out at 60° C. to 80° C. The above process to produce compounds of the present invention was preferably carried out at about atmospheric pressure although higher or lower pressures were used if desired. Preferably, 2-3 eq. KOAc, 1-1.5 eq. bis(pinacol)borane, 0.03-1 eq. Pd(OAc)$_2$, and 0.09-3 eq. 1,3-bis(2,6-diisopropylphenyl)imidazolium chloride were used although higher or lower amounts were used if desired. Additionally, other suitable reaction conditions for the conversion of $Q^1$-$A^{111}$ to $Q^1$-B(OR)$_2$ can be found in the literature which involve a variety of $Q^1$-$A^{111}$ or aryl/heteroarylhalides and a variety of conditions (Biooganic & Medicinal Chemistry Letters, 2003, 12(22), 4001; Biooganic & Medicinal Chemistry Letters, 2003, 13(18), 3059; Chemical Communications (Cambridge, UK), 2003, 23, 2924; Synthesis, 2002, 17, 2503; Angewandte Chemie, International Ed., 2002, 41(16), 3056; Journal of the American Chemical Society, 2002, 124(3), 390; Organic Letters, 2002, 4(4), 541; Tetrahedron, 2001, 57(49), 9813; Journal of Organic Chemistry, 2000, 65(1), 164; Journal of Organic Chemistry, 1997, 62(19), 6458; Journal of Organometallic Chemistry, 1983, 259(3), 269). In some cases, compounds of Formula XIII-Z ($Q^1$-$A^{111}$) and XIV-Z ($Q^1$-B(OR)$_2$) are commercially available or synthesized according to literature procedures. In cases where neither are available, compounds of Formula XIII-Z ($Q^1$-$A^{111}$) and XIV-Z ($Q^1$-B(OR)$_2$) were synthesized via procedures described in the experimental section herein.

Both $R^3$ and $Q^1$ in the compounds described herein in some instances contain functional groups that can be further manipulated. It would be appreciated by those skilled in the art that such manipulation of functional groups can be accomplished with key intermediates or with late stage compounds. Such functional group transformations are exemplified in the following Schemes 16-26 as well as in the experimental section but are in no way meant to limit the scope of such transformations. Additionally, the chemistry shown in Schemes 16-26 can also be applied to compounds of I-AAA, II-Z, and II-Z'.

The compounds of Formula I-A (compounds of Formula I-AA where $R^3$=Z—CONR$^{312}$R$^{322}$) were prepared as shown below in Scheme 17.

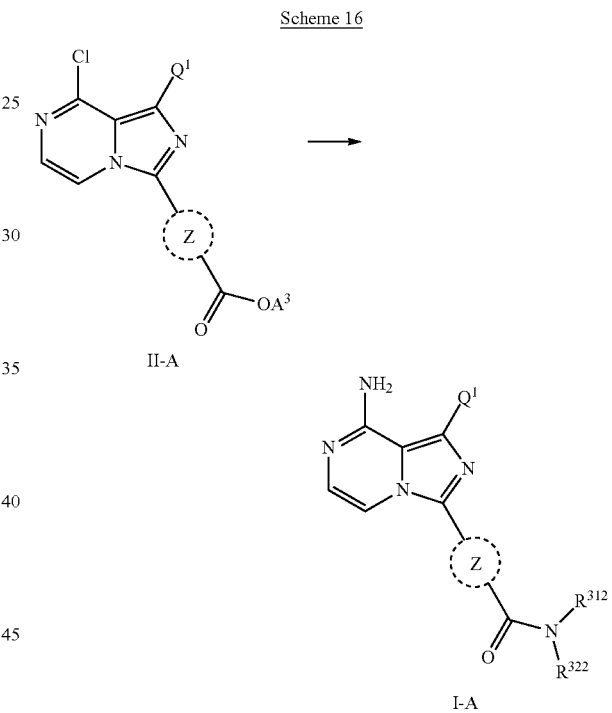

where $Q^1$, $R^{312}$ and $R^{322}$ are as defined previously for compound of Formula I and $A^3$=hydrogen or alkyl such as methyl or ethyl.

In a typical preparation of compound of Formula I-A, when $A^3$=alkyl and $R^{312}$ and $R^{322}$ were both equal to H, reaction of compound of Formula II-A (compounds of Formula II where $R^3$=Z—CO$_2$A$^3$) with ammonia in a suitable solvent, afforded compound of Formula I-A. Suitable solvents for use in the above process included, but were not limited to, ethers such as tetrahydrofuran (THF), glyme, and the like; dimethylformamide (DMF); dimethyl sulfoxide DMSO); acetonitrile; alcohols such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvents were isopropanol and a mixture of isopropanol/THF. The above process was carried out at temperatures between about −78° C. and about 120° C. Preferably, the reaction was carried out between 80° C. and about 120° C. The above process to produce compounds of the present invention was preferably carried out at about atmospheric pressure although higher or lower pressures were used if desired. Substantially equimolar amounts of reactants were preferably used although higher or lower amounts were used if desired. Additionally, in a typical preparation of compound of Formula I-A, compound of Formula II-A (when $A^3$=H) was reacted with $HNR^{312}R^{322}$ followed by ammonia in a suitable solvent. When $A^3$=H, typical coupling procedures as described in Scheme 3 (conversion of $CO_2H$ to COCl via treatment with $SOCl_2$ or oxalyl chloride followed by reaction with $HR^{312}R^{322}$ or treatment of $CO_2H$ and $HR^{312}R^{322}$ with EDC or DCC in conjunction with DMAP, HOBT, or HOAt and the like) were employed to afford the transformation of a carboxylic acid to an amide. When $A^3$=alkyl such as methyl or ethyl, treatment of the ester with $Al(NR^{312}R^{322})$ afforded conversion of $CO_2A^3$ to $CO(NR^{312}R^{322})$. Subsequent treatment with ammonia afforded compounds of Formula I-A.

The compounds of Formula I-A' (compounds of Formula I-AA where $R^3$=Z—$CO_2A^3$) and I-A" (compounds of Formula I-AA where $R^3$=Z—$CO_2H$ were prepared as shown below in Scheme 17:

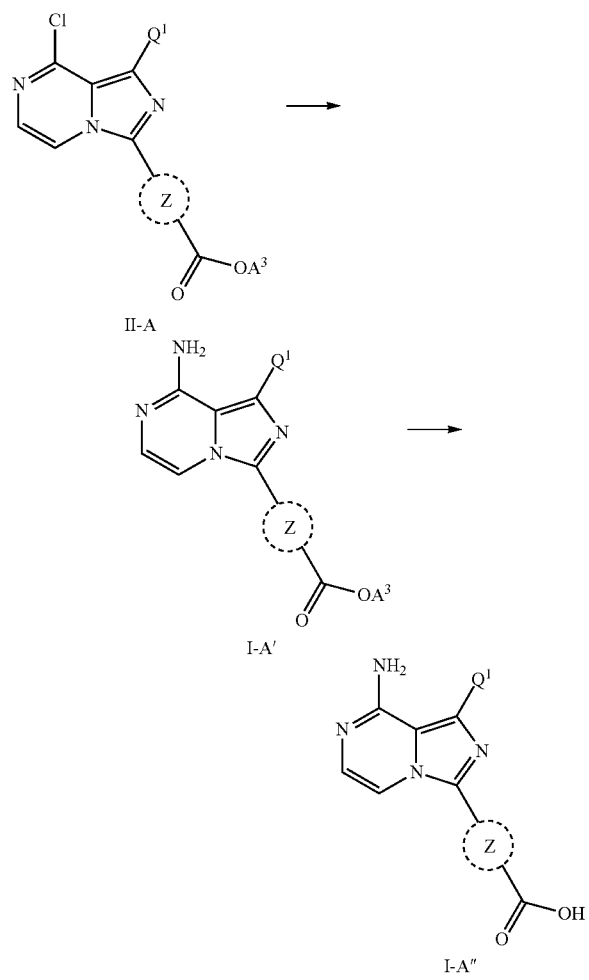

In a typical preparation of compound of Formula I-A', compound of Formula II-A was reacted with ammonia in a suitable solvent. Suitable solvents for use in the above process included, but were not limited to, ethers such as tetrahydrofuran (TH-F), glyme, and the like; dimethylformamide DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about −78° C. and about 120° C. Preferably, the reaction was carried out between 100° C. and about 120° C. The above process to produce compounds of the present invention was preferably carried out at about atmospheric pressure although higher or lower pressures were used if desired. In most cases, the reactions were run in a sealed tube. Substantially equimolar amounts of reactants were preferably used although higher or lower amounts were used if desired. Typically, an excess of ammonia was used and the reaction was monitored in order to ensure that additional of ammonia to the ester moiety did not occur to an appreciable extent. Additionally, in a typical preparation of compound of Formula I-A", compound of Formula I-A' was reacted under typical saponification conditions such as NaOH in $THF/H_2O/$ MeOH. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was a mixture of $THF/H_2O/MeOH$. The above process was carried out at temperatures between about −78° C. and about 120° C. Preferably, the reaction was carried out between rt and about 60° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula II-B (compounds of Formula II where $R^3$=Z—$CH_2OH$) and I-B (compounds of Formula I-AA where $R^3$=Z—$CH_2OH$) were prepared as shown below in Scheme 18:

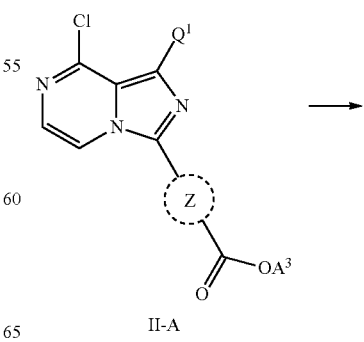

where $Q^1$ is as defined previously for compounds of Formula I and $A^3$=alkyl such as methyl or ethyl.

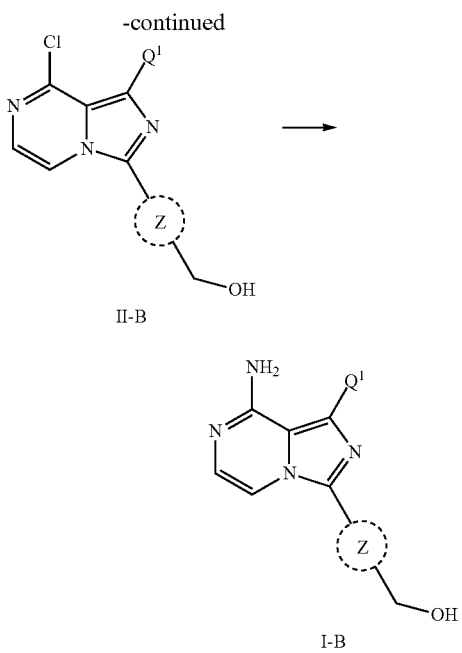

where $Q^1$ is as defined previously for compound of Formula I and $A^3$=hydrogen or alkyl such as methyl or ethyl.

In a typical preparation of compound of Formula I-B, compound of Formula II-A is treated with a suitable reducing agent such as lithium aluminum hydride in a suitable solvent, such as THF to afford compound of Formula II-B. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used. The preferred solvent was THF. The above process was carried out at temperatures between about −78° C. and about 120° C. Preferably, the reaction was carried out between 0° C. and about 50° C. The above process to produce compounds of the present invention was preferably carried out at about atmospheric pressure although higher or lower pressures were used if desired. Substantially equimolar amounts of reactants were preferably used although higher or lower amounts were used if desired. Subsequent treatment of compound of Formula II-B under previously described ammonolysis conditions (ammonia in isopropanol in a sealed tube at 120° C.), afforded compound of Formula I-B.

The compounds of Formula II-C (compounds of Formula II where $R^3=Z\text{---}CH_2A^4$), II-D (compounds of Formula II where $R^3=Z\text{---}CH_2A^5(R^{313})(R^{323})_{aa}$), I-B (compounds of Formula I-AA where $R^3=Z\text{---}CH_2OH$) and I-C (compounds of Formula I-AA where $R^3=Z\text{---}CH_2A^5(R^{313})(R^{323})_{aa}$) were prepared as shown below in Scheme 19:

Scheme 19

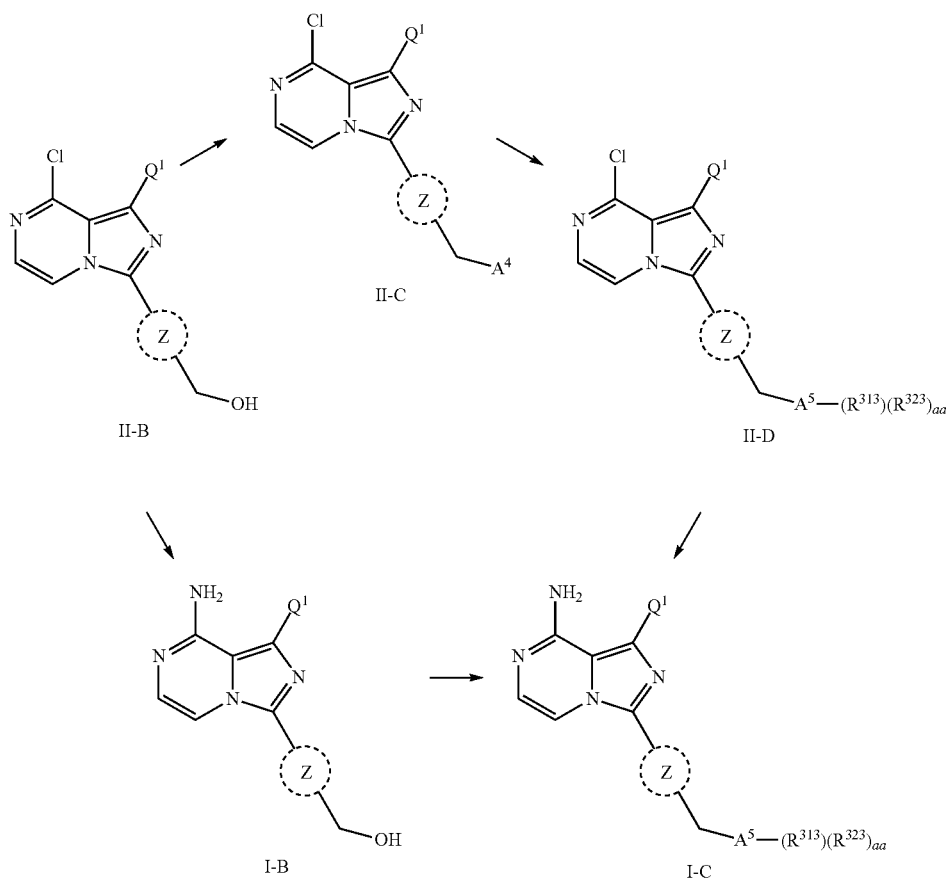

where $Q^1$, $R^{313}$, and $R^{323}$ are as defined previously for compound of Formula I, $A^4$=suitable leaving group such as OTs, OMs, OTf, or halo such as chloro, bromo, or iodo; d=0 or 1; and $A^5$=N, O or S.

In a typical preparation of compound of Formula I-C, the hydroxy group of compound of Formula II-B was converted to a suitable leaving group, $A^4$, such as Cl or OTs, OMs, or OTf, by reaction with $SOCl_2$ or $Ts_2O$, $Ms_2O$, or $Tf_2O$ to afford compound of Formula II-C. Reaction of compound of Formula II-C with $HA^5(R^{313})(R^{323})_{aa}$ afforded compound of Formula II-D. Subsequent reaction of compound of Formula II-D) under previously described ammonolysis conditions afforded compound of Formula I-C. Additionally, compound of Formula II-B was converted to compound of Formula I-B as described previously in Scheme 18. Further conversion of compound of Formula I-B to compound of Formula I-C was accomplished by following the previously described conditions for the conversion of compound of Formula II-B to compound of Formula II-C and the further conversion of compound of Formula II-C to compound of Formula II-D (in the net conversion of OH to $A^5(R^{313})(R^{323})_{aa}$). Furthermore, compound of Formula II-B can be directly converted to compound of Formula II-D by treating compound of Formula II-B with various alkylating agent or with phenols via the Mitsunobu reaction to afford compounds Formula II-D (compounds of Formula II where $R^3=CH_2-Z-A^5(1R^{313})(R^{323})_{aa}$) in which $A^5$=O, aa=0, and $R^{313}$=alkyl or aryl).

The compounds of Formula I-C' (compounds of Formula I-AA where $R^3=Z-CH_2-A^2$), I-C" (compounds of Formula I-AA where $R^3=Z-CH_2-NH_2$), and I-C''' (compounds of Formula I-AA where $R^3=Z-CH_2-N(R^{313})(R^{323})$)) were prepared as shown below in Scheme 20:

Scheme 20

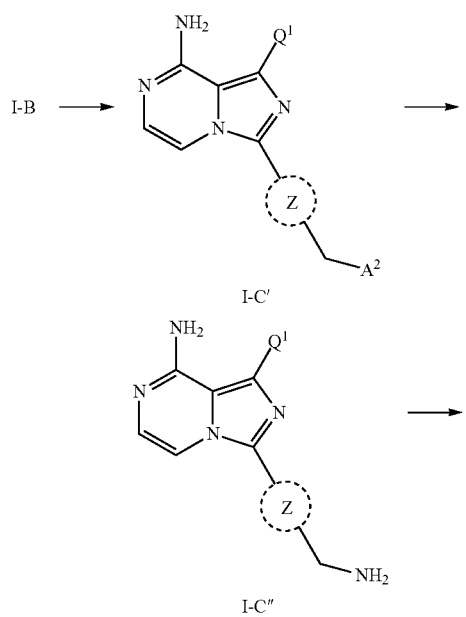

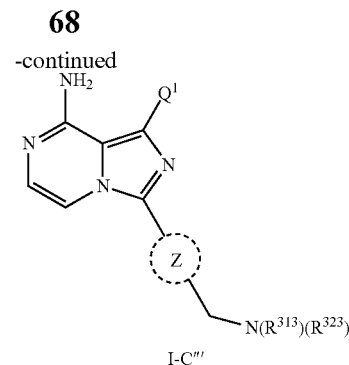

I-C''' where $Q^1$, $R^{313}$, and $R^{323}$ are as defined previously for compound of Formula I and $A^2$=phthalimido or $N_3$.

In a typical preparation of compounds of Formula I-C', I-C", and I-C''', the hydroxy group of compound of Formula I-B was converted to $A^2$, following the procedures as described in Scheme 5 for the conversion of compound of Formula VII to compound of Formula VI. Reaction of compound of Formula I-C' under conditions described in Scheme 4 afforded compound of Formula I-C"C". Reaction of compound of Formula I-C" with, but not limited to various alkylating agents, various aldehydes/ketones under reductive amination conditions, various acylating agents such as acetic anhydride, benzoyl chlorides, or with carboxylic acids in the presence of EDC or DCC with HOBT or HOAT, or with sulphonylating agents such as $Ts_2O$ or $MeSO_2Cl$ afforded compounds of Formula I-C'''. For example, in a typical preparation of compounds of Formula I-C''', a compound of Formula I-C" is treated with a suitable acylating agent in the presence of a suitable base in a suitable solvent. Suitable solvents for use in the above process included, but were not limited to, ethers such as tetrahydrofuran (IMP), glyme, and the like; and chlorinated solvents such as methylene chloride ($CH_2Cl_2$) or chloroform ($CHCl_3$). If desired, mixtures of these solvents were used, however, the preferred solvent was chloroform. Suitable bases for use in the above process included, but were not limited to, trialkylamines such as diisopropylethylamine, triethylamine, or resin bound trialkylamines such as PS-DIEA. The preferred base was PS-DIEA. In the case where the suitable acylating agent was acetic anhydride, the conversion of compound of Formula I-C" to compound of Formula I-C''' where $R^{313}$=H and $R^{323}$=$COCH_3$ was accomplished. The above process was carried out at temperatures between about −78° C. and about 120° C. Preferably, the reaction was carried out between 0° C. and about 20° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula I-D (compounds of Formula I-AA where $R^3=(CH_2)_n-Z^2$-H and $Z^2$ is a heterocyclyl ring containing a nitrogen atom connected to H) and I-E (compounds of Formula I-AA where $R^3=(CH_2)_n$-$Z^2$—$R^{31}$ and $Z^2$ is a heterocyclyl ring containing a nitrogen atom connected to $R^{31}$) were prepared as shown below in Scheme 21:

Scheme 21

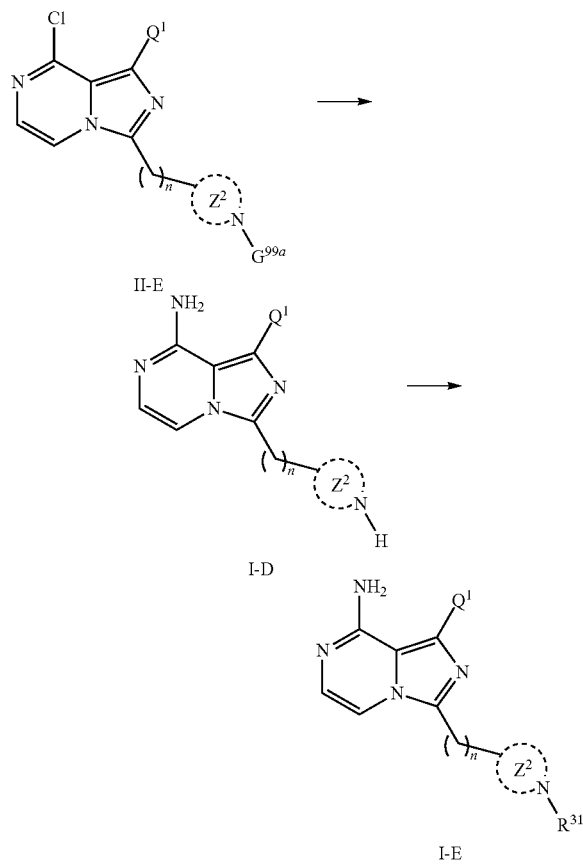

where $Q^1$ and $R^{31}$ are as defined previously for compound of Formula I, $G^{99a}$ is $C(=O)A^6$ or $CO_2A^6$, n=0-5, and $A^6$=alkyl, aryl, or aralkyl.

In a typical preparation of compound of Formula I-E, compound of Formula II-E is treated with suitable reagents capable of converting N-$G^{99a}$ to N—H and therefore afford compound of Formula I-D. For example, treatment of compound of Formula II-E (when $G^{99a}$ is equal to $CO_2Bn$) under previously described ammonolysis conditions followed by treatment with concentrated HCl and a suitable basic workup, affords compound of Formula I-D. Compound of Formula I-D can be subjected to various conditions including but not limited to reductive aminations, alkations and ar(hetar)ylations, and acylations to afford amides, ureas, guanidines, carbamates, thiocarbamates, sulphonamides, and variously substituted nitrogen adducts to afford the net conversion of NH to $NR^2$.

The compounds of Formula II-G (compounds of Formula II where $R^3=Z^3$—OH), II-H (compounds of Formula II where $R^3=Z-A^5(R^{313})(R^{323})_{aa}$), I-F (compounds of Formula I-AA where $R^3=Z$—OH), and I-G (compounds of Formula I-AA where $R^3=Z-A^5(R^{313})(R^{323})_{aa}$) were prepared as shown below in Scheme 22:

Scheme 22

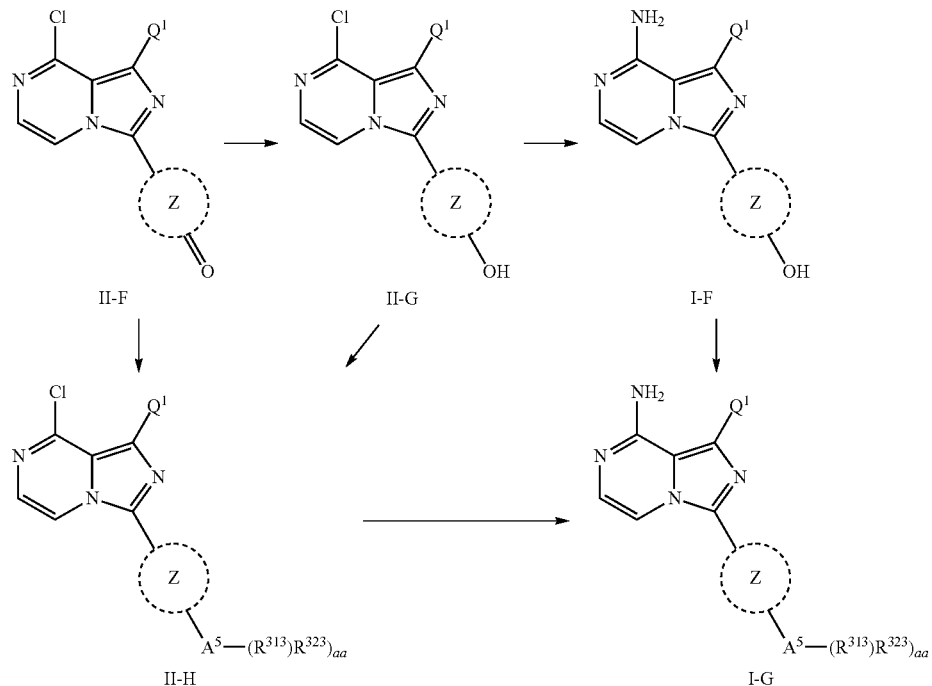

where $Q^1$, $R^{313}$, and $R^{323}$ are as defined previously for compound of Formula I; aa =0 or 1; and $A^5$=N, O or S.

In a typical preparation of compound of Formula I-F and 1-G, the following transformations occurred: Compound of Formula II-F was reduced with a suitable reducing agent in a suitable solvent, such as sodium borohydride in methanol to afford compound of Formula II-G. Compound of Formula II-G was subjected to previously described ammonolysis conditions to afford compound of Formula I-F. Additionally, compounds of Formula II-F can be reacted with various amines under reductive amination conditions (NaBH$_3$CN or NaBH(OAc)$_3$ with HA$^5$(R$^{313}$)(R$^{323}$)$_{aa}$ where d=0, A$^5$=N, and R$^{313}$ and R$^{323}$ are as previously described for compound of Formula I) to afford compounds of Formula II-H where d=0, A$^5$=N, and R$^{313}$ and R$^{323}$ are as previously described for compound of Formula I. Subsequent reaction of compounds of Formula II-H (compounds of Formula II where R$^3$=Z-A$^5$(R$^{313}$)(R$^{323}$)$_{aa}$ where d=0, A$^5$=N, and R$^{313}$ and R$^{323}$ are as previously described for compound of Formula I) with previously described ammonolysis conditions afforded compounds of Formula I-G. Furthermore, compounds of Formula II-H from II-G and I-G from I-F can be synthesized according to the conditions described in Scheme 19 for the transformations of II-B to II-D and I-B to I-C, respectively.

The compounds of Formula I-C''' (compounds of Formula I-AA where R$^3$=Z—CH$_2$—N(R$^{313}$)(R$^{323}$)) were prepared as shown below in Scheme 23:

Scheme 23

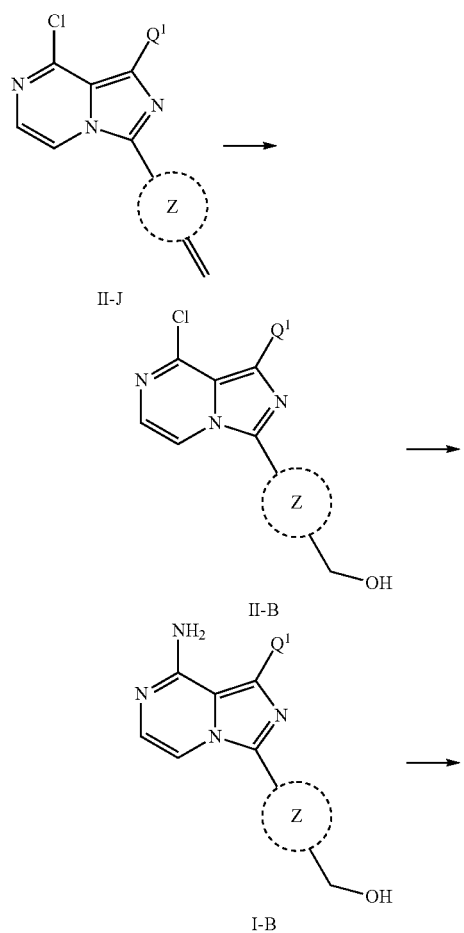

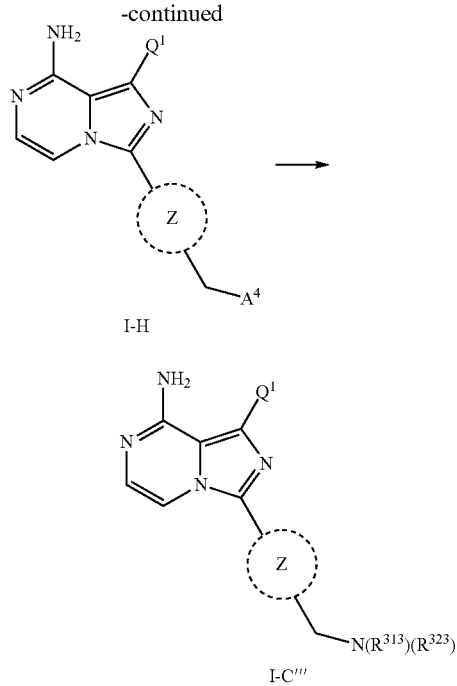

where $Q^1$, $R^{313}$, and $R^{323}$ are as defined previously for compound of Formula I and A$^4$=suitable leaving group such as Cl, OTs, OMs or OTf.

In a typical preparation of compound of Formula I-C''' (compounds of Formula I-AA where R$^3$=Z—CH$_2$—N(R$^{313}$)(R$^{323}$), the following transformations occurred: Compounds of Formula II-J (compounds of Formula II where R$^3$=Z=CH$_2$) were reacted with a suitable hydroborating agent such as diborane, 9-borabicyclo[3.3.1]nonane (9-BBN), catecholborane and the like, in a suitable solvent such as THF followed by treatment with an suitable oxidizing agent such as hydrogen peroxide in basic aqueous solution or NaBO$_3$.H$_2$O to afford compounds of Formula II-B. Further reaction of compounds of Formula II-B with previously described ammonolysis conditions afforded compounds of Formula I-B. The hydroxy group of compounds of Formula I-B was then converted to a suitable leaving group, A$^4$, such OTs, OMs, or OTf, by reaction with Ts$_2$O, Ms$_2$O, or Tf$_2$O, respectively, to afford compounds of Formula I-H. Further reaction of compounds of Formula I-H with HN(R$^{313}$)(R$^{323}$) where R$^{313}$ and R$^{323}$ are as previously described for compounds of Formula I afforded compound of Formula I-C''' (compounds of Formula I-AA where R$^3$=Z—CH$_2$—N(R$^{313}$)(R$^{323}$)).

The compounds of Formula I-C''' (compounds of Formula I-AA where R$^3$=Z—OH(CH$_2$OH)), I-K (compounds of Formula I-AA where R$^3$=Z=O), and I-L (compounds of Formula I-AA where R$^3$-Z—NR$^{313}$R$^{323}$) were prepared as shown below in Scheme 24:

Scheme 24

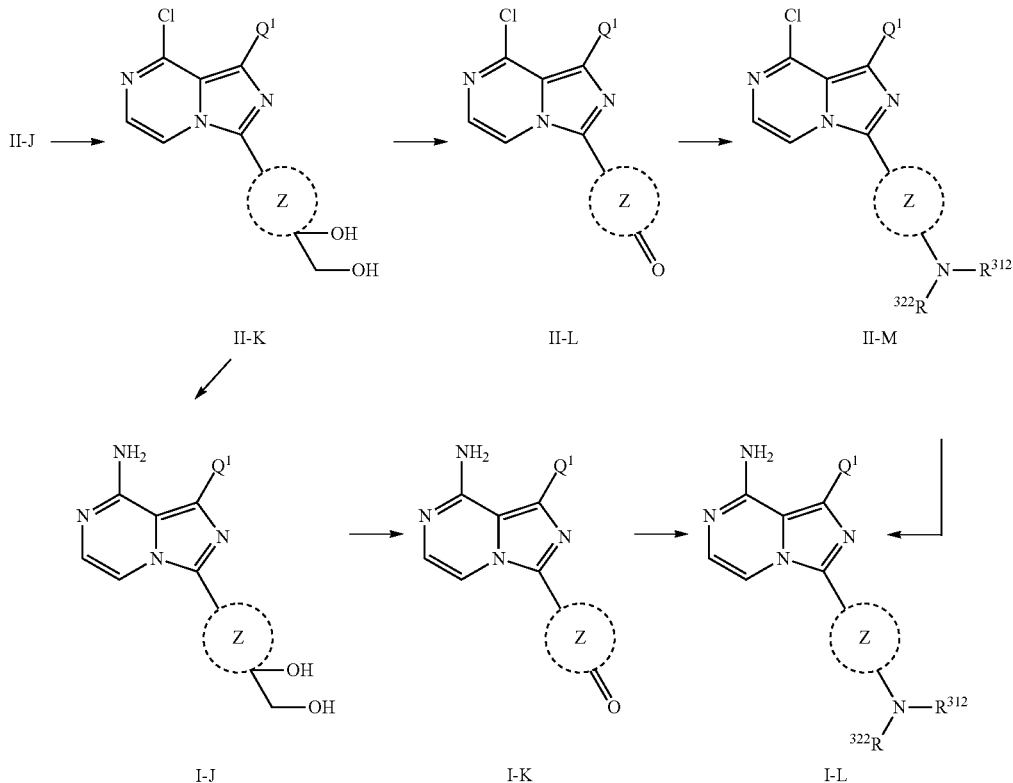

where $Q^1$, $R^{312}$ and $R^{322}$ are as defined previously for compound of Formula I.

In a typical preparation of compound of Formula I-J (compounds of Formula I-AA where $R^3=Z$—OH($CH_2OH$)), I-K (compounds of Formula I-AA where $R^3=Z$=O), and I-L (compounds of Formula I-AA where $R^3=Z$—$NR^{312}R^{322}$) compound of Formula II-J was treated under (compounds of Formula II where $R^3=Z$=$CH_2$) was reacted with a suitable dihydroxylating agent such as osmium tetraoxide in the presence of NMO in a suitable solvent such as THF to afford compound of Formula I-K (compounds of Formula II where $R^3=Z$—OH($CH_2OH$)) as a mixture of cis and trans isomers. Compounds of Formula II-K (compounds of Formula II where $R^3=Z$—OH($CH_2OH$)) were treated with a suitable oxidizing agent, such as but not limited to, $NaIO_4$, converting the diol into a ketone moiety, affording compound of Formula II-L (compounds of Formula II where $R^3=Z$=O). Compound of Formula II-L (compounds of Formula II where $R^3=Z$=O) was then treated under typical reductive amination conditions, involving a suitable amine, $HNR^{312}R^{322}$ and a suitable reducing agent, such as but not limited to, $NaBH(OAc)_3$ or $NaBH(CN)_3$, affording compound of Formula II-M (compounds of Formula II where $R^3=Z$—$NR^{312}R^{322}$). Compound of Formula II-M (compounds of Formula II where $R^3=Z$—$NR^{312}R^{322}$) was treated under ammonolysis conditions, ammonia in isopropanol in a stainless steel bomb at 110° C., to afford compound of Formula I-L (compounds of Formula I-AA where $R^3=Z$—$NR^{312}R^{322}$). Moreover, compound of Formula II-K (compounds of Formula II where R=Z—OH ($CH_2OH$)) was treated under the ammonolysis conditions described above to afford compound of Formula I-J (compounds of Formula I-AA where $R^3=Z$—OH($CH_2OH$)) as a mixture of isomers. Compound of Formula I-J (compounds of Formula I-AA where $R^3=Z$—OH($CH_2OH$) was treated with a suitable oxidizing agent, such as but not limited to, $NaIO_4$, converting the diol into a ketone moiety, affording compound of Formula I-K (compounds of Formula I-AA where $R^3=Z$=O), which was treated under the typical reductive amination conditions described above to afford compound of Formula I-L (compounds of Formula I-AA where $R^3=Z$—$NR^{312}R^{322}$).

The compounds of Formula I-N (compounds of Formula I-AA where $R^3=Z$—OH($CH_2NR^{313}R^{323}$)) were prepared as shown below in Scheme 25:

Scheme 25

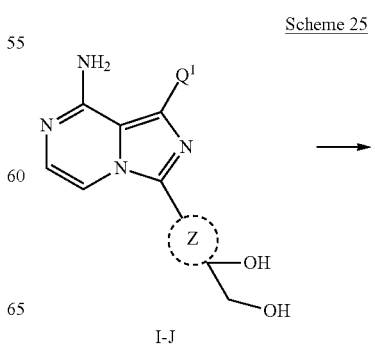

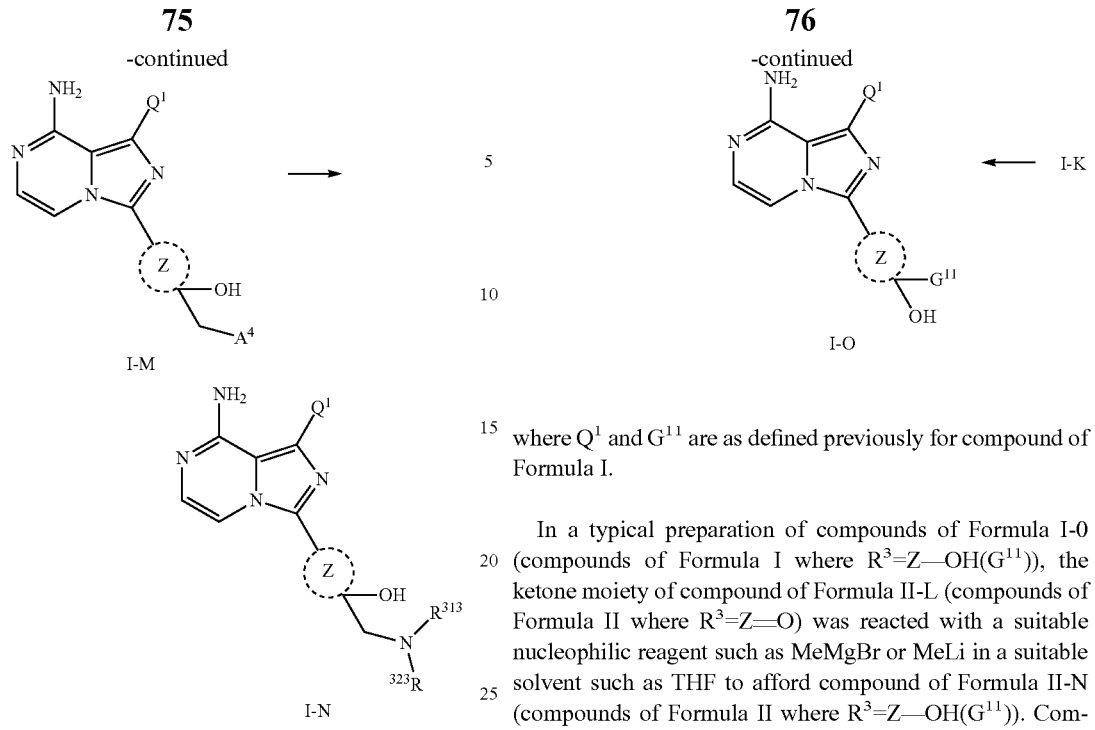

where $Q^1$, $R^{313}$, and $R^{323}$ are as defined previously for compound of Formula I; $A^4$=suitable leaving group such as OTs, OMs, or OTf.

In a typical preparation of compounds of Formula I-N (compounds of Formula I-AA where $R^3$=Z—OH(CH$_2$NR$^{313}$R$^{323}$)), the primary hydroxyl group of compound of Formula I-J (compounds of Formula I-AA where $R^3$=Z—OH(CH$_2$OH) was converted to a suitable leaving group, $A^4$, such as OTs, OMs, or OTf, by reaction with Ts$_2$O, Ms$_2$O, or Tf$_2$O in the presence of a suitable base such as diisopropylamine or pyridine and solvent such as THF or methylene chloride to afford compound of Formula I-M (compounds of Formula I-A where $R^3$=Z—OH(CH$_2$A$^4$)). Reaction of compound of Formula I-M (compounds of Formula I-AA where $R^3$=Z—OH(CH$_2$A$^4$)) with HN(R$^{313}$)(R$^{323}$) in a suitable solvent such as THF or methylene chloride afforded compound of Formula I-N (compounds of Formula I where $R^3$=Z—OH(C$_2$NR$^{313}$R$^{323}$)).

The compounds of Formula I-O (compounds of Formula I where $R^3$=Z$^3$—OH(G$^{11}$)) were prepared as shown below in Scheme 26:

Scheme 26

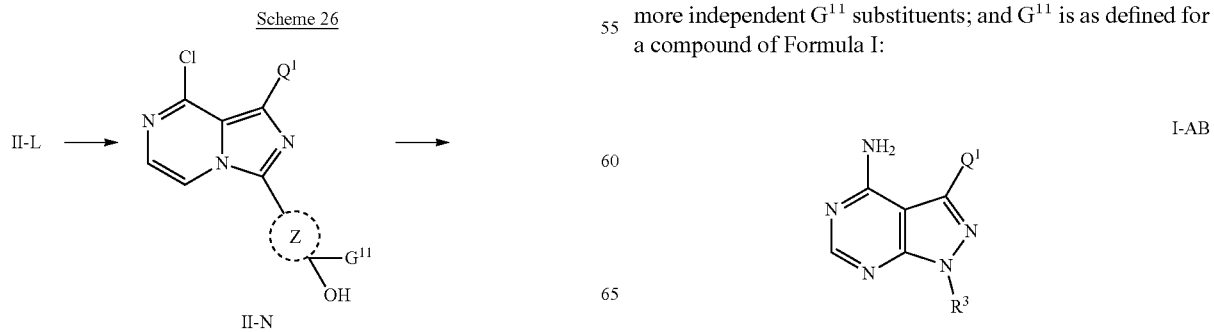

where $Q^1$ and $G^{11}$ are as defined previously for compound of Formula I.

In a typical preparation of compounds of Formula I-0 (compounds of Formula I where $R^3$=Z—OH(G$^{11}$)), the ketone moiety of compound of Formula II-L (compounds of Formula II where $R^3$=Z=O) was reacted with a suitable nucleophilic reagent such as MeMgBr or MeLi in a suitable solvent such as THF to afford compound of Formula II-N (compounds of Formula II where $R^3$=Z—OH(G$^{11}$)). Compound of Formula II-N (compounds of Formula II where $R^3$=Z—OH(G$^{11}$)) was reacted under ammonolysis conditions, ammonia in isopropanol in a stainless steel bomb at 110° C., to afford compound of Formula I-0 (compounds of Formula I where $R^3$=Z—OH(G$^{11}$)). Additionally, compound of Formula I-0 (compounds of Formula I where $R^3$=Z—OH (G$^{11}$)) was prepared by reacting compound of Formula I-K (compounds of Formula I-AA where $R^3$=Z=O) with a suitable nucleophilic reagent such as MeMgBr or MeLi in a suitable solvent such as THF.

The conversion of compounds of Formula I-PP' and I-P' to compounds of Formula I-RR an I-R, respectively may be accomplished by reaction with a boronic acid ester using so-called "Liebeskind-Srogl" conditions such as those described in *Organic Letters*, (2002), 4(6), 979 or Synlett, (2002), (3), 447.

A compound of Formula I-A Bis equal to compound of Formula I wherein $X_1$=CH, $X_2$, $X_4$ and $X_5$=N, and $X_3$, $X_6$ and $X_7$=C; $Q^1$ is as defined for a compound of Formula I; $R^3$ is $C_{0-10}$alkyl, cycloC$_{3-10}$alkyl, aminomethylcycloC$_{3-10}$alkyl, bicycloC$_{5-10}$alkyl, aryl, heteroaryl, aralkyl, heteroaralkyl, heterocyclyl, heterobicycloC$_{5-10}$alkyl, spiroalkyl, or heterospiroalkyl, any of which is optionally substituted by one or more independent G$^{11}$ substituents; and G$^{11}$ is as defined for a compound of Formula I:

Method AB was used when preparing compounds of Formula I-AB as shown below in Scheme 28:

Method AB:

Scheme 28

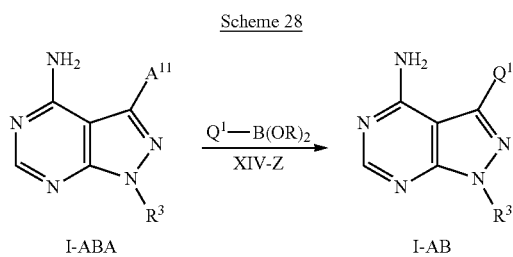

I-ABA          I-AB where $Q^1$ and $R^3$ are as defined previously for compound of Formula I-AB, $A^{11}$=halogen such as Cl, Br, or I, and $Q^1$-B(OR)$_2$=suitable boronic acid/ester.

In a typical preparation of compounds of Formula I-AB, compound of Formula I-ABA was reacted with a suitable boronic acid/ester of Formula XIV-Z ($Q^1$-B(OR)$_2$) in a suitable solvent via typical Suzuki coupling procedures. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride (CH$_2$Cl$_2$) or chloroform (CHCl$_3$). If desired, mixtures of these solvents were used, however, the preferred solvent systems were THF/water and DMF/water. The above process was carried out at temperatures between about 20° C. and about 120° C. Preferably, the reaction was carried out between 80° C. and about 100° C. The above process to produce compounds of the present invention was preferably carried out at about atmospheric pressure although higher or lower pressures were used if desired. Substantially equimolar amounts of reactants were preferably used although higher or lower amounts were used if desired.

One skilled in the art will appreciate that alternative methods may be applicable for preparing compounds of Formula I-AB from I-ABA. For example, compound of Formula I-ABA could be reacted with a suitable organotin reagent $Q^1$-SnBu$_3$ or the like in a suitable solvent via typical Stille coupling procedures.

The compounds of Formula I-ABA wherein $R^3$ is $C_{1-10}$alkyl, cycloC$_{3-10}$alkyl, bicycloC$_{5-10}$alkyl, aralkyl, heteroaralkyl, heterocyclyl, heterobicycloC$_{5-10}$alkyl, spiroalkyl, or heterospiroalkyl, any of which is optionally substituted by one or more independent G$^{11}$ substituents, of Scheme 28 were prepared as shown below in Scheme 29:

Scheme 29

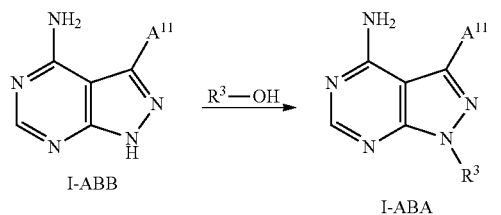

I-ABB          I-ABA where $R^3$ is $C_{1-10}$alkyl, cycloC$_{3-10}$alkyl, bicycloC$_{5-10}$alkyl, aralkyl, heteroaralkyl, heterocyclyl, heterobicycloC$_{5-10}$alkyl, spiroalkyl, or heterospiroalkyl, any of which is optionally substituted by one or more independent G$^{11}$ substituents; G$^{11}$ is as defined previously for compound of Formula I, and $A^{11}$=halogen such as Cl, Br, or I.

In a typical preparation of a compound of Formula I-ABA, a compound of Formula I-ABB was reacted with an alcohol $R^3$—OH under typical Mitsunobu conditions in a suitable solvent in the presence of suitable reactants. Suitable solvents for use in the above process included, but were not limited to, ethers such as tetrahydrofuran (THF), glyme, and the like; dimethylfomamide DMF); dimethyl sulfoxide (DMSO); acetonitrile (CH$_3$CN); chlorinated solvents such as methylene chloride (CH$_2$Cl$_2$) or chloroform (CHCl$_3$). If desired, mixtures of these solvents were used, however, the preferred solvent was THF. Suitable reactants for use in the above process included, but were not limited to, triphenylphosphine and the like, and an azodicarboxylate (DIAD, DEAD, DBAD). The preferred reactants were triphenylphosphine or resin-bound triphenylphosphine and DIAD. The above process may be carried out at temperatures between about –78° C. and about 100° C. Preferably, the reaction was carried out between about 0° C. and 25° C. The above process to produce compounds of the present invention was preferably carried out at about atmospheric pressure although higher or lower pressures were used if desired. Substantially equimolar amounts of reactants were preferably used although higher or lower amounts were used if desired. Generally, one equivalent of triphenylphosphine, DL), and RASH was used per equivalent of compound of Formula I-ABB.

Alternatively, the compounds of Formula I-ABA may be prepared by alkylating compounds of Formula I-ABB with an alkylating agent $R^3$-LG, wherein LG is a leaving group including, but not limited to, chloride, bromide, iodide, tosylate, mesylate, trifluoromethanesulfonate, under typical alkylation conditions known to someone skilled in the art.

Preferably, in compounds of Formula I-ABB, $A^{11}$=Br and I. These compounds are known ($A^{11}$=I: H. B. Cottam et al., *J. Med. Chem.* 1993, 36(22), 3424-3430; $A^{11}$=Br: T. S. Leonova et al., *Khim. Geterotsikl. Soedin.* 1982, (7), 982-984).

Compound of Formula I-AC is equal to compound of Formula I wherein $X_1$ and $X_5$=CH, $X_2$ and $X_4$=N, and $X_3$, $X_6$ and $X_7$=C; $Q^1$ is as defined for a compound of Formula I; $R^3$ is $C_{0-10}$alkyl, cycloC$_{3-10}$alkyl, bicycloC$_{5-10}$alkyl, aryl, heteroaryl, aralkyl, heteroaralkyl, heterocyclyl, heterobicycloC$_{5-10}$alkyl, spiroalkyl, or heterospiroalkyl, any of which is optionally substituted by one or more independent G$^{11}$ substituents; and G$^{11}$ is as defined for a compound of Formula I:

Method AC was used when preparing compounds of Formula I-AB as shown below in Scheme 30:

Method AC:

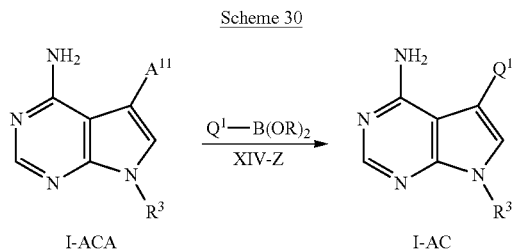

where $Q^1$ and $R^3$ are as defined previously for compound of Formula I-AC, $A^{11}$=halogen such as Cl, Br, or I and $Q^1$-B$(OR)_2$=suitable boronic acid/ester.

In a typical preparation of compounds of Formula I-AC, compound of Formula I-ACA was reacted with a suitable boronic acid/ester XIV-Z ($Q^1$-B$(OR)_2$) in a suitable solvent via typical Suzuki coupling procedures. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired mixtures of these solvents were used, however, the preferred solvent systems were THF/water and DMF/water. The above process was carried out at temperatures between about 20° C. and about 120° C. Preferably, the reaction was carried out between 80° C. and about 10° C. The above process to produce compounds of the present invention was preferably carried out at about atmospheric pressure although higher or lower pressures were used if desired. Substantially equimolar amounts of reactants were preferably used although higher or lower amounts were used if desired.

One skilled in the art will appreciate that alternative methods may be applicable for preparing compounds of formula I-AC from I-ACA. For example, compound of Formula I-ACA could be reacted with a suitable organotin reagent $Q^1$-SnBu$_3$ or the like in a suitable solvent via typical Stille coupling procedures.

The compounds of Formula I-ACA of Scheme 30 were prepared as shown below in Scheme 31:

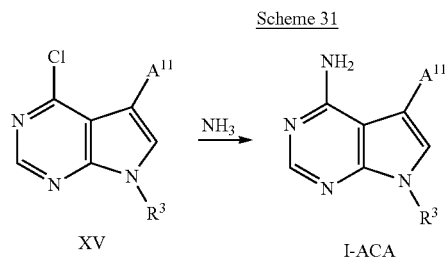

where $R^3$ is as defined previously for compound of Formula I-AC, and $A^{11}$=halogen such as Cl, Br, or I.

In a typical preparation of compounds of Formula I-ACA, compound of Formula XV was reacted with ammonia in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about −78° C. and about 120° C. Preferably, the reaction was carried out between 80° C. and about 100° C. The above process to produce compounds of the present invention was preferably carried out in a glass pressure tube or a stainless steel reactor. Preferably, an excess of ammonia was used.

The compounds of Formula XVA (=compounds of Formula XV of Scheme 31 wherein $R^3$ is $C_{1-10}$alkyl, cycloC$_{3-10}$alkyl, bicycloC$_{5-10}$alkyl, aralkyl, heteroaralkyl, heterocyclyl, heterobicycloC$_{5-10}$alkyl, spiroakyl, or heterospiroalkyl, any of which is optionally substituted by one or more independent $G^{11}$ substituents) were prepared as shown below in Scheme 32:

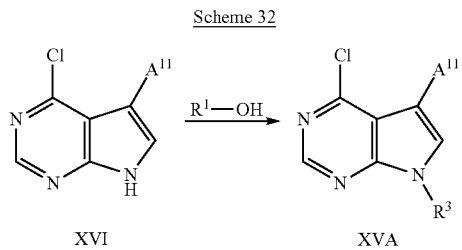

where $R^3$ is $C_{1-10}$alkyl, cycloC$_{3-10}$alkyl, bicycloC$_{5-10}$alkyl, aralkyl, heteroaralkyl, heterocyclyl, heterobicycloC$_{5-10}$alkyl, spiroalkyl, or heterospiroalkyl, any of which is optionally substituted by one or more independent $G^{11}$ substituents; $G^{11}$ is as defined previously for compound of Formula I; and $A^{11}$=halogen such as Cl, Br, or I.

In a typical preparation of a compound of Formula XVA, a compound of Formula XVI was reacted with an alcohol R$^3$OH under typical Mitsunobu conditions in a suitable solvent in the presence of suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile (CH$_3$CN); chlorinated solvents such as methylene chloride (CH$_2$Cl$_2$) or chloroform (CHCl$_3$). If desired, mixtures of these solvents were used, however, the preferred solvent was THF. Suitable reactants for use in the above process included, but were not limited to, triphenylphosphine and the like, and an azodicarboxylate (DIAD, DEAD, DBAD). The preferred reactants were triphenylphosphine or resin-bound triphenylphosphine and DIAD. The above process may be carried out at temperatures between about −78° C. and about 100° C. Preferably, the reaction was carried out between about 0° C. and 25° C. The above process to produce compounds of the present invention was preferably carried out at about atmospheric pressure although higher or lower pressures were used if desired. Substantially equimolar amounts of reactants were preferably used although higher or lower amounts were used if desired. Generally, one equivalent of triphenylphosphine, DIAD, and R$^3$—OH was used per equivalent of compound of Formula XVI.

Alternatively, the compounds of Formula XVA may be prepared by alkylating compounds of Formula XVI with an alkylating agent R$^3$-LG, wherein LG is a leaving group including, but not limited to, chloride, bromide, iodide, tosylate, mesylate, trifluoromethanesulfonate, under typical alkylation conditions known to someone skilled in the art.

The compounds of Formula XVB (compounds of Formula XV of Scheme 31 wherein $R^3$ is aryl or heteroaryl, optionally substituted by one or more independent $G^{11}$ substituents) were prepared as shown below in Scheme 33:

Scheme 33

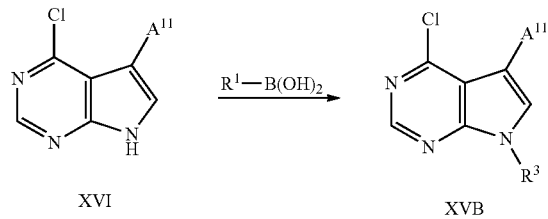

where $R^3$ is aryl or heteroaryl, optionally substituted by one or more independent $G^{11}$ substituents, $G^{11}$ is as defined previously for compound of Formula I; and $A^{11}$=halogen such as Cl, Br, or I.

In a typical preparation of compounds of Formula XVB, compound of Formula XVI was reacted with a suitable boronic acid of Formula $R^3$—$B(OH)_2$ in a suitable solvent via typical copper(II)-mediated coupling procedures. Suitable solvents for use in the above process included, but were not limited to, ethers such as tetrahydrofuran (THF), glyme, 1,4-dioxane, and the like; dimethylformamide (DMF); N-methylpyrrolidinone (NMP); chlorinated solvents such as methylene chloride ($CH_2Cl_2$). If desired, mixtures of these solvents were used, however, the preferred solvent was methylene chloride ($CH_2Cl_2$). Suitable reactants for use in the above process included, but were not limited to, copper(II) acetate ($Cu(OAc)_2$, copper(II) triflate ($Cu(OTf)_2$), and the like, and a base pyridine, and the like). The preferred reactants were $Cu(OAc)_2$ and pyridine. The above process to produce compounds of the present invention was preferably carried out at about atmospheric pressure under air, although higher or lower pressures could be used if desired. Preferably, the reaction was cried out at about 22C. Generally, 1.5 eq, of copper (II) acetate, 2 eq. of pyridine, and 2 eq. of boronic acid of Formula $R^3$—$B(OH)$ were used per equivalent of compound of Formula XVI.

All compounds of Formula XVI are known in the literature ($A^{11}$=I: L. B. Townsend et al., *J. Med. Chem.* 1990, 33, 1984-92; $A^{11}$=Br, Cl: L. B. Townsend et al., *J. Med. Chem.*, 1988, 31, 2086-2092). Preferably, $A^{11}$=Br and I.

Both $R^3$ and $Q^1$ in the compounds described herein in some instances contain functional groups that can be further manipulated. It would be appreciated by those skilled in the art that such manipulation of functional groups could be accomplished with key intermediates or with late stage compounds. Such functional group transformations are exemplified in the following Schemes 3435 as well as in the experimental section but are in no way meant to limit the scope of such transformations.

The compounds of Formula I-ACA' (=compounds of Formula I-ACA where $R^3$=Z—$CORN^{312}R^{322}$) were prepared from compounds of Formula XV' (=compounds of Formula XV where $R^3$=Z—$CO_2A^3$) as shown below in Scheme 34:

Scheme 34

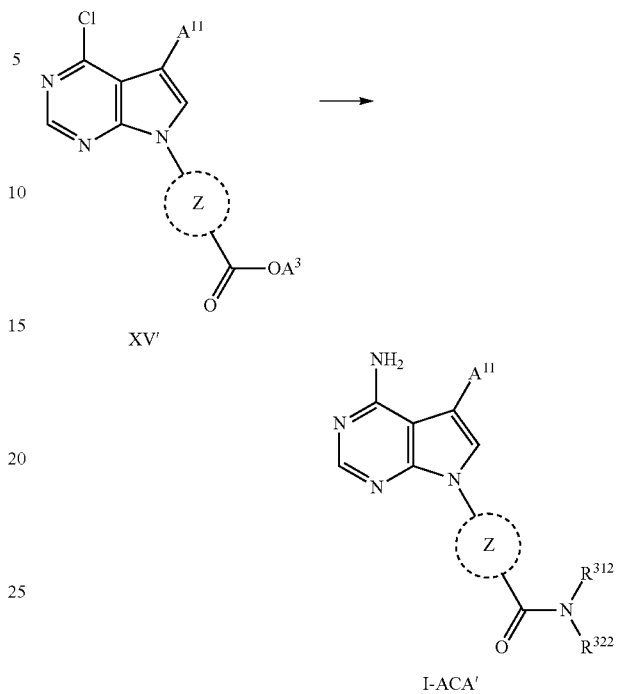

where $R^{312}$ and $R^{322}$ are as defined previously for compound of Formula I; $A^{11}$=halogen such as Cl, Br, or I; and $A^3$=hydrogen or alkyl such as methyl or ethyl.

In a typical preparation of compound of Formula I-ACA', when $A^3$=alkyl and $R^{312}$ and $R^{322}$ were both equal to H, reaction of compound of Formula XV' with ammonia in a suitable solvent, afforded compound of Formula I-ACA'. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about −78° C. and about 120° C. Preferably, the reaction was carried out between 80° C. and about 100° C. The above process to produce compounds of the present invention was preferably carried out in a glass pressure tube or a stainless steel reactor. Preferably, an excess of ammonia was used. Additionally, in a typical preparation of compound of Formula I-ACA' (compounds of Formula I-ACA where $R^3$=Z—$CORN^{312}R^{322}$), compound of Formula XV' (compounds of Formula XV' where $R^3$=Z—$CO_2A^3$) was reacted with $HNR^{312}R^{322}$ followed by ammonia in a suitable solvent. When $A^3$=H, typical coupling procedures (such as conversion of —$CO_2H$ to -COCl via treatment with $SOCl_2$ or oxalyl chloride followed by reaction with $HNR^{312}R^{322}$ or treatment of —$CO_2H$ and $HNR^{312}R^{322}$ with EDC or DCC in conjunction with DMAP, HOBT, or HOAt and the like) were employed to afford the transformation of a carboxylic acid to an amide. When $A^3$ alkyl such as methyl or ethyl, treatment of the ester with $Al(NR^{312}R^{322})$ afforded conversion of —$CO_2A^3$ to -$CO(NR^{312}R^{322})$. Subsequent treatment with ammonia afforded compounds of Formula I-ACA'.

The chemistry shown in Scheme 34 can also be applied to compounds with $Q^1$ in place of $A^{11}$.

The compounds of Formula XVIII (compounds of Formula XV, I-ACA, or I-AC where $R^3=Z-CH_2OH$), XIX (compounds of Formula XV, I-ACA, or I-AC where $R^3=Z-CH_2LG$), and XX (compounds of Formula XV, I-ACA, or I-AC where $R^3=Z-CH_2A^5(R^{313})R^{323})_{aa}$) were prepared as shown below in Scheme 35:

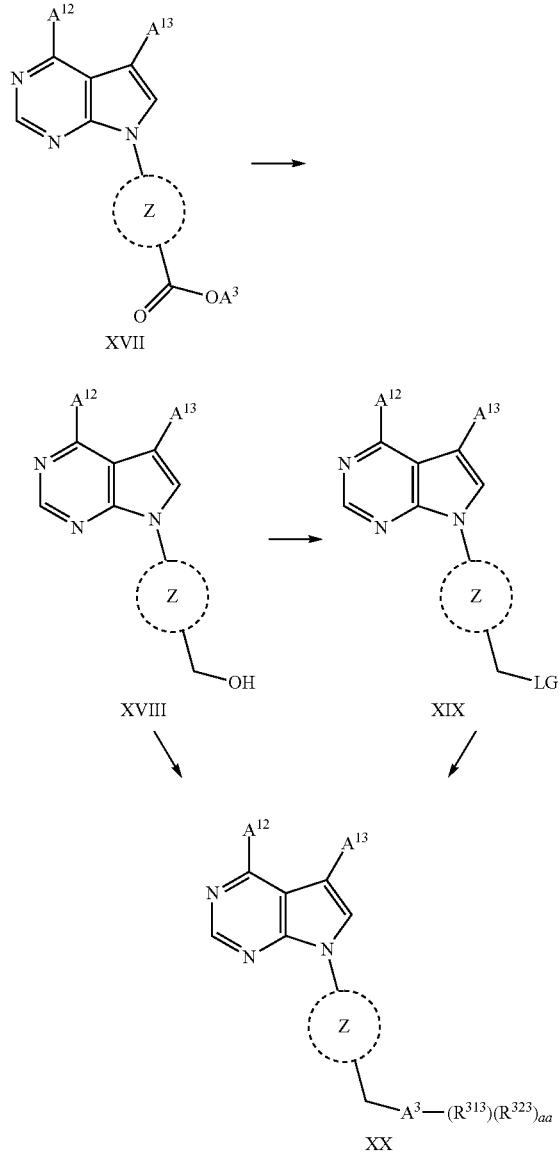

where $Q^1$, $R^{313}$, and $R^{323}$ are as defined previously for compound of Formula I; LG=suitable leaving group such as tosylate, mesylate, trifluoromethanesulfonate, or halo such as chloro, bromo, or iodo; aa =0 or 1; $A^3$=hydrogen or alkyl such as methyl or ethyl; $A^{11}$=halogen such as Cl, Br, or I; $A^{12}$=C or $NH_2$; $A^{13}=A^{11}$ or $Q^1$; and $A^5$=N, O or S.

The following table indicates the relations between the compounds of Formulas XVII-XX, $A^{12}$, $A^{13}$, compounds of Formulas I-AC, I-AC, and XV, and $R^3$.

| Compound of Formula ... | wherein $A^{12}=$ | and $A^{13}=$ | ... is equal to Formula ... | wherein $R^3=$ |
|---|---|---|---|---|
| XVII | Cl | $A^{11}$ | XV | $Z-CO_2A^3$ |
| XVII | $NH_2$ | $A^{11}$ | I-ACA | $Z-CO_2A^3$ |
| XVII | $NH_2$ | $Q^1$ | I-AC | $Z-CO_2A^3$ |
| XVIII | Cl | $A^{11}$ | XV | $Z-CH_2OH$ |
| XVIII | $NH_2$ | $A^{11}$ | I-ACA | $Z-CH_2OH$ |
| XVIII | $NH_2$ | $Q^1$ | I-AC | $Z-CH_2OH$ |
| XIX | Cl | $A^{11}$ | XV | $Z-CH_2LG$ |
| XIX | $NH_2$ | $A^{11}$ | I-ACA | $Z-CH_2LG$ |
| XIX | $NH_2$ | $Q^1$ | I-AC | $Z-CH_2LG$ |
| XX | Cl | $A^{11}$ | XV | $Z-CH_2A^5R^2(R^4)_d$ |
| XX | $NH_2$ | $A^{11}$ | I-ACA | $Z-CH_2A^5R^2(R^4)_d$ |
| XX | $NH_2$ | $Q^1$ | I-AC | $Z-CH_2A^5R^2(R^4)_d$ |

In a typical preparation of compound of Formula XVII (compounds of Formula XV, I-ACA, or I-AC, where $R^3=Z-CH_2OH$), compound of Formula XVII (compounds of Formula XV, I-ACA, or I-AC, where $R^3=Z-CO_2A^3$) is treated with a suitable reducing agent, such as lithium aluminum hydride or diisobutylaluminum hydride, in a suitable solvent, such as THF or methylene chloride, to afford compound of Formula XVIII. In a typical preparation of compound of Formula XX (compounds of Formula XV, I-ACA, or I-AC, where $R^3=Z-CH_2A^5(R^{313})(R^{323})_{aa}$), the hydroxy group of compound of Formula XVIII was converted to a suitable leaving group, LG, such as Cl or tosylate, mesylate, or triflate, by reaction with $SOCl_2$ or $Ts_2O$, $Ms_2O$, or $Tf_2O$ to afford compound of Formula XIX (compounds of Formula XV, I-ACA, or I-AC, where $R^3=Z-CH_2LG$). Reaction of compound of Formula XIX with $HA^5(R^{313})(R^{323})_{aa}$ afforded compound of Formula XX. Furthermore, compound of Formula XVIII can be directly converted to compound of Formula XX by treating compound of Formula XVIII with various alkylating agents or under typical Mitsunobu reaction conditions to afford compounds of Formula XX (compounds of Formula XV, I-ACA, or I-AC, where $R^3=Z-CH_2A^5(R^{313})(R^{323})_{aa}$) in which $A^5=O$, aa=0, and $R^{313}$=alkyl or aryl). Someone skilled in the an will choose the most appropriate stage during the sequence shown in Scheme 35 to convert $A^{12}=Cl$ to $A^{12}=NH_2$ as described in Scheme 31, and to convert $A^{13}=A^{11}$ to $A^{13}=Q^1$ as described in Scheme 30, if applicable.

An alternative preparation of compounds of Formula I-AC is shown in Scheme 36.

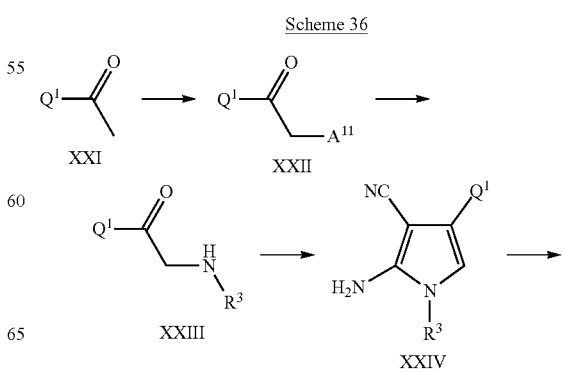

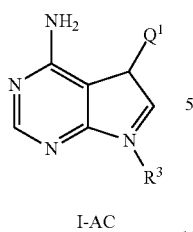

I-AC where $Q^1$ and $R^3$ are as defined previously for compound of Formula I; and $A^{11}$=halogen such as Cl, Br, or I.

The compounds of Formula XXI may be prepared from aldehydes $Q^1$-CHO (see Scheme 14 for their preparation) by addition of methyllithium or a methyl Grignard reagent, followed by oxidation of the resulting alcohol to the ketone of Formula XXI. Other compounds are commercially available or can be prepared by methods well known to someone skilled in the art, see: Larock, R. C. *Comprehensive Organic Transformations*, $2^{nd}$ ed.; Wiley and Sons: New York, 1999, 1197 ff. Reaction of compounds of Formula XXI under typical halogenation conditions with typical halogenating agents including, but not limited to, $Br_2$, NBS, pyridinium perbromide, or $CuBr_2$ (for $A^{11}$=Br), or NCS or $SO_2Cl_2$ (for $A^{11}$=Cl) gives the compounds of Formula XXII. Their reaction with amines of Formula $H_2N$—$R^3$ gives the aminoketones of Formula XXIII that are converted to aminocyanopyrroles of Formula XXIV by reaction with malononitrile under basic conditions. Finally, reaction of compounds of Formula XXIV under typical cyclization conditions gives the compounds of Formula I-AC. Conditions for this cyclization include, but are not limited to, heating with formamide; heating with formamide and ammonia; sequential treatment with a trialkyl orthoformate, ammonia, and a base; sequential treatment with formamidine and ammonia.

It would be appreciated by those skilled in the art that in some situations, a substituent that is identical or has the same reactivity to a functional group which has been modified in one of the above processes, will have to undergo protection followed by deprotection to afford the desired product and avoid undesired side reactions. Alternatively, another of the processes described within this invention may be employed in order to avoid competing functional groups. Examples of suitable protecting groups and methods for their addition and removal may be found in the following reference: "Protective Groups in Organic Syntheses", T. W. Greene and P. G. M. Wuts, John Wiley and Sons, 1989.

Compound of Formula I-AQ is equal to compound of Formula I wherein $X_1$=CH; $X_2$, $X_3$ and $X_5$=N; $X_4$, $X_6$, and $X_7$=C and J=H or $NH_2$

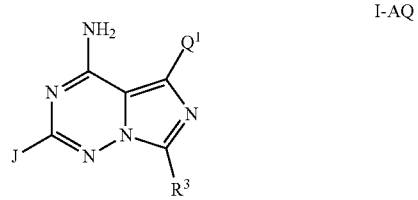

I-AQ

Method AQ was used when preparing compounds of Formula I-AQ as shown below in Scheme 37:

Method AQ:

Scheme 37

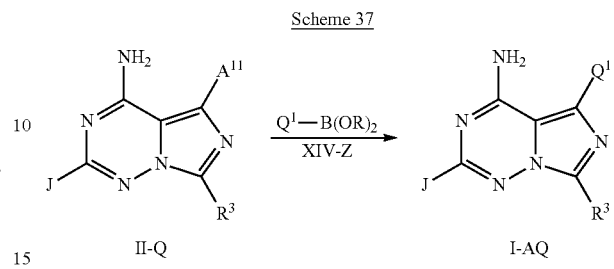

II-Q            I-AQ where $Q^1$ and $R^3$ are as defined previously for compound of Formula I, $A^{11}$=halogen such as Cl, Br, or I; $B(OR)_2$=suitable boronic acid/ester and J=H or $NH_2$.

In a typical preparation of compounds of Formula I-AQ, compound of Formula II-Q was reacted with a suitable boronic acid/ester ($Q^1$-$B(OR)_2$) in a suitable solvent via typical Suzuki coupling procedures. Suitable solvents for use in the above process included, but were not limited to, water, ethers such as tetrahydrofuran (THF), glyme, and the like; dimethylformamide (DMF); dimethyl sulfoxide DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was glyme/water. The above process was carried out at temperatures between about $-78°$ C. and about $120°$ C. Preferably, the reaction was carried out between $80°$ C. and about $100°$ C. The above process to produce compounds of the present invention was preferably carried out at about atmospheric pressure although higher or lower pressures were used if desired. Substantially equimolar amounts of reactants were preferably used although higher or lower amounts were used if desired.

One skilled in the art will appreciate that alternative methods may be applicable for preparing compounds of Formula I-AQ from II-Q. For example, compound of Formula II-Q could be reacted with a suitable organotin reagent $Q^1$-$SnBu_3$ or the like in a suitable solvent via typical Stille coupling procedures.

The compounds of Formula II-Q of Scheme 37 were prepared as shown below in Scheme 38.

Scheme 38

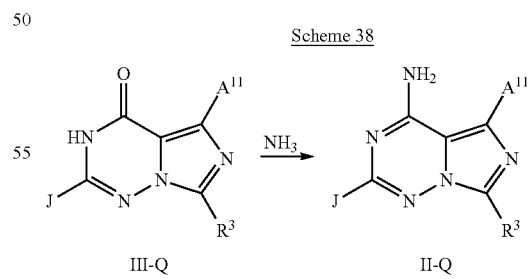

III-Q            II-Q where $R^3$ is as defined previously for compound of Formula I and $A^{11}$=halogen such as Cl, Br, or I; and J=H or $NH_2$.

In a typical preparation of compounds of Formula II-Q, compound of Formula II-Q was reacted with phosphorus oxychloride ($POCl_3$) and triazole, and pyridine followed by ammonia ($NH_3$) in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was carried out at temperatures between about −20° C. and about 50° C. Preferably, the reaction was carried out between 0° C. and about 25° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula III-Q of Scheme 38 were prepared as shown below in Scheme 39.

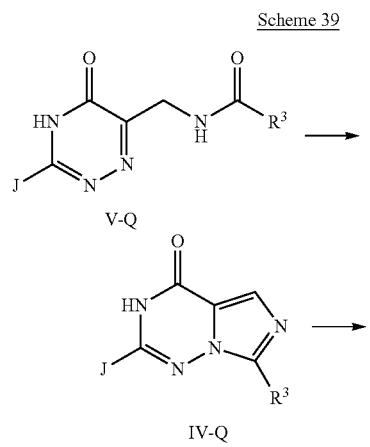

where $R^3$ is as defined previously for compound of Formula I; $A^{11}$=halogen such as Cl, Br, or I; and J=H or $NH_2$.

In a typical preparation of a compound of Formula III-Q, intermediate V-Q was converted to compound of Formula IV-Q. Intermediate of Formula V-Q was treated with phosphorus oxychloride ($POCl_3$) in a suitable solvent at a suitable reaction temperature. Suitable solvents for use in the above process included, but were not limited to, ethers such as tetrahydrofuran (THF), glyme, and the like, chlorinated solvents such as methylene chloride ($CH_2Cl_2$) or chloroform ($CHCl_3$), and acetonitrile. If desired, mixtures of these solvents were used. The preferred solvent was acetonitrile. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Intermediate for Formula III-Q was prepared by reacting intermediate of Formula IV-Q with a suitable halogenating agent. Suitable halogenating agents included, but were not limited to, $Br_2$, $I_2$, $Cl_2$, N-chlorosuccinimide, N-bromosuccinimide, or N-iodosuccinimide. The preferred halogenating agent was N-iodosuccinimide. Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was DMF. The above process was carried out at temperatures between about −78° C. and about 120° C. Preferably, the reaction was carried out between 40° C. and about 75° C. The above process to produce compounds of the present invention was preferably carried out at about atmospheric pressure although higher or lower pressures were used if desired. Substantially equimolar amounts of reactants were preferably used although higher or lower amounts were used if desired.

Compounds of Formulae IV-Q and III-Q where J=$NH_2$ can be respectively converted into the compounds of Formulae IV-Q and III-Q where J=H, by diazotisation procedures known to those skilled in the art. A typical procedure includes the treatment of a compound of Formula IV-Q or III-Q where J=$NH_2$ with tert-butylnitrite in a suitable solvent such a THF or DMF.

The compounds of Formula V-Q of Scheme 39 were prepared as shown below in Scheme 40:

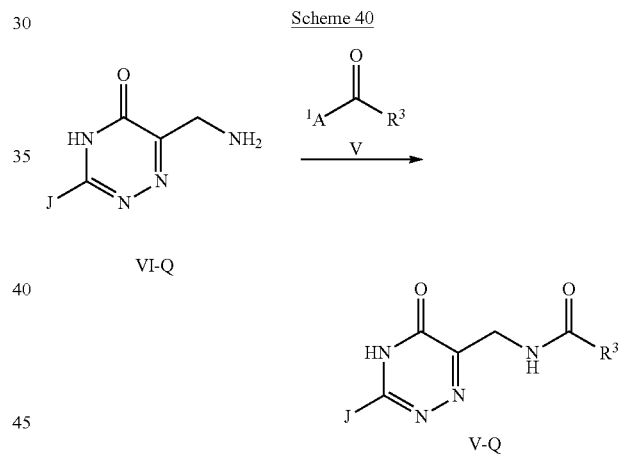

where $R^1$ is as defined previously for compound of Formula I; $A^1$=OH, alkoxy, or a leaving group such as chloro or imidazole; and J=H or $NH_2$.

In a typical preparation, of a compound of Formula V-Q, a compound of Formula VI-Q and compound of Formula V were reacted under suitable amide-coupling conditions. Suitable conditions include but are not limited to treating compounds of Formula VI-Q and V (when $A^1$=OH) with coupling reagents such as DCC or EDC in conjunction with DMAP, HOBt, HOAt and the like, or reagents like EEDQ. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was methylene chloride. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired. Alternatively, compounds of Formula VI-Q and V (where $A^1$=F, Cl, Br, I) were reacted with bases such as triethylamine or ethyldiisopropylamine and the like in conjunction with DIP and the like. Suitable solvents for use in this process included, but were not limited to, ethers such as tetrahydrofuran (THF), glyme, and the like; dimethylformamide (0M); dimethyl sulfoxide DMSO); acetonitrile; pyridine; halogenated solvents such as chloroform or methylene chloride. If desired, mixtures of these solvents were used, however the preferred solvent was DMF. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially equimolar amounts of compounds of Formula VI-Q and V (where $A^1$=F, Cl, Br, I) and base and substoichiometric amounts of DMAP were preferably used although higher or lower amounts were used if desired. Additionally, other suitable reaction conditions for the conversion of an amine (compound of Formula VI-Q) to an amide (compound of Formula V-Q) can be found in Larock, R. C. *Comprehensive Organic Transformations*, $2^{nd}$ ed.; Wiley and Sons: New York, 1999, pp 1941-1949.

The compounds of Formula VI-Q of Scheme 40 where J=H were prepared as shown below in Scheme 41:

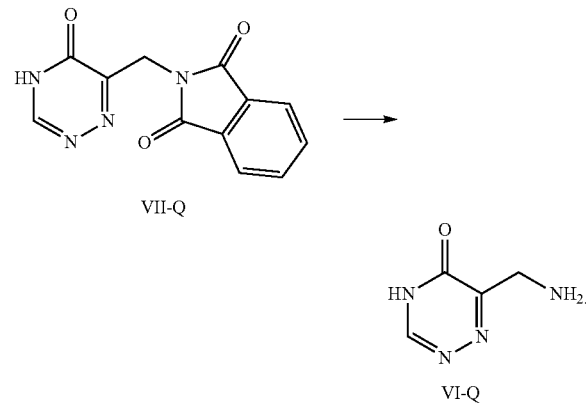

In a typical preparation, of a compound of Formula VI-Q, a compound of Formula VII-Q is reacted under suitable reaction conditions in a suitable solvent. Suitable conditions include treatment of compound of Formula VII-Q with hydrazine or methyl hydrazine in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride; alcoholic solvents such as methanol and ethanol. If desired, mixtures of these solvents may be used, however the preferred solvents were ethanol and methylene chloride. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired.

Compounds of Formula VI-Q where $J=NH_2$ may be prepared according to the procedures described in *J. Het. Chem.*, (1984), 21, 697.

The compounds of Formula VII-Q of Scheme 41 were prepared as shown below in Scheme 42:

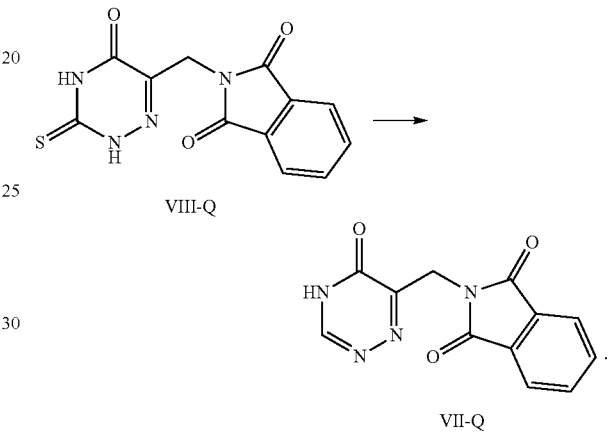

In a typical preparation of a compound of Formula VII-Q, a compound of Formula VIII-Q was reacted with Raney Nickel in a suitable solvent Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); alcohols such as methanol, ethanol, isopropanol, trifluoroethanol, and the like; chlorinated solvents such as methylene chloride ($CH_2Cl_2$) or chloroform ($CHCl_3$). If desired, mixtures of these solvents were used, however, the preferred solvent was ethanol. The above process may be carried out at temperatures between about rt and about 100° C. Preferably, the reaction was carried out at about 80° C. The above process to produce compounds of the present invention was preferably carried out at about atmospheric pressure although higher or lower pressures were used if desired. Substantially equimolar amounts of reactants were preferably used although higher or lower amounts were used if desired. Additionally a compound of Formula VII-Q can be prepared by reacting a compound of Formula VIII-Q with a suitable oxidizing agent in a suitable solvent. A suitable oxidizing agent includes, but is not limited to hydrogen peroxide ($H_2O_2$), 3-chloro peroxybenzoic acid (mCPBA) and the like. Suitable solvents for use in the above process included, but were not limited to, ethers such as THF, glyme, and the like; DMF; DMSO; $CH_3CN$; and dimethylacetamide (DMA); chlorinated solvents such as $CH_2Cl_2$ or $CHCl_3$ If desired, mixtures of these solvents were used, however, the preferred solvent was DMA. The above process may be carried out at temperatures between about 0° C. and 100° C. Preferably, the reaction was carried out at about rt to 70° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula VIII-Q of Scheme 42 were prepared as shown below in Scheme 43:

Scheme 43

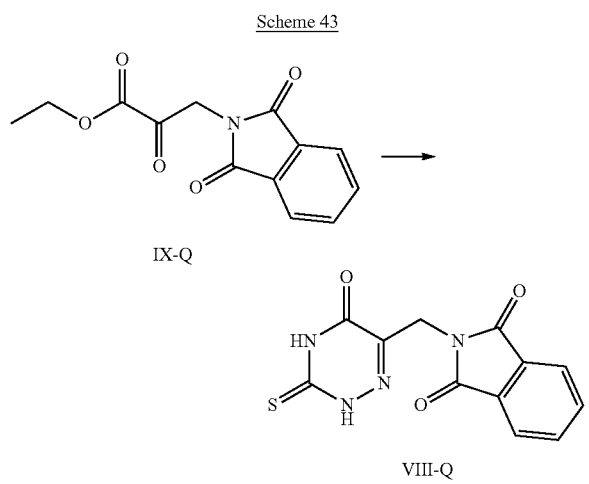

IX-Q

VIII-Q

In a typical preparation of a compound of Formula VIII-Q, a compound of Formula IX-Q was reacted with thiosemicarbazide and a suitable base in a suitable solvent. Suitable bases include, but were not limited to triethylamine, ethyldiisopropylamine and the like. Suitable solvents for use in the above process included, but were not limited to, ethers such as tetrahydrofuran (THF), glyme, and the like, dimethylformamide (DMF); dimethylacetamide (DMA); dimethyl sulfoxide (DMSO); acetonitrile ($CH_3CN$); alcohols such as methanol, ethanol, isopropanol, trifluoroethanol, and the like; chlorinated solvents such as methylene chloride ($CH_2Cl_2$) or chloroform ($CHCl_3$). If desired, mixtures of these solvents were used, however, the preferred solvent was ethanol. The above process may be carried out at temperatures between about rt and about 10° C. Preferably, the reaction was carried out between about 40° C. and 80° C. The above process to produce compounds of the present invention was preferably carried out at about atmospheric pressure although higher or lower pressures were used if desired. Substantially equimolar amounts of reactants were preferably used although higher or lower amounts were used if desired. Compound of Formula IX-Q can be prepared according to literature procedures Knutsen, Lars J. S. et. al., *J. Chem. Soc. Perkin Trans 1: Organic and Bio-Organic Chemistry* (1972-1999), 1984, 229-238.

It would be appreciated by those skilled in the art that in some situations, a substituent that is identical or has the same reactivity to a functional group which has been modified in one of the above processes, will have to undergo protection followed by deprotection to afford the desired product and avoid undesired side reactions. Alternatively, another of the processes described within this invention may be employed in order to avoid competing functional groups. Examples of suitable protecting groups and methods for their addition and removal may be found in the following reference: "Protective Groups in Organic Syntheses", T. W. Greene and P. G. M. Wuts, John Wiley and Sons, 1989.

Method A W was also used when preparing compounds of Formula II-Q as shown below in Scheme 44:
Method AW:

Scheme 44

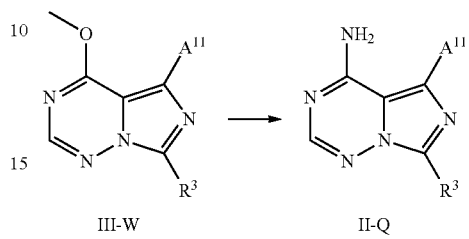

III-W      II-Q where $Q^1$ and $R^3$ are as defined previously for compound of Formula I, and $A^{11}$=halogen such as Cl, Br, or I.

In a typical preparation of compounds of Formula II-Q, compound of Formula III-W was reacted with ammonia in a suitable solvent. Suitable solvents for use in the above process included, but were not limited to, ethers such as tetrahydrofuran (THF), glyme, and the like; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was isopropanol. The above process was cared out at temperatures between about 0° C. and about 50° C. Preferably, the reaction was carried out at between 0° C. and about 22° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula III-W of Scheme 44 were prepared as shown below in Scheme 45.

Scheme 45

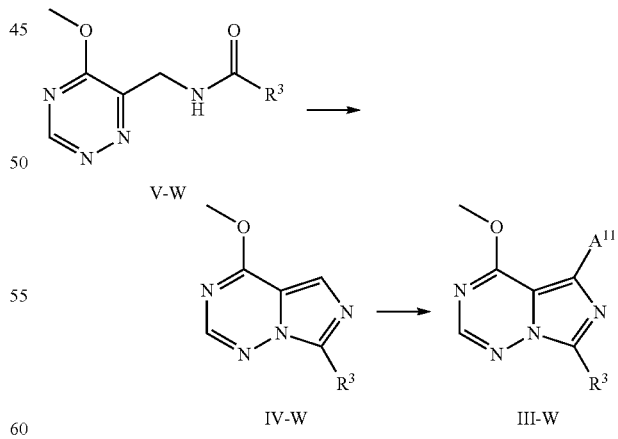

V-W

IV-W      III-W where $R^3$ is as defined previously for compound of Formula I and $A^{11}$=halogen such as Cl, Br, or I.

In a typical preparation of a compound of Formula III-W, compound V-W was converted to compound of Formula IV-W. Compound of Formula V-W was treated with phosphorus oxychloride ($POCl_3$) or the isolated "Vilsmeir salt"

[CAS# 33842-02-3] in a suitable solvent at a suitable reaction temperature. Suitable solvents for use in the above process included, but were not limited to, ethers such as tetrahydrofuran (THF), glyme, and the like, chlorinated solvents such as methylene chloride ($CH_2Cl_2$) or chloroform ($CHCl_3$), and acetonitrile ($CH_3CN$). If desired, mixtures of these solvents were used. The preferred solvent was acetonitrile. The above process was cared out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Compounds of Formula III-W were prepared by reacting compound of Formula IV-W with a suitable halogenating agent Suitable halogenating agents included, but were not limited to, $Br_2$, $I_2$, $Cl_2$, N-chlorosuccinimide, N-bromosuccinimide, or N-iodosuccinimide. The preferred halogenating agent was N-iodosuccinimide, Suitable solvents for use in the above process included, but were not limited to, ethers such as tetrahydrofuran (THF), glyme, and the like; dimethylformamide (DMF); dimethyl sulfoxide (DMSO); acetonitrile; alcohols such as methanol, ethanol, isopropanol, trifluoroethanol, and the like; and chlorinated solvents such as methylene chloride ($CH_2Cl_2$) or chloroform ($CHCl_3$). If desired, mixtures of these solvents were used, however, the preferred solvent was DMF. The above process was carried out at temperatures between about −78° C. and about 120° C. Preferably, the reaction was carried out between 40° C. and about 75° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula VI-W of Scheme 45 were prepared as shown below in Scheme 46.

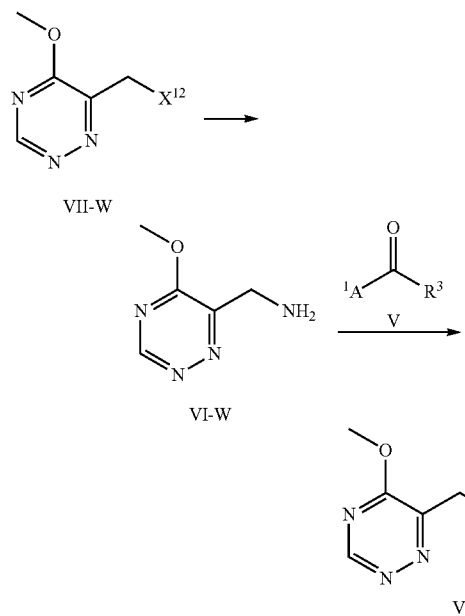

where $R^3$ is as defined previously for compound of Formula I, $X^{12}$=azido, or mono- or di-protected amino and $A^1$=OH, alkoxy or a leaving group such as chloro or imidazole.

In a typical preparation of a compound of Formula V-W, compound VI-W was reacted with compound V under suitable amide coupling conditions. Suitable conditions include but are not limited to those described for the conversion of compound XIII to compound XII as shown in Scheme 10. Compounds of Formula VI-W were prepared from compounds of Formula VII-W. A typical procedure for the conversion of compounds of Formula VII-W to compounds of Formula VI-W involves subjecting a compound of Formula VII-W, where $X^{12}$=azido, to reducing conditions such as, but not limited to, catalytic hydrogenation in a suitable solvent at a suitable reaction temperature. Suitable solvents for use in the above process included, but were not limited to, ethers such as tetrahydrofuran (THF), glyme, and the like, alcoholic solvents such as methanol, ethanol and the like, esters such as ethyl acetate, methyl acetate and the like. If desired, mixtures of these solvents were used. The preferred solvents were ethyl acetate and methanol. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Alternatively, when $X^{12}$=azido, the reduction to compounds of Formula VI-W could be achieved by treatment of a compound of Formula VII-W with triaryl- or trialkylphosphines in the presence of water in a suitable solvent at a suitable reaction temperature. Suitable solvents for use in the above process included, but were not limited to, ethers such as tetrahydrofuran (THF), dioxane and the like, alcoholic solvents such as methanol, ethanol and the like, esters such as ethyl acetate, methyl acetate and the like, DMF, acetonitrile, and pyridine. If desired, mixtures of these solvents were used. The preferred solvents were THF and acetonitrile. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

Where $X^{12}$=mono- or di-protected amino, the deprotection could be effected by the procedures known to those skilled in the art and as disclosed in: "Protective Groups in Organic Syntheses", T. W. Greene and P. G. M. Wuts, John Wiley and Sons, 1989.

The compounds of Formula VII-W of Scheme 46 were prepared as shown below in Scheme 47:

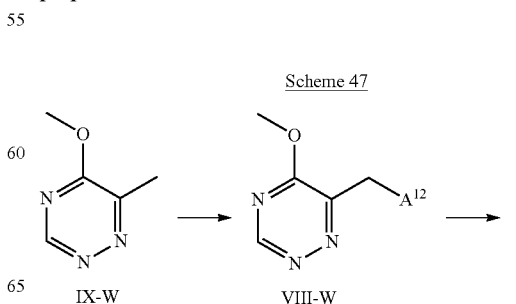

-continued

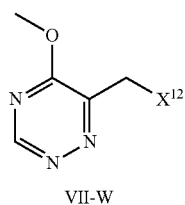
VII-W where $R_3$ is as defined previously for compound of Formula I, $X^{12}$ is as defined for a compound of Formula VII-W and $A^{12}$=iodo, bromo, chloro, tosylate, mesylate or other leaving group.

In a typical preparation of a compound of Formula VII-W where $X^{12}$=azide, compound VIII-W was reacted with an azide salt, such as lithium or sodium azide in suitable solvent at a suitable reaction temperature. Suitable solvents for use in the above process included, but were not limited to, alcoholic solvents such as ethanol, butanol and the like, esters such as ethyl acetate, methyl acetate and the like, DMF, acetonitrile, acetone DMSO. If desired, mixtures of these solvents were used. The preferred solvents were acetone and DMF. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Alternatively, where $X^{12}$=mono- or di-protected amino, compounds of Formula VIII-W were reacted with suitably protected amines where the protecting group is chosen such that the nucleophilic nature of the nitrogen is either retained or where it can be enhanced by the action of a reagent such as a base. Those skilled in the art will recognize that such protecting groups include, but are not limited to, benzyl, trityl, allyl, and alkyloxycarbonyl derivatives such as BOC, CBZ and FMOC.

Compounds of Formula VIII-W where $A^{12}$=halogen, are prepared from compounds of Formula XI-W. In a typical procedure, compounds of Formula XI-W are treated with halogenating reagents such as but not limited to N-iodosuccinimide, N-bromosuccinimide, N-chlorosuccinimide, trichloroisocyanuric acid, N,N'-1,3-dibromo-5,5-dimethylhydantoin, bromine and iodine, preferably in the presence of one or more radical sources such as dibenzoyl peroxide, azobisisobutyronitrile or light in suitable solvent at a suitable reaction temperature. Suitable solvents for use in the above process included, but were not limited to, chlorinated solvents such as carbon tetrachloride, dichloromethane, α,α,α-trifluorotoluene and the like, esters such as methyl formate, methyl acetate and the like, DMF, acetonitrile. If desired, mixtures of these solvents were used. The preferred solvents were carbon tetrachloride and α,α,α-trifluorotoluene. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

Alternatively, compounds of Formula VIII-W where $A^{12}$=tosylate or mesylate were prepared from compounds of Formula X-W as shown in Scheme 48. In a typical preparation of a compound of Formula VIII-W, a compound of Formula X-W was reacted with a sulfonylating reagent such as methanesulfonyl chloride or p-toluenesulfonyl chloride in the presence of a base such as, but not limited to DIPEA or triethylamine in a suitable solvent at a suitable reaction temperature. Suitable solvents for use in the above reaction included, but were not limited to, chlorinated solvents such as dichloromethane, 1,2-dichloroethane and the like, ethers such THF, diethylether and the like, DMF and acetonitrile. If desired, mixtures of these solvents were used. The preferred solvents were THF and dichloromethane. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

Scheme 48

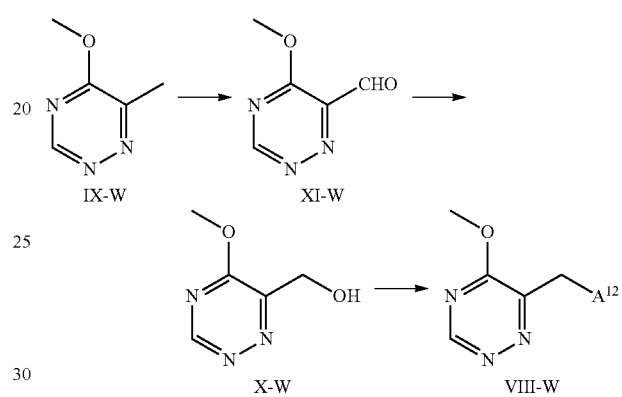

Compounds of Formula X-W were prepared from compounds of Formula XI-W. In a typical preparation of a compound of Formula X-W, a compound of Formula XI-W was reacted with a reducing reagent such as, but not limited to, sodium borohydride, lithium borohydride or lithium aluminum hydride in a suitable solvent at a suitable reaction temperature. Suitable solvents for use in the above reaction included, but were not limited to, ethers such THF, diethylether and the like, and alcohols such as ethanol, methanol, isopropanol and the like. If desired, mixtures of these solvents were used. The preferred solvents were THF and methanol. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

Compounds of Formula XI-W were prepared from compounds of Formula XI-W. In a typical preparation of a compound of Formula XI-W, a compound of Formula IX-W was reacted with an oxidizing reagent such as, but not limited to, selenium dioxide, manganese dioxide, potassium permanganate and the like, in a suitable solvent at a suitable reaction temperature. Suitable solvents for use in the above reaction included, but were not limited to, chlorinated solvents such as dichloromethane, 1,2-dichloroethane and the like, water, acetic acid and sulfolane. If desired, mixtures of these solvents were used. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

Those skilled in the art will appreciate that compounds of Formula IX-W can be made by routes disclosed in the literature, for example as in *Bulletin de la Societe Chimique de France*, (1973), (6)(Pt. 2), 2126.

Compounds of Formula I-AQ and/or their precursors may be subjected to various functional group interconversions as a means to access some functionalities that may not be introduced directly as a result of incompatible chemistries. Examples of such functional group manipulations applicable to compounds of Formula I-AQ and their precursors are similar, but not limited to, those described in Schemes 16-27, 34 and 35 that related to compounds of Formula I-AA, I-P, I-P', I-Q, I-R, I-AB and I-AC.

Experimental Procedures

8-Chloro-3-cyclobutyl-imidazo[1,5α]pyrazine

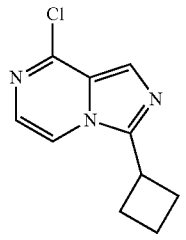

This compound was prepared using procedures analogous to that described for trans-methyl 4-(8-chloroimidazo[1,5-α]pyrazin-3-yl)cyclohexanecarboxylate and its precursor trans-methyl 4-({[(3-chloropyrazin-2-yl)methyl]amino}carbonyl)cyclohexanecarboxylate, using cyclobutanecarboxylic acid in place of 4<methoxycarbonyl)cyclohexanecarboxylic acid.

8-Chloro-3-cyclobutyl-1-iodoimidazo[1,5-α]pyrazine

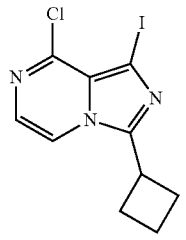

8-Chloro-3-cyclobutylimidazo[1,5-α]pyrazine (1058 mg, 5.1 mmol) and NIS (1146 mg, 5.1 mmol) in anh DMF (10 mL) were stirred at 60° C. under Ar for 6 h. The reaction was diluted with DCM (~400 mL), washed (H$_2$O, brine), dried (Na$_2$SO$_4$) and concentrated under reduced pressure. Purification of the crude material by flash chromatography on silica gel (50 g cartridge, 10:1-8:1-7:1-6:1 hexanes:EtOAc) afforded the title compound as a pale yellow solid; $^1$H NMR (400 MHz, CDCl$_3$) δ 7.51 (d, J=4.8 Hz, 1H), 7.26 (d, J=4.8 Hz, 1H), 3.75 (quintetd, J=1.2 Hz, 8.4 Hz, 1H), 2.62-2.42 (m, 4H), 2.32-1.98 (m, 2H); MS (ES+): m/z 334.0 (100) [MH$^+$]; HPLC: t$_R$=3.38 min (OpenLynx, polar_5min).

3-Cyclobutyl-1-iodoimidazo[1,5-α]pyrazin-8-amine

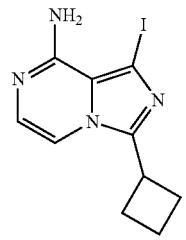

A Parr bomb containing 8-chloro-3-cyclobutyl-1-iodoimidazo[1,5-α]pyrazine (759 mg, 2.3 mmol) in IPA (100 ml) was saturated with NH$_3$(g) for 5 min at 0° C. then sealed and heated at 115° C. for 38 h. The reaction mixture was then concentrated under reduced pressure, partitioned between DCM (200 mL) and H$_2$O (50 mL) and extracted with DCM (50 mL). Combined organic fractions were washed with brine, dried (Na$_2$SO$_4$) and concentrated under reduced pressure to provide the title compound as a white solid; $^1$H NMR (400 MHz, CDCl$_3$) δ 7.13 (d, J=4.8 Hz, 1H), 7.01 (d, J=5.2 Hz, 1H), 5.63 (br, 2H), 3.73 (quintetd, J=0.8 Hz, 8.4 Hz, 1H), 2.60-2.38 (m, 4H), 2.20-1.90 (m, 2H); MS (ES+): m/z 315.9 (100) [MH$^+$]; HPLC: t$_R$=1.75 min (OpenLynx, polar-5 min).

7-Cyclohexyl-5-iodoimidazo[5,1-f][1,2,4]triazin-4-amine

To a suspension of 1H-1,2,4-triazole (1 g, 0.02 mol) in acetonitrile (23 mL) was added dropwise phosphoryl chloride (0.6 mL, 0.007 mol) and triethylamine (3 mL, 0.02 mol) at 0° C. To this mixture was added 7-cyclohexyl-5-iodoimidazo[5,1-f][1,2,4]triazin-4(3H)-one (77 mg, 0.224 mmol) and the resulting mixture refluxed overnight. The cooled mixture was then quenched with excess NH$_3$ in $^i$PrOH (pH 8) stirred at rt for 30 min. then filtered and the isolated solid washed with DCM. The filtrate was concentrated in vacuo and purified by chromatography over silica gel eluting with 2% MeOH in DCM to afford the 7-cyclohexyl-5-iodoimidazo[5,1-f][1,2,4]triazin-4-amine. $^1$H NMR (400 MHz-DMSO-d6) δ 1.14-1.91 (m, 10H), 3.11-3.18 (m, 1H), 6.75 (br.s, 1H), 7.84 (s, 1H) 8.42 (bs, 1H); MS (ES+): m/z: 344.01 (100) [MH+]. HPLC: t$_R$=3.10 min (OpenLynx: polar_5 min).

99

7-Cyclohexyl-5-iodoimidazo[5,1-f][1,2,4]triazin-4(3H)-one

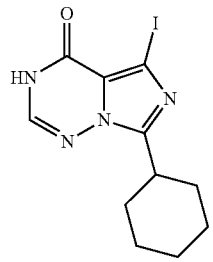

To a solution of 7-cyclohexylimidazo[5,1-f][1,2,4]triazin-4(3H)-one (130 mg, 0.6 mmol) in DMF (0.6 mL) was added N-iodosuccinimide (700 mg, 0.003 mol) and the reaction mixture stirred at 55° C. for 20 h. After this time the mixture was diluted with water (50 mL) and extracted with EtOAc (4×40 mL). The organic extracts were washed with water (4×40 mL), treated with sodium thiosulfate and brine, dried over $Na_2SO_4$ and concentrated in vacuo to afford 7-cyclohexyl-5-iodoimidazo[5,1-f][1,2,4]triazin-4(3H)-one. $^1$H NMR (400 MHz-DMSO-d6) δ 1.34-1.37 (m, 3H), 1.52-1.56 (m, 2H), 1.76-1.88 (m, 5H), 3.06-3.08 (m, 1H) 7.87 (s, 1H) 11.78 (s, 1H); MS (ES+): m/z: 344.95 (100) [MH+]. HPLC: tr=2.95 min (OpenLynx: polar_5 min).

7-Cyclohexylimidazo[5,1-f][1,2,4]triazin-4(3H)-one

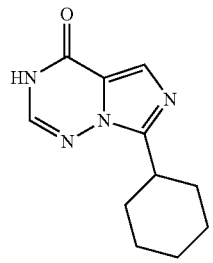

To a suspension of 6-aminomethyl-4H-[1,2,4]triazin-5-one (250 mg, 1.98 mmol) in DMF (7.5 mL) was added 2-(1H-benzotriazol-1-yl)-1,1,3,3-tetramethyluronium tetrafluoroborate (760 mg, 2.35 mmol), cyclohexanecarboxylic acid (305 mg, 2.38 mmol) and N,N-diisopropylethylamine (1.5 mL, 8.6 mmol). After 1 h acetonitrile (40 mL) was added to the mixture followed by dropwise addition of phosphoryl chloride (0.28 mL, 3.0 mmol) and the reaction mixture stirred at 55° C. for 1 h. The mixture was then concentrated in vacuo chromatographed over silica gel eluting with 3% MeOH in DCM, to afford 7-cyclohexylimidazo[5,1-f][1,2,4]triazin-4(3H)-one. $^1$H NMR (400 MHz-DMSO-d6) δ 1.24-1.91 (m, 10H), 3.08-3.16 (m, 1H), 7.68 (s, 1H) 7.88 (s, 1H) 11.76 (s, 1H); MS (ES+): m/z: 219.24 (100) [MH+]. HPLC: $t_R$=2.44 min (OpenLynx: polar_5 min).

100 trans-[4-(8-Amino-1-iodoimidazo[1,5-α]pyrazin-3-yl)cyclohexyl]methanol

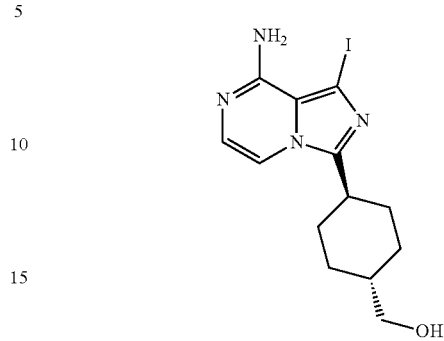

trans-[4-(8-chloro-1-iodoimidazo[1,5-α]pyrazin-3-yl)cyclohexyl]methanol (26.50 g, 67.66 mmol) was charged in a 400 ml steel bomb and was dissolved in 2M $NH_3$ in isopropanol (300 mL) and anhydrous THF (10 mL). The reaction mixture was cooled to −78° C. Ammonia gas was bubbled vigorously into the solution for 8 min; then the bomb was tightly sealed and heated to 120° C. for 20 h. The crude reaction mixture was concentrated in vacuo, then the reaction residue was taken up with MeOH/CHCl$_3$, loaded onto silica gel. The mixture was purified by a silica gel glass column chromatography [eluted with 1:1 $CH_2Cl_2$/EtOAc to 10%~7 N $NH_3$ in MeOH/CHCl$_3$] to afford the desired product as a beige cream white solid; MS (ES+): m/z 373.01 (100) [MH+], 373.98 (50) [MH+2]; $t_R$(polar-5min/openlynx) 1.57 min.

trans-[4(8-Chloro-1-iodoimidazo[1,5-α]pyrazin-3-yl)cyclohexyl]methanol

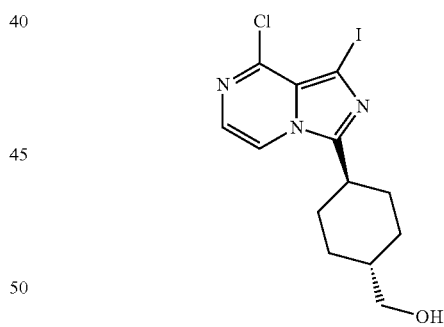

trans-[4-(8-Chloroimidazo[1,5-α]pyrazin-3-yl)cyclohexyl]methanol (18.00 g, 67.74 mmol) and N-iodosuccinimide (19.81 g, 88.06 mmol) in anhydrous DMF (360 mL) were stirred at 60° C. under $N_2$ for 6 h. The reaction was diluted with DCM (~600 mL), washed with water and brine, dried over anhydrous $Na_2SO_4$ and then concentrated in vacuo. The crude material was purified by a silica gel flash chromatography (eluted with 1:2 EtOAc/DCM to 1:1 EtOAc/DCM) to obtain the desired product as a pale yellow solid; By $^1$H NMR analysis, the product was contaminated with 0.35 eq. of NIS-impurity. The product was carried onto the next reaction without further purification; MS (ES+): m/z 391.92 (100) [MH+], 393.88 (50) [MH+2], 394.89 (10) [MH+3]; $t_R$(polar-5 min/openlynx) 2.79 min.

trans-[4(8-Chloroimidazo[1,5-α]pyrazin-3-yl)cyclohexyl]methanol

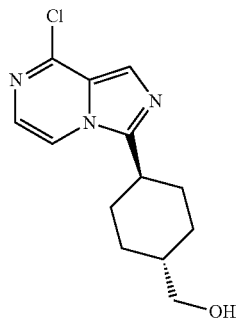

A THF solution (1.00 L) of trans-methyl 4-(8-chloroimidazo[1,5-α]pyrazin-3-yl)cyclohexanecarboxylate (29.70 g, 101.1 mmol) was cooled to −78° C. and was charged with LAB (1M in TH-F, 25-3 mmol, 25.3 mL) dropwise. After 30 min., the reaction mixture was charged with additional LAH (25.3 mmol) at −78° C. and then, allowed to stir at −78° C. for 1.5 h. The reaction was slowly warmed up to rt and stirred for additional 30 min. Ethyl acetate, Na$_2$SO$_4$.10H$_2$O, and silica gel were added to the reaction mixture and concentrated in vacuo to give an orange solid. The crude mixture was purified by a silica gel glass column chromatography (eluted with 2:3 EtOAc/DCM to 100% EtOAc) to obtain the title compound as a slightly yellow-tinted white solid; $^1$H NMR (CDCl$_3$, 400 MHz) δ 1.14-1.30 (m, 2H), 1.61-1.75 (m$_c$, 1H), 1.84 (dd, J=13.2, 13.2, 13.2, 3.2 Hz, 2H), 1.98-2.13 (m, 4H), 2.19 (s, br, —OH), 2.94 (tt, J=11.6, 3.2 Hz, 1H), 3.56 (d, J=6.0 Hz, 2H), 7.31 (d, J=5.2 Hz, 1H), 7.64 (dd, J=5.2, 1.2 Hz, 1H), 7.79 (d, J=0.8 Hz, 1H); MS (ES+): m/z 266.21/268.17 (100/89) [MH$^+$]. HPLC: t$_R$=2.38 min (OpenLynx, polar__5 min). MS (ES+): m/z 266.21 (100) [MH$^+$], 268.17 (80) [MH$^+$2], 289.18 (20) [MH$^+$3]; t$_R$(polar__5 min/openlynx) 2.36 min.

General Procedure for the Hydrolysis of Carboxylic Esters

To a solution/slurry of the carboxylic ester (30.17 mmol) in ethanol (200 mL) was added 3.0 M of sodium hydroxide in water (15.1 mL) and the mixture was stirred at 40° C. for 4 h. The solvent was removed under reduced pressure at 40° C. and to the residue was added water (10 mL) and ethanol (10 ml) and the slurry was filtered. The filter cake was washed with ethanol (2×10 mL) and dried under vacuum to yield the sodium salt. For the isolation of the free acid, water was added to this salt and the slurry was acidified with formic acid, stirred for 10 min at RT and filtered. The filter cake was washed with water followed by ethanol to yield the carboxylic acid.

trans-Methyl 4(8-chloroimidazo[1,5-α]pyrazin-3-yl)cyclohexanecarboxylate

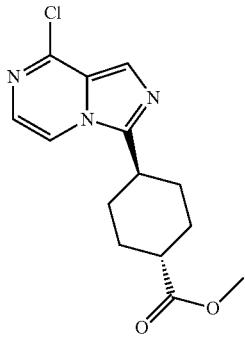

trans-Methyl 4-({[(3-chloropyrazin-2-yl)methyl]amino}carbonyl)-cyclohexanecarboxylate trans-Methyl 4-({[(3-chloropyrazin-2-yl)methyl]amino}carbonyl)-cyclohexanecarboxylate (29.00 g, 93.02 mmol) was dissolved in anhydrous acetonitrile (930 mL) and anhydrous DMF (9 mL) and heated at 55° C. under nitrogen for 3 h. The reaction mixture was concentrated in vacuo, then, the solid residue was taken up in DCM, then, basified to pH 10 with 2M ammonia in isopropanol. The mixture was concentrated in vacuo, re-dissolved in DCM, and then loaded onto TEA-basified silica gel. The crude product was purified by a silica gel column chromatography (eluted with 2:3 EtOAc/DCM) to obtain the title compound as a yellow powder; $^1$H NMR (CDCl$_3$, 400 MHz) δ 1.63 (ddd, J=13.2, 13.2, 13.2, 3.2 Hz, 2H), 1.85 (ddd, J=13.2, 13.2, 13.2, 2.8 Hz, 2H), 2.10 (dd, J=14.4, 3.2 Hz, 2H), 2.19 (dd, J=14.0, 3.2 Hz, 2H), 2.46 (t, J=12.4, 3.6 Hz, 1H), 2.96 (tt, J=116, 3.2 Hz, 1H), 3.70 (s, 3H), 7.33 (dd, J=5.2, 1.2 Hz, 1H), 7.61, J=4.8 Hz, 1H), 7.79 (s, 1H). MS (ES+): m/z 294.17/296.14 (100/86) [MH$^+$]. HPLC: t$_R$=2.85 min (OpenLynx, polar__5 min).

trans-Methyl 4({[(3-chloropyrazin-2-yl)methyl]amino}carbonyl)cyclohexanecarboxylate

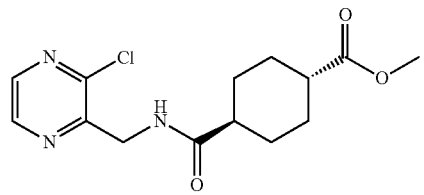

A THF (370 mL) solution of 4-(methoxycarbonyl)cyclohexanecarboxylic acid (15.14 g, 81.30 mmol) and CDI (13.18 g, 81.30 mmol) was placed under a nitrogen atmosphere and stirred at 60° C. for 4 h. The reaction mixture was cooled to rt, then, (3-chloropyrazin-2-yl)methylamine bis-hydrochloride salt (16.00 g, 73.91 mmol) and DIPEA (31.52 g, 244.00 mmol, 42.5 mL) was added. After stirring at 60° C. for 20 h, the reaction was concentrated in vacuo. The crude reaction mixture was purified by a silica gel glass column chromatography (eluted with 3:2 DCM/EtOAc) to obtain the pure desired product as a slightly yellowish creamy white powder, $^1$H NMR (CDCl$_3$, 400 MHz) δ 1.43-1.65 (m, 4H), 2.01-2.14 (m, 4H), 2.25 (tt J=12.0, 36 Hz, 1H), 2.34 (tt, J=11.6, 3.2 Hz, 1H), 3.68 (s, 3H), 4.70 (d, J=4.4 Hz, 2H), 6.81 (s, br, —NH), 8.32-8.36 (m, 1H), 8.46 (d, J=2.4 Hz, 1H); MS (ES+): m/z 312.17/314.12 (84132) [MH$^+$]; HPLC: t$_R$=2.44 min (OpenLynx, polar__5 min).

[3-(8-Amino-1-iodoimidazo[1,5a]pyrazin-3-yl)cyclobutyl]methanol

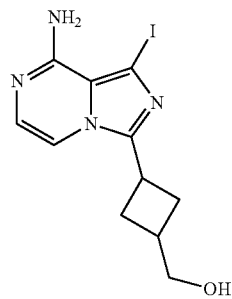

[3-(8-Chloro-1-iodoimidazo[1,5-a]pyrazin-3-yl)cyclobutyl]methanol (6.9 g) in i-PrOH (200 mL) was saturated with NH₃(g), by passing a slow a slow stream of ammonia for 10 min at −20° C., and then heated in a Parr bomb at 110° C. for 2 d. The reaction mixture was then cooled to rt, filtered through a sintered glass and the solid residue and the Parr vessel were rinsed with i-PrOH several times. The filtrate was concentrated under reduced pressure to provide an orange solid still containing NH₄Cl. The material was taken up into refluxing MeCN (250 mL) and filtered hot. The step was repeated with another portion of hot MeCN (200 mL). The combined MeCN filtrates were concentrated under reduced pressure to give the title compound as an orange solid; HPLC: (polar5min) 0.53 and 1.51 min; MS (ES+): 345.1 (100, M⁺+1); ¹H NMR (400 MHz, DMSO-d6) δ 7.50 (d, J=5.2 Hz, 1 H), 7.44 (d, J=5.2 Hz, 0.27 H, minor isomer), 6.95 (d, J=5.2 Hz, 1.29 H overlapped with the minor isomer) 6.63 (br, 2H), 4.61 (t, J=5.2 Hz, 0.27H, minor isomer), 4.52 (t, J=5.2 Hz, 1H), 3.69 (quintet J=5.6 Hz, 0.32H, minor isomer), 3.54 (quintet, J=5.6 Hz, 1H), 2.52-2.25 (m, 4H), 2.10-2.00 (m, 1H).

[3-(8-Chloro-1-iodo-imidazo[1,5-a]pyrazin-3-yl) cyclobutyl]-methanol

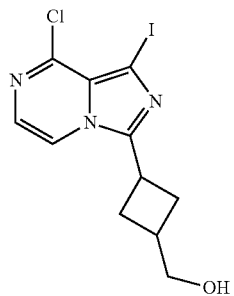

To a solution of NIS (6.31 g, 28.0 mmol) in anh DMF (100 mL) under Ar was added dry [3-(8-chloroimidazo[1,5-α]pyrazin-3-yl)cyclobutyl]methanol (6.67 g) dissolved in anh DMF (30 mL). The flask containing [3-(8-chloroimidazo[1,5-α]pyrazin-3-yl)cyclobutyl]methanol was rinsed with another portion of anh DMF (20 mL) and the rinse was added to the reaction mixture. The reaction was heated to 60° C. (rt→60° C.∼30 min) and the stirred at this temperature for 3 h. The mixture was then cooled to rt, partitioned between 1M aq Na₂S₂O₃ (60 ml), brine (60 mL) and DCM (160 mL). The aq layer was extracted with DCM (3×100 mL). The combined organics were dried (Na₂SO₄), concentrated under reduced pressure and purified by flash chromatography on SiO₂ (0-8% MeOH in DCM) to provide a material, homogenous by UV on both TLC and HPLC, still containing DMF. The material was dissolved in DCM (200 mL) and washed with water (3×40 mL), dried (Na₂SO₄) and concentrated under reduced pressure to provide the title compound as a pale yellow solid; HPLC (polar 5 min) 2.52 min; MS (ES+): m/z (rel. int.) 364.0 (100, M⁺+1); ¹H NMR (400 MHz, CDCl₃) δ 7.59 (d, J=4.8 Hz, 1 H), 7.49 (d, J=4.8 Hz, 0.22 H, minor isomer), 7.29 (d, J=4.8 Hz, 1 H), 7.28 (d, J=5.2 Hz, 0.23 H, minor isomer), 3.83-3.80 (m, 0.7 H), 3.72-3.62 (m, 3 H), 2.75-2.55 (m, 4 H), 2.42-2.32 (m, 1-2H).

[3-(8-Chloro-imidazo[1,5-a]pyrazin-3-yl)cyclobutyl]-methanol

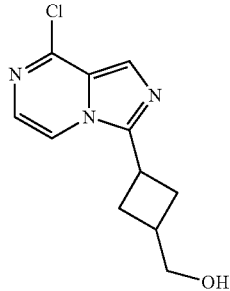

To a solution of 8-chloro-3-(3-methylenecyclobutyl)imidazo[1,5-a]pyrazine (4.48 g, 20.4 mmol) in anh THF (255 mL) at −78° C. under Ar, 9-BBN (61.2 mL, 0.5M in THF, 30.6 mmol) was added dropwise over 8 min (a suspension). The cooling bath was replaced with ice-H₂O and the reaction was allowed to warm slowly to rt. After being stirred for 17 h, H₂O (100 mL) was added followed by, after ∼5 min, NaBO₃.H₂O (12.2 g, 122.3 mmol) added in one lot. The reaction was stirred at rt for 5 h and then filtered through Celite. The Celite and residual solids were washed with DCM and EtOAc. The filtrate was concentrated under reduced pressure to yield an aq solution, which was saturated with NaCl and extracted with EtOAc (3×). The extracts were dried (Na₂SO₄) and concentrated under reduced pressure to yield a light yellow oil which was purified by flash chromatography on SiO₂ (9:1 DCM:MeOH) to afford the title compound as a light yellow oil; HPLC: t_R (mass-directed HPLC, polar 7 min) 2.52 min; MS (ES+): 238.0. The addition may be carried out at 0° C. Suspension quickly clears up after the exchange of cooling baths. The final product contained 1,5-cis-octanediol derived from 9-BBN. Based on ¹H NMR estimated roughly to be 66% target material and 33% of the byproduct. The crude product was taken onto next step crude, stereoselectivity of the product was 4-5:1 as judged by ¹H NMR.

(8-Chloro-3-(3-methylene-cyclobutyl)-imidazo[1,5-α]pyrazine)

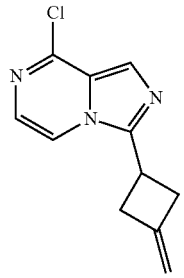

3-Methylene-cyclobutanecarboxylic acid (3-chloropyrazin-2-ylmethyl)-amide (52.1 g, 219.2 mmol) was dissolved in 1.0 L of anhydrous MeCN. Followed by the addition of DMF (1.0 mL) and POCl₃ (100 mL, 1.09 mol). The reaction was heated to 55° C. for 30 min. with a slow N₂ bubbling the reaction. The reaction was then concentrated in vacuo, basified with cold 2.0M NH₃ in IPA with CH₂Cl₂. The IPA/CH₂Cl₂ was concentrated in vacuo and the salts were dissolved with minimal water and extracted with CH₂Cl₂ (4×). The organic layers where combined and washed with sat. NaHCO₃ (1×), dried over sodium sulfate, filtered and concentrated in vacuo. The crude product was purified via silica gel column chromatography [eluting with 2:1 Hex:EtOAc] to yield the title compound as a light yellow solid; ¹H NMR (400 MHz, CDCl₃) δ 3.24-3.30 (4 H, m), 3.78-3.85 (1 H, m), 4.89-4.94 (2 H, m), 7.33 (1 H, d, J=4.99 Hz), 7.53 (1 H, d, J=5.09 Hz), 7.82 (1 H, s); MS (ES+): m/z 220.28/222.30 (100/80) [MH⁺]; HPLC: t_R=2.87 min (OpenLynx, polar_5 min).

3-Methylene-cyclobutanecarboxylic acid (3-chloropyrazin-2-ylmethyl)amide

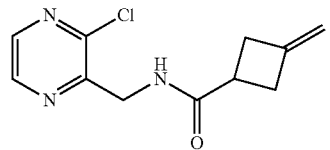

C-(3-Chloropyrazin-2-yl)-methylamine bis-HCl (1.0 g, 4.62 mmol), N-ethyl-N'-(3-dimethylaminopropyl)carbodiimide (EDC) (1.31 g, 6.47 mmol, 1.4 eq.), 4-dimethylamino pyridine DMAP (0.141 g, 1.15 mmol, 0.25 eq.), and diisopropylethylamine (DIPEA) (2.42 mL, 1.79 g, 13.9 mmol, 3.0 eq.) were dissolved in anhydrous CH₂Cl₂ (25 mL). To this solution, a solution of 3-methylenecyclobutanecarboxylic acid (0.622 g, 5.54 mmol, 1.2 eq.) in anhydrous CH₂Cl₂ (25 mL) was added under N₂ and the reaction was allowed to stir overnight at rt. Reaction mixture was concentrated in vacuo and the resulting residue was dissolved in EtOAc, washed with water (2×), NaHCO₃ (1×), water (1×), and brine (1×), dried over Na₂SO₄, filtered, and concentrated in vacuo, giving crude title compound, as a brown oil. The crude material was purified by chromatography on silica gel [Jones Flashmaster, 20 g/70 mL cartridge, eluting with EtOAc:Hex 10%→20%→40%→70%], affording the title compound as a pale yellow solid. Additionally, the title compound could be prepared by the following route: 1,1'—Carbonyldiimidazole (CDT) (0.824 g, 5.08 mmol, 1.1 eq.) and 3-methylenecyclobutanecarboxylic acid (0-570 g, 5.08 mmol, 1.1 eq.) were dissolved in anhydrous THF (12 mL) and allowed to stir at 60° C. for 2 h. A solution of C-(3-chloropyrazin-2-yl)-methylamine bis-HCl (1.0 g, 4.62 mmol) and diisopropylethylamine (DIPEA) (2.42 mL, 1.79 g, 13.9 mmol, 3.0 eq.) in anhydrous CH₂Cl₂ (13 mL) was added to the acid mixture and the reaction was allowed to stir at 60° C., under N₂, overnight. The reaction mixture was concentrated in vacuo and the resulting residue was dissolved in EtOAc, washed with NaHCO₃ (2×) and brine (1×), dried over Na₂SO₄, filtered, and concentrated in vacuo, giving crude title compound, as a brown oil. The crude material was purified by chromatography on silica gel [Jones Flashmaster, 20 g/70 mL cartridge, eluting with EtOAc:Hex 10%→20%→40%→70%], affording the title compound as a pale yellow solid; ¹H NMR (CDCl₃, 400 MHz) δ 2.86-2.96 (m, 2H), 3.03-3.19 (m, 3H), 4.72 (dd, J=4.4, 0.8 Hz, 2H), 4.79-4.84 (m, 2H), 6.78 (s, —NH), 8.32-8.34 (m, 1H), 8.46 (d, J=2.8 Hz, IRS); MS (ES+): m/z 238.19 (90) [MH⁺]; HPLC: t_R=2.67 min (OpenLynx, polar_7 min).

3-(8-Amino-1-iodoimidazo[1,5-α]pyrazin-3-yl)cyclobutanol

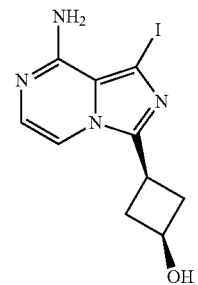

In a Parr pressure reactor 3-(8-chloro-1-iodo-imidazo[1,5-α]pyrazin-3-yl)-cyclobutanol (4.159 g, 0.0119 mol) was dissolved with 2.0M ammonia in isopropyl alcohol (40 mL). The mixture was cooled to −20° C. and saturated with ammonia. The reaction was heated at 110° C. for 63 h at which point it was cooled and concentrated in vacuo. The crude product was purified using HPFC Jones 25 g silica gel column eluting with 5-8% MeOH:CH₂Cl₂ to yield the title compounds; MS (ES+): m/z 330.88 (100) [MH⁺], 331.89 (10) [MH⁺⁺]; HPLC: t_R=0.48 min (OpenLynx, polar_5 min); ¹H NMR (CDCl₃, 400 MHz) δ 2.55-2.76 (m, 2 H) 3.06-3.22 (m, 2 H) 3.32-3.50 (m, 1 H) 4.51-4.69 (m, 1 H) 6.15 (br.s., 2 H) 7.24 (d, J=5.05 Hz, 1 H) 7.39 (d, J=5.05 Hz, 1 H).

3-(8-Chloro-1-iodoimidazo[1,5-α]pyrazin-3-yl)cyclobutanol

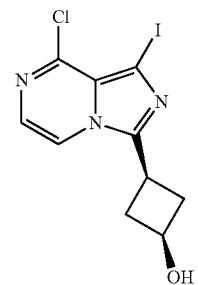

3-(8-Chloro-1-iodo-imidazo[1,5-a]pyrazin-3-yl)-cyclobutanone (5.0 g, 14 mmol) was dissolved in a 1:1 mixture of methanol (35.0 mL) and CH₂Cl₂ (35.0 mL). To the solution mixture sodium tetrahydroborate (560 mg, 14.0 mmol) was added slowly, gas evolution was observed. After 4.5 h at rt under nitrogen, the reaction was concentrated in vacuo. The crude mix was dissolved in EtOAc and washed with water. The organic layer was dried over sodium sulfate, filtered and concentrated in vacuo. The crude product was purified using HPFC Jones 50 gram silica gel column eluting with 50% EtOAc:Hex to 100% EtOAc, to yield the title compound as a light yellow solid; MS (ES+): m/z 349.81 (100) [MH⁺], 351.50 (30) [MH⁺⁺⁺]; HPLC: t_R=2.49 min (OpenLynx, polar_5 min); ¹H NMR (CDCl₃, 400 MHz) 2.41-2.54 (m, 2

H) 2.78-3.05 (m, 1 H) 3.12-3.32 (m, 1 H) 4.08-4.75 (m, 1 H) 5.30 (s, 1 H) 7.31 (d, J=5.05 Hz, 1 H) 7.57 (d, J=4.80 Hz, 1 H)

1-{4-[3-(8-Amino-1-iodoimidazo[1,5-α9 pyrazin-3-yl)cyclobutyl]piperazin-1-yl}ethanone

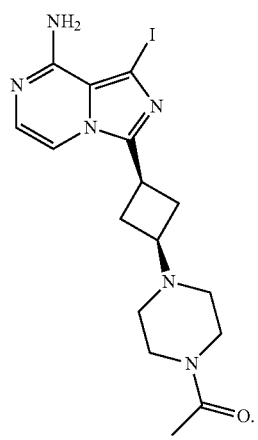

1-{4-[3-(8-Chloro-1-iodoimidazo[1,5-α]pyrazin-3-yl)cyclobutyl]piperazin-1-yl}ethanone (13.2 g, 0.029 mol) was dissolved in isopropyl alcohol (100 mL) into a Parr pressure reactor. The vessel was cooled to −78° C. and saturated with ammonia gas and sealed. The reaction was heated for 19 h at 110° C., at which point the reaction was cooled and the solvent concentrated in vacuo. The crude product was purified via silica gel chromatography eluting with 5-10% MeOH (7M NH₃): CH₂Cl₂ to yield the title compounds as an off white solid; MS (ES+): m/z 440.89 (100) [MH⁺], 441.89 (20) [MH⁺⁺]; HPLC: $t_R$=0.46 min (OpenLynx, polar_5min); ¹H NMR (CDCl₃, 400 MHz) δ 2.09 (s, 3 H) 2.28-2.48 (m, 6 H) 2.54-2.71 (m, 2 H) 2.80-2.99 (m, 1 H) 3.27-3.43 (m, 1 H) 3.43-3.54 (m, 2 H) 3.56-3.70 (m, 2 H) 7.02 (d, #5.05 Hz, 1 H) 7.16 (d, J=5.05 Hz, 2 H).

1-{4-[3-(8-Chloro-1-iodoimidazo[1,5-α]pyrazin-3-yl)cyclobutyl]piperazin-1-yl}ethanone

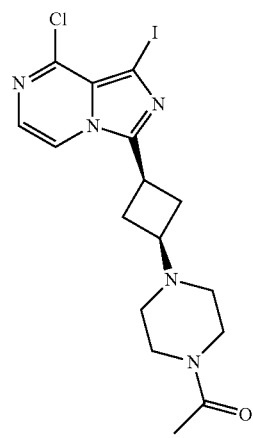

Into a RBF 3-(8-chloro-1-iodoimidazo[1,5-α]pyrazin-3-yl)cyclobutanone (1.00 g, 0.0029 mol) and sodium triacetoxyborohydride (1.30 g, 0.006 mol) were dissolved in 1,2-dichloroethane (65.0 mL) and a solution of 1-acetylpiperazine (0.39 g, 0.003 mol) in 1,2-dichloroethane was added to the reaction. The reaction mixture was stirred at rt for 2 h. The crude product was concentrated in vacuo and the dissolved in CH₂Cl₂ (25.0 mL) and washed with saturated NaHCO₃ solution (1×40 mL). The product was dried with sodium sulfate and concentrated in vacuo to yield a light yellow solid; MS (ES+): m/z 459.84 (100) [MH⁺], 461.80 (40) [MH⁺⁺⁺]; HPLC: $t_R$=1.81 min (OpenLynx, polar_5 min); ¹H NMR (CDCl₃, 400 MHz) δ 2.04-2.15 (m, 3 H) 2.26-2.50 (m, 6 H) 2.55-2.72 (m, 2 H) 2.83-2.99 (m, 1 H) 3.29-3.52 (m, 3 H) 3.56-3.67 (m, 2 H) 7.29 (d, 1 H) 7.58 (d, 1 H).

(1-Iodo-3-[3-(4-methyl-piperazin-1-yl)-cyclobutyl]-imidazo[1,5-a]pyrazin-8-ylamine)

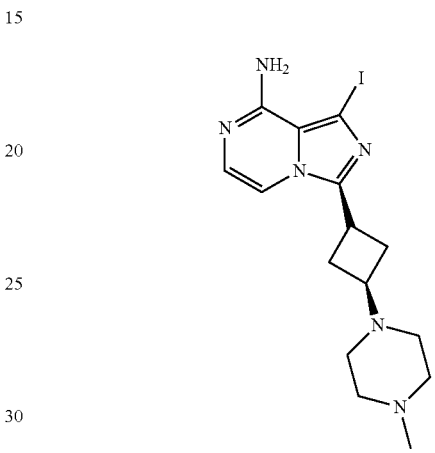

A solution of 2N ammonia in isopropyl alcohol (350 ml) and THF (30 mL, 0.4 mol) was added to 8-chloro-1-iodo-3-[3-(4-methyl-piperazin-1-yl)-cyclobutyl]-imidazo[1,5-α]pyrazine (19.91 g, 0.04612 mol) in a Parr bomb and cooled to −78° C. Ammonia was bubbled into the solution for 8-10 min. The bomb was sealed, stirred and heated to at 110° C. over 3 d. The solvent was then evaporated in vacuo and purified by flash silica gel chromatography (wetted with CHCl₃, dried loaded with silica, and eluted with 8% (7N NH₃) MeOH in CHCl₃), which afforded the title compound; ¹H NMR (CDCl₃, 400 MHz) δ 7.31 (1 H, d, J=5.01), 7.16 (1 H, d, J=6.25), 5.83 (2 H, s), 3.49 (1 H, m), 3.06 (1 H, m), 2.76 (4 H, m), 2.64 (8 H, m), 2.46 (3H, s); MS (ES+): m/z 412.89/413.91 (50/10) [MH⁺]; HPLC: $t_R$=0.31 min. (OpenLynx, polar_5 min.).

(8-Chloro-1-iodo-3-[3-(4-methylpiperazin-1-yl)cyclobutyl]imidazo[1,5-α]pyrazine)

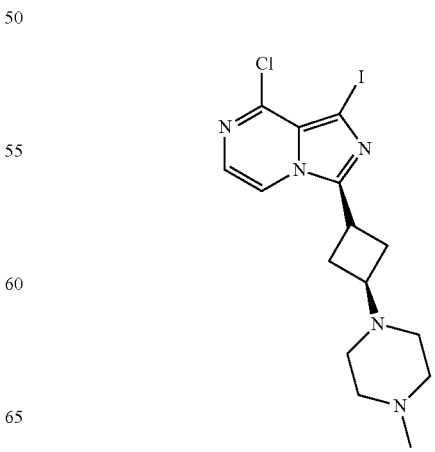

1-Methyl piperazine (5.75 mL, 0.0514 mol) in 1,2-dichloroethane (1096.7 mL, 13.892 mol) was added to 3-(8-chloro-1-iodoimidazo[1,5-α]pyrazin-3-yl)cyclobutanone (17.00 g, 0.04892 mol) and sodium triacetoxyborohydride (21.8 g, 0.0978 mol). The reaction stirred at rt for 3 h. The reaction was concentrated, dissolved in CH$_2$Cl$_2$, and then washed with saturated NaHCO$_3$ solution and brine. The product was dried over sodium sulfate, filtered, and concentrated in vacuo. The product was flushed through a quick silica gel plug (wetted with 100% CHCl$_3$, eluted with 8% (7N NH$_3$) MeOH in CHCl$_3$), to afford the title compound; $^1$H NMR (CDCl$_3$, 400 MHz) δ 7.63 (1 H, d), 7.30 (1 H, d), 3.42 (1H, m), 2.94 (1H, m), 2.65 (4 H, m), 2.44 (8 H, m), 2.32 (3H, s); MS (ES+): m/z 431.85/433.87 (100/45) [MH$^+$]; HPLC: t$_R$=1.82 min. (OpenLynx, polar_5 min.).

3-(8-Chloroimidazo[1,5-α]pyrazin-3-yl)-1-methyl-cyclobutanol

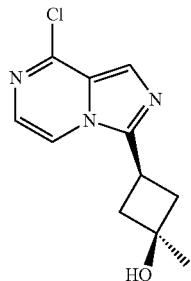

3-(8-Chloroimidazo[1,5-α]pyrazin-3-yl)cyclobutanone (1.95 g, 8.80 mmol) in anhydrous THF (77.78 mL) at −78° C. under an atmosphere of nitrogen was treated slowly with a 3.0 M solution of methylmagnesium chloride in THF (5.9 mL). The solution stirred for 3 hr at −78° C. then quenched with 40 mL of semi-saturated aqueous NH$_4$Cl (NH$_4$Cl dilution in 1:1 mixture with water) at −78° C. and allowed to warm up to rt. The mixture was then extracted with EtOAc (3×40 mL) and the combined extracts washed with brine (30 mL), dried over magnesium sulfate, filtered and concentrated in vacuo. The crude solid was purified by chromatography over silica gel eluting with 1:1 EtOAc/DCM to 4% MeOH in (1:1) EtOAc/DCM to afford desired product. $^1$H-NMR (400 MHz, CDCl$_3$) δ ppm 1.54 (s, 3 H), 2.74-2.60 (m, 4 H), 3.75-3.39 (m, 1 H), 7.35 (d, J=5.04 Hz, 1 H), 7.71 (d, J=5.00 Hz, 1 H) and 7.86 (s, 1 H). MS (ES+): m/z 238.15 and 240.17 [MH$^+$].

3-(8-Chloro-1-iodoimidazo[1,5-α]pyrazin-3-yl)-1-methylcyclobutanol

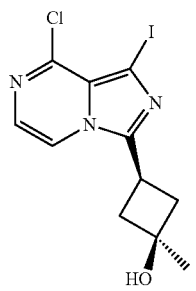

3-(8-Chloroimidazo[1,5-α]pyrazin-3-yl)-1-methylcyclobutanol (2.20 g, 9.26 mmol) and NIS (2.71 g, 12.0 mmol) were dissolved in DMF (36.6 mL, 0.472 mol) and stirred at 60° C. for 4 h. The mixture was then concentrated in vacuo and the residue reconstituted in EtOAc (100 mL). This solution was washed with sodium bicarbonate (2×20 mL) and these washes back-extracted with EtOAc (2×20 mL). The organic layers were combined, dried with sodium sulfate, filtered and concentrated in vacuo. The crude solid was purified by chromatography over silica gel eluting with 1:1 EtOAc:hexanes to afford desired product. $^1$H-NMR (400 MHz, CDCl$_3$) δ ppm 1.53 (s, 3 H), 2.72-2.59 (m, 4 H), 3.37-3.29 (m, 1 H), 7.32 (d, J=4.91 Hz, 1 H) and 7.60 (d, J=4.96 Hz, 1 H). MS (ES+): m/z 363.95 and 365.91 [MH$^+$].

3-(8-Amino-1-iodoimidazo[1,5-α]pyrazin-3-yl)-1-methylcyclobutanol

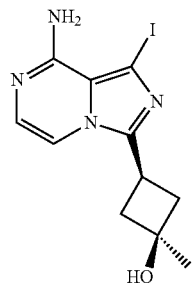

A solution of 2M ammonia in isopropanol (80 mL) and THF (5 mL) was added to 3-(8-chloro-1-iodoimidazo[1,5-α]pyrazin-3-yl)-1-methylcyclobutanol (2.77 g, 7.62 mmol) in a Parr pressure reactor. The mixture was cooled to at −78° C. then ammonia gas was bubbled into the solution for 4-6 min. The reactor was sealed then heated at 110° C. for 15 h. The solvent was then removed in vacuo and the residue purified by chromatography over silica gel eluting with 7% MeOH in DCM to afford desired product. $^1$H NMR (400 MHz, DMSO-d6) δ ppm 1.44 (s, 3 H), 2.32-2.51 (m, 4 H), 3.33-3.52 (m, 1 H), 6.61 (br.s., 2 H), 7.03 (d, J=5.05 Hz, 1 H) and 7.62 (d, J=5.05 Hz, 1 H).

(3-(8-Chloro-1-iodoimidazo[1,5-α]pyrazin-3-yl)cyclobutanone)

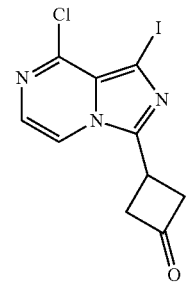

A solution of 3-(8-chloro-1-iodoimidazo[1,5-α]pyrazin-3-yl)-1-hydroxymethylcyclobutanol (4.08 g, 0.011 mol) in THF (120 mL) and water (40 mL) was charged with sodium periodate (2.8 g, 0.013 mol) at 0° C. The reaction warmed to rt and stirred for h. The reaction mixture was diluted with ethyl acetate and then washed with brine. The organic phase was dried over Na$_2$SO$_4$, filtered, and concentrated in vacuo to afford the title compound as a yellow solid; $^1$H NMR (CDCl$_3$, 400 MHz) δ 7.56 (1 H, d, J=4.94), 7.32 (1 H, d, J=4.98), 3.64 (5 H, m); MS (ES+): m/z 347.82 and 349.85 [MH$^+$]; HPLC: t$_R$=2.89 min. (OpenLynx, polar_5 min.).

3-(8-Chloro-1-iodoimidazo[1,5-α]pyrazin-3-yl)-1-hydroxymethylcyclobutanol

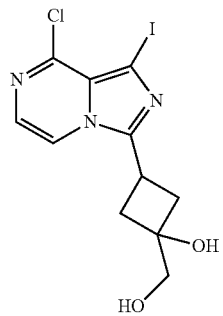

Under inert atmosphere N-iodosuccinimide (3.6 g, 0.016 mol) and 3-(8-chloroimidazo[1,5-α]pyrazin-3-yl)-1-hydroxymethylcyclobutanol (3.16 g, 0.012 mol) were dissolved in N,N-dimethylformamide (30 mL) and heated at 60° C. for 3.0 h. The reaction mixture was then concentrated in vacuo to a dark oil and purified by HPFC Jones 20 g silica gel column, eluting with 5% MeOH:CH$_2$Cl$_2$ to yield a light brown fluffy solid which was triturated with diethyl ether and hexanes to afford the title compound; MS (ES+): m/z 379.85 and 381.80 [MH$^+$]; HPLC: t$_R$=2.30 min (OpenLynx, polar_5 min).

3-(8-Chloroimidazo[1,5-α]pyrazin-3-yl)-1-hydroxymethylcyclobutanol

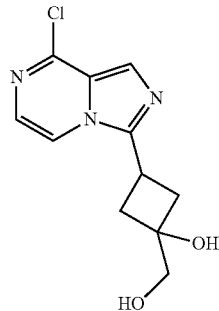

To a THF solution (170 mL) of 8-chloro-3-(3-methylenecyclobutyl)imidazo[1,5-α]pyrazine (3.1 g, 14 mmol), water (18 mL), 50% N-methylmorpholine-N-oxide in water (3.2 mL) and potassium osmate, dehydrate (200 mg, 0.70 mmol) were added and the reaction was allowed to stir at rt for 4 h. Sodium sulfite (8.0 g, 70.0 mmol) was added to the reaction mixture and allowed to stir for 30 min at which point the reaction was concentrated in vacuo. The crude product was extracted from the aqueous with EtOAc. The organics were washed with brine and the combined aqueous washes were back extracted with EtOAc (5×50 μL). The combined organics were dried over sodium sulfate, filtered, and concentrated in vacuo to yield the title compounds as a sticky tan/off-white solid; MS (ES+): m/z 254.17 (100) [MH$^+$], 256.19 (50) [MH$^{++}$]; HPLC: t$_R$=1.95 min (OpenLynx, polar_5 min).

3-Methylene-cyclobutanecarboxylic Acid

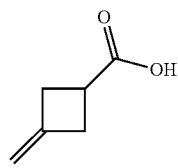

To a solution of 3-methylenecyclobutanecarbonitrile (100.0 g, 1.042 mol) in ethanol (1.00 L) and water (1.00 L) was added potassium hydroxide (230.0 g, 4.2 mol). The resulting mixture was heated at reflux for 7 hr then the EtOH was removed in vacuo and the solution was cooled to 0° C. and acidified with (300.0 mL) of conc. HCl to pH=1. The mixture was extracted with diethyl ether (4 ×1 L) and the combined organic phases were dried over sodium sulfate, filtered and concentrated in vacuo to yield desired product. $^1$H NMR (400 MHz, CDCl$_3$) δ ppm 2.64-3.44 (m, 5H), 4.60-4.98 (m, 2H) and 10.64 (br. s., 1H).

Ethyl 3-methylenecyclobutanecarboxylate

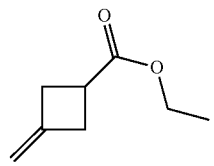

Iodoethane (7.5 mL, 93.0 mol) was added at rt to a mixture of 3-methylenecyclobutanecarboxylic acid (10.0 g, 80.0 mmol) and cesium carbonate (56.0 g, 170.0 mmol) in anhydrous N,N-dimethylformamide (500.00 mL) under an atmosphere of nitrogen. The reaction was stirred for 16 hr then partitioned between diethyl ether (1 L) and brine (1 L). The aqueous layer was extracted with diethyl ether (3×500 mL) and the combined organic phases washed with water (2×1 L), dried over sodium sulfate, filtered and concentrated in vacuo to yield desired product $^1$H NMR (400 MHz, CDCl$_3$) δ ppm 1.26 (t, 3H), 2.71-3.27 (m, 5H), 4.15 (q, J=7.07 Hz, 2H) and 4.53-4.96 (m, 2H).

N-[(3-chloropyrazin-2-yl)methyl]-3-methylenecyclobutanecarboxamide

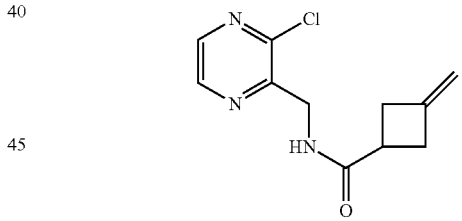

1,1'—Carbonyldiimidazole (CDI) (8.24 g, 50.81 mmol) and 3-methylenecyclobutanecarboxylic acid (5.70 g, 50.81 mmol) were dissolved in anhydrous THF (100 mL) and allowed to stir at 60° C. for 4 h. A solution of C-(3-Chloropyrazin-2-yl)methylamine bis-hydrochloride (10.0 g, 46.19 mmol) and diisopropylethylamine DIPEA) (32.30 mL, 184.76 mmol) in anhydrous CH$_2$Cl$_2$ (150 mL) was added to the mixture and the reaction was allowed to stir at rt for 24 h. The mixture was concentrated in vacuo, the residue dissolved in EtOAc and the resulting solution washed with saturated NaHCO$_3$ (aq.) water H$_2$O and Brine. The combined organic layers were dried over sodium sulfate, filtered and concentrated in vacuo to afford crude product, which was purified by chromatography over silica gel eluting with 50-70% EtOAc/hexane to yield desired product. $^1$H NMR (400 MHz, CDCl$_3$) δ ppm 2392-2.94 (2 H, m), 3.05-3.14 (2 H, m), 4.60 (2 H, d, J=4.24 Hz), 4.80-4.84 (2 H, m), 6.75 (1 H, brs), 8.33 (1 H, d, J=4.22 Hz) and 8.45 (1 H, d, J=2.54 Hz). MS (ES+): m/z 238 and 240 [MH+].

8-Chloro-3-(3-methylenecyclobutyl)imidazo[1,5-α]pyrazine

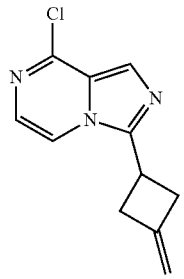

N-[(3-Chloropyrazin-2-yl)methyl]-3-methylenecyclobutanecarboxamide (52.1 g, 219.2 mmol) in anhydrous MeCN (1.0 L) was treated with DMF (1.0 mL) and POCl₃ (100 mL, 1.09 mol) and the mixture was stirred at 55° C. for 30 min. under a gentle stream of N₂. The reaction was then concentrated in vacuo and the residue reconstituted in CH₂Cl₂ and treated with cold 2.0 M NH₃ in IPA. This mixture was concentrated in vacuo, water added to dissolve the salts, and then extracted with CH₂Cl₂ (4×60 mL). The organic layers where combined and washed with sat. NaHCO₃ (1×70 mL) dried over sodium sulfate, filtered and concentrated in vacuo. The crude material was purified by chromatography over silica gel eluting with 2:1 hexane:EtOAc to yield desired product. ¹H NMR (400 z, CDCl₃) δ ppm 3.24-3.30 (4 H, m), 3.78-3.85 (1 H, m), 4.89-4.94 (2 H, m), 7.33 (1 H, d, J=4.99 Hz), 7.53 (1 H, d, J=5.09 Hz) and 7.82 (1 H, s). MS (ES+): m/z 220.28 and 222.30 [MH+].

C-(3-Chloropyrazin-2-yl)methylamine bis-hydrochloride

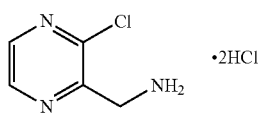

A solution of 2-(3-chloropyrazin-2-ylmethyl)-isoindole-1,3-dione (10.0 g, 36.5 mmol) in anhydrous CH₂Cl₂ (200 mL) was charged with hydrazine (2.87 mL, 2.93 g, 91.3 mmol, 2.5 eq.) at rt, under N₂ atmosphere. After 2.5 h, MeOH (30 mL) was added and the reaction was heated until the solution was homogenous. The reaction mixture was allowed to stir for 19 h. The white ppt that had formed (2,3-dihydrophthalazine-1,4-dione byproduct), was filtered off and washed several times with ether. The clear filtrate was concentrated in vacuo and the concentrate was dissolved in EtOAc and filtered again to remove white ppt. All solvent was removed, giving a yellow oil, which was dissolved into EtOAc and ether and charged with HCl (g). The title compound, a pale yellow solid, instantly precipitated. The title compound was dried in a 40° C. oven for 72 h, affording the title compound, as a dark yellow solid; ¹H NMR (400 MHz, CD₃OD) δ 4.55 (2 H, s), 8.27 (1 H, d, J=2.52 Hz), 8.54 (1 H, d, J=2.56 Hz); MS (ES+): #m/z 143.96/145.96 (100/60) [MH⁺]; HPLC: t_R=0.41 min (OpenLynx, polar_7 min).

1-{[(3-Oxocyclobutyl)carbonyl]oxy}pyrrolidine-2,5-dione

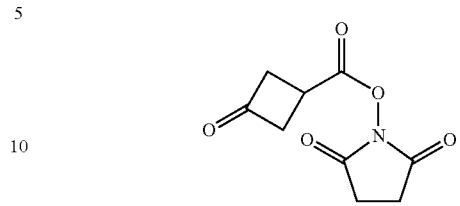

Into a 5 L reactor equipped with a nitrogen flow and an overhead stirrer was added N-hydroxysuccinimide (250.0 g, 2.172 mol) and 3-oxo-cyclobutanecarboxylic acid (248 g, 2.17 mol). Ethyl acetate (3.4 L) was added and the reaction was cooled to 16° C. A solution of 25% DCC in EtOAc (2.17 mol) was added slowly via an addition funnel to the reaction mixture over 7 minutes then the mixture was then heated at 45° C. After 2 h, the mixture was filtered and the filtrate was washed once with EtOAc (1 L×1) and evaporated to dryness in vacuo to afford the desired product. ¹H NMR (400 MHz DMSO-d6) δ 2.83 (bs, 4H), 3.30-3.39 (m, 2H), 3.52-3.60 (m, 2H) and 3.67-3.73 (m, 1H).

3-(8-Chloroimidazo[1,5-α]pyrazin-3-yl)cyclobutanone

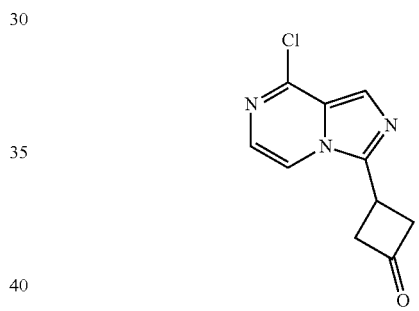

Into a round bottom 1-neck flask (5 L), 3-oxo-cyclobutanecarboxylic acid 2,5-dioxo-pyrrolidin-1-yl ester (217.2 g, 0.937 mol), C-(3-chloro-pyrazin-2-yl)-methylamine hydrochloride salt (153.3 g, 0.852 mol), and THF (760 mL) were added. A solution of 10% NaHCO3 (1.07 kg) was then added and after 20 min, the layers were allowed to separate and the aqueous layer was removed. The aqueous layer was back extracted with EtOAc (1×700 mL, 1×300 mL). The combined organics were washed with brine (350 mL), dried over MgSO₄, filtered, and concentrated in vacuo to provide the title compound. This solid was resuspended in ethyl acetate (915 mL) and DMF (132 mL) and the solution was put under an atmosphere of nitrogen and cooled to 10.5° C. Phosphorus oxychloride (159 mL, 1.70 mol) was then added over 15 minutes and the reaction was allowed to stir for 45 min. The reaction solution was then poured slowly into a 22% aqueous Na₂CO₃ solution at 10° C. Water (1 L) was added and the layers were allowed to separate. The organic layer was removed and the aqueous was back extracted with EtOAc (1×1 L, 1×0.5 L). The combined organic phases were dried over MgSO₄, filtered, and concentrated in vacuo until about 0.5 L of solvent remained. Heptane was added and the slurry was concentrated in vacuo until most of the EtOAc was removed. The resultant slurry was filtered to give desired product. ¹H NMR (400 Adz, CDCl₃) δ 3.59-3.68 (m, 2H), 3.72-3.79 (m, 2H), 3.86-3.94 (m, 1H), 7.40 (d, 1H, J=5.2 Hz), 7.60 (d, 1H, J=5.2 Hz) and 7.85 (s, 1H).

115

3-(1-Bromo-8-chloroimidazo[1,5-α]pyrazin-3-yl)cyclobutanone

3-(8-Chloroimidazo[1,5-α]pyrazin-3-yl)cyclobutanone (47.7 g, 215 mmol) was dissolved in DMF (200 mL) under an atmosphere of nitrogen and cooled to 4° C. N-Bromosuccinimide (40.3 g, 226 mmol) was dissolved in DMF (140 mL) and slowly added to the reaction mixture. After 5 min, water (400 mL) was added and the resulting solid isolated by filtration and washed with solid with water to give the title compound. $^1$H NMR (DMSO-d6, 400 MHz): δ 3.45-3.53 (m, 2H), 3.58-3.67 (m, 2H), 4.08-4.16 (m, 1H), 7.45 (d, 1H, J=5.2 Hz) and 8.30 (d, 1H, J=4.8 Hz).

3-(1-Bromo-8-chloroimidazo[1,5-α]pyrazin-3-yl)-1-methylcyclobutanol

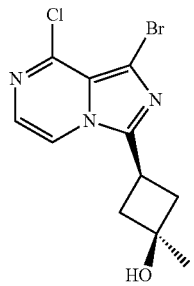

3-(1-Bromo-8-chloroimidazo[1,5-α]pyrazin-3-yl)cyclobutanone (51.988 g, 0.17 mot) in anhydrous THF (550 g, 620 mL) under nitrogen at −78° C. was treated with a 3.0 M solution of methyl magnesium chloride in THF (130 mL, 0.38 mol) over 30 min. The mixture was stirred at −78° C. for 30 min and then the cooling bath was removed and the mixture quenched with 14% NH$_4$Cl (132 g). EtOAc was added to the aqueous phase and the pH was adjusted to ~5 with 20% HCl and the layers separated. The combined organic phases were concentrated in vacuo to a slurry and 0.5 L of toluene was added and the mixture concentrated in vacuo until the EtOAc was removed. The slurry was heated at reflux until homogeneous then allowed to coot to provide desired product, which was isolated by filtration and dried in vacuo. $^1$H NMR (DMSO-d$_6$, 400 MHz): δ 1.37 (s, 3H), 2.35-2.49 (m, 4H), 3.52 (dddd, 1H, J=9.6, 9.6, 9.6, 9.6 Hz), 5.18 (bs, 1H), 7.37 (d, 1H, J=5.2 Hz) and 8.26 (d, 1H, J=5.2 Hz).

116

3-(Amino-1-bromoimidazo[1,5-α]pyrazin-3-yl)-1-methylcyclobutanol

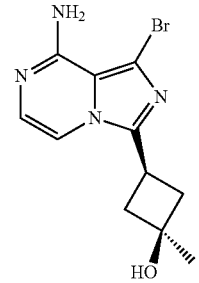

A 35% ammonia solution (132 ml, 2.9 moles) was added to a suspension of 3-(1-bromo-8-chloroimidazo[1,5-α]pyrazin-3-yl)-1-methylcyclobutanol (22.0 g, 0.06463 mol) in 2-butanol (81 ml). The mixture was heated at 90° C. in a pressure vessel for 15 hr then concentrated to 130 ml, cooled to room temperature and the solid collected by filtration. This material was washed with water (3×22 mL) and dried at 40° C. under vacuum. To afford the desired product. $^1$H NMR (DMSO-d$_6$, 400 MHz): δ 7.5 (d, 1H), 7.0 (d, 1H), 6.6 (bs, 2H), 5.1 (s, 1H), 3.4 (pentet, 1H), 2.3-2.4 (m, 4H) and 1.4 (s, 3H).

7-Cyclobutyl-5-iodoimidazo[5,1-f][1,2,4]triazin-4-ylamine

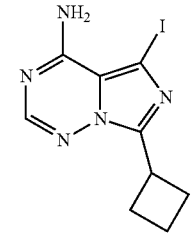

To a solution of 1,2,4-triazole (1.28 g, 18.59 mmol) in anhydrous pyridine (10 mL) was added phosphorus oxychloride (POCl$_3$) (0.578 mL, 6.20 mmol) and stirred at rt for 15 min. This mixture was dropwise charged (3.5 min) with a solution of 7-cyclobutyl-5-iodo-3H imidazo[5,1-f][1,2,4]triazin-4-one (0.653 mg 2.07 mmol) in anhydrous pyridine (14 ml) and stirred for 1.5 h. The reaction mixture was cooled to 0° C. quenched with 2M NH$_3$ in isopropanol (IPA) until basic then allowed to reach rt and stirred for an additional 2 h. The reaction mixture was filtered through a fritted Buchner funnel and washed with DCM. The filtrate was concentrated in vacuo and purified by chromatography on silica gel [eluting with 30% EtOAc in DCM] resulting in the title compound as an off-white solid; $^1$H NMR (CDCl$_3$, 400 MHz) δ 1.93-2.04 (m, 1H), 2.05-2.18 (m, 1H), 2.35-2.45 (m, 2H), 2.49-2.62 (m, 2H), 4.00-4.12 (m, 1H), 7.82 (s, 1H); MS (ES+): m/z 316.08 (100) [MH$^+$], HPLC: t$_R$=2.59 min (MicromassZQ, polar_5 min).

7-Cyclobutyl-5-iodo-3H-imidazo[5,1-f][1,2,4]triazin-4-one

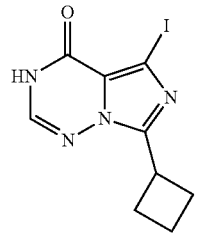

A solution of 7-cyclobutyl-3H-imidazo[5,1-f][1,2,4]triazin-4-one (789 mg 4.15 mmol) and N-iodosuccinimide (NIS, 933 mg, 4.15 mmol) in anhydrous DMF (40 mL) was stirred overnight at rt. An additional 4 eq. of NIS was added and reaction was heated to 55° C. for 6 h. The reaction mixture was concentrated in vacuo and partitioned between DCM and H$_2$O and separated. The aqueous layer was washed with DCM (3×) and the combined organic fractions were washed with 1M sodium thiosulfate (Na$_2$S$_2$O$_3$) (1×), brine (1×), dried over sodium sulfate (Na$_2$SO$_4$), filtered, and concentrated in vacuo. The solid was triturated with 20% EtOAc in DCM and filtered through a fritted Buchner funnel resulting in the title compound as an off-white solid; $^1$H NMR (DMSO-d$_6$, 400 MHz) δ 1.84-1.96 (m, 1H), 1.98-2.13 (m, 1H), 2.25-2.43 (m, 4H), 3.84-3.96 (m, 1H), 7.87 (s, 1H); MS (ES+): m/z 317.02 (100) [MH$^+$], HPLC: t$_R$=2.62 min (MicromassZQ, polar_5 min).

7-Cyclobutyl-3H-imidazo[5,1-f][1,2,4]triazin-4-one

A crude solution of cyclobutanecarboxylic acid (5-oxo-4,5-dihydro-[1,2,4]triazin-6-ylmethyl)amide (1.33 g, 6.39 mmol) in phosphorus oxychloride (POCl$_3$) (10 mL) was heated to 55° C. The reaction was heated for 2 h then concentrated in vacuo and the crude oil was cooled to 0° C. in an ice-bath and quenched with 2M NH$_3$ in isopropanol (IPA) until slightly basic. This crude reaction mixture was concentrated in vacuo and was partitioned between DCM and H$_2$O and separated. The aqueous layer was extracted with DCM (3×) and the combined organic fractions were dried over sodium sulfate (Na$_2$SO$_4$), filtered and concentrated in vacuo. The crude material was purified by chromatography on silica gel [eluting with 5% MeOH in DCM], resulting in the title compound as an off-white solid; $^1$H NMR (DMSO-d$_6$, 400 MHz) δ 1.86-1.96 (m, 1H), 2.00-2.13 (m, 1H); 2.26-2.46 (m, 4H); 3.87-4.00 (m, 1H); 7.71 (s, 1H); 7.87 (d, J=3.6 Hz, 1H); 11.7 (brs, 1H); MS (ES+): m/z 191.27 (100) [MH$^+$], HPLC: t$_R$=2.06 min (MicromassZQ, polar_5 min).

Cyclobutanecarboxylic Acid (5-oxo-4,5-dihydro-[1,2,4]triazin-6-ylmethyl)amide

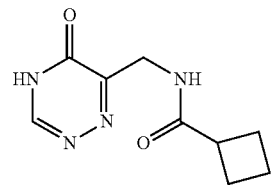

To a solution of 6-aminomethyl-4H-[1,2,4]triazin-5-one (500 mg, 3.96 mmol) and N,N-diisopropylethylamine (DIEA) (0.829 mL, 4.76 mmol) in anhydrous N,N-dimethylformamide (DMF) (20 mL) and anhydrous pyridine (2 mL) was dropwise charged with cyclobutanecarbonyl chloride (0.451 mL, 3.96 mmol) at 0° C. then warmed to rt and stirred for an additional 1.5 h. The reaction mixture was quenched with H$_2$O (2 mL) and concentrated in vacuo and was purified by chromatography on silica gel [eluting with 5% MeOH in DCM (200 mL)→10% MeOH in DCM (800 mL)], affording the title compound; $^1$H NMR (DMSO-d$_6$, 400 MHz) δ 1.7-1.82 (m, 1H), 1.70-1.92 (m, 1H); 1.97-2.07 (m, 2H); 2.07-2.19 (m, 2H); 3.55-3.67 (m, 1H); 4.19 (d, 2H); 7.97 (brt, J=5.6 Hz, 1H); 8.67 (s, 1H); MS (ES+): m/z 209.25 (100) [MH$^+$], HPLC: t$_R$=1.56 min (MicromassZQ, polar_5 min).

6-Aminomethyl-4H-[1,2,4]triazin-5-one

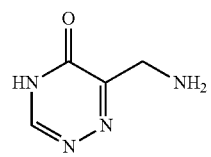

A slurry of 2-(5-oxo-4,5-dihydro-[1,2,4]triazin-6-ylmethyl)isoindole-1,3-dione (4 g, 15.6 mmol) in DCM/EtOH (1:1) (150 mL) was charged with anhydrous hydrazine (1.23 mL, 39.0 mmol) and stirred at rt for 18 h. The reaction mixture was concentrated in vacuo and the off-white solid was triturated with warm CHCl$_3$ and filtered through a fritted funnel. The solid was then triturated with hot boiling methanol (MeOH) and filtered through a fritted funnel resulting in an off-white solid. The material was triturated a second time as before and dried overnight resulting in the title compound as a white solid, which was taken on to the next step without further purification; $^1$H NMR (DMSO-d$_6$, 400 MHz) δ 3.88 (s, 2H), 8.31 (2, 1H); MS (ES+): m/z 127.07 (100) [MH$^+$], HPLC: t$_R$=0.34 min (MicromassZQ, polar_5 min).

2-(5-Oxo-4,5-dihydro-[1,2,4]triazin-6-ylmethyl)isoindole-1,3-dione

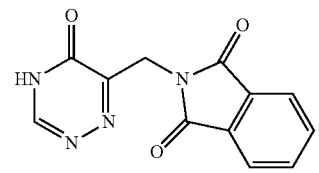

A slurry of 2-(5-oxo-3-thioxo-2,3,4,5-tetrahydro-[1,2,4]triazin-6-ylmethyl)isoindole-1,3-dione (1.0 g, 3.47 mmol) in EtOH (40 mL) was charged with excess Raney Ni (3 spatula) and heated to reflux for 2 h. The reaction mixture was filtered hot through a small pad of celite and washed with a hot mixture of EtOH/THF (1:1) (100 mL) and the filtrate was concentrated in vacuo resulting in the title compound as an off-white solid; $^1$H NMR (DMSO-d$_6$, 400 MHz) δ 4.75 (s, 2H), 7.84-7.98 (m, 4H), 8.66 (s, 1H); MS (ES+): m/z 257.22 (100) [MH$^+$].

2-(5-Oxo-3-thioxo-2,3,4,5-tetrahydro-[1,2,4]triazin-6-ylmethyl)indan-1,3-dione

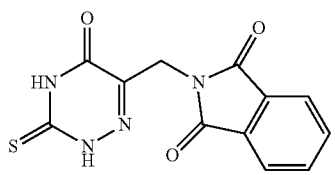

A slurry of 3-(1,3-dioxo-1,3-dihydroisoindol-2-yl)-2-oxopropionic acid ethyl ester (20 g, 76.6 mmol) in anhydrous EtOH (300 mL) was charged with thiosemicarbazide (6.98 g, 76.6 mmol) in one portion and heated to 80° C. for 2 h. The reaction mixture was charged with N,N-diisopropylethylamine (DIEA) (26.7 mL, 76.56 mmol) and heated to 40° C. for 6 h then stirred at Tt for an additional 10 h. The reaction mixture was concentrated in vacuo and solid was triturated with hot EtOH/EtOAc filtered and washed with EtOAc. The solid was dried overnight in a vacuum oven (40° C.) resulting in the title compound as an off-white solid; $^1$H NMR (DMSO-d$_6$, 400 MHz) δ 4.68 (s, 2H), 7.85-7.95 (m, 4H); MS (ES+): m/z 289.2 (100) [MH$^+$].

2-[(3-Methyl-5-oxo-4,5-dihydro-1,2,4-triazin-6-yl)methyl]-1H-isoindole-1,3(2H)-dione

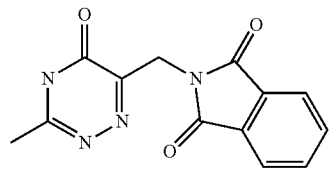

A solution of ethyl 3-(1,3-dioxo-1,3-dihydro-2H-isoindol-2-yl)-2-oxopropanoate [*J. Org. Chem.*, (1985), 50 (1), 91] (4.29 g, 16.4 mmol), acetamidrazone hydrochloride (1.80 g, 16.4 mmol) in anhydrous EtOH (85.8 mL) was heated to 80° C. for 3 h then cooled to rt and stirred for an additional 16 h. The reaction mixture was filtered through a flitted funnel resulting in 3.28 g, (73% yield) of the title compound as a white solid. $^1$H NMR (400 MHz, DMSO-d6) δ ppm 2.28 (s, 3H), 4.73 (s, 2H) and 7.74-8.12 (m, 4H); MS (ES+): m/z 271.08 [MH+].

6-(Aminomethyl)-3-methyl-1,2,4-triazin-5(4H)-one

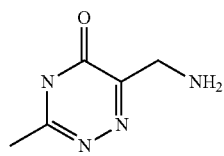

A solution of 2-[(3-methyl-5-oxo-4,5-dihydro-1,2,4-triazin-6-yl)methyl]-1H-isoindole-1,3(2B)-dione (2.00 g, 7.40 mmol) in DCM (10.0 mL) and EtOH (10.0 mL) was charged with hydrazine (0.58 mL, 181.5 mmol) and stirred at rt for 8 h, then heated to 45° C. for an additional 16 h. The reaction was charged with an additional 0.5 equiv of hydrazine (0.116 mL, 3.70 mmol) and heated to 45° C. for 4 h. The reaction mixture was allowed to cool to rt then filtered through a fritted funnel and the cake was washed with 2 portions of cold 1:1 EtOH/DCM (75 mL) and the filtrate was concentrated resulting in 622 mg of a pale yellow solid which was taken on to the next step without further purification. $^1$H NMR (400 MHz, DMSO-d$_6$) δ ppm 2.21 (s, 3H), 3.72 (s, 2H); MS (ES+): m/z 141.06 [MH+].

trans-4-({[(Benzyloxy)carbonyl]amino}methyl)cyclohexanecarboxylic Acid

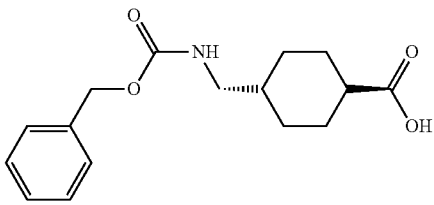

trans-4-(Aminomethyl)cyclohexanecarboxylic acid (10.00 g, 0.06361 mol), in a 10% aq solution of NaOH (5.60 g in 55 mL) was cooled to 0° C. and treated over 15 min with vigorous stirring, with benzyl chloroformate (11 mL, 0.076 mol). After one hour the solution was acidified (1M HCl(aq)) and the resulting the white precipitate collected by filtration, washed with water and hexane then dried in vacuo oven overnight to afford 17.23 g of the title compound. $^1$H NMR (400 MHz, CDCl$_3$): δ 0.93-0.99 (m, 2H), 1.38-1.46 (m, 2H), 1.82-1.85 (m, 2H), 2.03-2.06 (m, 2H), 2.25 (m, 1H), 3.06 (t, J=5.6 Hz, 2H), 4.83 (m, 1H), 5.09 (s, 2H), 7.31-7.36 (m, 5H). MS (ES+): m/z 292 [MH+].

Benzyl [(trans-4-{[(3-chloropyrazin-2-yl)methyl]carbamoyl}cyclohexyl)methyl]carbamate

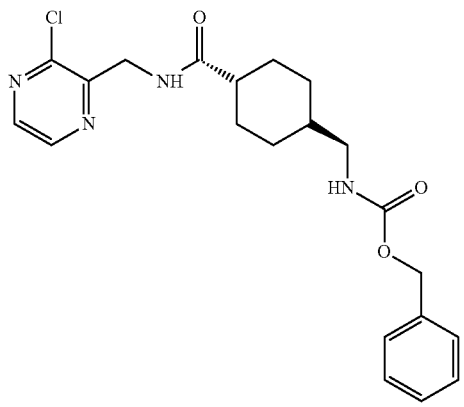

To a solution of C-(3-chloropyrazin-2-yl)methylamine hydrochloride salt (0.100 g, 0.533 mmol) in DCM (1.35 mL) was added N-(3-dimethylaminopropyl)-N-ethylcarbodiimide hydrochloride (0.16 g, 0.83 mmol), N,N-diisopropylethylamine (0.14 mL, 0.83 mmol), 1-hydroxybenzotriazole (0.075 g, 0.56 mmol) and trans-4-({[(benzyloxy)carbonyl]amino}methyl)cyclohexanecarboxylic acid (0.21 g, 0.70 mmol). The reaction was stirred at rt overnight then diluted with DCM, washed with sat. NaHCO$_3$ (aq) and brine, then dried over Na$_2$SO$_4$ and the solvent removed in vacuo. The residue thus isolated was chromatographed over silica gel eluting with EtOAc/hexane (1:1) to afford 0.173 g of the title compound. $^1$H NMR (400 MHz, CDCl$_3$): δ 1.00-1.03 (m, 2H), 1.45-1.51 (m, 2H), 1.83-1.89 (m, 2H), 1.99-2.03 (m, 2H), 2.20 (m, 1H), 3.05-3.12 (m, 3H), 4.68 (d, J=4.4 Hz, 2H), 4.79 (br, 1H), 5.10 (s, 2H), 6.79 (br, 1H), 7.31-7.37 (m, 5H), 8.33 (d, J=2.8 Hz, 1H), 8.46 (d, J=2.8 Hz, 1H). MS (ES+): m/z 417.14 [MH+].

Benzyl {[trans-4-(8-chloroimidazo[1,5-α]pyrazin-3-yl)cyclohexyl]methyl}carbamate

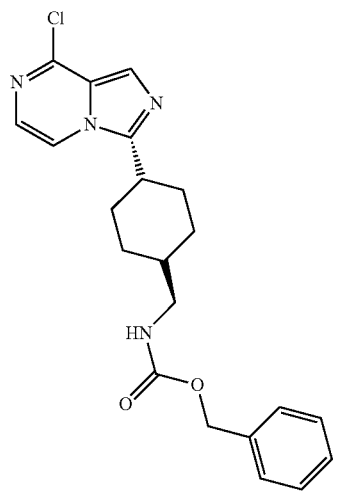

To a suspension of benzyl [(trans-4-{[(3-chloropyrazin-2-yl)methyl]carbamoyl}cyclohexyl)methyl]carbamate (0.100 g, 0.220 mmol) in EtOAc (0.9 mL) and DMF (0.068 mL) at 0° C. was added slowly POCl$_3$ (0.082 mL, 0.88 mmol). After stirring at rt for an hour, the mixture was cooled to 0° C. and solid NaHCO$_3$ was added. After a flyer 10 min at 0° C. and 20 min at rt, the mixture was re-cooled to 0° C. and water (20 nm) was added. The reaction mixture was extracted with EtOAc (3×20 mL) and the extracts washed with water (2×30 mL) and brine (30 mL) and then dried over Na$_2$SO$_4$ and concentrated in vacuo to afford 0.096 g of the title compound. $^1$H NMR (400 MHz, CDCl$_3$): δ 1.15-1.19 (m, 2H), 1.76-1.87 (m, 3H), 1.93-2.00 (m, 2H), 2.04-2.08 (m, 2H), 3.07 (m, 1H), 3.15 (t, J=6.4 Hz, 2H), 4.84 (br, 1H), 5.09 (s, 2H), 7.31-7.40 (m, 6H), 7.61 (d, J=4.8 Hz, 1H), 7.79 (s, 1H). MS (ES+): m/z 399.26 [MH+].

Benzyl {[trans-4-(8-chloro-1-iodoimidazo[1,5-α]pyrazin-3-yl)cyclohexyl]methyl}carbamate

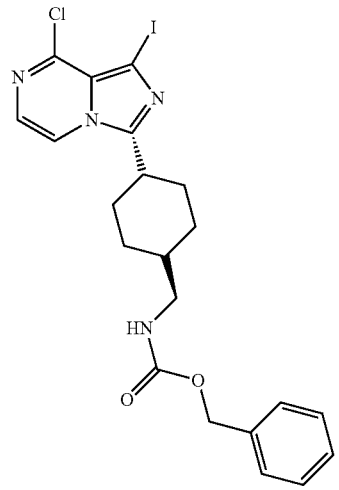

To a solution of benzyl {[trans-4-(8-chloroimidazo[1,5-α]pyrazin-3-yl)cyclohexyl]methyl}carbamate (1.49 g, 0.00374 mol) in DMF (0.6 mL) was added NIS (1.0 g, 0.0045 mol). The reaction mixture was stirred at 55° C. overnight then diluted with EtOAc (20 mL), washed with water (2×40 mL) and brine (20 mL), then dried over Na$_2$SO$_4$ and concentrated in vacuo. The crude mixture thus isolated was chromatographed over silica gel eluting with hexane hexane:EtOAc 1:1 to afford 1.7 g of the title compound. MS (ES+): m/z 525.01 [MH+].

Benzyl {[trans-4(8-amino-1-iodoimidazo[1,5-α]pyrazin-3-yl)cyclohexyl]methyl}carbamate

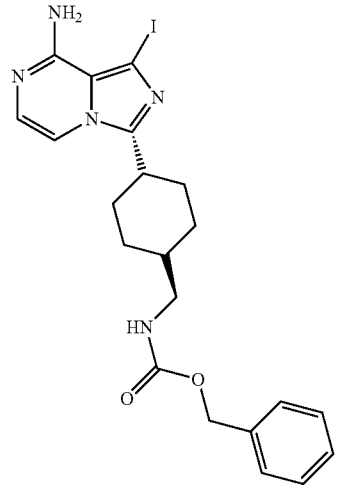

A solution of benzyl {[trans-4-(8-chloro-1-iodoimidazo[1,5-α]pyrazin-3-yl)cyclohexyl]methyl}carbamate (1.70 g, 0.00324 mol) in IPA (30 mL) was cooled to −78° C., treated with a stream of ammonia gas over 3 min. and then heated at 110° C. in a Parr vessel overnight. The reaction solution was concentrated in vacuo and residue washed with water to afford 1.37 g of desired product. $^1$H NMR (400 MHz, CDCl$_3$): δ=1.08-1.17 (m, 2H), 1.88 (m, 1H), 1.71-1.81 (m, 2H), 1.91-1.94 (m, 2H), 2.00-2.04 (m, 2H), 2.90 (m, 1H), 3.13 (t, J=6.4 Hz, 2H), 4.86 (br, 1H), 5.11 (s, 2H), 5.76 (br, 2H), 7.00 (d J=5.2 Hz, 1H), 7.22 (d J=5.2 Hz, 1H), 7.31-7.37 (m, 5H). MS (ES+): m/z 5.7.36 [MH+].

Benzyl 4-{[(3-chloropyrazin-2-yl)methyl]carbamoyl}piperidine-1-carboxylate

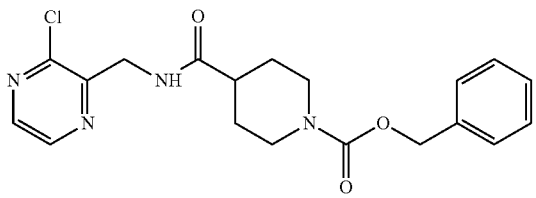

A solution of C-(3-Chloropyrazin-2-yl)methylamine bis-hydrochloride (2.00 g, 0.0107 mol) and N,N-diisopropyl-ethylamine (2.2 g, 0.017 mol) in DCM (27.0 mL) was treated with and N-(3-dimethylaminopropyl)-Al-ethylcarbodiimide hydrochloride (3.2 g, 0.017 mol), 1-hydroxybenzotriazole (1.5 g, 0.011 mol) and 1-[(benzyloxy)carbonyl]-4-piperidine carboxylic acid (3.8 g, 0.014 mol). The mixture was stirred at rt overnight then diluted with DCM (30 mL), washed with sat. NaHCO₃ (20 mL) and brine (20 mL), then dried over Na₂SO₄ and concentrated in vacuo. The crude material thus obtained was chromatographed over silica gel eluting with EtOAc:hexane 1:1 yielding 3.38 g of the title compound. $^1$H NMR (400 MHz, CDCl$_3$): δ 1.68-1.78 (m, 2H), 1.91-1.94 (m, 2H), 2.44 (m, 1H), 2.89-2.92 (m, 2H), 4.24-4.26 (m, 2H), 4.70 (d, J=4.8 Hz, 2H), 5.14 (s, 2H), 6.85 (br, 1H), 7.30-7.37 (m, 5H), 8.34 (d, J=2.8 Hz, 1H), 8.45 (d, J=2.8 Hz, 1H). MS (ES+): m/z 389.17 [MH+].

Benzyl 4(8-chloroimidazo[1,5-α]pyrazin-3-yl)piperidine-1-carboxylate

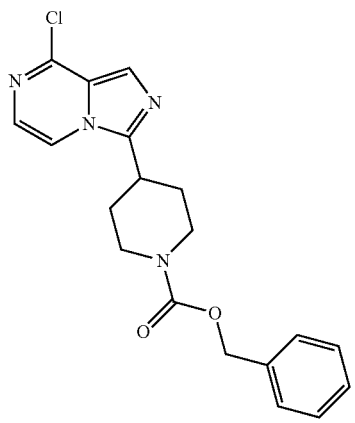

To a suspension of benzyl 4-{[(3-chloropyrazin-2-yl)methyl]carbamoyl}piperidine-4-carboxylate (0.100 g, 0.220 mmol) in EtOAc (0.9 mL) and DMF (0.068 mL) at 0° C. was slowly added POCl₃ (0.082 mL, 0.88 mmol). After stirring at rt for an hour the mixture was cooled to 0° C. then treated with solid NaHCO₃. The mixture was stirred for 20 min at rt, diluted with water and extracted with EtOAc (3×20 mL). The combined extracts were washed with water (2×30 mL) and brine (30 mL), then dried over Na₂SO₄, and concentrated in vacuo to yield 2.07 g of desired product. $^1$H NMR (400 MHz CDCl$_3$): δ 1.98-2.04 (m, 4H), 3.03-3.20 (m, 3H), 4.30-4.33 (m, 2H), 5.16 (s, 2H), 7.33 (d, J=5.2 Hz, 1H), 7.35-7.38 (m, 5H), 7.26 (d, J=4.4 Hz, 1H), 7.79 (s, 1H). MS (ES+): m/z 371.22 [MH+].

Benzyl 4(8-chloro-1-iodoimidazo[1,5-α]pyrazin-3-yl)piperidine-1-carboxylate

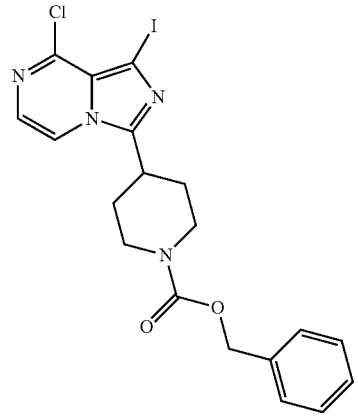

To a solution of benzyl 4-(8-chloroimidazo[1,5-α]pyrazin-3-yl)piperidine-1-carboxylate (1.31 g, 0.00354 mol) in DMF (0.6 mL) was added NIS (1.6 g, 0.0071 mol). The reaction mixture was left to stir at 55° C. for 20 h. then the mixture was diluted with EtOAc (20 mL), washed with water (2×40 mL) and brine, then dried over Na₂SO₄ and concentrated in vacuo. The crude reaction mixture was chromatographed over silica gel eluting with hexane→hexane:EtOAc 1:1 yielding 1.63 g of desired product. $^1$H NMR (400 MHz, CDCl$_3$): δ 1.95-2.04 (m, 4H), 3.02-3.15 (m, 3H), 4.29-4.32 (m, 2H), 5.15 (s, 2H), 7.32 (d, S=5.2 Hz, 1H), 7.34-7.37 (m, 5H), 7.66 (d, J=5.2 Hz, 1H). MS (ES+): m/z 497.03 [MH+].

Benzyl 4-(8-amino-1-iodoimidazo[1,5-α]pyrazin-3-yl)piperidine-1-carboxylate

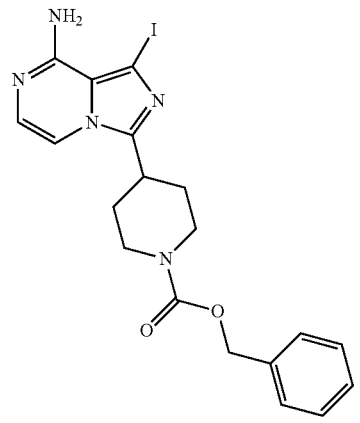

A mixture of benzyl 4-(8-chloro-1-iodoimidazo[1,5-α]pyrazin-3-yl)piperidine-1-carboxylate (0.500 g, 0.00101 mol) in IPA (20 mL) was cooled to at −78° C. and treated with a stream of ammonia gas over 3 minutes. The resulting solution was heated at 110° C. in a Parr vessel prior to concentration in vacuo, suspension in DCM and filtration through a bed of Celite. The filtrate was concentrated in vacuo to afford 0.504 g of desired product $^1$H NMR (400 Adz, CDCl$_3$): δ 1.88-2.02 (m, 2H), 2.99-3.10 (m, 3H), 4.24-4.41 (m, 2H), 5.15 s, 2H), 6.03 (br, 2H), 7.03 (d, J=4.8 Hz, 1H), 7.24 (d, J=5.2 Hz, 1H), 7.31-7.40 (m, 5H). MS (ES+): m/z 479.33 [MH+].

1-(2-Trimethylsilylethoxymethyl)-1H-pyrrolo[2,3-b]pyridine

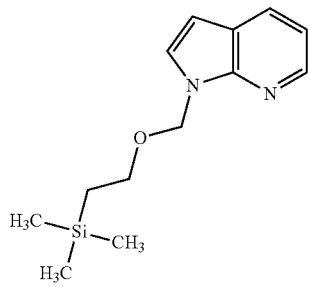

To a suspension of sodium hydride (934 mg, 0.0358 mol) in DMF (57 mL) was added dropwise under N$_2$, a solution of I H-pyrrolo[2,3-b]pyridine (3.00 g, 0.0254 mol) in DMF (20 mL). The mixture was stirred at r.t. for 45 min. then cooled to 0° C. and treated dropwise with [2-(trimethylsilyl)ethoxy]methyl chloride (6.32 mL, 0.0357 mol). The mixture was stirred at rt for 12 h. then poured into water (10 mL), stirred for 30 min. and extracted with Et2O (4×10 mL). The combined extracts were washed with brine (20 mL), dried over sodium sulfate, and concentrated in vacuo to give the crude product which was chromatographed over silica gel eluting with hexane 1:9 Et$_2$O:hexane to afford 6 g desired product.

N-(2-Trimethylsilyl-1-ethoxymethyl)-2-(tributylstannyl)-1H-pyrrolo[2,3-b]pyridine

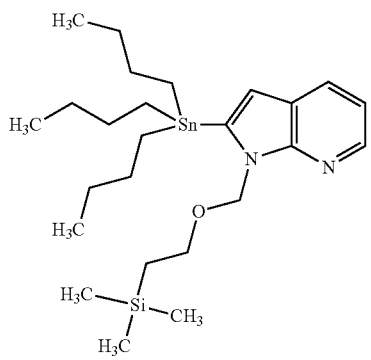

To a solution of 1-(2-trimethylsilylethoxymethyl)-1H-pyrrolo[2,3-b]pyridine (500 mg, 0.0020129 mol) in THF (5 mL) at −10° C. was added a 2.0 M of n-BuLi in cyclohexane (1.2 mL). After 10 min at −10° C., the mixture was cooled to −20° C. and tributyltin chloride (0.65 mL, 0.0024 mol) was added. The mixture was stirred at rt for 1 h, the poured into a 5% aqueous ammonium chloride (20 mL), extracted with EtOAc (3×20 mL) and the combined extracts dried over anhydrous MgSO$_4$ and concentrated in vacuo. The material thus obtained was chromatographed over silica gel eluting with 1:9 EtOAc:hexane to afford 0.7 g of the title compound. $^1$H NMR (400 MHz DMSO-d6) δ 0.01 (s, 9H), 0.10 (s, 2H), 0.92-0.94 (m, 9M, 1.14-1.27 (m, 6H), 1.37-1.46 (m, 6H), 1.60-1.72 (m, 6H), 3.48-3.52 (m, 2H), 5.71 (s, 2H), 6.74 (s, 1H), 7.16-7.19 (m, 1H), 8.02 (dd, J=1.6, 7.6 Hz, 1H) and 8.31 (dd, J=1.6, 4.4 Hz, 1H).

3-cyclobutyl-1-[1-(2-trimethylsilylethoxymethyl)-1H-pyrrolo[2,3-b]pyridin-2-yl]imidazo[1,5-α]pyrazin-8-amine

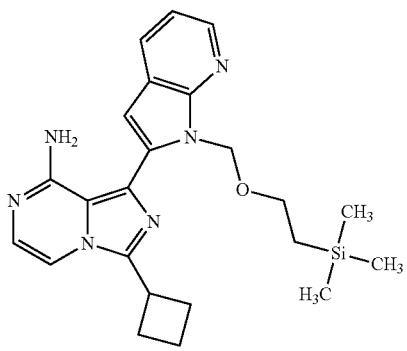

A mixture of N-(2-trimethylsilyl-1-ethoxymethyl)-2-(tributylstannyl)-1H-pyrrolo[2,3-b]pyridine (110 mg, 0.20 mmol), 3-cyclobutyl-1-iodoimidazo[1,5-α]pyrazin-8-amine (50 mg, 0.1592 mmol) and bis(triphenylphosphine)palladium(II) chloride (10 mg, 0.02 mmol) in ethanol (2 mL) was heated at reflux for 48 h. The mixture was then cooled to rt, filtered through a pad of Celite and concentrated in vacuo. The residue thus obtained was chromatographed over silica gel eluting with hex:EtOAc to afford 17.2 mg of the title compound. $^1$H NMR (400 MHz CDCl$_3$) δ 0.22 (s, 9H), 0.70 (t, 2H), 1.87-2.19 (m, 2H), 2.49-2.64 (m, 4H), 3.37 (t, 2H), 3.81-3.86 (m, 1H), 5.51 (bs, 2H), 6.07 (s, 2H), 6.67 (s, 1H), 7.10-7.16 (m, 3H), 7.93 (dd, J=1.6, 8.0 Hz, 1H) and 8.41 (dd, J=1.6, 4.8 Hz, 1H). MS (ES+): m/z: 435.21 [MH+].

4-Bromo-2-nitro-N-phenylamine

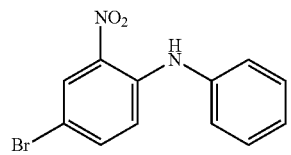

A mixture of 1-bromo-4-fluoro-3-nitrobenzene (2270 mg, 10.01 mol), aniline (3 ml) and DMF (20 ml) was heated at 100° C. under an atmosphere of Nitrogen for 7 h. The mixture was then concentrated in vacuo, and the residue triturated with heptane (30 ml) to give the desired product. 1H NMR (400 MHz, CDCl$_3$) δ=7.11 (d, 1 H, J=9.2 Hz), 7.25-7.29 (m, 3 H), 7.40-7.45 (m, 3 H), 8.35 (d, 1 H J=2.4 Hz) and 9.45(brs, 1 H).

4-Bromo-N-methyl-2-nitroaniline

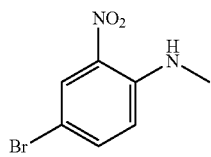

Prepared according to a procedure analogous to that described for 4-bromo-2-nitro-N-phenylaniline. $^1$H NMR (400 MHz, CDCl$_3$): δ=3.02 (d, 3 H, J=5.2 Hz), 6.76 (d, 1 H, J=9.6 Hz), 7.51-7.54 (m, 1 H), 8.02 (brs, 1 H) and 8.32 (d, 1 H, J=2.8 Hz). MS (ES+): m/z 231.05 and 233.08[MH+].

4-Bromo-N-ethyl-2-nitroaniline

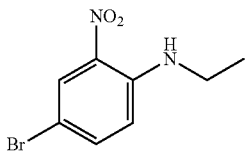

Prepared according to a procedure analogous to that described for 4-bromo-2-nitro-N-phenylaniline. $^1$H NMR (400 MHz, CDCl3) δ=1.37 (t, 3 H, J=7.2 Hz), 3.31-3.37 (m, 2 H), 6.76 (d, 1 H, J=8.8 Hz), 7.48-7.51 (m, 1 H, 7.95 (brs, 1 H) and 8.31 (d, 1 H, J=2.4 Hz). MS (ES+): m/z 245.07 and 247.11 [MH+].

N-Benzyl-4-bromo-2-nitroaniline

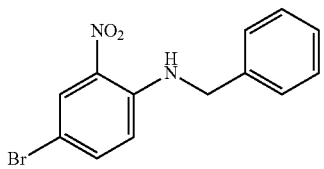

Prepared according to a procedure analogous to that described for 4-bromo-2-nitro-N-phenylaniline. $^1$H NMR (4006 MHz, CDCl$_3$) δ=4.54 (d, 2 H, J=5.6 Hz), 6.72 (d, 1 H, J=9.2 Hz), 7.30-7.40 (m, 5 H), 7.44 (ddd, 1 H, J=0.4 & 2.4 & 9.2 Hz), 8.34 (d, 1 H, J=2.4 Hz) and 8.41 (brs, 1 H). MS (ES+): m/z 245.07 and 247.11 [MH+].

4-Bromo-N$^1$-phenylbenzene-1,2-diamine

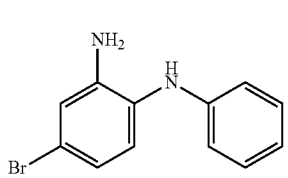

Prepared according to a procedure analogous to that described for 4-bromo-2-nitro-N-phenylaniline. $^1$H NMR (400 MHz, DMSO-d$_6$)=3.80 (brs, 2 H), 5.07 (br, s, 1 H), 6.70-6.75 (m, 2H), 6.82-6.86 (m, 2 H), 6.93 (d, 1 H, J=2.4 Hz), 6.97 (d, 1 H, J=8.0 Hz) and 7.17-7.24 (m, 2 H). MS (ES+): m/z 263.17 and 265.20 [MH+].

4-Bromo-N$^1$-methylbenzene-1,2-diamine

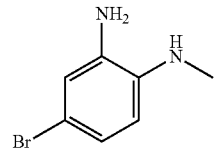

A suspension of 4-bromo-N-methyl-2-nitroaniline (5328 mg, 22.04 mmol) in EtOH (100 ml) was treated with SnCl$_2$.2H$_2$O (25.61 g, 110.2 mmol) and the resulting mixture heated at 70° C. under an atmosphere of Nitrogen for 5 h. The reaction mixture was then cooled to rt and treated with ice-water (50 ml) followed by aqueous NaOH (4 N) until pH>8. This basic mixture was then extracted with EtOAc (3×150 ml) and the combined extracts washed with brine (3×100 ml), dried over MgSO$_4$ and concentrated in vacuo to afford the title compound. $^1$H NMR (400 MHz, DMSO-d$_6$) δ ppm=2.68 (s, 3 H), 4.74 (brs, 3 H), 6.27 (d, 1 H, J=8.4 Hz), 6.61 (dd, 1 H, J=2.0 & 8.4 Hz) and 6.66 (d, 1 H, J=2.0 Hz). MS (ES+): m/z 201.10 and 203.12 [MH+].

4-Bromo-N'-ethylbenzene-1,2-diamine

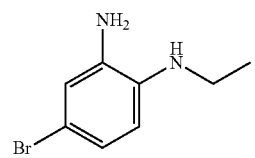

Prepared according to a procedure analogous to that described for 4-bromo-N'-methylbenzene-1,2-diamine. $^1$H NMR (400 Mhz, DMSO-d$_6$) δ ppm=1.19 (t, 3 H, J=6.8 Hz), 3.01 (quartet, 2 H, J=6.8 Hz), 4.46 (brs, 1 H), 4.81 (brs, 2 H), 6.30 (d, 1 H, J=8.4 Hz), 6.58 (dd, 1 H, J=2.4 & 8.4 Hz) and 6.66 (d, 1 H, J=2.0 Hz). MS (ES+): m/z 215.07 and 217.16 [MH+].

N$^1$—Benzyl-4-bromobenzene-1,2-diamine

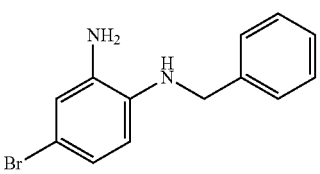

Prepared according to a procedure analogous to that described for 4-bromo-N$^1$-methylbenzene-1,2-diamine. $^1$H NMR (400 MHz, DMSO-d$_6$) δ ppm=3.39 (brs, 2 H), 3.61

(brs, 1 H), 4.28 (s, 2 H, 6.51 (d, 1 H, J=8.4 Hz), 6.85-6.89 (m, 2 H) and 7.27-7.38 (m, 5 H). MS (ES+): m/z 277.20 and 279.20 [MH+].

1-Benzyl-5-bromo-2-phenyl-1H-benzimidazole

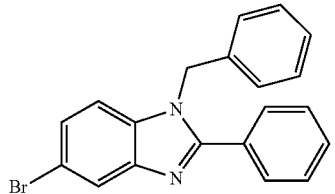

p-TsOH.H$_2$O (311.7 mg, 1.606 mmol) was added to a DCM (50 ml) solution of N'-benzyl-4-bromobenzene-1,2-diamine (4451 mg, 16.06 mmol) and trimethyl orthobenzoate (3096 µl, 17.66 mmol) and the resulting mixture was stirred at rt under an atmosphere of Nitrogen for 40 h. The reaction mixture was then concentrated in vacuo to give a yellow solid which was triturated with 40% MeOH/water (375 mL), filtered, washed with saturated NaHCO$_3$ (20 ml)+H$_2$O (80 ml) twice and 40% MeOH/H$_2$O (2×50 ml), and dried to give the title compound. $^1$H NMR (400 MHz, DMSO-d$_6$) δ ppm=5.44 (s, 2 H, 7.05-7.08 (m, 3 H), 7.30-7.36 (m, 4 H), 7.44-7.50 (m, 3 H), 7.66-7.68 (m, 2 H) and 7.99 (dd, 1 H, J=0.4 & 1.6 Hz). MS (ES+): m/z 363.20 and 365.26 [MH+].

5-Bromo-1-methyl-2-phenyl-1H-benzimidazole

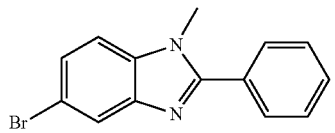

Prepared according to a procedure analogous to that described for 1-benzyl-5-bromo-2-phenyl-1 H-benzimidazole. $^1$H NMR (400 z, CDCl$_3$) δ ppm=3.86 (s, 3 H), 7.26-7.29 (m, 1H), 7.42 (dd, 1 H, J=2.0 & 8.4 Hz), 7.53-7.56 (m, 3 H), 7.74-7.76 (m, 2 H) and 7.95 (dd, 1 H, J=0.4 & 1.6 Hz). MS (ES+): m/z 287.18 and 289.14 [M+].

5-Bromo-1-ethyl-2-phenyl-1 H-benzimidazole

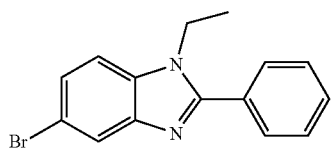

Prepared according to a procedure analogous to that described for 1-benzyl-5-bromo-2-phenyl-1 H-benzimidazole $^1$H NMR (400 MHz, CDCl$_3$) δ ppm=1.46 (t, 3 H, J=7.2 Hz), 4.27 (quartet, 2 H, J=7.2 Hz), 7.27 (m, 1 H), 7.30 (dd, 1 H, J=0.4 & 8.8 Hz), 7.42 (dd, 1 H, J=1.6 & 8.8 Hz), 7.53-7.55 (m, 3 H), 7.70-7.72 (m, 2 H) and 7.96 (dd, 1 H, J=0.4 & 1.6 Hz). MS (ES+): m/z 301.18 and 303.11 [MH+].

5-Bromo-1,2-diphenyl-1H-benzimidazole

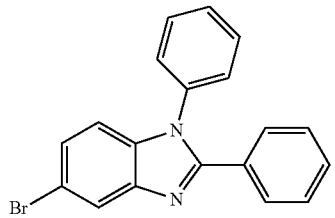

Prepared according to a procedure analogous to that described for 1-benzyl-5-bromo-2-phenyl-1H-benzimidazole. $^1$H NMR (400 MHz, CDCl$_3$): δ=7.11 (dd, 1 H, J=0.4 & 8.4 Hz), 7.27-7.39 (m, 6 H), 7.48-7.56 (m, 5 H) and 8.01 (dd, 1H, J=0.4 & 1.6 Hz). MS (ES+): m/z 349.20 and 351.22 [MH+].

1-Methyl-2-phenyl-5-(4,4,5,5-tetramethyl-[1,3,2]dioxaborolan-2-yl)-1H-benzimidazole

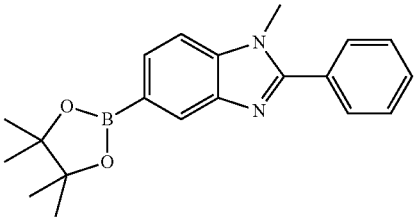

A mixture of 5-bromo-1-methyl-2-phenyl-1H-benzimidazole (616 mg, 2.14 mmol), [1,1'—Bis(diphenylphosphino)ferrocene]dichloropalladium(II) complex with dichloromethane (1:1) (52.6 mg, 0.0644 mmol), bis(pinacolato)diboron (667 mg, 2.57 mmol), 1,1'-bis(diphenylphosphino)ferrocene (36.8 mg, 0.0644 mmol) and AcOK (638 mg, 6.44 mmol) in 1,4-dioxane (10 ml) was purged with N$_2$ for 5 min, and was then heated at 100° C. under an atmosphere of Nitrogen for 16 h. The mixture was then treated with saturated NH$_4$Cl (20 ml), extracted with EtOAc (3×20 ml) and the combined extracts washed with brine (3×20 ml), dried over MgSO$_4$ and concentrated in vacuo to afford crude product which was purified by chromatography over silica gel eluting with 30% (250 ml) and 40% (250 ml) EtOAc/Heptane to give a white solid that was triturated with 50% EtOAc/Heptane (10 ml) to yield the title compound. $^1$H NMR (400 MHz, CDCl$_3$) δ ppm=1.38 (s, 12 H), 3.86 (s, 3 H), 7.39 (dd, 1 H, J=1.2 & 8.0 Hz), 7.50-7.55 (m, 3H), 7.76-7.79 (m, 3H) and 8.29 (d, 1 H, J=0.8 Hz). MS (ES+): m/z 335.29 (100) [MH+].

1-Ethyl-2-phenyl-5(4,4,5,5-tetramethyl-[1,3,2]dioxaborolan-2-yl)-1H-benzimidazole

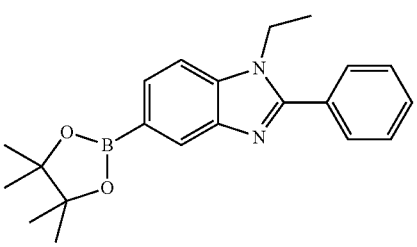

Prepared according to a procedure analogous to that described for 1-Methyl-2-phenyl-5-(4,4,5,5-tetramethyl-[1,3,2]dioxaborolan-2-yl)-1H-benzimidazole. ¹H NMR (400 MHz, CDCl₃) δ ppm=1.38 (s, 12 H), 1.45 (t, 3 H, J=7.2 Hz), 4.28 (quartet, 2 H, J=7.2 Hz), 7.42 (dd, 1 H, J=0.8 & 8.0 Hz), 7.51-7.54 (m, 3H), 7.71-7.74 (m, 2M, 7.77 (dd, 1 H, J=0.8 & 8.0 Hz) and 8.31 (s, 1H). MS (ES+): m/z 349.33 [MH+].

1-Benzyl-2-phenyl-5-(4,4,5,5-tetramethyl-[1,3,2]dioxaborolan-2-yl)-1H-benzimidazole

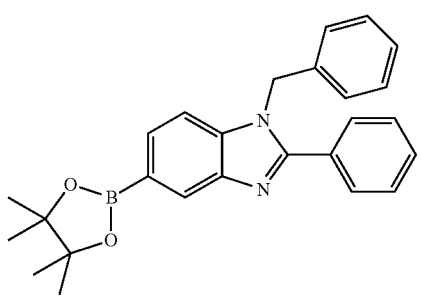

Prepared according to a procedure analogous to that described for 1-Methyl-2-phenyl-5-(4,4,5,5-tetramethyl-[1,3,2]dioxaborolan-2-yl)-1H-benzimidazole. ¹H NMR (400 z, CDCl₃) δ ppm=1.36 (s, 12 H), 5.45 (s, 2 H), 7.05-7.08 (m, 1 H), 7.21 (dd, 1 H, J=0.8 & 8.0 Hz), 7.26-7.31 (m, 3H), 7.44-7.48 (m, 3H), 7.66-7.71 (m, 3H) and 8.36 (m, 1 H). MS (ES+): m/z 411.42 [MH+].

1,2-Diphenyl-5-(4,4,5,5-tetramethyl-[1,3,2]dioxaborolan-2-yl)-1H-benzimidazole

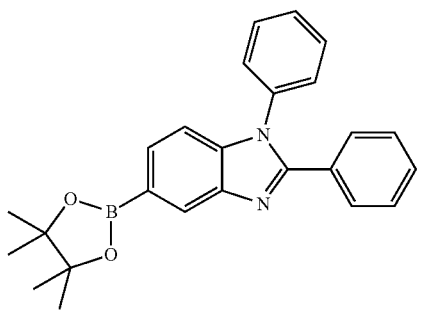

Prepared according to a procedure analogous to that described for 1-Methyl-2-phenyl-5-(4,4,5,5-tetramethyl-[1,3,2]dioxaborolan-2-yl)-1H-benzimidazole. ¹H NMR (400 MHz, CDCl₃) δ ppm=1.38 (s, 12 H), 7.22 (dd, 1 H, J=0.8 & 8.0 Hz), 7.29-7.35 (m, 5 H), 7.47-7.50 (m, 3 H), 7.55-7.57 (m, 2 H) and 7.71 (dd, 1 H, J=0.8 & 8.0 Hz), 8.38 (m, 1 H). MS (ES+): m/z 397.43 [MH+].

7-Chloro-2-(4,4,5,5-tetramethyl-[1,3,2]dioxaborolan-2-yl-1H-indole

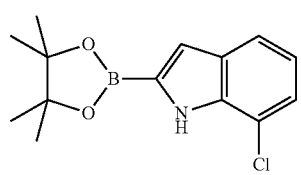

A flask containing Ir(Ome)₂(COD)₂ [Inorganic Syntheses (1985), 23, 126] (850 mg, 0.0013 mol), 4,4'-di-tert-butyl-[2,2']bipyridinyl (686 mg, 0.00256 mol) and 4,4,4',4',5,5,5',5'-octamethyl-2,2'-bi-1,3,2-dioxaborolane (15.2 g, 0.0600 mol) was evacuated and refilled with Ar (3×), then charged with anhydrous DIE (400 mL, 3 mol) and a solution of 7-chloro-1H-indole (0.086 mol) in DE (10 mL). The resulting mixture was stirred under Ar for 16 h then concentrated and chromatographed over silica gel eluting with 10% EtOAc/Heptane to afford the desired product as a waxy solid in a 96% yield. ¹H NMR (400 MHz, CDCl₃) δ ppm 1.39 (s, 12 H), 7.04 (t, J=7.71 Hz, l H), 7.15 (d, J=2.27 Hz, 1 H), 7.21-7.30 (m, 1 H), 7.58 (d, J=8.08 Hz, 1 H) and 8.72 (br. s., 1 H).

4-Methoxy-2-(4,4,5,5-tetramethyl-[1,3,2]dioxaborolan-2-yl)-1H-indole

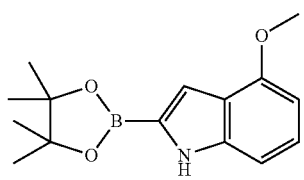

Prepared according to a procedure analogous to that described for 7-chloro-2-(4,4,5,5-tetramethyl-[1,3,2]dioxaborolan-2-yl)-1H-indole using 4-methoxy-1H-indole.

7-Bromo-4-methoxy-2-(4,4,5,5-tetramethyl-[1,3,2]dioxaborolan-2-1H-indole

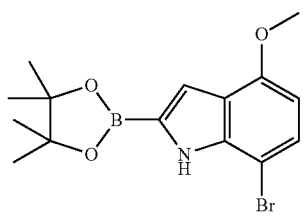

Prepared according to a procedure analogous to that described for 7-chloro-2-(4,4,5,5-tetramethyl-[1,3,2]dioxaborolan-2-yl)-1H-indole using 7-bromo-4-methoxy-1H-indole.

7-Methyl-2-(4,4,5,5-tetramethyl-[1,3,2]dioxaborolan-2-yl)-1H-indole

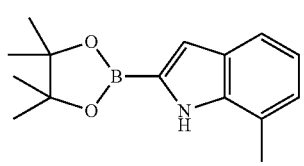

Prepared according to a procedure analogous to that described for 7-chloro-2-(4,4,5,5-tetramethyl-[1,3,2]dioxaborolan-2-yl)-1H-indole using 7-methyl-1H-indole.

133

7-Fluoro-2-(4,4,5,5-tetramethyl-[1,3,2]dioxaborolan-2-yl-1H-indole

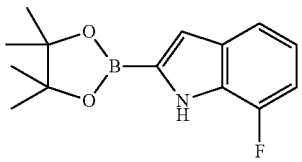

Prepared according to a procedure analogous to that described for 7-chloro-2-(4,4,5,5-tetramethyl-[1,3,2]dioxaborolan-2-yl)-1H-indole using 7-fluoro-1H-indole.

4-Methyl-2-(4,4,5,5-tetramethyl-[1,3,2]dioxaborolan-2-yl-1H-indole

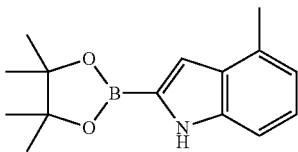

Prepared according to a procedure analogous to that described for 7-chloro-2-(4,4,5,5-tetramethyl-[1,3,2]dioxaborolan-2-yl)-1H-indole using 4-methyl-1H-indole.

4-Methoxy-1-methyl-2-(4,4,5,5-tetramethyl-[1,3,2]dioxaborolan-2-yl)-1H-indole

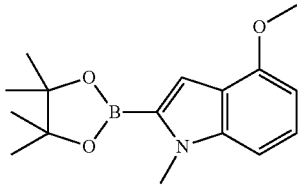

Prepared according to a procedure analogous to that described for 7-chloro-2-(4,4,5,5-tetramethyl-[1,3,2]dioxaborolan-2-yl)-1H-indole using 4-methoxy-1-methyl-1H-indole.

7-Ethyl-2-(4,4,5,5-tetramethyl-[1,3,2]dioxaborolan-2-yl)-1I-indole

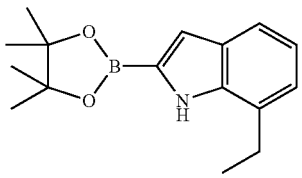

Prepared according to a procedure analogous to that described for 7-chloro-2-(4,4,5,5-tetramethyl-[1,3,2]dioxaborolan-2-yl)-1H-indole using 7-ethyl-1H-indole.

134

4,7-Dimethoxy-2-(4,4,5,5-tetramethyl-[1,3,2]dioxaborolan-2-yl)-1H-indole

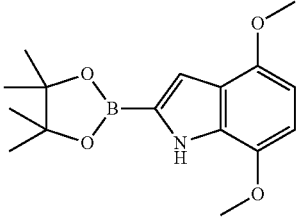

Prepared according to a procedure analogous to that described for 7-chloro-2-(4,4,5,5-tetramethyl-[1,3,2]dioxaborolan-2-yl)-1H-indole using 4,7-dimethoxy-1H-indole.

2-(4,4,5,5-Tetramethyl-[1,3,2]dioxaborolan-2-yl)-1H-indol-4-yl acetate

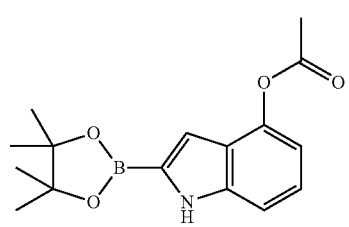

Prepared according to a procedure analogous to that described for 7-chloro-2-(4,4,5,5-tetramethyl-[1,3,2]dioxaborolan-2-yl)-1H-indole using 1H-indol-4-yl acetate.

2-(4,4,5,5-Tetramethyl-[1,3,2]dioxaborolan-2-yl)-1H-indol-4-carboxylic Acid, Methyl Ester

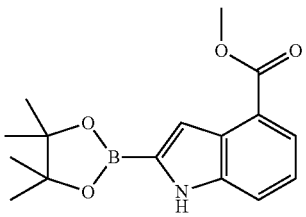

Prepared according to a procedure analogous to that described for 7-chloro-2-(4,4,5,5-tetramethyl-[1,3,2]dioxaborolan-2-yl)-1H-indole using 1H-indole-4-carboxylic acid, methyl ester.

7-Methoxy-2-(4,4,5,5-tetramethyl-[1,3,2]dioxaborolan-2-yl)-benzofuran

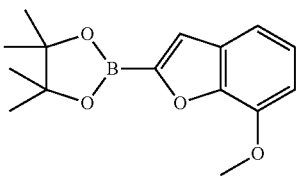

Prepared according to a procedure analogous to that described for 7-chloro-2-(4,4,5,5-tetramethyl-[1,3,2]dioxaborolan-2-yl)-1H-indole using 7-methoxy-benzofuran.

4,4,5,5-Tetramethyl-2-(3-methyl-benzo[b]thiophen-2-yl)[1,3,2]dioxaborolane

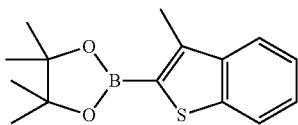

Prepared according to a procedure analogous to that described for 7-chloro-2-(4,4,5,5-tetramethyl-[1,3,2]dioxaborolan-2-yl)-1H-indole using 3-methyl-benzo[b]thiophene.

3-Methyl-2-(4,4,5,5-tetramethyl-[1,3,2]dioxaborolan-2-yl)-benzofuran

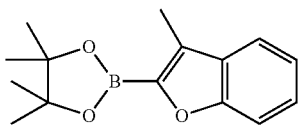

Prepared according to a procedure analogous to that described for 7-chloro-2-(4,4,5,5-tetramethyl-[1,3,2]dioxaborolan-2-yl)-1H-indole using 3-methyl-benzofuran.

7-Bromo-2-(4,4,5,5-tetramethyl-[1,3,2]dioxaborolan-2-yl)-1H-indole

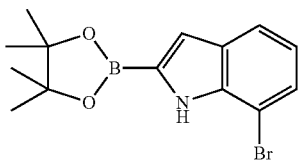

Prepared according to a procedure analogous to that described for 7-chloro-2-(4,4,5,5-tetramethyl-[1,3,2]dioxaborolan-2-yl)-1H-indole using 7-bromo-1H-indole.

3-Methyl-2-(4,4,5,5-tetramethyl-[1,3,2]dioxaborolan-2-yl)-1H-indole

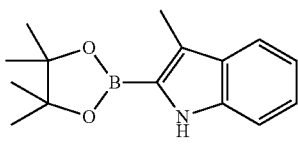

Prepared according to a procedure analogous to that described for 7-chloro-2-(4,4,5,5-tetramethyl-[1,3,2]dioxaborolan-2-yl)-1H-indole using 3-methyl-1H-indole.

7-Methyl-2-(4,4,5,5-tetramethyl-[1,3,2]dioxaborolan-2-yl)-benzofuran

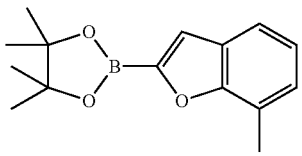

Prepared according to a procedure analogous to that described for 7-chloro-2-(4,4,5,5-tetramethyl-[1,3,2]dioxaborolan-2-yl)-1H-indole using 7-methyl-benzofuran.

7-Methoxy-2-(4,4,5,5-tetramethyl-[1,3,2]dioxaborolan-2-yl)-1H-indole

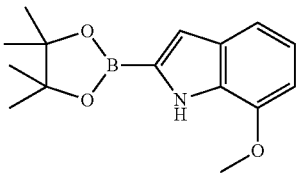

Prepared according to a procedure analogous to that described for 7-chloro-2-(4,4,5,5-tetramethyl-[1,3,2]dioxaborolan-2-yl)-1H-indole using 7-methoxy-1H-indole.

7-Ethoxy-1H-indole

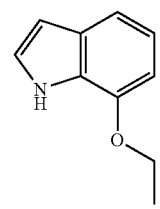

To a stirred solution of 1H-indol-7-ol (500 mg, 3.75 mmol) in acetone (10 mL) at r.t. was added potassium carbonate (3.11 g, 22.5 mmol), followed by iodoethane (0.45 mL, 5.63 mol). The mixture was stirred at r.t for 16 h then solvent removed under reduced pressure. The crude product thus obtained was purified by chromatography over silica gel to afford 7-ethoxy-1H-indole: $^1$H NMR (400 MHz, MeOD) δ ppm 1.51 (t, J=6.95 Hz, 3 H), 4.22 (q, J=6.91 Hz, 2 H), 6.42 (d, J=3.03 Hz, 1H), 6.63 (d, J=7.58 Hz, 1 H), 6.92 (t, J=7.83 Hz, 1 H), 7.04-7.23 (m, 2 H); MS (ES+): m/z 162.20 (MH+).

7-Ethoxy-2-(4,4,5,5-tetramethyl-[1,3,2]dioxaborolan-2-yl)-1H-indole

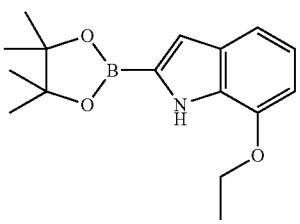

Prepared according to a procedure analogous to that described for 7-chloro-2-(4,4,5,5-tetramethyl-[1,3,2]dioxaborolan-2-yl)-1H-indole using 7-ethoxy-1H-indole.

7-Isopropoxy-1H-indole

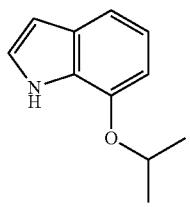

Made according to the procedure described for 7-ethoxy-1H-indole using 2-iodopropane.

7-Isopropoxy-2-(4,4,5,5-tetramethyl-[1,3,2]dioxaborolan-2-yl)-1H-indole

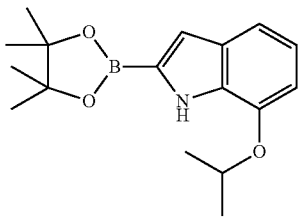

Prepared according to a procedure analogous to that described for 7-chloro-2-(4,4,5,5-tetramethyl-[1,3,2]dioxaborolan-2-yl)-1H-indole using 7-isopropoxy-1H-indole.

7-Trifluoromethyl-2-(4,4,5,5-tetramethyl-[1,3,2] dioxaborolan-2-yl)-1H-indole

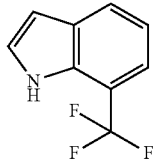

To a stirred mixture of 7-trifluoromethyl-1H-indole-2,3-dione (116 mg) in THF (5.00 mL) was added boron trifluoride etherate (0.205 mL, 1.62 mmol) followed by sodium borohydride (71.4 mg, 1.88 mmol). The resulting mixture was stirred at −20° C. for 2 hrs, then water (1 mL) was added and the mixture was stirred at 0° C. for 10 min. The solution was acidified to pH=1 with 2N HCl, warmed to r.t. and stirred at r.t. for 20 min prior to extraction with EtOAc. The extracts were dried over magnesium sulphate, concentrated in vacuo and the residue purified by chromatography over silica gel eluting with hexane to give 7-trifluoromethyl-1H-indole. $^1$H NMR (400 MHz, CDCl$_3$) δ ppm 6.63-6.68 (1 H, m), 7.20 (1 H, t, J=7.71 Hz), 7.30-7.35 (1 H, m), 7.47 (1 H, d, J=7.33 Hz), 7.83 (1 H, d, J=8.08 Hz), and 8.56 (1 H, br. s.).

7-Trifluoromethyl-2-(4,4,5,5-tetramethyl-[1,3,2] dioxaborolan-2-yl)-1H-indole

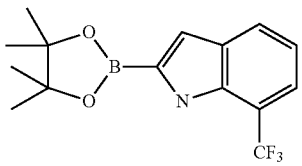

Prepared according to a procedure analogous to that described for 7-chloro-2-(4,4,5,5-tetramethyl-[1,3,2]dioxaborolan-2-yl)-1H-indole using 7-trifluoromethyl-1H-indole.

Ethyl N-[2(trifluoromethoxy)phenyl]carbamate

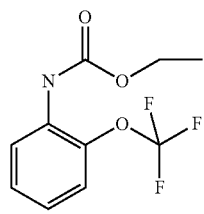

Ethyl chloroformate (4.4 mL, 0.046 mol) was added to a mixture of 2-(trifluoromethoxy)aniline (8.25 g, 0.0466 mol), sodium carbonate (15 g, 0.14 mol), 1,4-dioxane (70 mL) and water (70 mL) at 0° C. and the reaction mixture stirred at room temperature overnight. The reaction mixture was then washed with ether, acidified (pH 3) and the product extracted into EtOAc (3×40 mL). The combined extracts were washed with water (40 mL) and brine (40 mL), dried over Na2SO4 and the solvent removed in vacuo to give the desired product in a 84% yield. $^1$H NMR (400 MHz, CDCl$_3$): δ 1.33 (t, J=5.2 Hz, 3H), 4.25 (q, J=6.8 Hz, 2H), 6.91 (br, 1H), 7.04 (m, 1H), 7.23 (m, 1H), 7.28 (m, 1H) and 8.2 (m, 1H). MS (ES+): m/z 250.12 [MH+].

Ethyl N-[2-iodo-6-(trifluoromethoxy)phenyl]carbamate

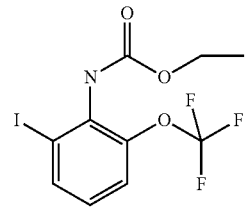

A 1.4 M solution of sec-butyllithium in cyclohexane (3.0 mL) was added drop-wise to a solution of ethyl N-[2-(trifluoromethoxy)phenyl]carbamate (0.5000 g, 0.002006 mol) in THF (9 mL) at −70° C. After stirring for 1 hour a solution of iodine (0.51 g, 0.002 mol) in THF (1.0 mL) was added drop-wise at −70° C. Stirring was continued for another 1 hour then the mixture was quenched with saturated ammonium chloride solution. Water (50 mL) was added and the mixture extracted with diethyl ether (3×40 mL). The combined organic phases was washed with 40% sodium meta-bisulfite solution, water and brine, then dried over Na2SO4 and the solvent removed in vacuo to give the desired product in a 73% yield. $^1$H NMR (400 MHz, CDCl$_3$): δ 1.29-1.36 (m, 3H), 4.21-4.28 (m, 2H), 6.21 (br, 1H), 7.05 (t, J=8.0 Hz, 1H), 7.30 (m, 1H) and 7.80 (dd, J=6.8, 1.2 Hz, 1H). MS (ES+): m/z 375.78 [MH+].

Ethyl [2-trifluoromethoxy-6-(trimethylsilanylethynylphenyl)]carbamate

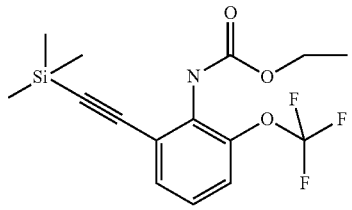

A mixture of Pd(PPh3)2Cl2 (83 mg, 0.00012 mol) and copper (I) iodide (23 mg, 0.00012 mol) in triethylamine (44 mL, 0.32 mol) was heated at 40° C. for 20 min then cooled tort and ethyl [2-iodo-6-(trifluoromethoxy)phenyl]carbamate (4.50 g, 0.0120 mol) was added in one portion. The mixture was stirred at room temperature for 30 min, then (trimethylsilyl)acetylene (1.6 mL, 0.011 mol) was added and the mixture stirred for a further 2 hours. The solvent was removed in vacuo and the residue was partitioned between water and diethyl ether (60 mL of each). The organic was washed with 1N HCl and brine, then dried over Na2SO4 then the solvent removed in vacuo. The reaction was chromatographed over silica gel eluting with 20% EtOAc/hexane to afford the desired product in 80% yield. MS (ES+): m/z 345.99 [MH+].

7-Trifluoromethoxy-1H-indole

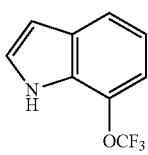

Sodium ethoxide (0.65 mL, 0.0017 mol, 2.6M) was added to a solution of ethyl [2-trifluoromethoxy-6-(trimethylsilanylethynylphenyl)]carbamate in EtOH (5.0 mL) and the mixture stirred at 72° C. for 14 hours. The solvent was removed under reduced pressure and the residue was partitioned between diethyl ether and water (30 mL of each). The ether phase was washed with brine and dried over $Na_2SO_4$ yielding the desired compound in 59% yield. $^1$H NMR (400 Adz, $CDCl_3$): δ 6.60-6.61 (m, 1H), 7.07-7.09 (m, 2H), 7.25 (d, J=5.6 Hz, 1H), 7.55-7.57 (m, 1H) and 8.42 (br, 1H). MS (ES+): m/z 202.18 [MH+].

7-Trifluoromethoxy-2-(4,4,5,5-tetramethyl-[1,3,2]dioxaborolan-2-yl)-indole

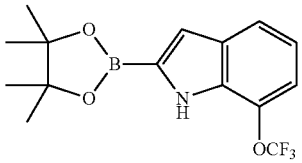

Prepared according to a procedure analogous to that described for 7-chloro-2-(4,4,5,5-tetramethyl-[1,3,2]dioxaborolan-2-yl)-1H-indole using 7-trifluoromethoxy-1H-indole.

7-Phenyl-1H-indole

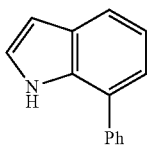

To a suspension of 7-bromo-1H-indole (196 mg, 0.00100 mol) in 1,4-dioxane (4 mL) and water (1 mL) was added phenylboronic acid (146 mg, 0.00120 mol), potassium carbonate (414 mg, 0.00300 mol) and [1,1'-bis(diphenylphosphino)ferrocene]dichloropalladium(II), complex with dichloromethane (1:1) (82 mg, 0.00010 mol). The flask was evacuated and refilled with nitrogen, three times then the mixture was heated at 100° C. overnight. The mixture was diluted with EtOAc (30 mL), washed with sat. aq. $NaHCO_3$ (10 mL) and brine (10 mL), then dried over anhydrous sodium sulfate and the solvent removed in vacuo. The crude material was purified by chromatography over silica gel eluting with hexane/EtOAc to give the title compound (180 mg, 93% yield). $^1$H NMR ($CDCl_3$, 400 MHz): δ 6.64 (dd, J=3.0, 2.0 Hz, 1H), 7.18-7.26 (m, 3H), 7.41 (t, J=7.5 Hz, 1H), 7.48-7.57 (m, 2H), 7.61-7.70 (m, 3H) and 8.43 (br s, 1H) ppm. LC-MS (ES+): 194 [MH+].

7-Phenyl-2-(4,4,5,5-tetramethyl-[1,3,2]dioxaborolan-2-yl)-1H-indole

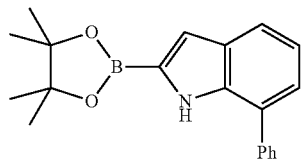

Prepared according to a procedure analogous to that described for 7-chloro-2-(4,4,5,5-tetramethyl-[1,3,2]dioxaborolan-2-yl)-1H-indole using 7-phenyl-1H-indole.

7-Cyclopropyl-2-(4,4,5,5-tetramethyl-[1,3,2]dioxaborolan-2-yl)-1-indole

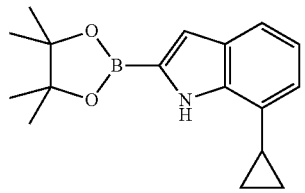

Prepared according to the procedures described above for 7-phenyl-2-(4,4,5,5-tetramethyl-[1,3,2]dioxaborolan-2-yl)-1H-indole using cyclopropylboronic acid in place of phenylboronic acid. $^1$H NMR ($CDCl_3$, 400 MHz): δ 0.75-0.82 (m, 2H), 0.95-1.04 (m, 2H), 2.08 (m, 1H), 6.59 (dd, J=3.0, 2.0 Hz, 1H), 6.96 (d, J=7.1 Hz, 1H), 7.06 (t, J=7.6 Hz, 1H), 7.25 (m, 1H), 7.52 (d, J=7.8 Hz, 1H) and 8.39 (br s, 1H) ppm. LC-MS (ES, Pos.): 158 [MH+].

6-Bromo-7-fluoro-1H-indole

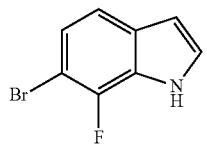

To a solution of 1-bromo-2-fluoro-3-nitrobenzene (2.5 g, 11.3 mmol) in THF (25 mL) at −50° C. was added vinyl magnesium bromide (34 mL, 34 mmol) and the mixture was stirred at 40° C. for 1 h. The reaction was quenched with saturated ammonium chloride solution and extracted with ethyl acetate. The organic layer was washed with brine, dried over anhydrous sodium sulfate and evaporated under reduced pressure to yield a gun, which was purified by column chromatography over silica gel eluting with EtOAc/hexane to afford pure 6-bromo-7-fluoro-1H-indole. $^1$H NMR (400

MHz, CDCl₃) δ=6.53-6.62 (m, 1H), 7.16-7.25 (m, 2H), 7.29 (d, J=8.34 Hz, 1H) and 8.36 (br. s., 1H); MS (ES+): m/z 214.08 [MH+].

6-Bromo-7-fluoro-1-methyl-1H-indole

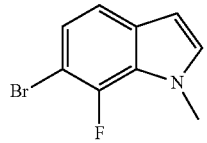

To a solution of 6-bromo-7-fluoro-1H-indole (470 mg, 2.19 mmol) in THF (7 mL) at −10° C. was added sodium hydride (175 mg, 4.39 mmol, 60% dispersion) and the mixture was stirred at 0° C. for 30 min. Methyl iodide was added at 0° C. and the reaction was allowed to warm to at 10° C. and stirred for 2 h. The reaction was quenched with saturated ammonium chloride and extracted with DCM. The DCM extract was washed with brine, dried over anhydrous sodium sulfate and evaporated under reduced pressure. The crude product was purified by column chromatography over silica gel eluting with EtOAc/hexane to afford 6-bromo-7-fluoro-1-methyl-1H-indole. ¹H NMR (400 MHz, CDCl₃) δ=3.95 (d, J=2.00 Hz, 1H), 6.42 (t, J=2.78 Hz, 1H), 6.94 (d, J=3.03 Hz, 1H), 7.09-7.15 (m, 1H) and 7.20 (d, J=8.34 Hz, 1H); MS (ES+): m/z 228.04 [MH+].

7-Fluoro-1-methyl-6-(4,4,5,5-tetramethyl-[1,3,2]dioxaborolan-2-yl)-1H-indole

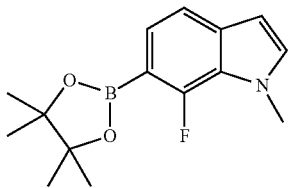

To a mixture of 6-bromo-7-fluoro-1-methyl-1H-indole (420 mg, 1.84 mmol), 4,4,4',4',5,5,5',5'-octamethyl-2,2'-bi-1,3,2-dioxaborolane (514 mg, 2.02 mmol), potassium acetate (542 mg 5.52 mmol), [1,1'-bis(diphenylphosphino)ferrocene]dichloropalladium(II) complex with dichloromethane (1:1 complex, 150 mg, 0.184 mmol) and 1,1'-bis(diphenylphosphino)ferrocene (102 mg, 0.184 mmol) was added dioxane (10 mL) and the mixture was degassed by bubbling through with nitrogen for 3 min. The reaction mixture was heated at 100° C. overnight then the dioxane was removed under reduced pressure and the residue was dissolved in DCM and filtered to remove inorganics. The filtrate was concentrated and the crude product was purified by column chromatography over silica gel eluting with EtOAc/hexane to afford pure 7-fluoro-1-methyl-6-(4,4,5,5-tetramethyl-[1,3,2]dioxaborolan-2-yl)-1H-indole. ¹H NMR (400 MHz, CDCl₃) δ=1.41 (s, 12H), 4.02 (d, J=2.02 Hz, 3H), 6.46 (t, J=2.65 Hz, 1H), 7.03 (d, J=3.03 Hz, 1H) and 7.28-7.47 (m, 2 H); MS (ES+): m/z 276.03 [MH+].

7-Trifluoromethyl-benzo[b]thiophene

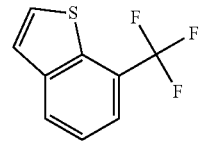

To a stirred solution of 2-(trifluoromethyl)benzenethiol (5.000 g, 0.028 mol) in acetone (50 mL) was added 2-bromo-1,1-diethoxyethane (6.08 g, 0.030 mol) and potassium carbonate (7.757 g, 0.056 mol). The resulting mixture was then stirred at 45° C. for 2 hours prior to removal of the solvent in vacuo and suspension of the residue in EtOAc. The inorganic salts were filtered off and the organic phase was concentrated to give crude product, which was used in next step without further purification. This residue was dissolved in toluene (50 mL), and to this solution was added PPA (10 g) and the resulting mixture stirred at 95-100° C. for 2 hours. The mixture was allowed to cool to r was poured into ice-water, then extracted with EtOAc (3×50 ml). The combined extracts were washed with aqueous sodium bicarbonate followed by brine, then dried over anhydrous sodium sulfate and evaporated under reduced pressure to yield an oil. This was purified by column chromatography over silica gel eluting with hexane to give 7-trifluoromethyl-benzo[b]thiophene. ¹H NMR (400 MHz, MeOD) δ ppm 7.49-7.57 (m, 2H), 7.70 (d, J=7.33 Hz, 1H), 7.74 (d, J=5.56 LIZ, 1H) and 8.10 (d, J=8.08 Hz, 1H).

7-Trifluoromethylbenzo[b]thiophene-2-boronic Acid

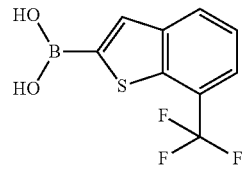

To a solution of 7-trifluoromethyl-benzo[b]thiophene (0.52 g, 0.0026 mol) in THF (30 mL) at −78° C. was added 2.5 M of n-BuLi in hexane (1.4 mL). The reaction was then slowly warmed up to −30° C. over 30 min. and stirred at this temperature for 10 min prior to recooling to −78° C. and treatment with triisopropyl borate (0.7255 g, 0.0038 mol). The reaction was then slowly warmed up to 0° C. then was quenched with saturated ammonium chloride and the solvent removed in vacuo. To the residue was added aqueous sodium hydroxide (10 mL, 2N solution) followed by water (30 mL) then this mixture was extracted with DCM. The aqueous solution was acidified using dilute sulfuric acid (2N solution), filtered and the residue dried in vacuo to yield 7-trifluoromethylbenzo[b]thiophen-2-boronic acid. ¹H NMR (400 MHz, MeOD) δ ppm 7.55 (1 H, t, J=7.45 Hz), 7.75 (1 H, d, J=7.07 Hz), 8.02 (1 H, s) and 8.17 (1 H, d, J=#7.83 Hz).

N-Methylindole-6-boronic Acid

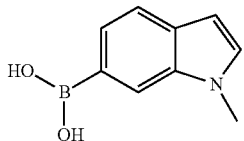

A mixture of indole-6-boronic acid (0.100 g, 0.615 mol), sodium hydride (0.07 g, 20 mmol) and THF (5 mL, 60 mmol) was stirred at rt for 20 min. then methyl iodide (100 uL, 20 mmol) was added and the mixture was allowed to stir at rt for 3 hours. The reaction was quenched with sat. NH$_4$Cl solution, washed with brine and dried over Na$_2$SO$_4$, then the solvent was removed in vacuo. The crude product was purified by chromatography over silica gel eluting with 1:9 EtOAc/hexane and 1% MeOH, yielding the desired product. $^1$H NMR (400 MHz, CDCl$_3$) δ ppm 3.99 (s, 3H), 6.58 (m, 1H). 7.23 (m, 1H), 7.81 (m, 1H), 8.08 (m, 1H) and 8.34 (m, 1H). MS (ES+): m/z 176.15 [MH+].

4-Bromo-3-methyl-2-nitrophenol

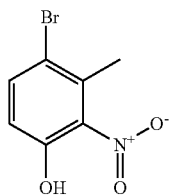

To a solution of 3-methyl-2-nitrophenol (2.0 g, 13.06 mmol) in acetic acid (40 mL) was added bromine (0.70 mL, 13.71 mmol) and the mixture was stirred at RT for 5 h. The reaction was poured in to ice water and the yellow precipitate formed was filtered and washed with water and dried in vacuo to yield 4-bromo-3-methyl-2-nitrophenol. $^1$H NMR (400 MHz, CDCl$_3$) δ=2.61 (s, 3H), 2.62 (s, 5H), 6.92 (d, J=8.84 Hz, 1H), 7.66 (d, J=9.09 Hz, 1H) and 9.28 (s, 1 H); MS (ES+): m/z 215.00 [M-17].

1-Bromomethoxy-2-methyl-3-nitrobenzene

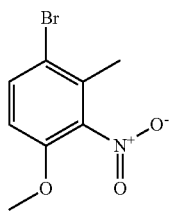

To a solution of 4-bromo-3-methyl-2-nitrophenol (2.200 g, 9.48 mmol) in acetone (35 mL) was added potassium carbonate (3.276 g, 23.70 mmol) and methyl iodide (1.47 mL, 23.70 mmol) and the mixture was heated to reflux for 4 h. The reaction was cooled to rt, filtered and the filtrate was evaporated under reduced pressure to afford the crude product. Purification of the crude product by column chromatography over silica gel eluting with EtOAc/hexane afforded pure 1-bromo-4-methoxy-2-methyl-3-nitrobenzene as pale yellow solid. $^1$H NMR (400 MHz, CDCl$_3$) δ=2.33 (s, 2H), 3.87 (s, 3H), 6.78 (d, J=8.84 Hz, 1H) and 7.58 (d, J=8.84 Hz, 1H); MS (ES+): m/z 247.26 [MH+].

1-[(E)-2-(6-bromo-3-methoxy-2-nitrophenyl)vinyl]pyrrolidine

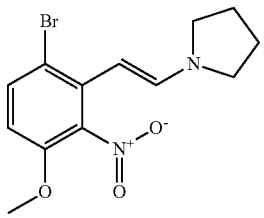

To a solution of 1-bromo-4-methoxy-2-methyl-3-nitrobenzene (1.400 g, 5.68 mmol) and 1,1-dimethoxy-N,N-dimethylethanamine (0.884 mL, 6.657 mmol) in DMF (10.0 mL) was added pyrrolidine (0.555 mL, 6.656 mmol) and the mixture was heated to at 110° C. for 4 h. The DMF was removed and the residue was recrystallized from DCM:methanol (1:6) mixture to afford 1-[(E)-2-(6-bromo-3-methoxy-2-nitrophenyl)vinyl]pyrrolidine.

4-Bromo-7-methoxy-1H-indole

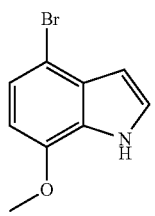

To a solution of 1-[(E)-2-(6-bromo-3-methoxy-2-nitrophenyl)vinyl]pyrrolidine (1.3 g, 3.97 mmol) in THF (6 mL) and methanol (6 mL) was added Raney Ni (≈500 mg) followed by hydrazine (0.19 mL). (CAUTION: Exothermic reaction with vigorous gas evolution). Hydrazine (0.19 mL) was added again, two times, after 30 min and 1 h. The reaction was stirred at 45° C. for 2 h, filtered through a pad of celite. The filtrate was concentrated in vacuo and the residue purified by chromatography over silica gel eluting with EtOAc/hexane to afford pure 4-bromo-7-methoxy-1H-indole. H NMR (400 MHz, CDCl$_3$)=3.94 (s, 3H), 6.52 (d, J=8.08 Hz, 1H), 6.56 (dd, J=3.16, 2.40 Hz, 1H), 7.17 (d, J=8.08 Hz, 1H), 7.22 (t, J=2.78 Hz, 1H) and 8.47 (br. s., 1H); MS (ES+): m/z 226.12 [MH+].

2-Phenyl-5-(4,4,5,5-tetramethyl-[1,3,2]dioxaborolan-2-yl)-1,3-benzothiazole

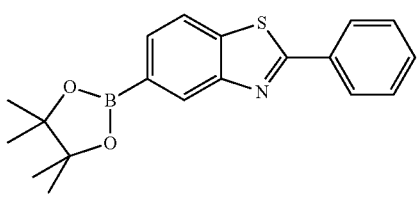

A stirred solution of 5-bromo-2-phenylbenzothiazole (0.500 g, 0.00172 mol), bis(pinacolato)diboron (0.508 g, 0.00200 mol), 1,3-bis(2,6-diisopropylphenyl)imidazol-2-ylidene hydrochloride (0.044 g, 0.10 mmol), Pd(OAc)$_2$ (0.019 g, 0.086 mmol) and AcOK (0.423 g, 0.00431 mol) in anhydrous THF (9.78 mL, 0.121 mol) was heated at 72° C. under Argon for 29 h. The mixture was filtered through a multi-layered pad of anhydrous sodium sulfate, silica gel and celite and the filtrate was concentrated in vacuo and the solids triturated multiple times with hexanes to give the title compound. $^1$H NMR (400 MHz, CHLOROFORM-d) δ ppm=1.39 (s, 12 H), 7.49-7.56 (m, 3 H), 7.83 (dd, J=8.08, 1.01 Hz, 1 H, 7.92 (d, J=7.33 Hz, 1 H), 8.12-8.18 (m, 2 H) and 8.60 (s, 1 H); MS (ES+): m/z 337.91 [MH+].

4-(Methoxycarbonyl)-4-methylcyclohexanecarboxylic Acid

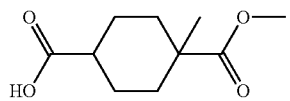

N,N-Diisopropylamine (1.18 mL, 8.35 mmol) was added dropwise to a 2M solution of "butyllithium (4.18 mL, 8.4 mmol) at −78° C. under nitrogen. After 15 min at this temperature the solution was raised to and held at 0° C. for 15 min prior to re-cooling to −78° C. and treatment with a solution of 4-(methoxycarbonyl)cyclohexanecarboxylic acid (0.62 g, 3.34 mmol) in THF (8 mL). After 30 min., iodomethane (0.31 mL, 5 mmol) was added dropwise and the mixture was allowed to warm to rt over 2 hr. The mixture was cooled to at 0° C., quenched with 2 N HCl (10 mL) then was extracted with EtOAc (2×10 mL), washed with brine (3×15 mL), and dried over anhydrous magnesium sulfate. Concentration of the combined organic extracts afforded a yellow solid. NMR (CDCl$_3$) consistent with crude, desired product.

Methyl trans-4-{[(2,5-dioxopyrrolidin-1-yl)oxy]carbonyl}cyclohexanecarboxylate

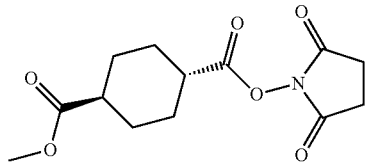

A solution of N-hydroxysuccinimide (6.18 g, 0.0537 mol) and trans-4-(methoxycarbonyl)cyclohexanecarboxylic acid (10.00 g, 0.05370 mol) in THF (100.00 mL) was charged with (N,N'-dicyclohexylcarbodiimide (11.08 g, 0.0537 mol) in THF (16 mL). This reaction was stirred at rt for an additional 16 h then stirred at 45° C. for 1 h. The reaction mixture was filtered while still warm through a flitted funnel. The cake was washed with 3 more portions of THF and the filtrate was concentrated in vacuo and was crystallized from i-PrOH (300 mL) and filtered through a flitted funnel resulting in 11.8 g, (78% yield) of the title compound as a white crystals. $^1$H NMR (400 MHz, CDCl3) δ ppm 1.45-1.69 (m, 4H), 2.07- 2.16 (m, 2H), 2.18-2.28 (m, 2H), 2.29-2.39 (m, 1H), 2.59-2.71 (m, 1H) 2.84 (br. s., 4H) and 3.68 (s, 3H); MS (ES+): m/z 284.09 [MH+].

Methyl trans-4-{[3-amino-5-oxo-4,5-dihydro-1,2,4-triazin-6-yl)methyl]carbamoyl}cyclohexanecarboxylate

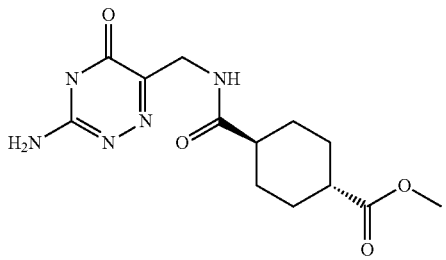

A solution of 3-amino-6-(aminomethyl)-1,2,4-triazin-5(4H)-one [J. Heterocyclic Chem., (1984), 21 (3), 697] (2.00 g, 0.0113 mol) in H$_2$O (60.0 mL, 3.33 mol) was cooled to 0° C. and drop wise charged with 1.00 M of NaHCO$_3$ in H$_2$O (22.5 mL) and allowed to warm to rt. This mixture was charged with methyl trans-4-{[(2,5-dioxopyrrolidin-1-yl)oxy]carbonyl}cyclohexanecarboxylate (3.8 g, 0.012 mol) in 1:1 THF/MeCN (40 mL). After 30 min a precipitate began to form in the reaction. This was allowed to stir at rt for an additional 16 h and was filtered through a fritted funnel and washed with H$_2$O (2×), diethyl ether (2×), and dried in vacuo resulting in the title compound 2.92 g, (84% yield) as an off-white solid. $^1$H NMR (400 MHz, DMSO-d$_6$) δ ppm 1.24-1.55 (m, 4H), 1.83 (s, 2H), 1.98 (d, J=10.61 Hz, 2H), 2.27 (s, 2H), 3.64 (s, 3H), 4.10 (d, J=5.81H 2H), 6.81 (br. s., 2H), 7.91 (t, J=5.56 Hz, 1H) and 11.98 (br. s., 1H); MS (ES+): m/z 310.05 [MH+].

Methyl trans-4(2-amino-4-oxo-3,4-dihydroimidazo[5,1-f][1,2,4]triazin-7-yl)cyclohexanecarboxylate

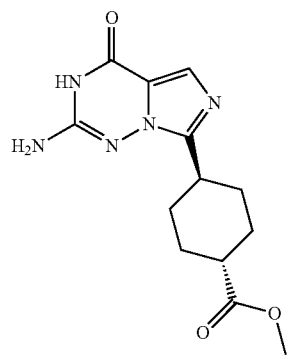

A solution of methyl trans-4-{[(3-amino-5-oxo-4,5-dihydro-1,2,4-triazin-6-yl)methyl]carbamoyl}cyclohexanecarboxylate (2.00 g, 0.00646 mol) in 1,2-dichloroethane (130 mL) was charged with POCl$_3$ (4.2 mL, 0.045 mol) and heated to reflux for 3 h. The reaction mixture was concentrated in vacuo then partitioned between EtOAc and sat. NaHCO$_3$ and separated. The aqueous was re-extracted with EtOAc (3×) and the combined organic fractions were dried over Na$_2$SO$_4$, filtered, and concentrated in vacuo resulting in 1.43 g, (76% yield) of the title compound as an off-white solid. $^1$H NMR (400 MHz, DMSO-d$_6$) δ ppm 1.43 (q, J=11.79 Hz, 2H), 1.61 (q, J=12.55 Hz, 2H), 1.85-2.11 (m, 4H), 2.38 (t, J=11.87 Hz, 1H), 2.98 (t, J=11.75 Hz, 1H), 3.61 (s, 3 H), 6.17 (br. s., 2 H), 7.49 (s, 1H) and 10.90 (br. s., 1H); MS (ES+): m/z 292.25 [MH+].

Methyl trans-4-(2-amino-4-oxo-3,4-dihydroimidazo[5,1-f][1,2,4]triazin-7-yl)cyclohexanecarboxylate

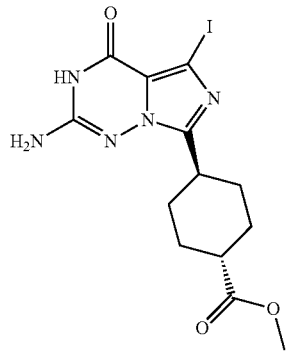

A solution of methyl trans-4-(2-amino-4-oxo-3,4-dihydroimidazo[5,1-f][1,2,4]triazin-7-yl)cyclohexanecarboxylate (0.200 g, 0.000686 mol) and N-iodosuccinimide (0.278 g, 0.00124 mol) in anhydrous DMF (4.0 mL) was stirred at rt for 48 h. The reaction was concentrated in vacuo then partitioned between H$_2$O and EtOAc. The aqueous material was re-extracted with EtOAc (3×) and the combined organic fractions were washed with H$_2$O (2×), Na$_2$S$_2$O$_3$ (2×) and brine (1×). The aqueous was re-extracted with CHCl$_3$ and combined with the EtOAc fractions dried over Na$_2$SO$_4$, filtered and concentrated in vacuo resulting in 229 mg, (79.9% yield) of the title compound as a light orange solid. $^1$H NMR (400 MHz, DMSO-d$_6$) δ ppm 1.34-1.65 (m, 4H), 1.88-2.06 (m, 4H), 2.33-2.45 (m, 1H), 2.91-3.01 (m, 1H), 3.61 (s, 3H), 6.17 (s, 2H) and 10.82 (br. s., 1H); MS (ES+): m/z 417.82 [MH+].

Methyl trans-4-(5-iodo-4-oxo-3,4-dihydroimidazo[5,1-f][1,2,4]triazin-7-yl)cyclohexanecarboxylate

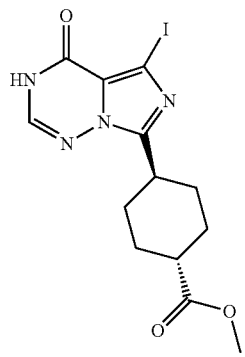

A solution of methyl trans-4-(2-amino-5-iodo-4-oxo-3,4-dihydroimidazo[5,1-f][1,2,4]triazin-7-yl)cyclohexanecarboxylate (0.880 g, 0.00211 mol) in anhydrous THF (74 mid) and DMF (13.2 mL) was charged with tert-butyl nitrite (1.2 mL, 0.010 mol) and stirred at rt for 2 h. The reaction was concentrated in vacuo and was purified by chromatography over silica gel [eluting with 5% MeOH in CHCl$_3$] resulting in 570 mg, (67% yield) of the title compound as a pale orange solid. ($^1$H NMR (400 MHz, DMSO-d$_6$) δ ppm 1.40-1.54 (m, 2H), 1.56-1.69 (m, 2H), 1.92-2.06 (m, 4H), 2.36-2.46 (m, 1H), 3.02-3.14 (m, 1H), 3.61 (s, 3H), 7.89 (d, J=3.28 Hz, 1 H) and 11.79 (br. s., 1H); MS (ES+): m/z 402.86 [MH+].

Methyl trans-4-(4-amino-5-iodoimidazo[5,1-f][1,2,4]triazin-7-yl)cyclohexanecarboxylate

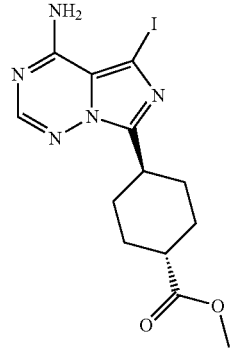

A solution of 1H-1,2,4-triazole (0.881 g, 0.0128 mol) in pyridine (3.00 mL) was charged with POCl$_3$ (0.396 mL, 0.00425 mol) and stirred at rt for 15 min. To this mixture was drop wise added methyl trans-4-(5-iodo-4-oxo-3,4-dihydroimidazo[5,1-f][1,2,4]triazin-7-yl)cyclohexanecarboxylate (0.570 g, 0.00142 mol) in pyridine (6.00 mL) and stirred at rt for an additional 2.45 h. The reaction was quenched with excess 2 M of NH$_3$ in i-PrOH (40.00 mL) at 0° C. and allowed to stir at rt for an additional 3 h. The reaction was concentrated in vacuo and partitioned between EtOAc and sat. NaHCO$_3$ and separated. The aqueous was washed with EtOAc (3×) and the combined organic fractions were washed with brine (1×). The aqueous was re-extracted with CHCl$_3$ (3×) and the organic was added to the EtOAc fractions. The combined organic fractions were dried over Na$_2$SO$_4$, filtered and concentrated in vacuo. The crude brown/red solid was purified by chromatography over silica gel [eluting with 5% MeOH in CHCl$_3$] resulting in 438 mg, (76% yield) of the title compound as a light yellow solid. $^1$H NMR (400 MHz, DMSO-d$_6$) δ ppm 1.39-1.54 (m, 2H), 1.55-1.71 (m, 2H), 1.92-2.07 (m, 4H), 2.35-2.46 (m, 1H), 3.06-3.19 (m, 1H), 3.61 (s, 3H), 6.77 (br. s., 1H) 7.86 (s, 1H) and 8.44 (br. s., 1H); MS (ES+): m/z 401.85 [MH+].

1-Chloro-2-[(2,2-diethoxyethyl)thio]benzene

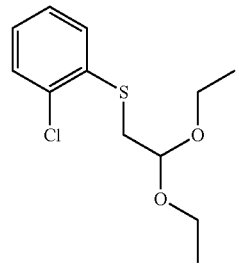

To a solution of 2-chlorobenzenethiol (5.0 g, 34.5 mmol) in acetone (35 mL) was added 2-bromo-1,1-diethoxyethane (7.15 g, 36.3 mmol) followed by potassium carbonate (9.55 g, 69.1 mmol). The mixture was heated at reflux for 3 h. then cooled to rt, filtered and the filtrate evaporated under reduced pressure to yield the crude product. This material was purified by chromatography over silica gel eluting with ethyl acetate in hexanes (0→2%) to afford pure 1-chloro-2-(2,2-diethoxyethylsulfanyl)benzene (7.3, 80%). $^1$H NMR (400 MHz, CDCl$_3$) δ=1.20 (t J=7.07 Hz, 6H), 3.15 (d, J=5.56 Hz, 2H), 3.51-3.61 (m, 2H), 3.63-3.74 (m, 2H), 4.69 (t, J=5.56 Hz, 1H), 7.12 (td, J=7.58, 1.52 Hz, 1H), 7.20 (td, J=7.58, 1.52 Hz, 1H), 7.36 (dd J=−7.83, 1.52 Hz, 1H), 7.39 (dd, J=8.08, 1.52 Hz, 1H); MS (ES+): m/z 187.17 [M-74].

7-Chlorobenzo[b]thiophene

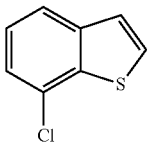

To a solution of 1-chloro-2-(2,2-diethoxyethylsulfanyl)benzene (3.95 g, 15.14 mmol) in toluene (40 mL) was added polyphosphoric acid (15 g, 137.5 mmol). The mixture was heated at reflux for 4 h. then was poured in to ice water, stirred for 30 min and extracted with toluene. The combined toluene extracts were washed with aqueous sodium bicarbonate followed by brine, dried over anhydrous sodium sulfate and evaporated under reduced pressure to yield the crude product. This material was purified by chromatography over silica gel eluting with hexane to afford pure 7-chlorobenzo[b]thiophene (1.72 g, 67.5%). $^1$H NMR (400 MHz, CDCl$_3$) δ=7.13-7.30 (m, 3H), 7.38 (d, J=5.31 Hz, 1H), 7.62 (dd, J=7.33, 1.52 Hz, 1H); MS (ES+): m/z 169.06 [MH+].

7-Chlorobenzo[b]thiophene-2-boronic Acid

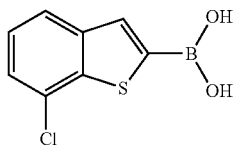

To a solution of 7-chlorobenzo[b]thiophene (1.0 g, 5.92 mmol) in THF (25 mL) at −78° C. was added "butyllithium (7.41 mL 11.8 mmol, 1.6 M solution). The reaction was allowed to warm to −30° C. then was cooled back to −78° C. and triisopropyl borate (2.23 g, 11.8 mmol) was added. The mixture was allowed to warm to 0° C., saturated ammonium chloride added and the organic phase separated off and concentrated in vacuo. To the residue was added aqueous sodium hydroxide (10 mL, 2N solution) followed by water (30 mL) and the mixture was washed with DCM. The aqueous phase was acidified with 2N sulfuric acid, and the resulting precipitate isolated by filtration and dried under vacuum to yield 7-chlorobenzo[b]thiophene-2-boronic acid (1.21 g, 96%) as white solid. $^1$H NMR (400 MHz, CDCl$_3$) δ=7.41 (t, J=7.70 Hz 1H), 7.50 (d, J=7.70 Hz, 1H), 7.91 (d, J=7.70 Hz, 1H), 8.03 (s, 1H), 8.63 (s, 2H); MS (ES+): m/z 211.86 [M+].

7-(methylthio-1H-indole

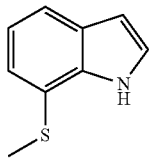

To a solution of 7-bromo-1H-indole (3.0 g, 15.3 mmol) in THF (60 mL) at −78° C. was added 'BuLi (1.7 M, 33.8 at, 57.4 mmol) and the mixture was allowed to warm to 0° C. The reaction was re-cooled to −78° C. and a solution of dimethyl disulfide (2.0 mL, 22.9 mmol) was added and the reaction was allowed to warm to 0° C. The reaction was quenched with saturated ammonium chloride and extracted with ethyl acetate. The organic layer was washed with brine, dried over anhydrous sodium sulfate and evaporated under reduced pressure to yield the crude product. This material was purified by chromatography over silica gel eluting with ethyl acetate in hexanes (0-2%) to afford pure 7-(methylthio)-1H-indole (1.4 g, 55%). $^1$H NMR (400 MHz CDCl$_3$) δ=2.50 (s, 3 H), 6.58 (dd, J=3.03, 2.02 Hz, 1H), 7.09 (t, J=7.58 Hz, 1H), 7.18-7.31 (m, 2H), 7.56 (d, J=7.83 Hz, 1H), 8.45 (br. s., 1 H); MS (ES+): m/z 164.15 [MH+].

7-(Methylsulfonyl)-1H-indole

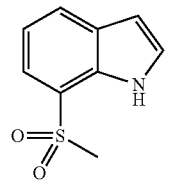

To a solution of 7-methylthio)-1H-indole (1.1 g, 6.7 mmol) in DCM (25 ml) at 40° C. was added m-chloroperbenzoic acid (3.02 g, 13.4 mmol) and the reaction was stirred at −40° C. for 30 min. The reaction mixture was then quenched with saturated sodium bicarbonate and extracted with DCM. The DCM extracts was washed with water, brine, dried over anhydrous sodium sulfate and evaporated under reduced pressure to yield the crude product. This material was purified by chromatography over silica gel eluting with hexanes (0→10%) to afford pure 7-(methylsulfonyl)-1H-indole (987 mg, 75%). $^1$H NMR (400 MEA CDCl$_3$) δ=3.12 (s, 1H), 6.66 (d, J=2.53 Hz, 1H), 7.24 (t, J=7.71 Hz, 1H), 7.35 (d, J=1.77 Hz, 1H), 7.68 (d, J=7.07 Hz, 1H), 7.90 (d, J=7.83 Hz, 1H), 9.68 (br. s., 1H); MS (ES+): m/z 196.08 [MH+].

Methyl trans-4-cyanocyclohexanecarboxylate

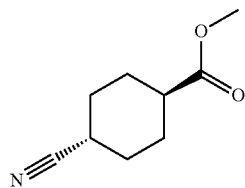

Chlorosulfonyl isocyanate (1.0 mL, 0.012 mol) was added to a solution of trans-4-(methoxycarbonyl)cyclohexanecarboxylic acid (2.00 g, 0.0107 mol) in DCM cooled to 0° C. The resulting solution was heated at reflux for 15 minutes and then cooled 0° C. and treated dropwise with DM. The mixture was stirred at room temperature overnight then poured onto ice water and the organic phase separated and washed with a saturated solution of sodium bicarbonate. The solvent was removed in vacuo and the crude material was taken up in ethyl acetate, washed with 1N aq. NaOH (10 mL) and the ethyl acetate removed in vacuo. The resulting crude product was used in subsequent steps without further purification. $^1$H NMR (400 MHz, CHLOROFORM-d) δ ppm 1.36-1.70 (4 H, m), 2.01-2.18 (4 H, m), 2.24-2.54 (2 H, m) and 3.68 (3 H, s).

Trans-4-cyanocyclohexanecarboxylic Acid

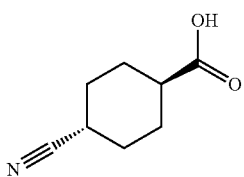

To a solution of methyl trans-4-cyanocyclohexanecarboxylate (996 mg, 5.96 mmol) in THF (37 mL) was added a solution of 0.5 M lithium hydroxide in water (20 mL). The mixture was stirred overnight then the THF was removed in vacuo and the residual aqueous solution acidified to pH 4. The resulting mixture was extracted with ether (2×30 mL), EtOAc (2×30 mL) and CHCl₃ (2×30 mL) then the combined extracts, dried over anhydrous sodium sulfate and concentrated in vacuo. This material was taken to the next step without any purification. ¹H NMR (400 Adz CHLOROFORM-d) δ ppm 1.43-1.73 (4 H, m), 2.05-2.22 (4 H, m) and 2.36-2.59 (2 H, m).

2-[Trans-4-(8-chloroimidazo[1,5-α]pyrazin-3-yl)cyclohexyl]propan-2-ol

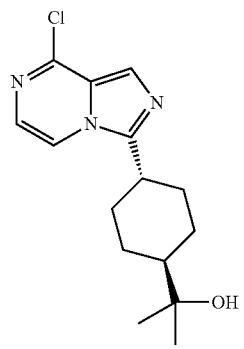

A solution of methyl trans-4-(8-chloroimidazo[1,5-α]pyrazin-3-yl)cyclohexanecarboxylate (4.0 g, 0.014 mol) in toluene (300 ml) and THF (70 mL) was cooled to 0° C. and treated with a 3.0 M solution of methylmagnesium bromide in ether (14 mL) maintaining the temperature at 0° C. The mixture was stirred at rt for 1.5 hours then cooled to 0° C. and an additional 3 eq of 3.0 M of methylmagnesium bromide in ether was added. The mixture was stirred at rt for 15 minutes then cooled to 0° C. and quenched with 1:1 NH₄Cl sat.:H₂O (50 mL total volume). The organic layer was separated and the aqueous layer was extracted with EtOAc (3×30 mL). The combined organic layers were dried over sodium sulfate and concentrated in vacuo and the crude product thus obtained, chromatographed over silica gel eluting with EtOAc to afford desired 2-[trans-4-(8-chloroimidazo[1,5-α]pyrazin-3-yl)cyclohexyl]propan-2-ol. ¹H NMR (400 MHz, CHLOROFORM-d) δ ppm 1.14-1.39 (m, 8 H), 1.41-1.60 (m, 1 H), 1.77-1.98 (m, 2 H), 2.01-2.20 (m, 4 H), 2.78-3.06 (m, 1 H), 7.35 (d, J=5.05 Hz, 1 H), 7.64 (d, J=5-05 Hz, 1 H) and 7.83 (s, 1 H).

Example 1

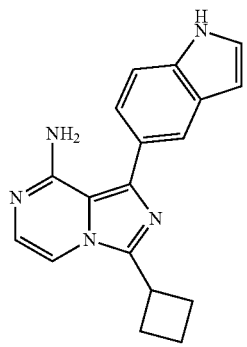

3-Cyclobutyl-1-(1H-indol-5-yl)imidazo[1,5α]pyrazin-8-amine

A dry mixture of 8-amino-3-cyclobutyl-1-iodoimidazo[3,4-a]pyrazine (30 mg, 0.096 mmol), cesium carbonate (35 mg, 0.117 mmol) and 5-(4,4,5,5-tetramethyl-1,3,2-dioxaborolan-2-yl)-1H-indole (26 mg, 0.107 mmol) was purged with Argon 3 times prior to the addition of tetrakistriphenylphosphino palladium (0) (6 mg, 0.005 mmol). The mixture was purged twice more and then treated with a degassed mixture of DME:water (5:1, 2 mL). The resulting solution was degassed twice more and then heated at 80° C. overnight. The resulting reaction mixture was concentrated in vacuo, the residue dissolved in 1:1 MeCN:MeOH (1.5 mL) and purified by mass directed preparative HPLC to afford 3-cyclobutyl-1-(1H-indol-5-yl)imidazo[1,5-α]pyrazin-8-amine H NMR (400 MHz, DMSO-d₆) δ ppm 1.82-1.92 (1 H, m) 1.95-2.08 (1 H, m) 2.32-2.41 (4 H, m) 3.82-3.93 (1 H, m) 5.91 (2 H, br. s.) 6.45 (1 H, d, J=3.03 Hz) 6.90 (1 H, d, J=5.05 Hz) 7.26 (1 H, dd, J=8.34, 1.52 Hz) 7.34 (1 H, d, J=5.05 Hz) 7.35-7.39 (1 H, m) 7.45 (1 H, d, J=8.34 Hz) 7.64-7.68 (1 H, m) 11.20 (1H, br. s.); MS (ES+): m/z 304.15 [MH+]. HPLC: t$_R$ 6.18 min (XTerra C18 5 uM, 4.6×15 mm, A: MeCN & B: 10 mmol NH₄OAc in 0.05% HOAc/aq., method Polar15).

Example 2

3-Cyclobutyl-1-(1H-indol-2-yl)imidazo[1,5-α]pyrazin-8-amine

Prepared as described above for EXAMPLE 1 using 1-(tert-butoxycarbonyl)-1H-indole-2-boronic acid in place of 5-(4,4,5,5-tetramethyl-1,3,2-dioxaborolan-2-yl)-1H-indole. The reaction conditions used effected significant cleavage of the N-(tert-butoxycarbamoyl) functionality. MS (ES+): m/z 304.10 [MH+].

Example 3

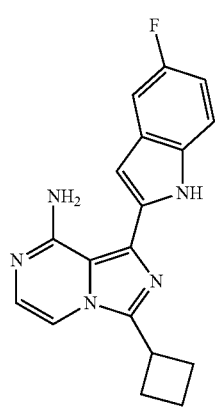

3-Cyclobutyl-1-(5-fluoro-If-indol-2-yl)imidazo[1,5-α]pyrazin-8-amine

Prepared as described above for EXAMPLE 1 using 1-(tert-butoxycarbonyl)-5-fluoro-1H-indole-2-boronic acid in place of 5-(4,4,5,5-tetramethyl-1,3,2-dioxaborolan-2-yl)-1H-indole. The reaction conditions used effected significant cleavage of the N-(tert-butoxycarbamoyl) functionality. MS (ES+): m/z 322.06 [MH+].

Example 4

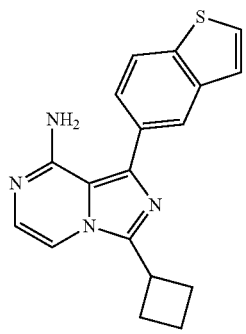

1-(1-Benzothien-5-yl)-3-cyclobutylimidazo[1,5-α]pyrazin-8-amine

Prepared as described above for EXAMPLE 1 using 2-(1-benzothiophen-5-yl)-4,4,5,5-tetramethyl-1,3,2-dioxaborolane in place of 5-(4,4,5,5-tetramethyl-1,3,2-dioxaborolan-2-yl)-1H-indole. MS (ES+): m/z 321.10 [MH+].

Example 5

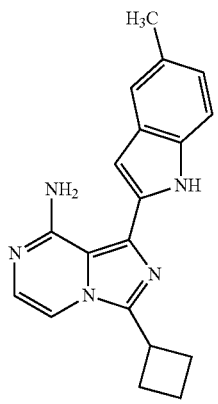

3-Cyclobutyl-1-(5-methyl-1H-indol-2-yl)imidazo[1,5-α]pyrazin-8-amine

Prepared as described above for EXAMPLE 1 using 1-(tert-butoxycarbonyl)-5-methyl-1H-indole-2-boronic acid in place of 5-(4,4,5,5-tetramethyl-1,3,2-dioxaborolan-2-yl)-1H-indole. MS (ES+): m/z 318.05 [MH+].

Example 6

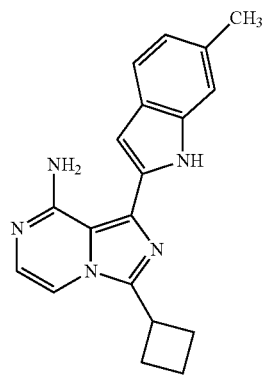

3-Cyclobutyl-1-(6-methyl-IM-indol-2-yl)imidazo[1,5-α]pyrazin-8-amine

Prepared as described above for EXAMPLE 1 using 1-(tert-butoxycarbonyl)-6-methyl-1H-indole-2-boronic acid in place of 5-(4,4,5,5-tetramethyl-1,3,2-dioxaborolan-2-yl)-1H-indole. MS (ES+): m/z 318.05 [MH+].

Example 7

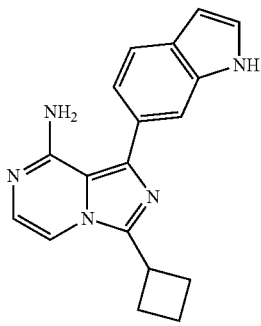

3Cyclobutyl-1-(1H-indol-6-yl)imidazo[1,5-α]pyrazin-8-amine

A mixture of 6-bromo-1H-indole (2 g, 10.00 mmol), 4,4,4',4',5,5,5',5'-octamethyl-2,2'-bi-1,3,2-dioxaborolane (2.00 g, 7.87 mmol) and potassium acetate (3.0 g, 31.00 mmol) was degassed three times, treated with (1, 1'-bis(diphenylphosphino)ferrocene) palladium dichloride (0.20 g, 0.28 mmol) and degassed twice more. 1,2-dimethoxyethane (28 mL) was added and the mixture was heated at 75° C. overnight. The cooled reaction mixture was then diluted with water, extracted with EtOAc and the extracts washed with water and brine, then dried over magnesium sulphate, and concentrated in vacuo to afford a brown/black semi-solid. This was triturated with ether to afford a brown powder, which was identified by LCMS to be desired indole-6-boronic acid, pinacol ester. $^1$H NMR (400 MHz, CHLOROFORM-D) δ ppm 1.37 (s, 12 H), 6.54-6.58 (m, 1 H), 7.26-7.28 (m, 1H), 7.55 (dd, J=7.83, 1.01 Hz, 1 H), 7.62-7.68 (m, 1 H), 7.90 (s, 1 H), 8.19 (br. s., 1 H); MS (ES+): m/z 244.25 [MH$^+$]; HPLC: $t_R$=3.52 min (OpenLynx, polar__5 min).

This material was used in place of 5-(4,4,5,5-tetramethyl-1,3,2-dioxaborolan-2-yl-1H-indole under the conditions described in EXAMPLE 1 to afford 3-cyclobutyl-1-(1H-indol-4-yl)imidazo[1,5-α]pyrazin-8-amine. MS (ES+): m/z 304.15 [MH+].

Example 8

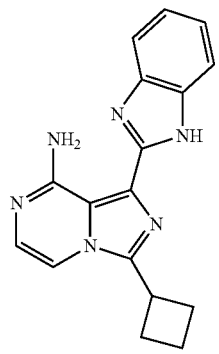

1-(1H-Benzimidazol-2-yl)-3-cyclobutylimidazo[1,5-α]pyrazin-8-amine

3-Cyclobutyl-1-iodoimidazo[1,5-α]pin-8-amine (500 mg, 2 mmol) and tetrakis(triphenylphosphine)palladium(0) (10 mg, 0.1 mmol) was degassed dry three times then treated with methanol (20 mL) and N,N-diisopropylethylamine (0.7 mL, 4.0 mmol) and the mixture heated at 70° C. under an atmosphere of carbon monoxide, with intermittent bubbling of this gas under the surface of the reaction mixture. After 3 d heating with extensive bubbling through of the solution with carbon monoxide and some addition of fresh catalyst after day 2, TLC (10% MeOH/DCM indicated the reaction to be complete. The reaction mixture was diluted with water, extracted with DCM and the extracts washed with water and brine, then dried over magnesium sulphate, and concentrated in vacuo to afford an orange solid which was recrystallised from acetonitrile to afford methyl 8-amino-3-cyclobutylimidazo[1,5-α]pyrazine-1-carboxylate. $^1$H NMR (400 Adz, CHLOROFORM-d) δ ppm 1.97-2.06 (m, 1 H), 2.10-2.26 (m, 1 H), 2.43-2.54 (m, 2 H), 2.53-2.68 (m, 2 H), 3.78 (dd, J=9.09, 8.08 Hz, 1 H), 4.01 (s, 3 H), 7.08 (d, J=4.80 Hz, 1 H), 7.22 (d, J=4.80 Hz, 1 H), 7.38 (br. s., 1 H), 7.69 (br. s., 1 H).

A suspension of 1,2-phenylenediamine (60 mg, 0.6 mmol) in toluene (2.0 mL) was treated with a 2M solution of trimethylaluminum in toluene (0.5 mL) effecting the formation of a pink solution. After 5 min this solution was treated with solid methyl 8-amino-3-cyclobutylimidazo[1,5-a]pyrazine-1-carboxylate (30 mg, 0.1 mmol) and the mixture heated at 120° C. for 30 min then stirred at rt overnight. The mixture was then partitioned between 2M NaOH (10 mL) & EtOAc (10 mL) and stirred for 15 min. The organic layer was separated and the aqueous layer extracted further with EtOAc (3×10 mL). The combined organics were washed with brine, dried and concentrated in vacuo to give ~85% pure 8-amino-N-(2-aminophenyl)-3-cyclobutylimidazo[1,5-α]pyrazine-1-carboxamide which was used without purification.

A solution of 8-amino-N-(2-aminophenyl)-3-cyclobutylimidazo[1,5-α]pyrazine-1-carboxamide (40.0 mg, 0.124 mmol) in acetic acid (1.2 mL) was microwaved at 120° C. for 10 min (300 W). The resulting solution was purified mass directed preparative HPLC to afford 1-(1H-benzimidazol-2-yl)-3-cyclobutylimidazo[1,5-α]pyrazin-8-amine. 1H NMR (400 MHz, DMSO-d6) δ ppm 1.92-2.05 (m, 1 H) 2.07-2.21 (m, 1 H) 2.53-2.59 (m, 4 H) 3.91-4.06 (m, 1 H) 7.08 (d, J=4.80 Hz, 1 H) 7.16-7.26 (m, 2 H) 7.38 (d, J=4.80 Hz, 1 H) 7.44 (br. s., 1 H) 7.55 (d, J=8.08 Hz, 1H) 7.62 (d, J=6.82 Hz, 1 H) 10.49 (br. s., 1 H) 12.76 (s, 1 H); MS (ES+): m/z 305.15 [MH$^+$].

Example 9

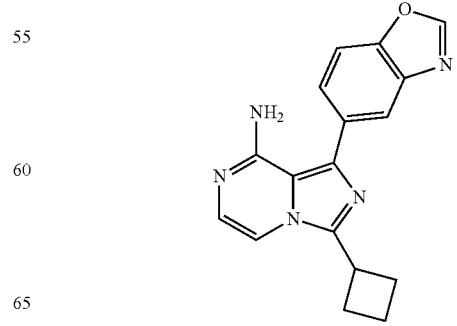

1-(1,3-Benzoxazol-5-yl)-3-cyclobutylimidazo[1,5-α]pyrazin-8-amine

A mixture of 5-chlorobenzoxazole (0.129 g, 0.84 mmol), 4,4,4',4',5,5,5',5'-octamethyl-2,2'-bi-1,3,2-dioxaborolane (0.4956 g, 1.95 mmol), potassium acetate (0.41 g, 4.2 mmol), 1,3-bis(2,6-diisopropylphenyl)imidazol-2-ylidene hydrochloride (43 mg, 0.10 mmol) and palladium acetate (11 mg, 0.05 mmol) was degassed, treated with tetrahydrofuran (10 mL) and the resulting mixture heated at 80° C. overnight. The mixture was diluted with water (100 mL), acidified to pH 6 and extracted with EtOAc (3×40 mL). The extracts were washed with water, dried and concentrated in vacuo. The residue so obtained was purified by chromatography over silica gel eluting with DCM to 10% MeCN/DCM to afford 1,3-benzoxazole-5-boronic acid, pinacol ester. $^1$H NMR (400 MHz, CHLOROFORM-d) δ ppm 1.37-1.39 (m, 12 H) 7.59 (d, J=8.34 Hz, 1 H) 7.86 (dd, J=8.08, 1.01 Hz, 1 H) 8.10 (s, 1 H) 8.26 (s, 1 H); MS (ES+): m/z 246.23 [MH$^+$].

This material was used in place of 5-(4,4,5,5-tetramethyl-1,3,2-dioxaborolan-2-yl)-1H-indole under the conditions described in example 1 to afford 1-(1,3-benzoxazol-5-yl)-3-cyclobutylimidazo[1,5-α]pyran-8-amine MS (ES+): m/z 306.16 [MH+].

Example 10

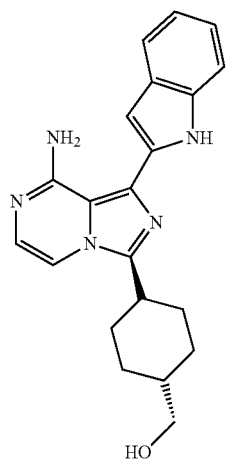

{trans-4-[8-Amino-1-(1H-indol-2-yl)imidazo[1,5-α]pyrazin-3-yl]cyclohexyl}methanol Prepared according to the procedure described in EXAMPLE 2 using trans-[4-(8-amino-1-iodoimidazo[1,5-α]pyrazin-3-yl)cyclohexyl]methanol in place of 8-amino-3-cyclobutyl-1-iodoimidazo[3,4-α]pyrazine. $^1$H NMR (DMSO-d6, 400 MHz) δ1.12-1.23 (m), 1.38-1.54 (m, 1H); 1.58-1.78 (m, 2H); 1.82-1.92 (m, 2H); 1.96-2.06 (m, 2H); 3.03-3.16 (m, 1H); 3.29 (t, J=5.6 Hz, 2H); 4.46 (t, J=5.3 Hz, 1H); 6.45 (brs, 2H); 6.63 (d, J=1.38 Hz, 1H); 7.02 (t, J=7.50 Hz, 1H); 7.06 (d, J=4.99 Hz, 1H); 7.12 (t, J=7.52, 1H), 7.46 (d, J=8.02 Hz, 1H), 7.58 (d, J=7.83 Hz, 1H, 7.66 (d, J=5.06 Hz, 1H), 11.43 (s, 1H); MS (ES+): m/z 362.07 (100) [MH+], HPLC: t$_R$=1.97 min (MicromassZQ, polar__5min).

Example 11

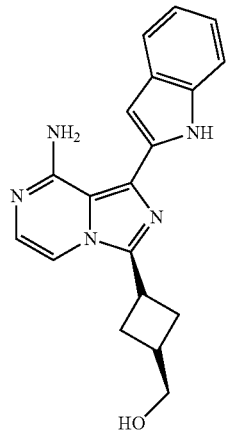

{cis-3-[8-Amino-1-(1H-indol-2-yl)imidazo[1,5-α]pyrazin-3-yl]cyclobutyl}methanol

Prepared according to the procedure described in EXAMPLE 2 using [3-(8-chloro-1-iodoimidazo[1,5-α]pyrazin-3-yl)cyclobutyl]methanol in place of 8-amino-3-cyclobutyl-1-iodoimidazo[3,4-α]pyrazine. MS (ES+): m/z 334.10[MH+].

Example 12

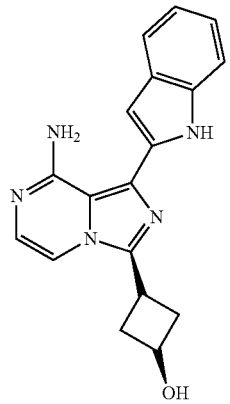

cis-3-[8-Amino-1-(1H-indol-2-yl)imidazo[1,5-α]pyrazin-3-yl]cyclobutanol

Prepared according to the procedure described in EXAMPLE 2 using 3-($-amino-1-iodoimidazo[1,5-α]pyrazin-3-yl)cyclobutanol in place of 8-amino-3-cyclobutyl-1-iodoimidazo[3,4-α]pyrazine. MS (ES+): m/z 320.03 [MH+].

Example 13

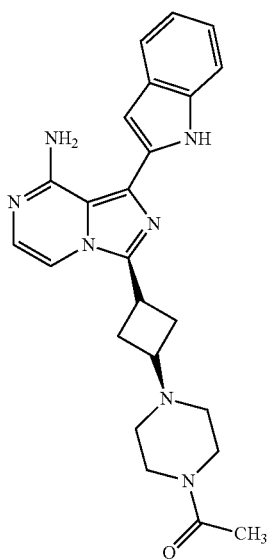

3-[cis-3-(4-Acetylpiperazin-1-yl)cyclobutyl]-1-(1H-indol-2-yl)imidazo[1,5-α]pyrazin-8-amine Prepared according to the procedure described in EXAMPLE 2 using 1-{4-[3-(8-amino-1-iodoimidazo[1,5-α]pyrazin-3-yl)cyclobutyl]piperazin-1-yl}ethanone in place of 8-amino-3-cyclobutyl-1-iodoimidazo[3,4-α]pyrazine. MS (ES+): m/z 430.08 [MH+].

Example 14

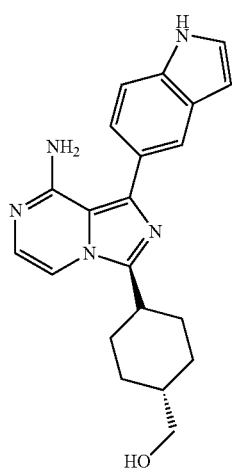

{trans-4-[S-Amino-1-(1H-indol-5-yl)imidazo[1,5-α]pyrazin-3-yl]cyclohexyl}methanol Prepared according to the procedure described in EXAMPLE 1 using trans-[4-(8-amino-1-iodoimidazo[1,5-α]pyrazin-3-yl)cyclohexyl]methanol in place of 9-amino-3-cyclobutyl-1-iodoimidazo[3,4-α]pyrazine. MS (ES+): m/z 362.07 [MH+].

Example 15

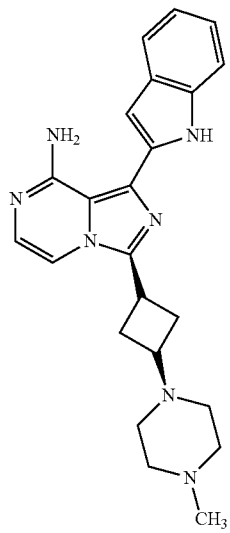

1-(1H-Indol-2-yl)-3-[cis-3-(methylpiperazin-1-yl)cyclobutyl]imidazo[1,5-α]pyrazin-8-amine Prepared according to the procedure described in EXAMPLE 2 using 1-iodo-3-[3-(4-methyl-piperazin-1-yl)cyclobutyl]imidazo[1,5-α]pyrazin-8-ylamine in place of 8-amino-3-cyclobutyl-1-iodoimidazo[3,4-α]pyrazine. MS (ES+): m/z 402.10 [MH+].

Example 16

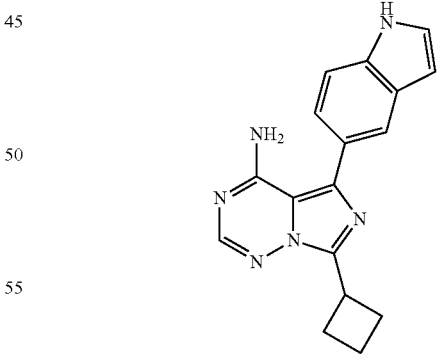

7-Cyclobutyl-5-(1H-indol-5-yl)imidazo[5,1-f][1,2,4]triazin-4-amine

Prepared according to the procedure described in EXAMPLE 1 using 7-cyclobutyl-5-iodoimidazo[5,1-f][1,2,4]triazin-4-ylamine in place of 8-amino-3-cyclobutyl-1-iodoimidazo[3,4-α]pyrazine. MS (ES+): m/z 305.16 [MH+].

Example 17

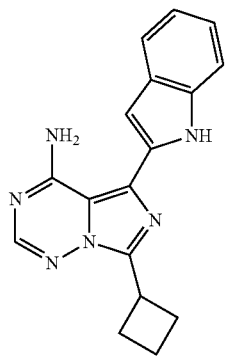

7-Cyclobutyl-5(1H-indol-2-yl)imidazo[5,1-f][1,2,4]triazin-4-amine

Prepared according to the procedure described in EXAMPLE 2 using 7-cyclobutyl-5-iodoimidazo[5,1-f][1,2,4]triazin-4-amine in place of 8-amino-3-cyclobutyl-1-iodoimidazo[3,4-α]pyrazine. MS (ES+): m/z 305.07 [MH+].

Example 18

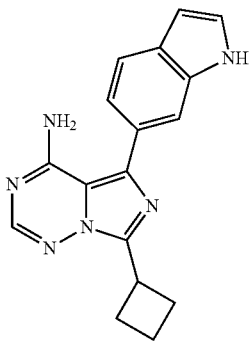

7-Cyclobutyl-5-(1H-indol-6-yl)imidazo[5,1-f][1,2,4]triazin-4-amine

Prepared according to the procedure described in EXAMPLE 7 using 7-cyclobutyl-5-iodoimidazo[5,1-f][1,2,4]triazin-4-ylamine in place of 8-amino-3-cyclobutyl-1-iodoimidazo[3,4-α]pyrazine. MS (ES+): m/z 305.07 [MH+].

Example 19

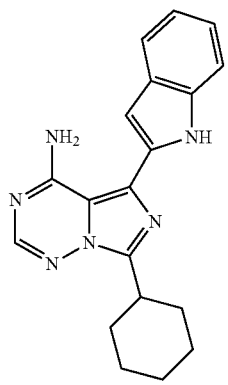

7-Cyclohexyl-5-(1H-indol-2-yl)imidazo[5,1-f][1,2,4]triazin-4-amine

Prepared according to the procedure described in EXAMPLE 2 using 7-cyclohexyl-5-iodoimidazo[5,1-f][1,2,4]triazin-4-amine in place of 8-amino-3-cyclobutyl-1-iodoimidazo[3,4-α]pyrazine. $^1$H NMR (400 MHz-DMSO-d6) δ 1.40-1.54 (m, 4H), 1.72-1.82 (m, 2H), 1.87-1.92 (m, 2H), 2.02-2.09 (m, 2H) 3.31-3.38 (m, 1H) 6.26 (bs, 2H) 6.73-6.74 (m, 1H), 7.13-7.17 (m, 1H), 7.22-7.25 (m, 1H), 7.44 (d, J=8.0 Hz, 1H) 7.64 (d, J=8.0 Hz, 1H), 7.91 (s, 1H), 9.18 (s, 1H). MS (ES+): m/z: 333.16 (100)[MH+]. HPLC: $t_R$=3.46 min (OpenLynx: polar_5 min).

Example 20

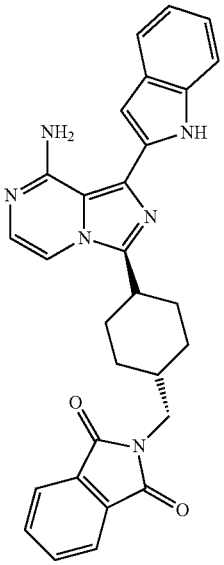

A mixture of {trans-4-[8-amino-1-(1H-indol-2-yl)imidazo[1,5-α]pyrazin-3-yl]cyclohexyl}methanol (400 mg, 0.001 mol), phthalimide (211.7 mg, 0.001439 mol), and triphenylphosphine resin (2.14 mmol/g loading; 1.03 g, 0.00221 mol; Argonaut) in THF (22 mL, 0.27 mol; Aldrich) was placed under nitrogen atmosphere and charged dropwise with diisopropyl azodicarboxylate (290.9 mg, 0.001439 mol). After 16 h, the resin was filtered off, washed with chloroform (5×20 mL) and the filtrate concentrated in vacuo to yield an orange oil which was chromatographed over silica gel eluting with chloroform→5% MeOH/chloroform to afford the title compound. $^1$H NMR (CDCl$_3$, 400 MHz): δ 7.90-7.85 (m, 2H) 7.77-7.70 (m, 2H), 7.64 (m, 1H), 7.43 (dd, J=8.0, 0.8 Hz, 1H), 7.27-7.15 (m, 2H), 7.14 (m, 1H), 7.09 (d, J=4.8 Hz, 1H), 6.77 (br s, 1H), 3.64 (d, J=6.4 Hz, 2H), 2.91 (m, 1H), 2.09 (m, 2H), 2.25-1.90 (m, 4H), 1.80 (ddd, J=13.2, 12.4, 2.4 Hz, 2H), 1.27 (ddd, J=13.2, 12.4, 2.4 Hz, 2H). MS (ES+): m/z 491.09 [MH+].

Example 21

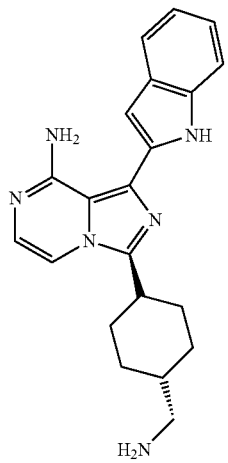

1-{trans-4-[8-Amino-1-(1H-indol-2-yl)imidazo[1,5-α]pyrazin-3-yl]cyclohexyl}methanamine A solution of benzyl {[trans-4-(g-amino-1-(1H-indol-2-yl)imidazo[1,5-α]pyrazin-3-yl)cyclohexyl]methyl}carbamate (0.163 g, 0.330 mmol) in conc. HCl (5 ml) was stirred at rt overnight. The reaction mixture was diluted with H₂O (20 mL), washed with Et₂O (30 mL), then basified with 1N NaOH (aq) and extracted with DCM (3×20 mL). The combined extracts were washed with water then dried over Na₂SO₄ and concentrated in vacuo To afford 0.085 g of desired compound. MS (ES+): m/z 361.30 [MH+].

Example 22

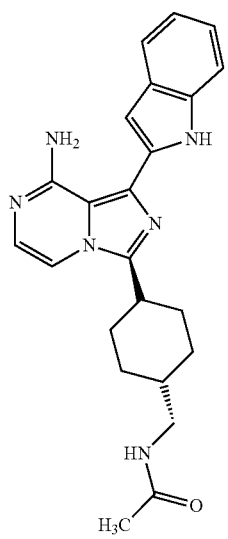

N-({trans-4-[8-Amino-1-(1H-indol-2-yl)imidazo[1,5α]pyrazin-3-yl]cyclohexyl}methyl)acetamide To a suspension of 1-{trans-4-[8-amino-1-(1H-indol-2-yl)imidazo[1,5-α]pyrazin-3-yl]cyclohexyl}methanamine (100.00 mg, 0.27 mmol), N-(3-dimethylaminopropyl)-N-ethylcarbodiimide hydrochloride (0.0798 g, 0.416 mmol), N,N-diisopropylethylamine (0.097 mL, 0.55 mmol), 1-hydroxbenzotriaxole Hydrate (0.0425 g, 0.277 mmol), and DMF (600 uL) in DCM (5 mL) was added AcOH (24 uL). The mixture was stirred at rt for 3 h under an atmosphere of nitrogen then diluted with DCM→(20 mL), washed with saturated NaHCO₃ (aq) (2×25 mL) and brine (2×25 mL), then dried over Na₂SO₄, filtered and concentrated in vacuo. The residue was chromatographed over silica gel eluting with DCM→2% 2M NH₃ in MeOH/DCM to afford 0.02 g of the title compound. MS (ES+): m/z 403.31 [MH+]. ¹H NMR (400 MHz, CDCl₃): δ 1.12-1.31 (m, 3H), 1.79-1.86 (m, 2H), 1.94-1.97 (m, 2H), 2.02 (s, 3H), 2.04-2.09 (m, 2H), 2.91 (m, 1H), 3.20 (t, J=6.4 Hz, 2H), 5.51 (hr, 1H), 5.66 (br, 2H), 6.79 (s, 1H), 7.10-7.16 (m, 2H), 7.20-7.25 (m, 2H), 7.43 (d, J=8.4 Hz, 1H), 7.44 (d, J=7.6 Hz, 1H), 9.07 r, 1H).

Example 23

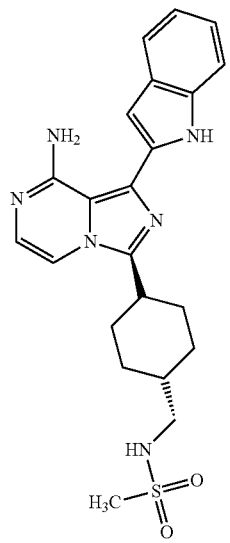

N-({4-[8-amino1-(1H-indol-2-yl)imidazo[1,5α]pyrazin-3-yl]cyclohexyl}methyl)methanesulfonamide Methanesulfonyl chloride (4.40 L, 0.057 mmol was added to a mixture of 1-{trans-4-[8-amino-1-(1H-indol-2-yl)imidazo[1,5-α]pyrazin-3-yl]cyclohexyl}methanamine (20.5 mg, 0.057 mol) and PS-DIEA (3.90 mmol/g loading; 60 mg, 0.2 mmol) in DCM (1.14 mL). The reaction mixture was stirred for 30 min at r.t. for 18 h. The crude reaction mixture was then concentrated and residue purified by mass directed preparative HPLC to afford 4 mg of desired product MS (ES+): m/z 439.10 (100) [MH+]. ¹H NMR (CD3OD, 400 MHz): δ 8.24 (br s, 2H), 7.61 (m, 2H), 7.46 (dd, J=8.4, 0.8 Hz, 1H), 7.19 (ddd, J=7.2, 1.2, 1.2 Hz, 1H), 7.08 (ddd, J=7.2, 1.2, 1.2 Hz, 1H), 6.75 (d, J=0.8 Hz, 1H), 3.14 (m, 1H), 2.07 (m, 4H), 1.85 (m, 2H), 1.64 (m, 1H), 1.26 (m, 2H).

Example 24

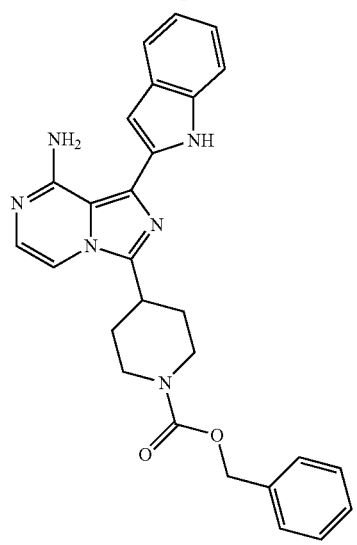

Benzyl 4-[8-amino-1-(1H-indol-2-yl)imidazo[1,5-α]pyrazin-3-yl]piperidin-1-carboxylate A mixture of benzyl 4-(8-amino-4-iodoimidazo[1,5-α]pyrazin-3-yl)piperidine-1-carboxylate (1.149 g, 0.002191 mol), 1-(tert-butoxycarbonyl)-1H-indole-2-boronic acid (0.629 g, 0.00241 mol), 1,2-dimethoxyethane (9.3 mL), water (1.8 mL) and cesium carbonate (1.43 g, 0.00438 mol) was degassed three times and then treated with tetrakis(triphenyl phosphine)palladium(0) (200 mg, 0.0002 mol). The mixture was once more degassed and then heated at 100° C. overnight. The resulting reaction mixture was diluted with EtOAc (30 mL) then washed with water (2×30 mL) and brine, dried over $Na_2SO_4$ and concentrated in vacuo. The crude product was chromatographed over silica gel eluting with hexane→EtOAc hexane 1:1.0.05 2M $NH_3$/MeOH to afford the desired product. $^1$H NMR (400 MHz $CDCl_3$): δ 2.02-2.06 (m, 4H), 3.03-3.17 (m, 3H), 4.29-4.33 (m, 2H), 5.16 (s, 2H), 5.66 (br, 2H), 6.79-6.80 (m, 1H), 7.11-7.16 (m, 2H), 7.20-7.25 (m, 2H), 7.31-7.45 (n4, 5H), 7.44 (m, 1H), 7.64 (d, J=7.6 Hz, 1H), 8.96 (br, 1H). MS (ES+): m/z 467.12 [MH+].

Example 25

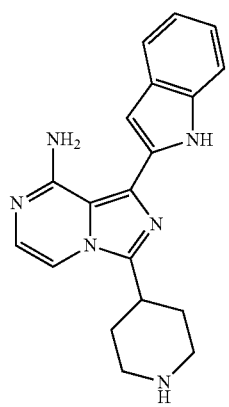

1-(1H-Indol-2-yl)-3-piperidin-4-ylimidazo[1,5α]pyrazin-8-amine

A solution of benzyl 4-[8-amino-1-(1H-indol-2-yl)imidazo[1,5-α]pyrazin-3-yl]piperidine-1-carboxylate (3.61 g, 0.00774 mol) in conc. HCl (100 ml) was stirred at rt overnight. The mixture was then diluted with water (200 mL), washed with $Et_2O$ (2×30 mL) then the aqueous layer concentrated in vacuo yielding 2.62 g of desired product as the trihydrochloride salt $^1$H NMR (400 MHz, MeOD): δ 2.19-2.32 (m, 4H), 3.26-3.30 (m, 2H), 3.53-3.36 (m, 2H), 3.70 (m, 1H), 7.06 (d, J=5.6 Hz, 1H), 7.10-7.14 (m, 1H), 7.23-7.26 (m, 2H), 7.50-7.52 (m, 1H), 7.67 (m, 1H), 7.93 (m, 1H). MS (ES+): m/z 333.27 [MH+].

Example 26

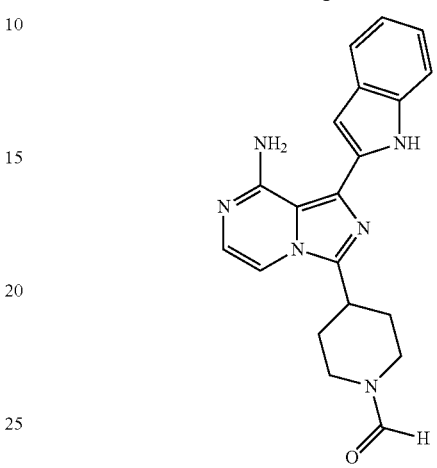

4-[8-Amino-1-(1H-indol-2-yl)imidazo[1,5-α]pyrazin-3-yl]piperidine-1-carbaldehyde To a solution of 1-(1H-Indol-2-yl)-3-piperidin-4-ylimidazo[1,5-α]pyrazin-8-amine hydrochloride (30.00 mg, 0.0068 mmol) in DCM (0.5 ml, 0.008 mol) was added N-(3-dimethylaminopropyl)-N-ethylcarbodiimide hydrochloride (0.0195 g, 0.102 mmol), N,N-diisopropylethylamine (0.047 mL), 1-hydroxbenzotriaxole hydrate (0.0104 g, 0.0679 mmol) and formic acid (4.7 mg, 0.10 mmol). The reaction was stirred at rt overnight then diluted with DCM, washed with saturated $NaHCO_3$ (2×25 mL) and brine (2×25), then dried over $Na_2SO_4$ and concentrated in vacuo. The material thus isolated was crystallized from EtOAc to afford 10.6 mg of desired product. $^1$H NMR (400 MHz, $CDCl_3$): δ 2.04-2.12 (m, 4H), 2.99-3.00 (m, 1H), 3.27-3.32 (m, 2H), 3.85 (m, 1H), 4.49 (m, 1H), 5.70 (br, 2H), 6.80 (s, 1H), 7.13-7.24 (m, 4H), 7.45 (d, J=8.4 Hz, 1H), 7.65 (d, J=8.0 Hz, 1H), 8.10 (s, 1H), 8.97 (br, 1H). MS (ES+): m/z 361.16 [MH+].

Example 27

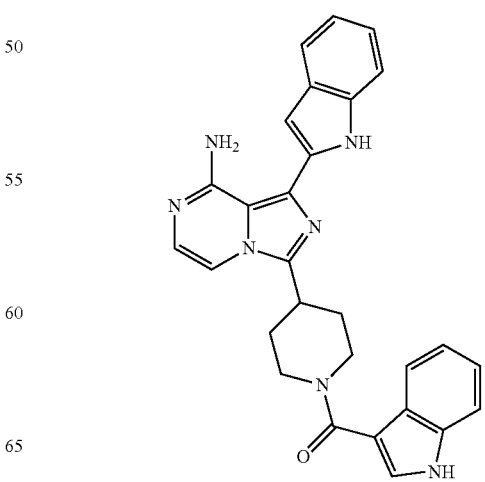

167

3-[1-(1H-Indol-3-ylcarbonyl)piperidin-4-yl]-1-(1H-indol-2-yl)imidazo[1,5-α]pyrazin-8-amine Prepared according to the procedure described above for EXAMPLE 26, except using indole-3-carboxylic acid in place of formic acid. MS (ES+): m/z 476.18 [MH+].

Example 28

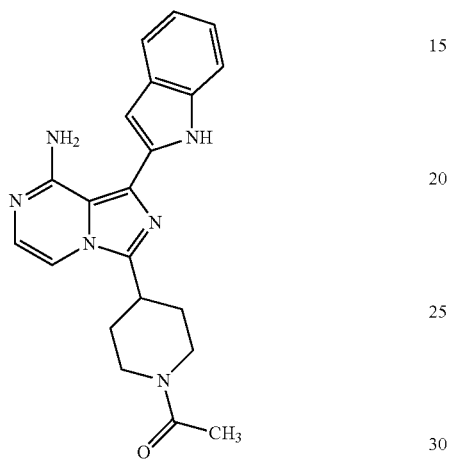

3-(1-Acetylpiperidin-4-yl)-1-(1H-indol-2-yl)imidazo[1,5-α]pyrazin-8-amine

Prepared according to the procedure described above for EXAMPLE 26, except using acetic acid in place of formic acid. MS (ES+): m/z 375.17 [MH+].

Example 29

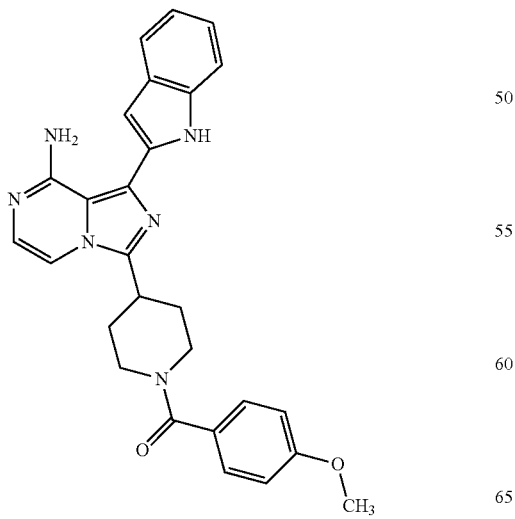

168

3-[1-(4-Methoxybenzoyl)piperidin-4-yl]-1-(1H-indol-2-yl)imidazo[1,5-α]pyrazin-amine Prepared according to the procedure described above for EXAMPLE 26, except using 4-methoxybenzoic acid in place of formic acid. MS (ES+): m/z 467.27 [MH+].

Example 30

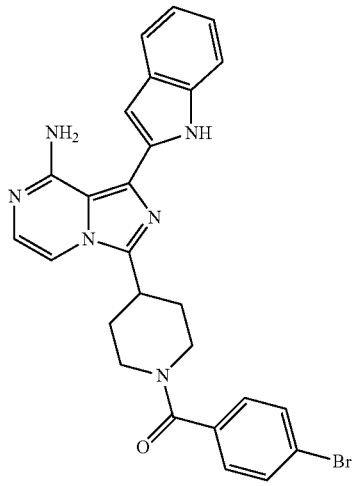

3-[1-(4-Bromobenzoyl)piperidin-4-yl]-1-(1H-indol-2-yl)imidazo[1,5-α]pyrazin-8-amine Prepared according to the procedure described above for EXAMPLE 26, except using 4-methoxybenzoic acid in place of formic acid. MS (ES+): m/z 515.17 & 517.17 [MH+].

Example 31

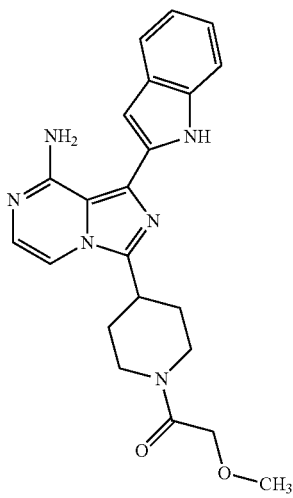

1-(1H-Indol-2-yl-3-[1-(methoxyacetyl)piperidin-4-yl]imidazo[1,5-α]pyrazin-8-amine Prepared according to the procedure described above for EXAMPLE 26, except using 2-methoxyacetic acid in place of formic acid. MS (ES+): m/z 405.10 [MH+].

Example 32

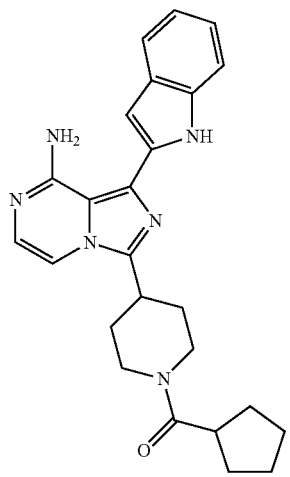

3-[1-(Cyclopentylcarbonyl)piperidin-4-yl]-1-(1H-indol-2-yl)imidazo[1,5-α]pyrazin-8-amine Prepared according to the procedure described above for EXAMPLE 26, except using cyclopentanecarboxylic acid in place of formic acid. MS (ES+): m/z 429.07 [MH+].

Example 33

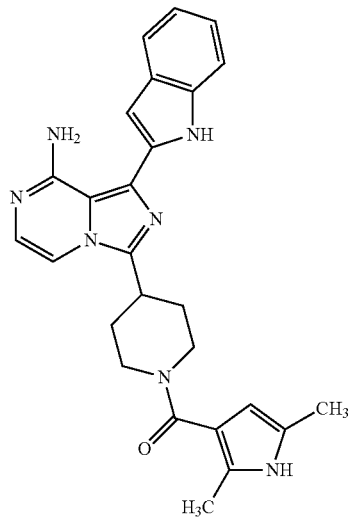

3-{1-[(2,5-Dimethyl-1H-pyrrol-3-yl)carbonyl]piperidin-4-yl}-1-(1H-indol-2-yl)imidazo[1,5-α]pyrazin-8-amine Prepared according to the procedure described above for EXAMPLE 26, except using 2,5-dimethylpyrrolecarboxylic acid in place of formic acid. MS (ES+): m/z 454.19 [MH+].

Example 34

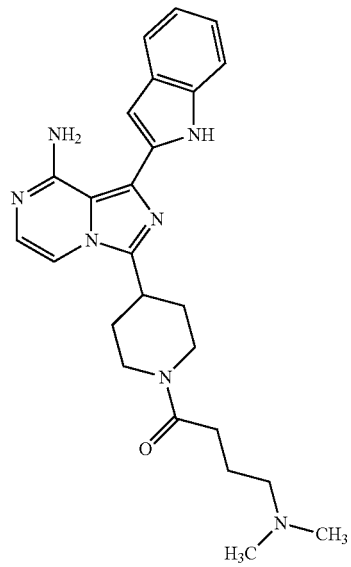

3-{1-[4-(Dimethylamino)butanoyl]piperidin-4-yl}-1-(1H-indol-2-yl) imidazo[1,5-α]pyrazin-gamine Prepared according to the procedure described above for EXAMPLE 26, except using 4-(dimethylamino)butanoic acid in place of formic acid. MS (ES+): m/z 446.22 [MH+].

Example 35

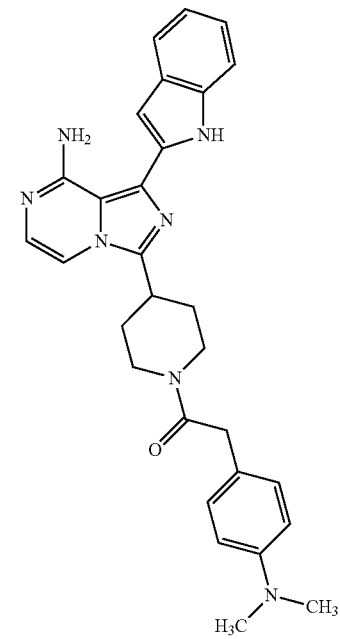

3-(1-[4-(Dimethylamino)phenacyl]piperidin-4-yl)-1-(1H-indol-2-yl)imidazo[1-α]pyrazin-8-amine Prepared according to the procedure described above for EXAMPLE 26, except using 4-(dimethylamino)phenylacetic acid in place of formic acid. MS (ES+): m/z 480.22 [MH+].

Example 36

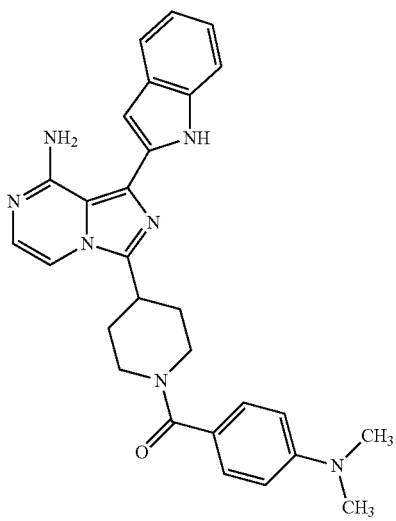

3-{1-[4-Dimethylamino)benzoyl]piperidin-4-yl}-1-(1H-indol-2-yl)imidazo[1,5-α]pyrazin-8-amine Prepared according to the procedure described above for EXAMPLE 26, except using 4(dimethylamino)benzoic acid in place of formic acid. MS (ES+): m/z 480.22 [MH+].

Example 37

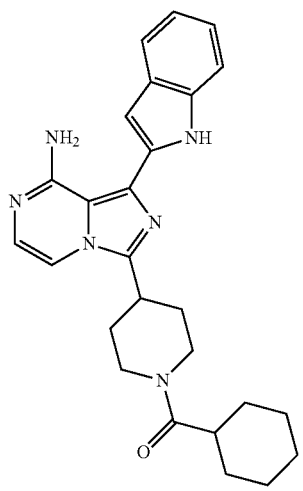

3-[1-(Cyclohexylcarbonyl)piperidin-4-yl]-1-(1H-indol-2-yl)imidazo[1,5-α]pyrazin-8-amine Prepared according to the procedure described above for EXAMPLE 26, except using cyclohexanecarboxylic acid in place of formic acid. MS (ES+): m/z 443.20 [MH+].

Example 38

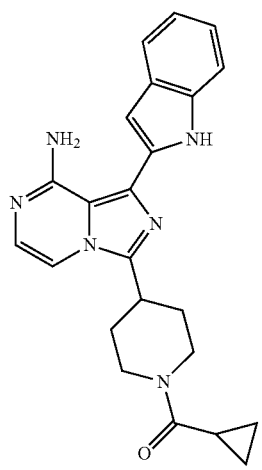

3-[1-(Cyclopropylcarbonyl)piperidin-4-yl]-1-(1-H-indol-2-yl)imidazo[1,5-α]pyrazin-8-amine Prepared according to the procedure described above for EXAMPLE 26, except using cyclopropanecarboxylic acid in place of formic acid. MS (ES+): m/z 401.19 [MH+].

Example 39

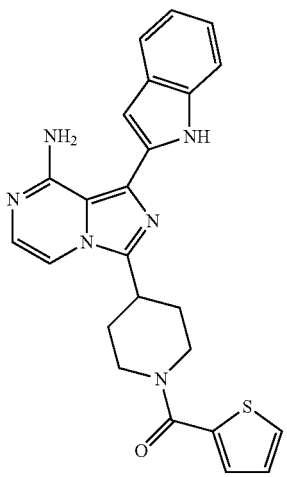

1-(1H-Indol-2-yl)-3-[1-(2-thienylcarbonyl)piperidin-4-yl]imidazo[1,5-α]pyrazin-8-amine Prepared according to the procedure described above for EXAMPLE 26, except using thiophene-2-carboxylic acid in place of formic acid. MS (ES+): m/z 443.22 [MH+].

Example 40

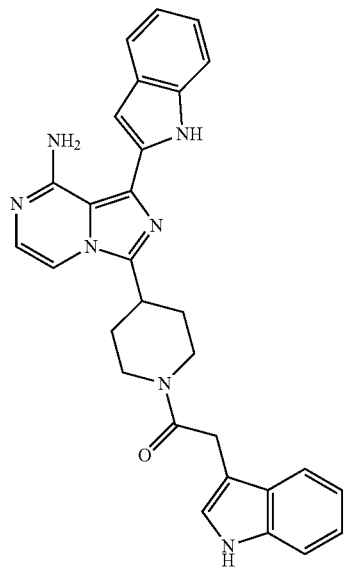

3-[1-(1H-Indol-3-ylacetyl)piperidin-4-yl]-1-(1H-indol-2-yl)imidazo[1,5-α]pyrazin-8-amine Prepared according to the procedure described above for EXAMPLE 26, except using indole-3-acetic acid in place of formic acid. MS (ES+): m/z 490.10 [MH+].

Example 41

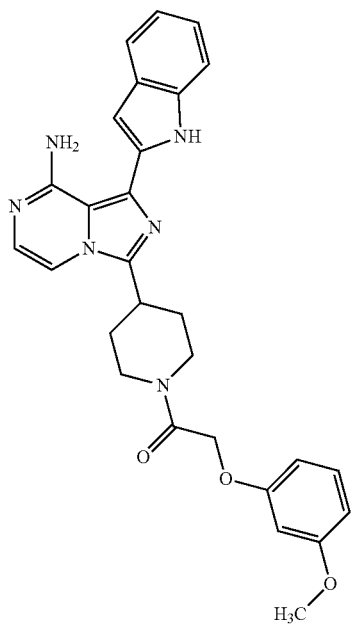

1-(1H-Indol-2-yl)-3-{1-[(3-methoxyphenoxy acetyl]piperidin-4-yl}imidazo[1,5-α]pyrazin-8-amine Prepared according to the procedure described above for EXAMPLE 26, except using (3-methoxyphenoxy)acetic acid in place of formic acid. MS (ES+): m/z 497.11 [MH+].

Example 42

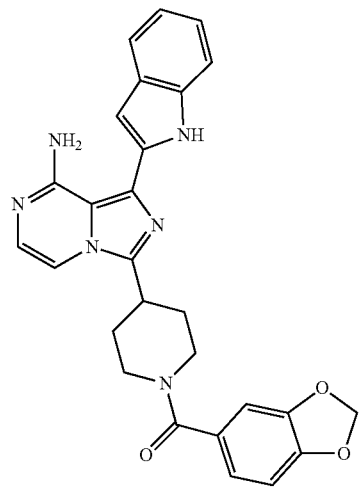

3-[1-(1,3-Benzodioxol-5-ylcarbonyl)piperidin-4-yl]-1-(1H-indol-2-yl)imidazo[1,5-α]pyrazin-8-amine Prepared according to the procedure described above for EXAMPLE 26, except using 1,3-benzodioxole-5-carboxylic acid in place of formic acid. MS (ES+): m/z 481.05 [MH+].

Example 43

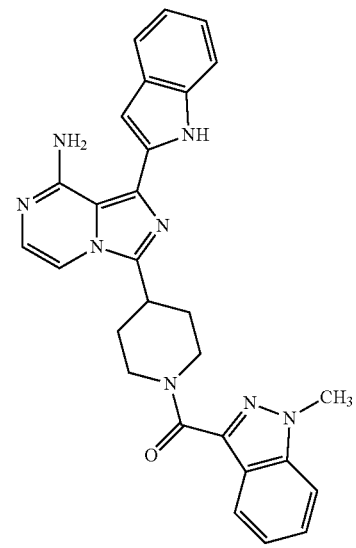

1-(1H-Indol-2-yl)-3-{1-[(1-methyl-1H-indazol-3-yl)carbonyl]piperidin-4-yl}imidazo[1,5-α]pyrazin-8-amine Prepared according to the procedure described above for EXAMPLE 26, except using 1-methyl-1H-indazole-3-carboxylic acid in place of formic acid. MS (ES+): m/z 491.04 [MH+].

Example 44

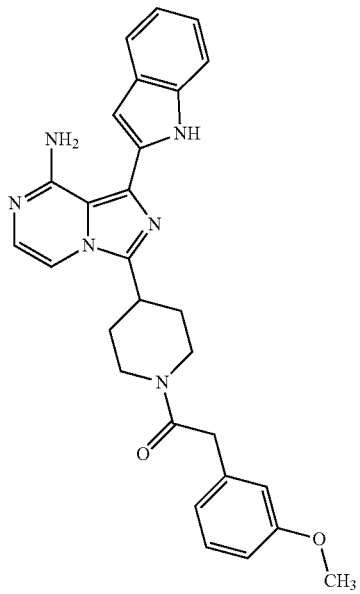

1-(1H-Indol-2-yl)-3-{1-[(3-methoxyphenyl)acetyl]piperidin-4-yl}imidazo[1,5-α]pyrazin-8-amine Prepared according to the procedure described above for EXAMPLE 26, except using 3-methoxyphenylacetic acid in place of formic acid. MS (ES+): m/z 481.09 [MH+].

Example 45

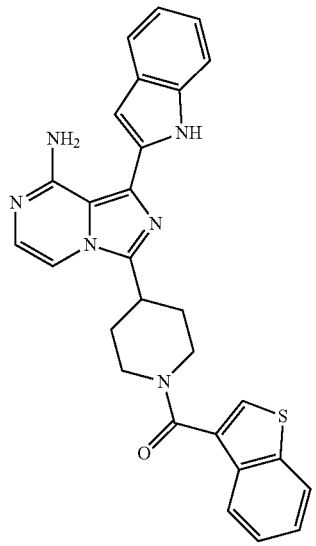

3-[1-(1-Benzothien-3-ylcarbonyl)piperidin-4-yl]-1-iodoimidazo[1,5-α]pyrazin-8-amine Prepared according to the procedure described above for EXAMPLE 26, except using benzothiophene-3-carboxylic acid in place of formic acid. MS (ES+): m/z 493.01 [MH+].

Example 46

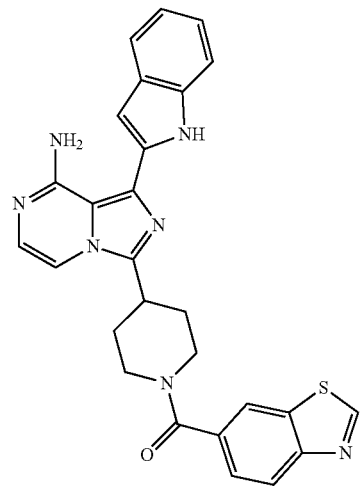

3-[1-(1,3-Benzothiazol-6-ylcarbonyl)piperidin-4-yl]-1-iodoimidazo[1,5-α]pyrazin-8-amine Prepared according to the procedure described above for EXAMPLE 26, except using benzothiazole-6-carboxylic acid in place of formic acid. MS (ES+): m/z 494.01 [MH+].

Example 47

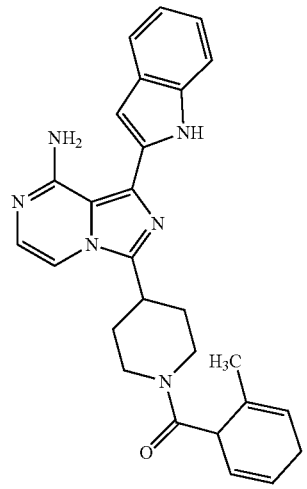

177

1-(1H-Indol-2-yl)-3-{1-[2-methylcyclohexa-2,5-dien-1-yl)carbonyl]piperidin-4-yl}imidazo[1,5-α]pyrazin-8-amine Prepared according to the procedure described above for EXAMPLE 26, except using 2-methylcyclohexa-2,5-diene-1-carboxylic acid in place of formic acid. MS (ES+): m/z 453.08 [MH+].

Example 48

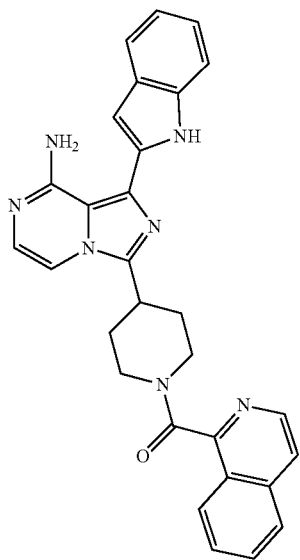

1-(1H-Indol-2-yl)-3-[1-(isoquinolin-1-ylcarbonyl)piperidin-4-yl]imidazo[1,5-α]pyrazin-8-amine Prepared according to the procedure described above for EXAMPLE 26, except using isoquinoline-1-carboxylic acid in place of formic acid. MS (ES+): m/z 488.01 [MH+].

Example 49

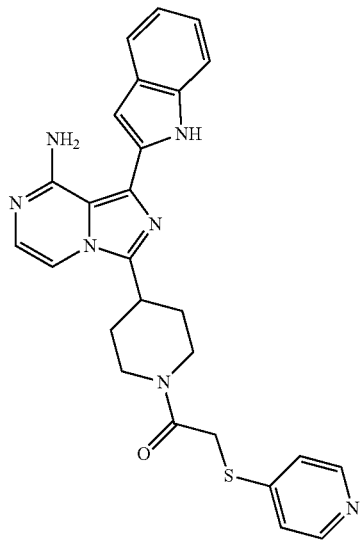

178

1-(1H-Indol-2-yl)-3-{1-[(pyridin-4-ylthio)acetyl]piperidin-4-yl}imidazo[1,5-α]pyrazin-8-amine Prepared according to the procedure described above for EXAMPLE 26, except using (pyridin-4-ylthio)acetic acid in place of formic acid. MS (ES+): m/z 484.04 [MH+].

Example 50

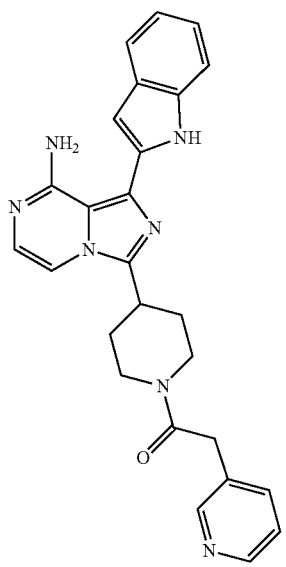

1-(1H-Indol-2-yl)-3-[1-(pyridin-3-ylacetyl)piperidin-4-yl]imidazo[1,5-α]pyrazin-8-amine Prepared according to the procedure described above for EXAMPLE 26, except using pyridin-3-ylacetic acid in place of formic acid. MS (ES+): m/z 452.07[MH+].

Example 51

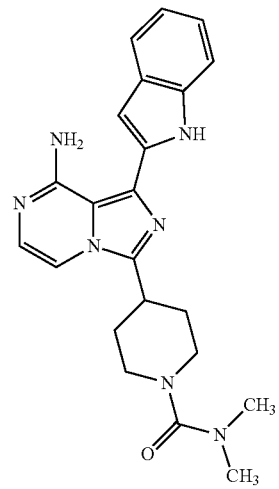

4-(8-Amino-1-(1H-indol-2-yl)imidazo[1,5-α]pyrazin-3-yl)N,N-dimethylpiperidine-1-carboxamide A mixture of 1-(1H-indol-2-yl)-3-piperidin-4-ylimidazo[1,5-α]pyrazin-8-amine hydrochloride (30.0 mg, 0.0679 mmol),N,N-diisopropylethylamine (59.1 μL, 0.340 mmol) and DMF (1.00 mL) was treated with N,N-dimethylcarbamoyl chloride (6-23 μL, 0.0679 mmol) and stirred at rt for 1 h prior to semi-preparative HPLC to afford the isolated title compound. $^1$H NMR (400 CD$_3$OD) ppm: 8.32 (br. s., 1H), 7.59-7.66 (m, 2H), 7.46 (d, 1H, J=8.3 Hz), 7.15-7.22 (m, 1H), 7.01-7.10 (m, 2H), 6.74 (s, 1H), 3.82 (d, 2H, J=12.6 Hz), 3.34-3.42 (m, 1H), 2.97-3.09 (m, 2H), 2.87 (s, 6H), 1.95-2.09 (m, 4H); MS (ES+): m/z 404.14 [MH+].

Example 52

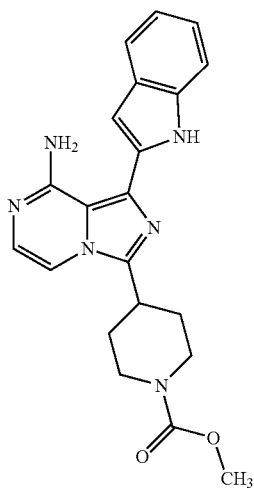

Methyl 4(8-amino-1-(1H-indol-2-yl)imidazo[1,5-α]pyrazin-3-yl)piperidine-1-carboxylate A mixture of 1-(1H-indol-2-yl)-3-piperidin-4-ylimidazo[1,5-α]pyrazin-8-amine hydrochloride (30.0 mg, 0.0679 mmol), N,N-diisopropylethylamine (59.1 μL, 0.3440 mmol) and DMF (1.00 mL) was treated with methyl chloroformate (5.25 μL, 0.0679 mmol) and stirred at rt for 1 h prior to semi-preparative HPLC to afford the isolation of the title compound. $^1$H NMR (400 MHz, CD$_3$OD) ppm: 8.32 (br. s., 1H), 7.58-7.66 (m, 2H), 7.46 (d, 1H, J=8.1 Hz), 7.14-7.22 (m, 1H), 7.00-7.12 (m, 2H), 6.73 (s, 1H), 4.26 (d, 2H, J=12.9 Hz), 3.71 (s, 3H), 3.33-3.37 (m, 3H), 2.9-3.17 (m, 2H), 1.85-2.06 (m, 4H); MS (ES+): m/z 391.06 [MH+].

Example 53

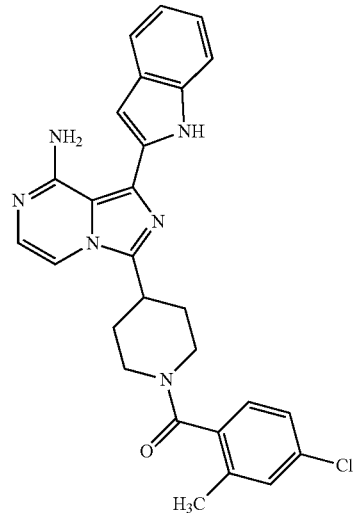

3-[1-(4-Chloro-2-methylbenzoyl)piperidin-4-yl]-1-(1H-indol-2-yl)imidazo[1,5-α]pyrazin-8-amine Prepared according to the procedure described above for EXAMPLE 26, except using 4-chloro-2-methylbenzoic acid in place of formic acid. MS (ES+): m/z 485.05 [MH+].

Example 54

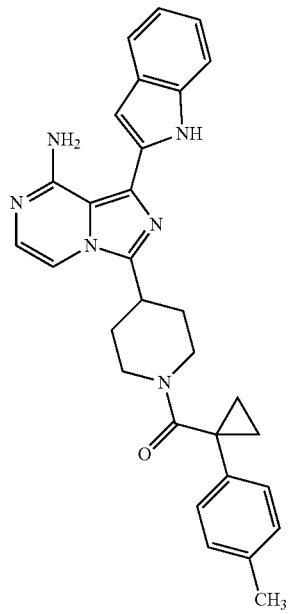

1-(1H-Indol-2-yl)-3-(1-{[1-(4-methylphenyl)cyclopropyl]carbonyl}piperidinyl)imidazo[1,5-α]pyrazin-8-amine Prepared according to the procedure described above for EXAMPLE 26, except using 1-(4-methylphenyl)cyclopropanecarboxylic acid in place of formic acid. MS (ES+): m/z 491.11 [MH+].

Example 55

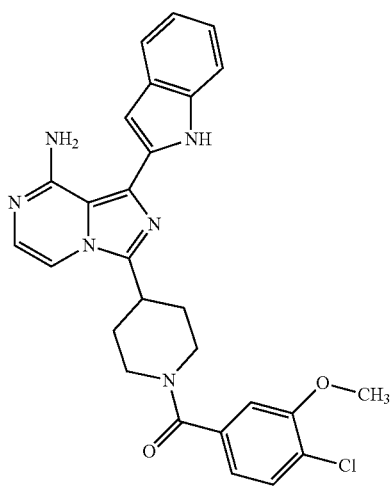

3-[1-(4-Chloro-3-methoxybenzoyl)piperidin-4-yl]-1-(1H-indol-2-yl)imidazo[1,5-α]pyrazin-8-amine Prepared according to the procedure described above for EXAMPLE 26, except using 4-chloro-3-methoxybenzoic acid in place of formic acid. MS (ES+): m/z 501.04 [MH+].

Example 56

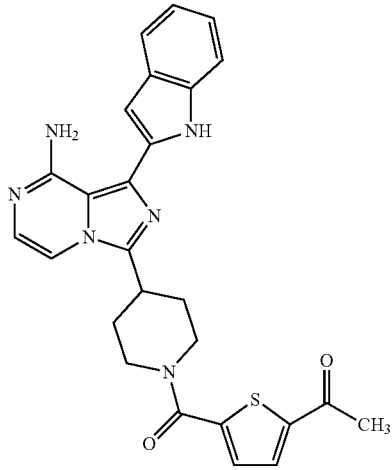

1-(5-{[4-(8-Amino-1-(1H-indol-2-yl)imidazo[1,5-α]pyrazin-3-yl)piperidin-1-yl]carbonyl}-2-thienyl)ethanone Prepared according to the procedure described above for EXAMPLE 26, except using 5-acetylthiophene-2-carboxylic acid in place of formic acid. MS (ES+): m/z 485.04 [MH+].

Example 57

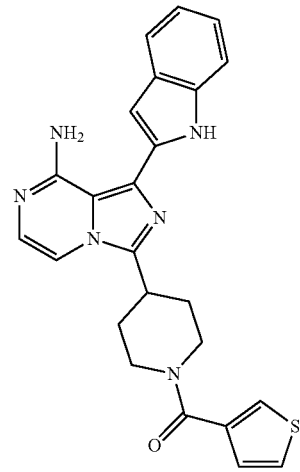

1-(1H-Indol-2-yl)-3-[1-(3-thienylcarbonyl)piperidin-4-yl]imidazo[1,5-α]pyrazin-8-amine Prepared according to the procedure described above for EXAMPLE 26, except using thiophene-3-carboxylic acid in place of formic acid. MS (ES+): m/z 443.04 [MH+].

Example 58

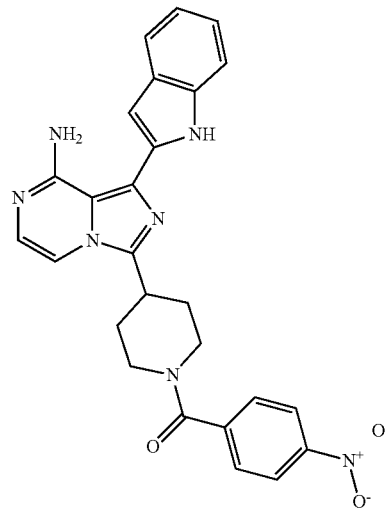

1-(1H-Indol-2-yl)-3-[1-(4-nitrobenzoyl)piperidin-4-yl]-imidazo[1,5-α]pyrazin-8-amine Prepared according to the procedure described above for EXAMPLE 26, except using 4-nitrobenzoic acid in place of formic acid. MS (ES+): m/z 482.07 [MH+].

Example 59

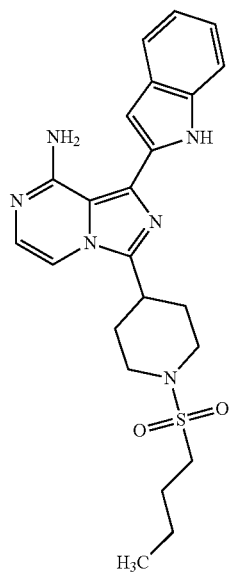

3-[1-(Butylsulfonyl)piperidin-4-yl]-1-(1H-indol-2-yl)imidazo[1,5-α]pyrazin-8-amine A solution of 1-(1H-indol-2-yl)-3-piperidin-4-ylimidazo[1,5-α]pyrazin-8-amine hydrochloride (33.233 mg, 0.075 mmol) in DMF (1 mL) was treated with N,N-diisopropylethylamine (0.05 mL, 0.3 mmol) and a solution of ″butanesulfonyl chloride (9.42 mg, 0.0602 mmol) in 1 mL of DMF. The mixture was left to stir at rt for 1 h and then subjected to mass-directed preparative HPLC to afford the title compound. $^1$H NMR (400 MHz-DMSO-d6) δ 0.91 (t, 3H), 1.40-1.45 (m, 2H), 1.66-1.69 (m, 2H), 1.86-1.90 (m, 2H) 2.04-2.09 (m, 2H) 3.02-3.11 (m, 5H) 3.73-3.77 (m, 2H), 6.47 (bs, 2M, 6.64 (s, 111, 7.00-7.05 (m, 1H) 7.09-7.12 (m, 2H), 7.45 (d, J=8.4 Hz, 1H), 7.58 (d, J=8.0 Hz, 1H), 7.69 (d, J=5.2 Hz, 1H). MS (ES+): m/z: 453.24 [MH+].

Example 60

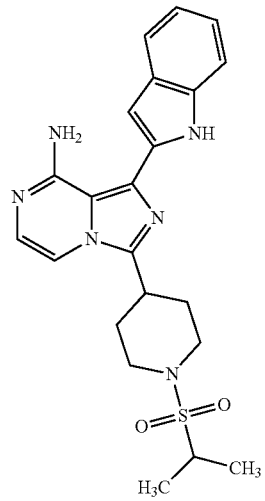

1-(1H-Indol-2-yl)-3-[1-(isopropylsulfonyl)piperidin-4-yl]imidazo[1,5-α]pyrazin-8-amine Prepared according to the procedure described above for EXAMPLE 59, except using isopropane-2-sulfonyl chloride in place of ″butanesulfonyl chloride. MS (ES+): m/z 439.27 [MH+].

Example 61

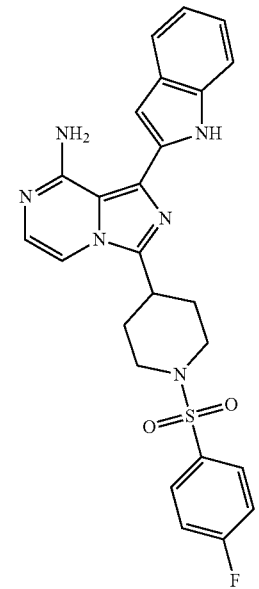

3-{1-[(—Fluorophenyl)sulfonyl]piperidin-4-yl}-1-(1H-indol-2-yl)imidazo[1,5-α]pyrazin-8-amine Prepared according to the procedure described above for EXAMPLE 59, except using 4-fluorobenzenesulfonyl chloride in place of "butanesulfonyl chloride. MS (ES+): m/z 491.15 [MH+].

Example 62

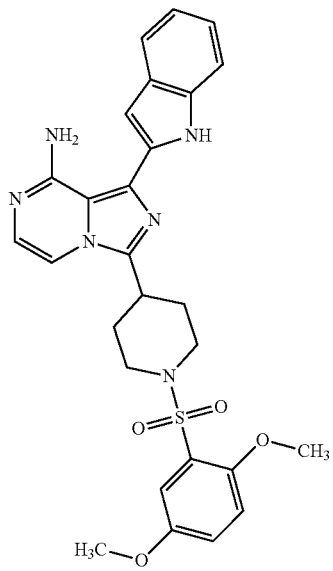

3-{1-[(2,5-Dimethoxyphenyl)sulfonyl]piperidin-4-yl}-1-(1H-indol-2-yl)imidazo[1,5-α]pyrazin-8-amine Prepared according to the procedure described above for EXAMPLE 59, except using 2,5-dimethoxybenzenesulfonyl chloride in place of "butanesulfonyl chloride. MS (ES+): m/z 533.17 [MH+].

Example 63

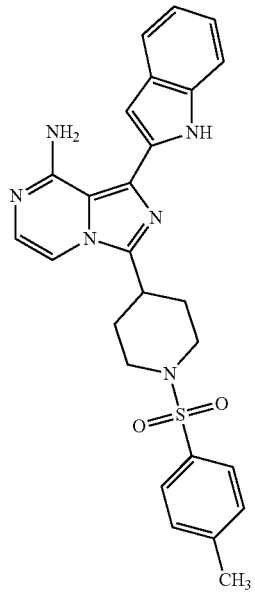

1-(1H-Indol-2-yl)-3-{1-[(4-methylphenyl)sulfonyl]piperidin-4-yl}imidazo[1,5-α]pyrazin-8-amine Prepared according to the procedure described above for EXAMPLE 59, except using 4-methylbenzenesulfonyl chloride in place of "butanesulfonyl chloride. MS (ES+): m/z 487.94 [MH+].

Example 64

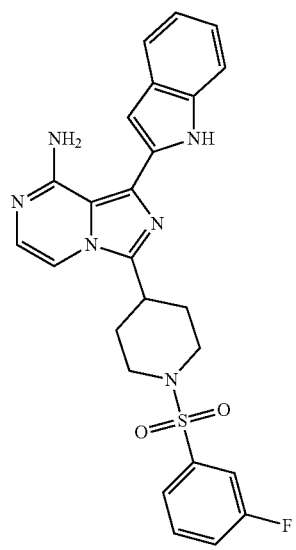

3-{1-[(3-Fluorophenyl)sulfonyl]piperidin 4-yl}-1-(1H-Indol-2-yl)imidazo[1,5-α]pyrazin-8-amine Prepared according to the procedure described above for EXAMPLE 59, except using 3-fluorobenzenesulfonyl chloride in place of "butanesulfonyl chloride. MS (ES+): m/z 491.92 [MH+].

Example 65

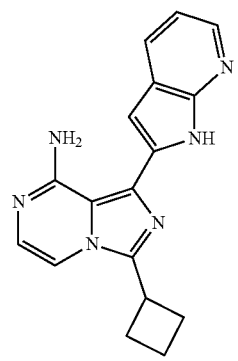

3-Cyclobutyl-1-(1H-pyrrolo[2,3-b]pyridin-2-yl)imidazo[1,5-α]pyrazin-8-amine

3-Cyclobutyl-1-[1-(2-trimethylsilylethoxymethyl)-1H-pyrrolo[2,3-b]pyridin-2-yl]imidazo[1,5-α]pyrazin-8-amine (35 mg, 0.08 mmol) was stirred with concentrated HCl for 15 min. The mixture was thien concentrated in vacuo and purified via mass directed preparative HPLC to afford the title compound. $^1$H NMR (400 MHz DMSO-d6) δ 1.92-2.00 (m, 1H), 2.07-2.14 (m, 1H), 2.43-2.47 (m, 4H), 3.93-4.01 (m, 1H), 6.35-6.49 (Us, 2H), 6.64-6.70 (m, 1H), 7.03-7.10 (m, 2H), 7.39-7.49 (m, 1H), 7.95-8.00 (m, 1H), 8.18-8.23 (m, 1H), 11.91 (bs, 1H). MS (ES+): m/z: 305.17 [MH+].

Example 66

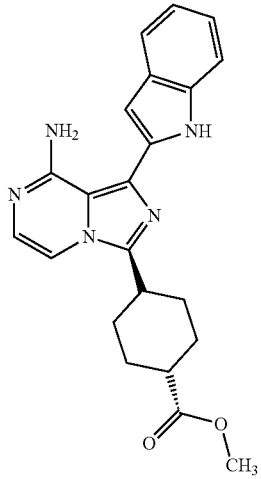

Methyl trans-4(8-amino-1-(1H-indol-2-yl)imidazo[1,5-α]pyrazin-3-yl)cyclohexanecarboxylate Starting from trans-methyl 4-(8-chloroimidazo[1,5-α]pyrazin-3-yl)cyclohexanecarboxylate, the title compound was prepared according to procedures analogous to those described for EXAMPLE 10. $^1$H NMR (d$_6$-DMSO, 400 MHz): δ 11.42 (br s, 1H), 7.70 (d, J=4.0 Hz, 1H), 7.58 (d, J=8.0 Hz, 1H), 7.46 (d, J=8.0 Hz, 1H), 7.30-4.90 (m, 3H), 6.63 (br s, 1H), 6.44 (br s, 1H), 3.64 (s, 3H), 3.18 (m, 1H), 2.44 (m, 1H), 2.03 (m, 4H), 1.80-1.50 (m, 4H). MS (ES+): m/z 390.28 [MH+].

Example 67

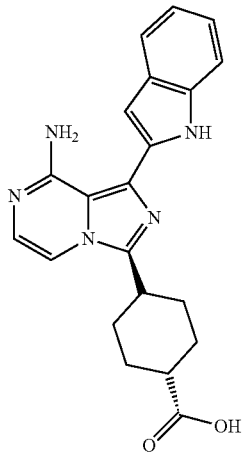

trans-4-(8-Amino-1-(1H-indol-2-yl)imidazo[1,5-α]pyrazin-3-yl)cyclohexanecarboxylic Acid A mixture of 37% HCl (30 mL) and methyl trans-4-(8-amino-1-(1H-indol-2-yl)imidazo[1,5-α]pyrazin-3-yl)cyclohexanecarboxylate (500.0 mg, 1.28 mmol) was stirred for 18 h at rt. The reaction mixture was then concentrated in vacuo, and the residue washed with diethyl ether (3×10 mL) and ethyl acetate (2×10 mL), then with ice-cold acetonitrile (10 mL) to afford 0.3 g of the desired product. $^1$H NMR (d6-DMSO, 400 MHz): δ 12.15 (br s, 1H), 11.69 (s, 1H), 8.45 (br s, 2H), 7.97 (d, J=6.4 Hz, 1H), 7.63 (d, J=8.0 Hz, 1H), 7.50 (dd, J=8.0, 0.4 Hz, 1H), 7.19 (m, 1H), 7.13 (d, J=6.0 Hz, 1H), 7.06 (m, 1H), 6.83 (d, J=1.6 Hz, 1H), 3.27 (td, J=11.6, 3.2, 3.2 Hz, 1H), 2.33 (td, J=10.8, 3.2, 3.2 Hz, 1H), 2.05 (m, 4H), 1.73 (m, 2H) and 1.58 (m/z, 2H). MS (ES+): m/z 376.05 [MH+].

Example 68

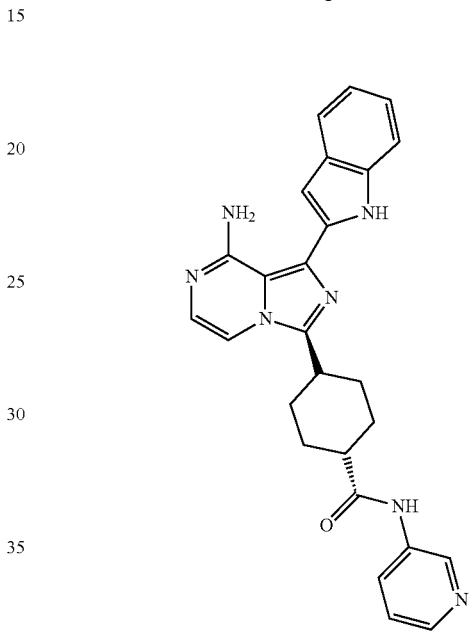

trans-4(8-Amino-1-(Yl-indol-2-yl)imidazo[1,5-α]pyrazin-3-yl)-N-pyridin-3-ylcyclohexanecarboxamide A suspension of 3-aminopyridine (40 mg, 0.43 mmol) in toluene (1.3 mL) was treated with a 2M toluene solution of trimethylaluminum (0.3 mL, 0.60 mmol). After 25 min, the resulting solution was treated with methyl trans-4-(8-amino-1-(1H-indol-2-yl)imidazo[1,5-α]pyrazin-3-yl)cyclohexanecarboxylate (30 mg, 0.08 mol) and the mixture stirred at rt overnight. The mixture was then stirred with 2M NaOH (20 mL) and ethyl acetate (20 mL) for 110 min., then the organic phase was separated and the aqueous extracted EtOAc (3×15 nm). The combined organic extracts were washed with water (20 mL) and brine (20 mL), then dried over Na$_2$SO$_4$ and concentrated in vacuo to give crude product which was subjected to mass-directed preparative HPLC to afford pure desired product. $^1$H NMR (d$_6$-DMSO, 400 MHz): δ 11.45 (br s, 1H), 10.12 (s, 1H), 8.77 (d, J=2.4 Hz, 1H), 8.25 (d, J=4.8 Hz, 1H), 8.14 (s, 1H), 8.08 (dd, J=8.0, 1.6 Hz, 1H), 7.71 (d, J=5.2 Hz, 1H), 7.59 (d, J=7.6 Hz, 1H), 7.46 (d, J=8.4 Hz, 1H), 7.34 (m, 1H), 7.15-7.00 (m, 3H), 6.65 (s, 1H), 6.42 (br s, 2H), 3.22 (m, 1H), 2.47 (m, 1H), 2.15-1.95 (m, 4H), and 1.85-1.65 (m, 4H). MS (ES+): m/z 452.17 [MH+].

Example 69

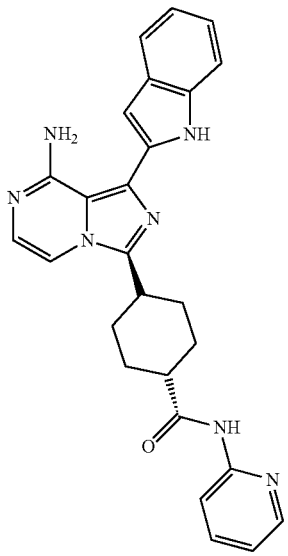

trans-4-(8-Amino-1-(1H-indol-2-yl)imidazo[1,5-α]pyrazin-3-yl)-N-pyridin-2-ylcyclohexanecarboxamide Prepared according to the procedure described above for EXAMPLE 68, except using 2-aminopyridine in place of 3-aminopyridine. MS (ES+): m/z 452.17 [MH+].

Example 70

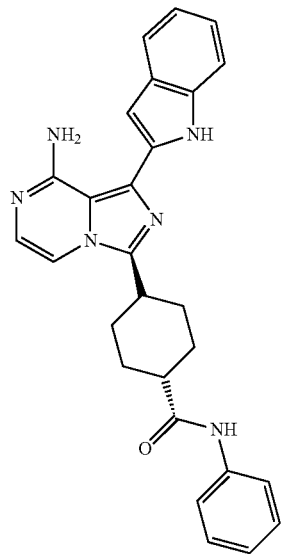

trans-4-(8-Amino-1-(1H-indol-2-yl)imidazo[1,5-α]pyrazin-3-yl)-N-phenylcyclohexane carboxamide Prepared according to the procedure described above for EXAMPLE 68, except using aniline in place of 3-aminopyridine. MS (ES+): m/z 451.16 [MH+].

Example 71

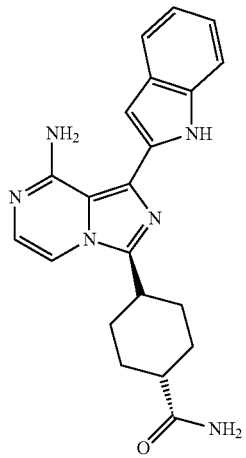

trans-4-(8-Amino-1-(1H-indol-2-yl)imidazo[1,5-α]pyrazin-3-yl)cyclohexanecarboxamide trans-4-(8-Amino-1-iodoimidazo[1,5-α]pyrazin-3-yl)cyclohexanecarboxamide (40 mg, 0.10 mmol), 1-(tert-butoxycarbonyl)-1H-indole-2-boronic acid (33 mg, 0.12 mmol), and sodium carbonate (33 mg, 0.31 mmol) were added to DME:Water (5:1) (2 mL) and the mixture degassed with Argon for 10 min. Tetrakis(triphenylphosphine)palladium(0) (8.0 mg, 0.007 mmol) was then added and the reaction mixture microwaved at 110° C. for 1 h, The mixture was concentrated in vacuo, taken up in DMSO, and purified by mass-directed preparative HPLC to afford desired product. $^1$H NMR (d$_6$-DMSO, 400 MHz): ☐ 11.50 (br s, 1H), 7.72 (m, 1H), 7.58 (m, 1H), 7.46 (dd, J=7.6, 0.4 Hz, 1H), 7.25 (br s, 1H), 7.13 (m, 1H), 7.08-7.00 (m, 2H), 6.70 (br s, 1H), 6.69 (br s, W, 3.16 (m, 1H), 2.20 (m, 1H), 2.10-1.80 (m, 4H) and 1.65 (m, 4H). MS (ES+): m/z 375.17 [MH+].

Example 72

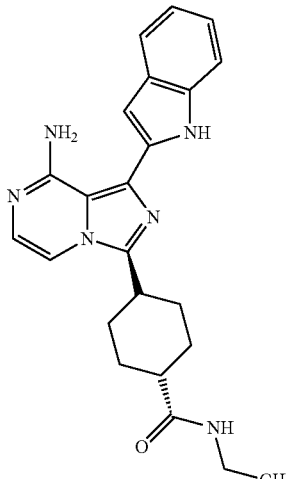

trans-4-(8-Amino-1-(1H-indol-2-yl)imidazo[1,5-α]pyrazin-3-yl)-N-ethylcyclohexanecarboxamide Ethylamine hydrochloride (30 mg, 0.37 mmol), 2-(1H-benzotriazol-1-yl)-1,1,3,3-tetramethyluronium tetrafluoroborate (35 mg, 0.11 mmol), and N,N-diisopropylethylamine (80 μL, 0.53 mmol) were added to a solution of trans-4-(8-Amino-1-(1H-indol-2-yl)imidazo[1,5-α]pyrazin-3-yl)cyclohexanecarboxylic acid (25 mg, 0.07 mmol) in anhydrous DMF (2 mL). Upon completion of reaction (as monitored by LCMS), the mixture was added to a saturated aqueous sodium bicarbonate solution (10 mL). The resulting precipitate was collected by filtration and washed with cold acetonitrile (3×10 mL) to afford 13 mg of the desired product. $^1$H NMR (d$_6$-DMSO, 400 MHz): δ 11.41 (br s, 1H), 7.75 (dd, J=4.0, 4.0 Hz, 1H), 7.69 (d, J=4.0 Hz, 1H), 7.58 (d, J=8.0, 4.0 Hz, 1H), 7.45 (d, J=4.0, 4.0 Hz, 1H), 7.12 (dd, J=8.0, 8.0 Hz, 1H), 7.08-7.00 (m, 2H), 6.63 (m, 1H), 6.43 (br s, 2H), 3.16 (m, 1H), 3.07 (m, 2H), 2.18 (m, 1H), 2.02 (m, 2H), 1.84 (m, 2H), 1.66 (m, 4H) and 1.02 (t, J=4.0 Hz, 3H). MS (ES+): m/z 403.09 [MH+].

Example 73

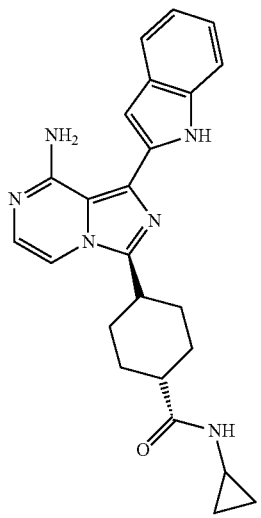

trans-4-(8-Amino-1-(1H-indol-2-yl)imidazo[1,5α]pyrazin-3-yl)-N-cyclopropylcyclo hexanecarboxamide Prepared according to the procedure described above for EXAMPLE 72, except using cyclopropylamine in place of ethylamine. MS (ES+): m/z 415.22 [MH+].

Example 74

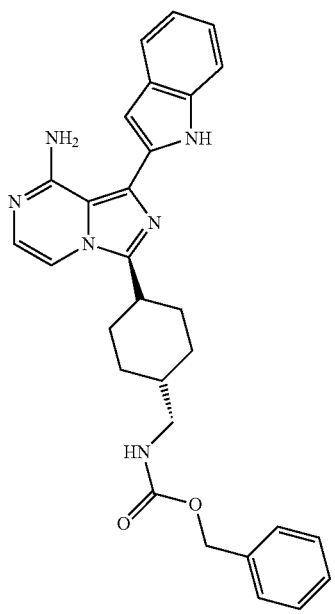

Benzyl {[trans-4(8-amino-1-(1H-indol-2-yl)imidazo[1,5-α]pyrazin-3-yl)cyclohexyl]methyl}carbamate A mixture of benzyl {[trans-4-(8-amino-1-iodoimidazo[1,5-α]pyrazin-3-yl)cyclohexyl]methyl}carbamate (1.00 g, 0.00180 mol), 1-(tert-butoxycarbonyl)-1H-indole-2-boronic acid (0.517 g, 0.00198 mol), 1,2-dimethoxyethane (7.7 mL), water (1.4 mL, 0.081 mol) and Cesium Carbonate (1.17 g, 0.00360 mol) degassed three times, treated with tetrakis(triphenylphosphine)palladium(0) (200 mg, 0.0002 mol) and degassed once more. The resulting mixture was heated at 100° C. overnight before being diluted with EtOAc (40 mL), washed with water (2×30 mL) and brine (20 mL) then dried over Na$_2$SO$_4$ and concentrated in vacuo. The crude product thus isolated was chromatographed over silica gel eluting with hexane→EtOAc:hexane: 5% 2M NH$_3$ in MeOH 1:1: 0.05 to afford the title compound. $^1$H NMR (400 MHz, CDCl$_3$): δ 1.13-1.22 (m, 2H), 1.75-1.86 (m, 2H), 1.94-1.97 (m, 2H), 2.11-2.13 (m, 2H), 2.86 (m, 1H), 3.12-3.16 (m, 2H), 4.82 (m, 1H) 5.12 (s, 2H), 5.69 (br, 2H), 6.78 (s, 1H), 7.13-7.15 (m, 2H), 7.19-7.25 (m, 2H), 7.32-7.38 (m, 5H), 7.42 (d, J=8.0 Hz, 1H), 7.64 (d, J=8.4 Hz, 1H), 9.09 (br, 1H). MS (ES+): m/z 495 [MH+].

Example 75

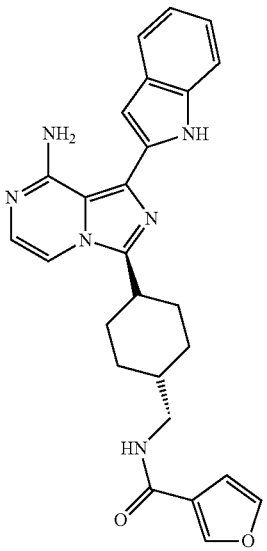

N-{[trans-4-(8-Amino]-(1H-indol-2-yl)imidazo[1,5-α]pyrazin-3-yl)cyclohexyl methyl}-3-furamide Prepared according to the procedure described above for EXAMPLE 22, except using 2-furoic acid in place of acetic acid. MS (ES+): m/z 455.20 [MH+].

Example 76

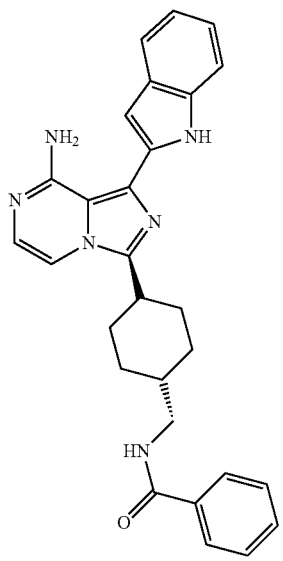

N-{[trans-4(8-Amino-1-(1-indol-2-yl)imidazo[1,5-α]pyrazin-3-yl)cyclohexyl]methyl}benzamide Prepared according to the procedure described above for EXAMPLE 22, except using benzoic acid in place of acetic acid. MS (ES+): m/z 465-25 [MH+].

Example 77

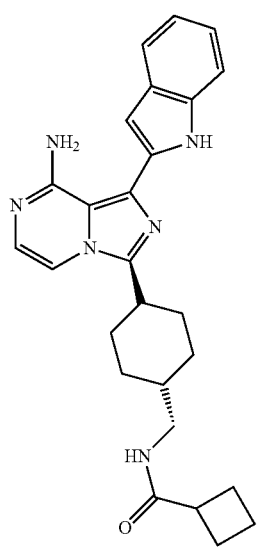

N-{[trans-4-(8-Amino-1-(1H-indol-2-yl)imidazo[1,5-α]pyrazin-3-yl)cyclohexyl]methyl}cyclobutanecarboxamide Prepared according to the procedure described above for EXAMPLE 22, except using cyclobutanecarboxylic acid in place of acetic acid. MS (ES+): m/z 443.25 [MH+].

Example 78

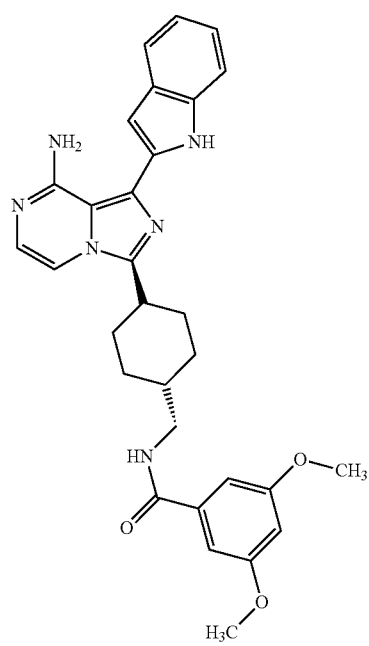

N-{[trans-4-(8-Amino1-(1H-indol-2-yl)imidazo[1,5-α]pyrazin-3-yl)cyclohexyl]methyl}-3,5-dimethoxy-benzamide Prepared according to the procedure described above for EXAMPLE 22, except using 3,5-dimethoxybenzoic acid in place of acetic acid. MS (ES+): m/z 525.35 [MH+].

Example 79

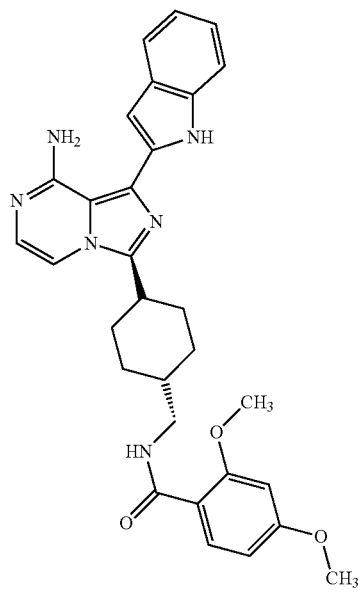

N-{[trans-4-(8-Amino-1-(1H-indol-2-yl)imidazo[1,5-α]pyrazin-3-yl)cyclohexyl]methyl}-2,4-dimethoxybenzamide Prepared according to the procedure described above for EXAMPLE 22, except using 2,4-dimethoxybenzoic acid in place of acetic acid. MS (ES+): m/z 525.33 [MH+].

Example 80

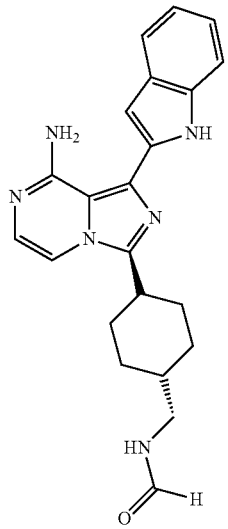

N-{[trans-4(8-Amino-1-(1H-indol-2-yl)imidazo[1,5-α]pyrazin-3-yl)cyclohexyl]methyl}formamide Prepared according to the procedure described above for EXAMPLE 22, except using formic acid in place of acetic acid. MS (ES+): m/z 389.10 [MH+].

Example 81

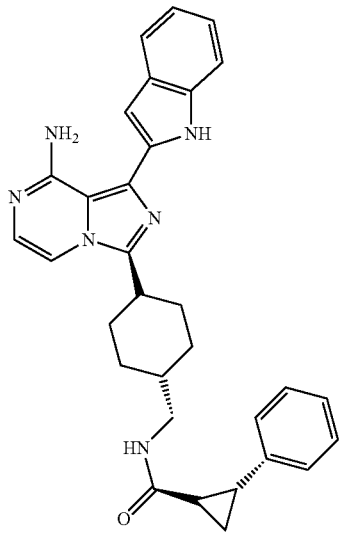

(1R,2R)—N-{[trans-4-(8-amino-1-(1H-indol-2-yl)imidazo[1,5-α]pyrazin-3-yl)cyclohexyl]methyl}-2-phenylcyclopropanecarboxamide Prepared according to the procedure described above for EXAMPLE 22, except using (1R,2R)-2-phenylcyclopropanecarboxylic acid in place of acetic acid. MS (ES+): m/z 505.30 [MH+].

Example 82

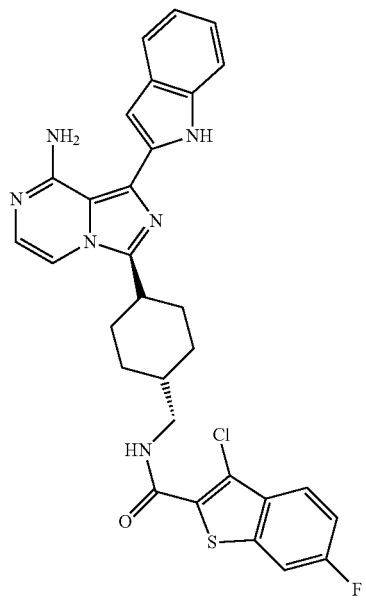

N-{[trans-4-(8-Amino-1-1H-indol-2-yl)imidazo[1,5-α]pyrazin-3-yl)cyclohexyl]methyl}-3-chloro-6-fluorobenzo[b]thiophene-2-carboxamide Prepared according to the procedure described above for EXAMPLE 22, except using 3-chloro-6-fluorobenzo[b]thiophene-2-carboxylic acid in place of acetic acid. MS (ES+): m/z 573.35 & 575.31 [MH+].

Example 83

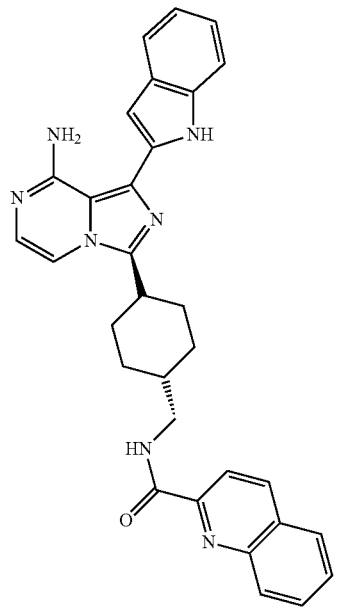

N-{[trans-4-(8-Amino-1-(If-indol-2-yl)imidazo[1,5-α]pyrazin-3-yl)cyclohexyl]methyl}isoquinoline-2-carboxamide Prepared according to the procedure described above for EXAMPLE 22, except using isoquinoline-2-carboxylic acid in place of acetic acid. MS (ES+): m/z 516.40 [MH+].

Example 84

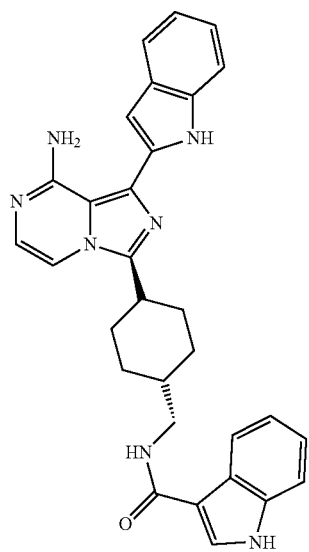

N-{[trans-(8-Amino-1-(1H-indol-2-yl)imidazo[1,5-α]pyrazin-3-yl)cyclohexyl]methyl}indole-3-carboxamide Prepared according to the procedure described above for EXAMPLE 22, except using indole-3-carboxylic acid in place of acetic acid. MS (ES+): m/z 505.46 [MH+].

Example 85

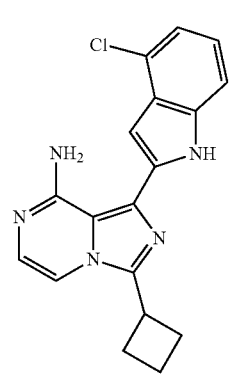

1-(4-Chloro-1H-indol-2-yl)-3-cyclobutylimidazo[1,5-α]pyrazin-8-amine

Prepared according to the procedure described above for EXAMPLE 2, except using 1-(tert-butoxycarbonyl)-4-chloro-1H-indole-2-boronic acid in place of 1-(tert-butoxycarbonyl)-1H-indole-2-boronic acid. $^1$H NMR (400 MHz-DMSO-d6) δ 1.91-1.98 (m, 1H), 2.08-2.15 (m, 1H), 2.42-2.46 (m, 4H), 3.97-4.00 (m, 1H), 6.42 (bs, 2H), 6.67 (s, 1H), 7.09-7.14 (m, 3H), 7.43-7.47 (m, 2H) and 11.83 (bs, 1H). MS (ES+): m/z 338.26 [MH+].

Example 86

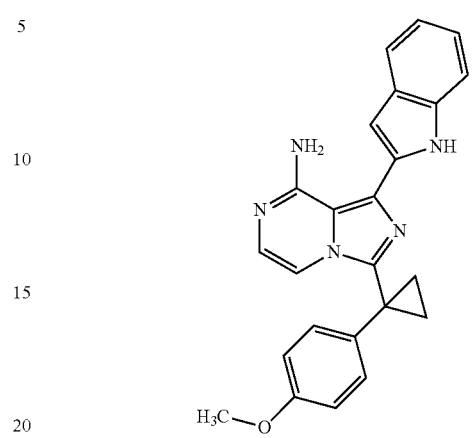

1-(1H-Indol-2-yl)-3-[1-(4-methoxyphenyl)cyclopropyl]imidazo[1,5-α]pyrazin-8-amine Prepared according to the procedure described above for EXAMPLE 2, except using 4-methoxyphenyl)cyclopropanecarboxylic acid in place of cyclobutanecarboxylic acid. $^1$H NMR (400 MHz, CHLOROFORM-d) δ ppm 1.46 (s, 2 H), 1.58 (s, 2 H), 3.76 (s, 3 H), 6.78 (d, J=8.80 Hz, 2 H), 6.77 (s, 1 H), 6.82 (s, 1 H), 6.98 (d, J=5.13 Hz, 1 H), 7.03 (d, J=8.80 Hz, 2 H), 7.15 (t, J=7.52 Hz, 1H), 7.23 (s, 2 H), 7.44 (d, J=8.07 Hz, 1 H), 7.65 (d, J=8.07 Hz, 1 H) and 9.36 (br. s., 1 H). MS (ES+): m/z 396.15 [MH+].

Example 87

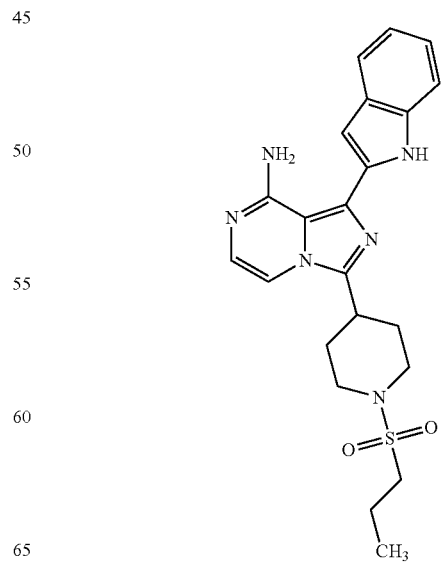

1-(1H-Indol-2-yl)-3-[1-(propylsulfonyl)piperidin-4-yl]imidazo[1,5-α]pyrazin-8-amine Prepared according to the procedure described above for EXAMPLE 59, except using propane-2-sulfonyl chloride in place of "butanesulfonyl chloride. MS (ES+): m/z 439.06 [MH+].

Example 88

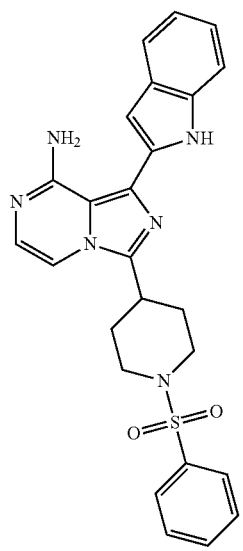

1-(1H-Indol-2-yl)-3-[1-(phenylsulfonyl)piperidin-4-yl]imidazo[1,5-α]pyrazin-8-amine Prepared according to the procedure described above for EXAMPLE 59, except using benzenesulfonyl chloride in place of "butanesulfonyl chloride. MS (ES+): m/z 473.29 [MH+].

Example 89

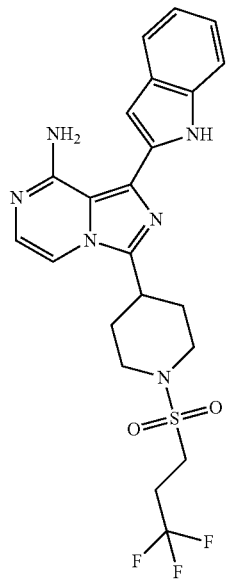

1-(1H-Indol-2-yl)-3-{1-[(3,3,3-trifluoropropyl)sulfonyl]piperidin-4-yl}imidazo[1,5-α]pyrazin-8-amine Prepared according to the procedure described above for EXAMPLE 59, except using 3,3,3-trifluoropropane-1-sulfonyl chloride in place of "butanesulfonyl chloride. MS (ES+): m/z 493.19 [MH+].

Example 90

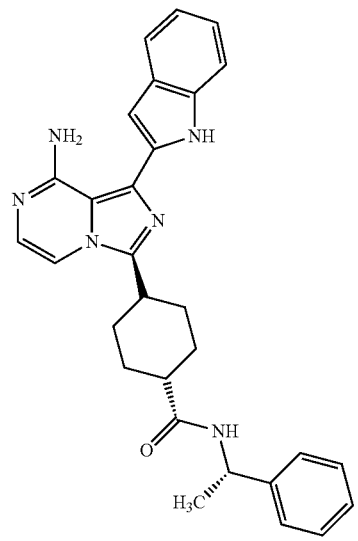

trans-3-(8-Amino-1-(1H-indol-2-yl)imidazo[1,5-α]pyrazin-3-yl)-N-[(1S)-1-phenylethyl]cyclohexanecarboxamide Prepared according to the procedure described above for EXAMPLE 72, except using (1S)-4-phenylethanamine in place of cyclopropylamine. MS (ES+): m/z 479.11 [MH+].

Example 91

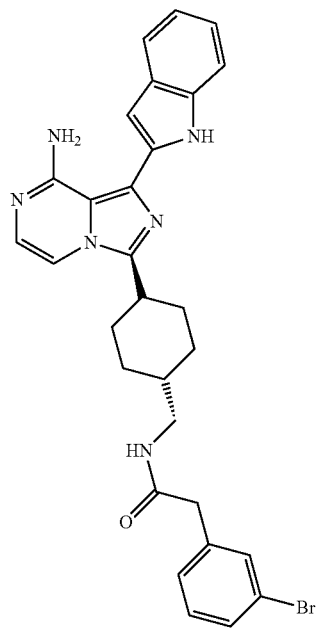

N-{[trans-4(8-Amino1-(1H-indol-2-yl)imidazo[1,5-α]pyrazin-3-yl)cyclohexyl]methyl}(3-bromophenyl)acetamide Prepared according to the procedure described above for EXAMPLE 22, except using 3-bromophenylacetic acid in place of acetic acid. MS (ES+): m/z 557.21 and 559.20 [MH+].

Example 92

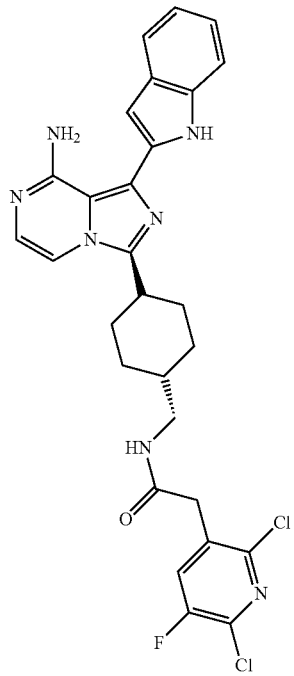

N-{[trans-4-(8-Amino-1-(1H-indol-2-yl)imidazo[1,5-α]pyrazin-3-yl)cyclohexyl]methyl}(2,6-dichloro-5-fluoropyridin-3-yl)acetamide Prepared according to the procedure described above for EXAMPLE 22, except using (2,6-dichloro-5-fluoropyridin-3-yl)acetic acid in place of acetic acid. MS (ES+): m/z 522.21 [MH+].

Example 93

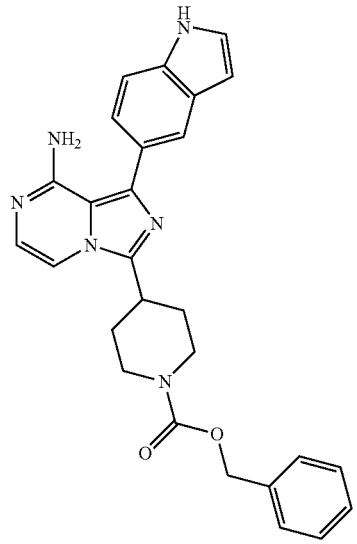

Benzyl 4-[8-amino-1-(1H-indol-5-yl)imidazo[1,5-α]pyrazin-3-yl]piperidine-1-carboxylate Prepared according to the procedure described above for EXAMPLE 24, except using indole-5-boronic acid in place of 1-(tert-butoxycarbonyl)-1H-indole-2-boronic acid. MS (ES+): m/z 494.97 [MH+].

Example 94

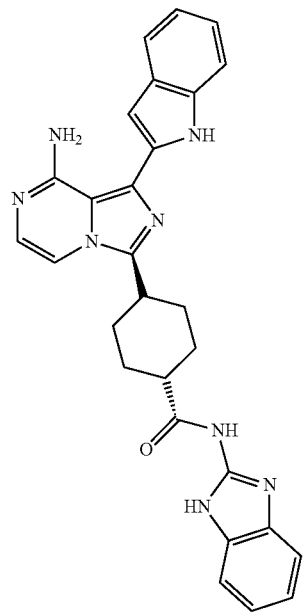

trans-4-(8-Amino-1-(1H-indol-2-yl)imidazo[1,5-α]pyrazin-3-yl)-N-benzimidazol-2-ylcyclohexanecarboxamide Prepared according to the procedure described above for EXAMPLE 68, except using 2-aminobenzimidazole in place of 3-aminopyridine. MS (ES+): m/z 490.97 [MH+].

Example 95

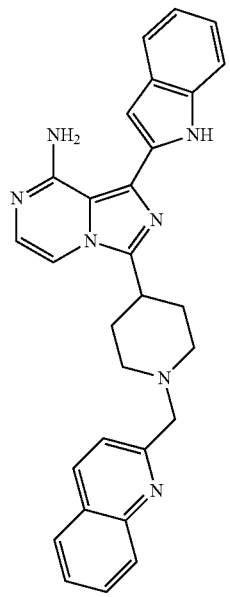

1-(1H-Indol-2-yl)-3-[1-(quinolin-2-ylmethyl)piperidin-4-yl]imidazo[1,5-α]pyrazin-8-amine A solution of 1-(1H-Indol-2-yl)-3-piperidin-4-ylimidazo[1,5-α]pyrazin-8-amine hydrochloride (30 mg, 0.09 mmol), 2-formylquinoline (17 mg, 0.11 mmol) and triethylamine (0.019 mL, 0.14 mmol) in 1,4-dioxane (1 mL) was treated with sodium cyanoborohydride (5.7 mg, 0.090 mmol) and microwaved at 300 watts, 120° C. for 20 min. The mixture was concentrated in vacuo, the residue was dissolved in methanol loaded onto an SCX ion exchange cartridge, and then eluted with 1M NH₄OH in methanol. The semi-pure material thus obtained was then subjected to semi-preparative HPLC to afford desired product. $^1$H NMR (400 h MeOD) δ ppm 2.13-2.33 (m, 4 H), 2.90 (t, J=10.86, 9.60 Hz, 2 H), 3.47 (d, J=10.11 Hz, 2 H), 4.29 (s, 2 H), 6.74 (s, 1 H), 7.02-7.11 (m, 2 H), 7.19 (t, J=8.08, 7.07 Hz, 1 H), 7.47 (d, J=39.09 Hz, 1 H), 7.58-7.65 (m, 3 H), 7.69 (d, J=8.59 Hz, 1 H), 7.80 (t, J=8.34, 6.82 Hz, 1 H), 7.96 (d, J=7.33 Hz, 1 H), 8.08 (d, J=8.34 Hz, 1 H) and 8.39 (d, J=8.59 Hz, 1 H). MS (ES+): m/z 474.23 [MH+].

Example 96

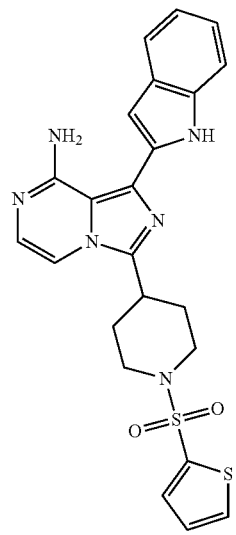

1-(1H-Indol-2-yl)-3-[1-(2-thienylsulfonyl)piperidin-4-yl]imidazo[1,5-α]pyrazin-8-amine Prepared according to the procedure described above for EXAMPLE 59, except using thiophene-2-sulfonyl chloride in place of "butanesulfonyl chloride. MS (ES+): m/z 479.16 [MH+].

Example 97

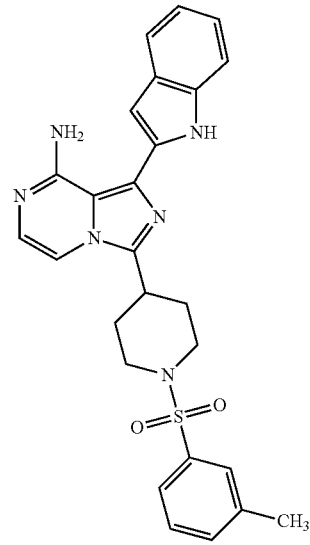

1-(1H-Indol-2-yl)-3-{1-[(3-methylphenyl)sulfonyl]piperidin-4-yl}imidazo[1,5-α]pyrazin-8-amine Prepared according to the procedure described above for EXAMPLE 59, except using 3-methylbenzenesulfonyl chloride in place of "butanesulfonyl chloride. MS (ES+): m/z 487.94 [MH+].

Example 98

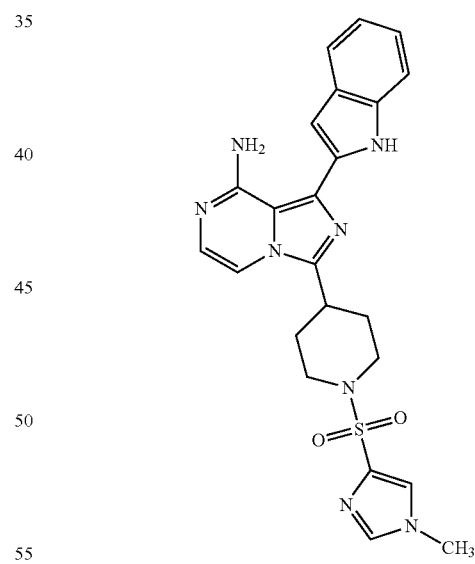

1-(1H-Indol-2-yl)-3-{1-[(1-methyl-1H-imidazol-4-yl)sulfonyl]piperidin-4-yl}imidazo[1,5-α]pyrazin-8-amine Prepared according to the procedure described above for EXAMPLE 59, except using 1-methyl-1H-imidazole-4-sulfonyl chloride in place of "butanesulfonyl chloride. MS (ES+): m/z 477.20 [MH+].

The following examples were prepared according to procedures analogous to those described above, utilizing where necessary known literature chemistries.

| Ex # | Structure | MH+ |
|---|---|---|
| 99 | 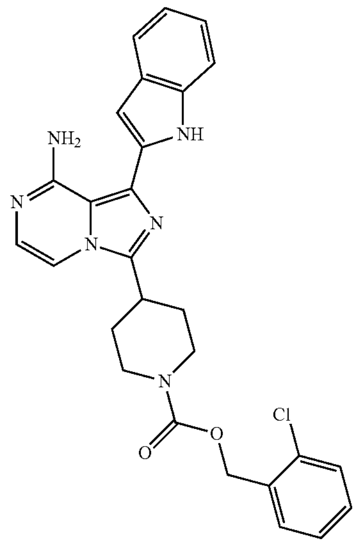 | 500.93
502.91 |
| 100 | | 433.06 |
| 101 | | 433.02 |

-continued
| Ex # | Structure | MH+ |
|---|---|---|
| 102 | 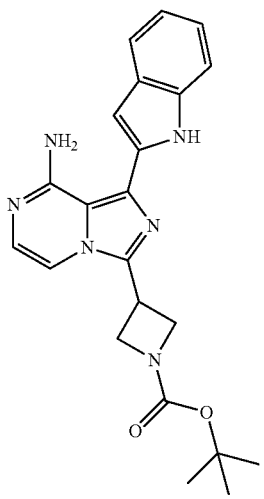 | 404.96 |
| 103 | 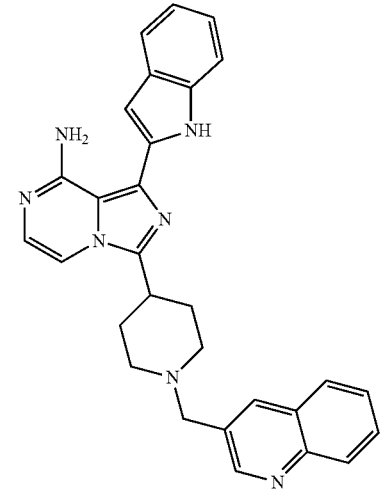 | 474.23 |
| 104 | 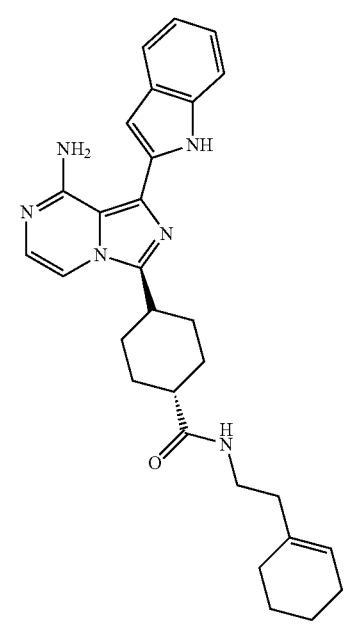 | 483.00 |

-continued
| Ex # | Structure | MH+ |
|---|---|---|
| 105 | 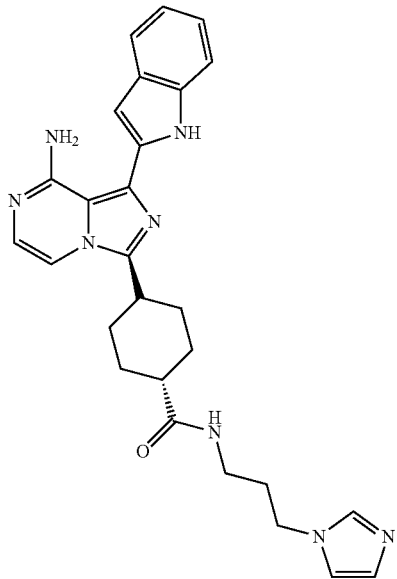 | 483.27 |
| 106 | 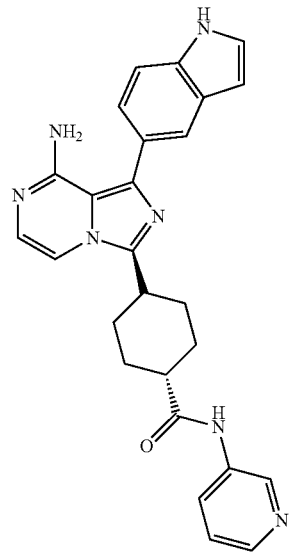 | 452.04 |

| Ex # | Structure | MH+ |
|---|---|---|
| 107 | 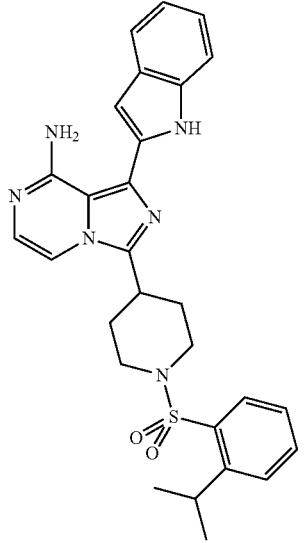 | 514.92 |
| 108 | 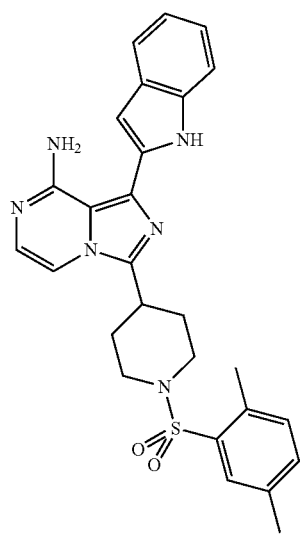 | 500.89 |

| Ex # | Structure | MH+ |
|---|---|---|
| 109 | 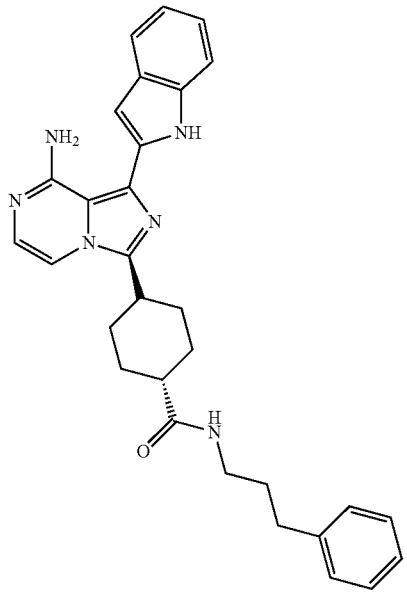 | 492.92 |
| 110 | 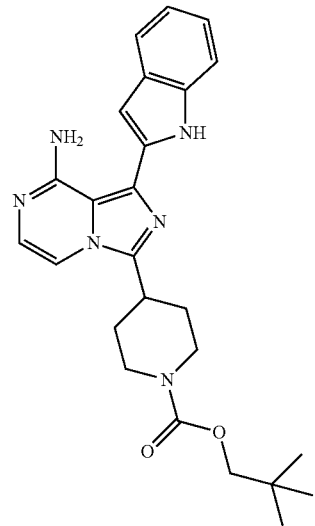 | 447.01 |

| Ex # | Structure | MH+ |
|---|---|---|
| 111 | 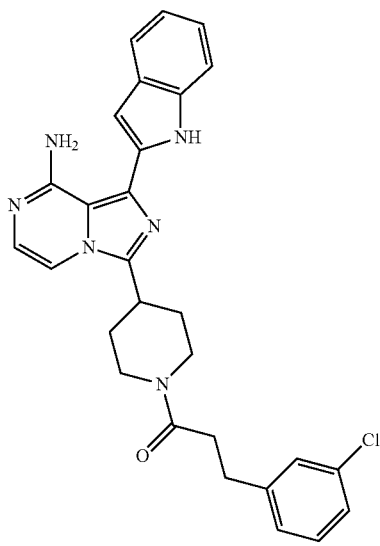 | 498.93<br>500.90 |
| 112 | 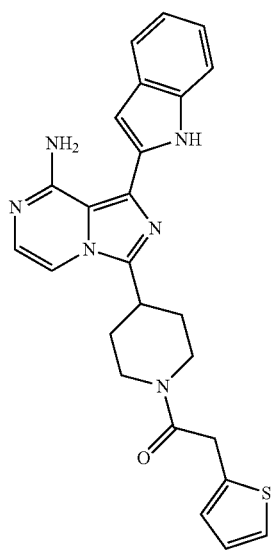 | 456.90 |
| 113 | 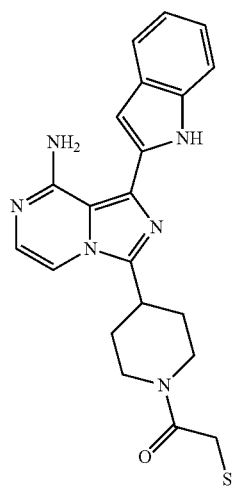 | 420.97 |

| Ex # | Structure | MH+ |
|---|---|---|
| 114 | 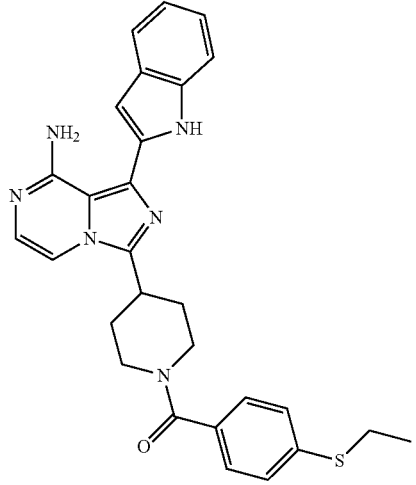 | 496.91 |
| 115 | 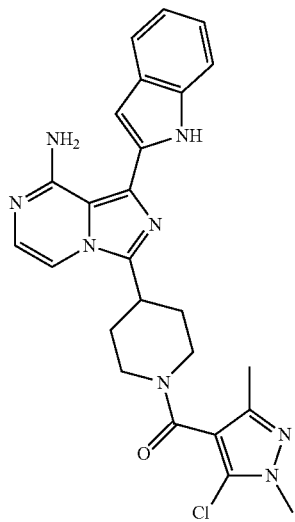 | 488.91 |
| 116 | 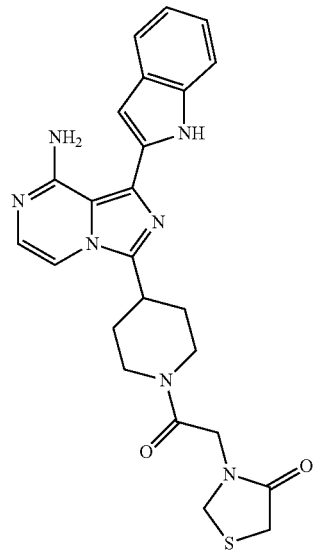 | 475.91 |

-continued

| Ex # | Structure | MH+ |
|---|---|---|
| 117 | 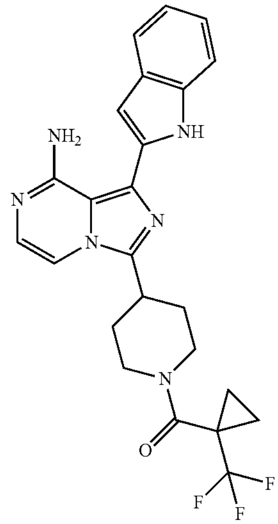 | 468.84 |
| 118 | 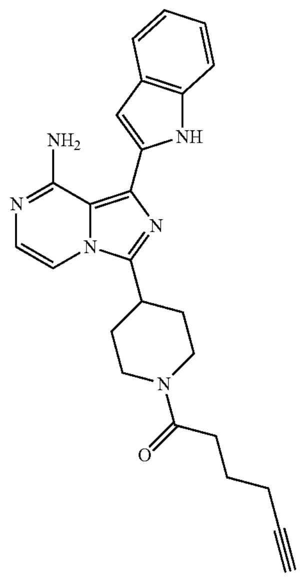 | 426.99 |
| 119 | 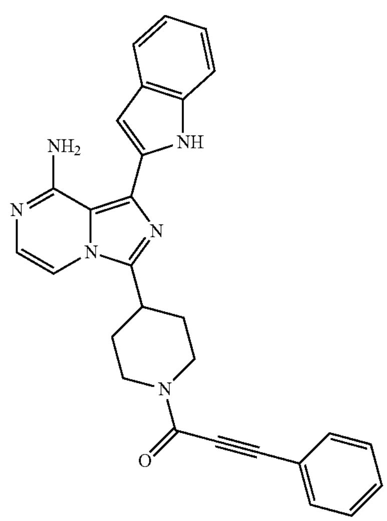 | 461.00 |

-continued

| Ex # | Structure | MH+ |
|---|---|---|
| 120 | 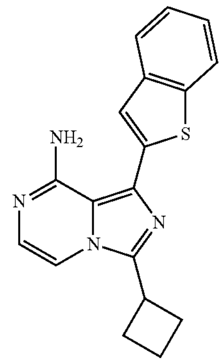 | 320.86 |
| 121 | 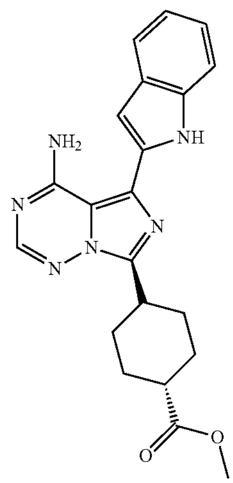 | 391.23 |
| 122 | 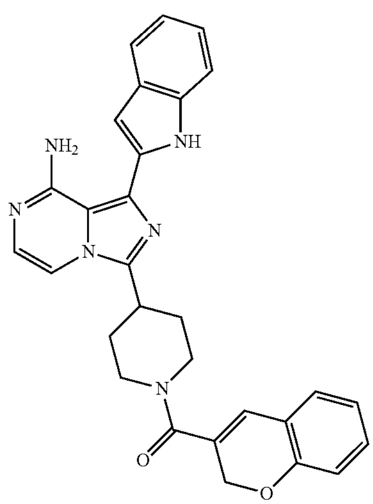 | 490.97 |

| Ex # | Structure | MH+ |
|---|---|---|
| 123 | 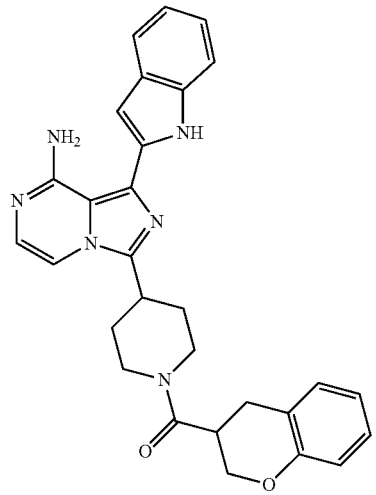 | 493.18 |
| 124 | 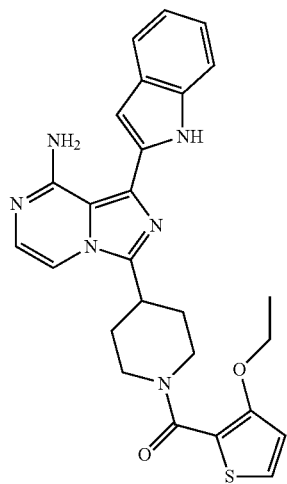 | 487.09 |
| 125 | 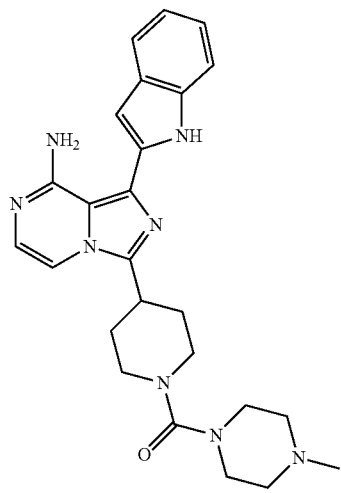 | 459.01 |

-continued
| Ex # | Structure | MH+ |
|------|-----------|-----|
| 126 | 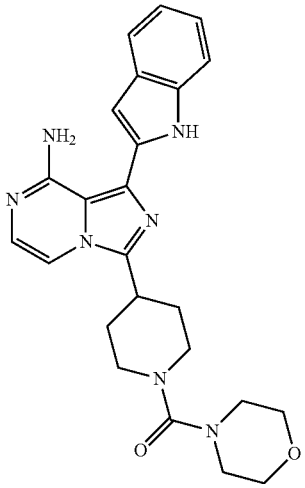 | 446.15 |
| 127 | 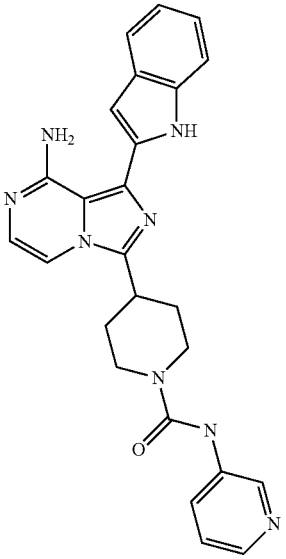 | 452.98 |
| 128 | 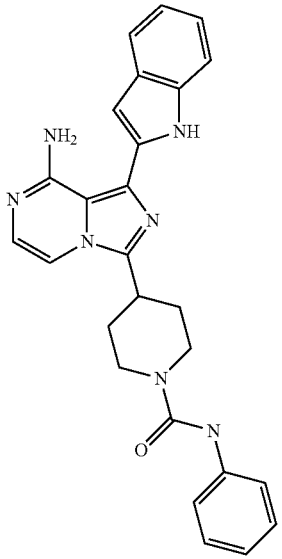 | 451.97 |

| Ex # | Structure | MH+ |
|---|---|---|
| 129 | 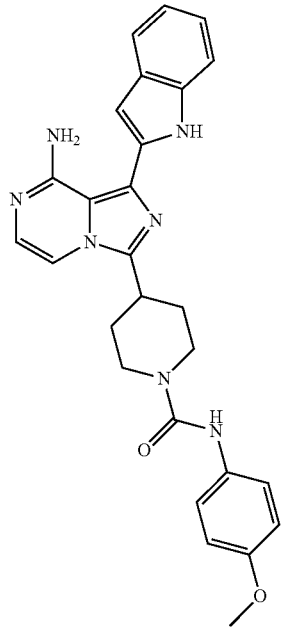 | 481.95 |
| 130 | 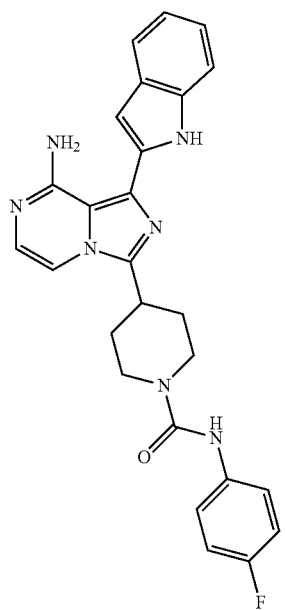 | 470.00 |

-continued
| Ex # | Structure | MH+ |
|---|---|---|
| 131 | 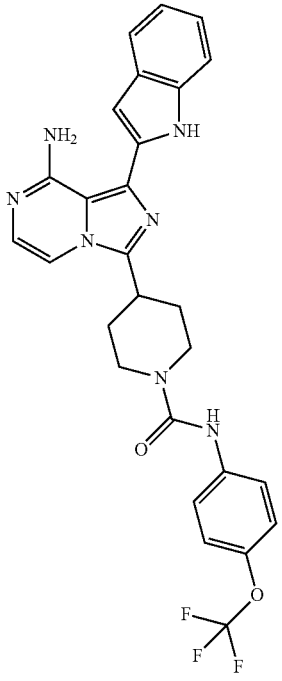 | 535.91 |
| 132 | 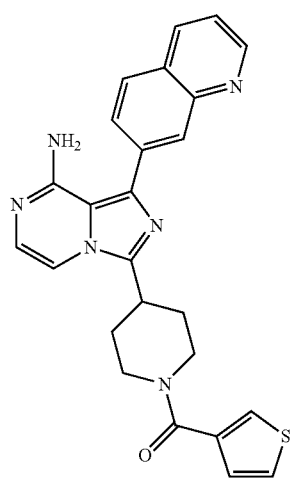 | 454.97 |

| Ex # | Structure | MH+ |
|---|---|---|
| 133 | 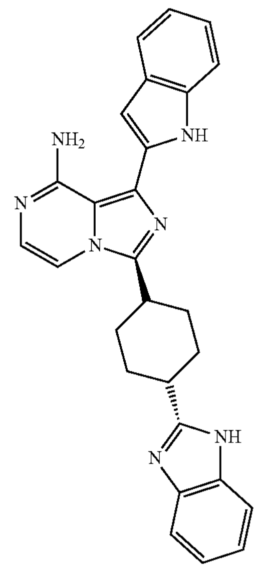 | 448.02 |
| 134 | 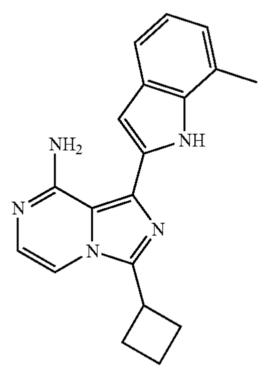 | 318.03 |
| 135 | 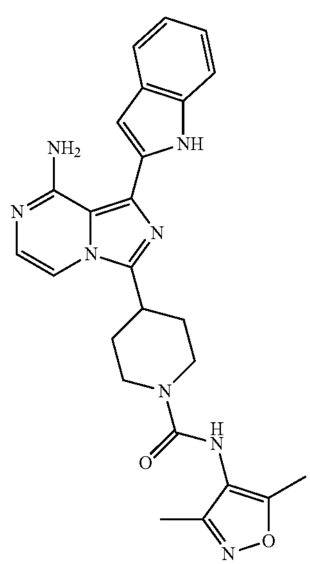 | 470.96 |

-continued

| Ex # | Structure | MH+ |
|---|---|---|
| 136 | 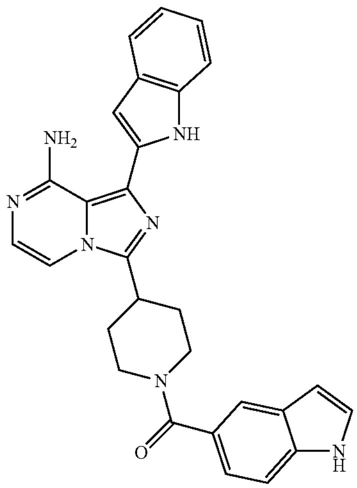 | 475.92 |
| 137 | 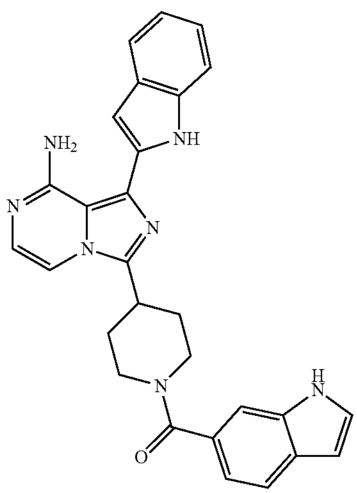 | 475.92 |
| 138 | 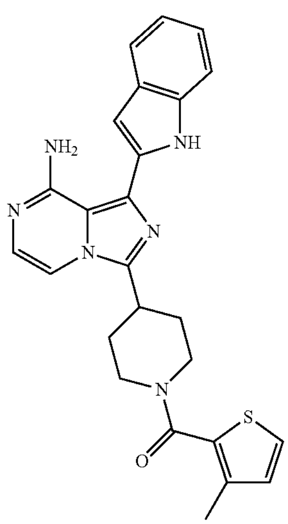 | 457.08 |

| Ex # | Structure | MH+ |
| --- | --- | --- |
| 139 | 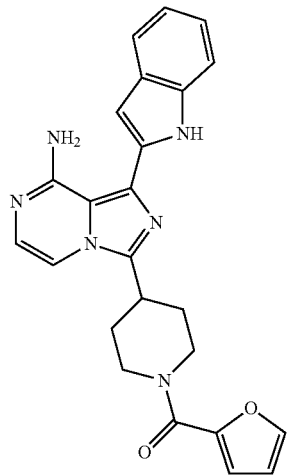 | 426.92 |
| 140 | 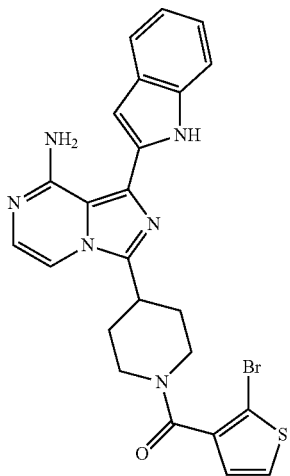 | 521.03<br>523.08 |
| 141 | 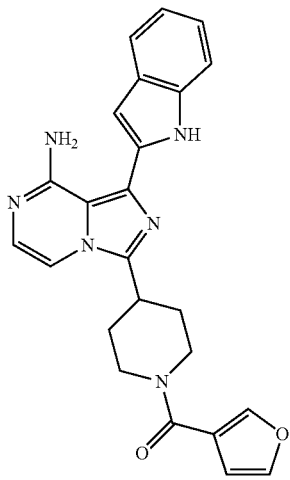 | 427.05 |

-continued

| Ex # | Structure | MH+ |
|---|---|---|
| 142 | 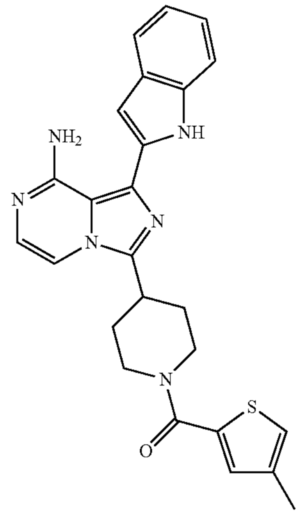 | 457.02 |
| 143 | 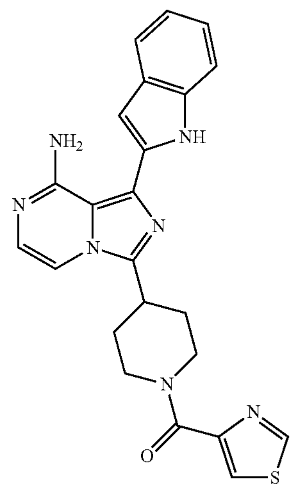 | 444.20 |
| 144 | 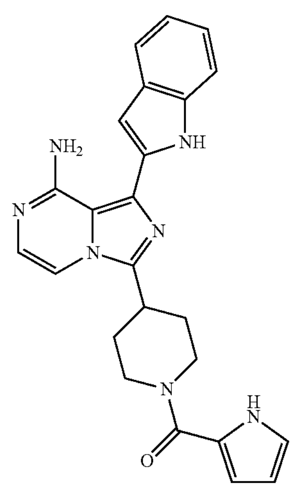 | 425.91 |

| Ex # | Structure | MH+ |
|---|---|---|
| 145 | 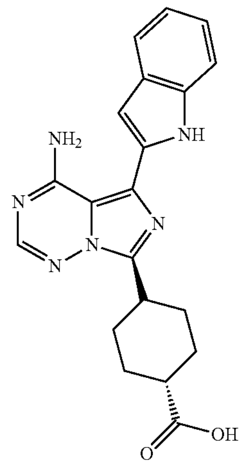 | 376.98 |
| 146 | 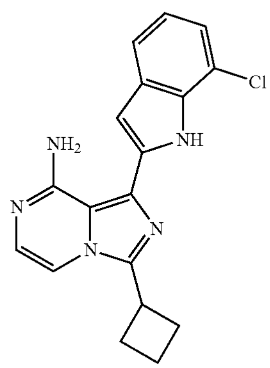 | 337.97<br>339.92 |
| 147 | 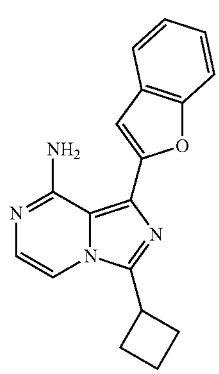 | 304.95 |

-continued
| Ex # | Structure | MH+ |
|---|---|---|
| 148 | 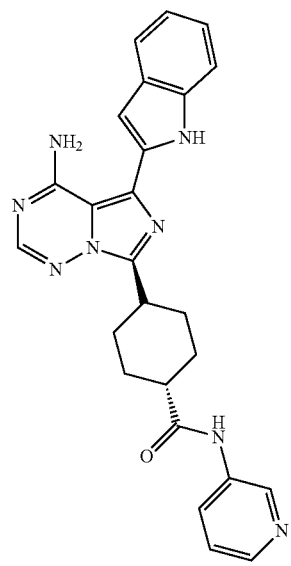 | 452.95 |
| 149 | 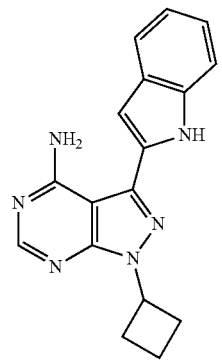 | 305.20 |
| 150 | 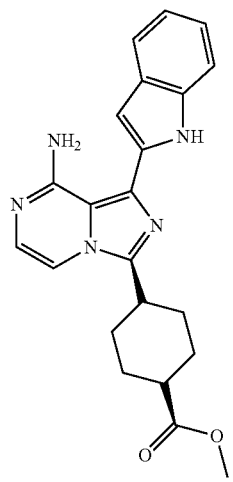 | 389.83 |

-continued

| Ex # | Structure | MH+ |
|---|---|---|
| 151 | 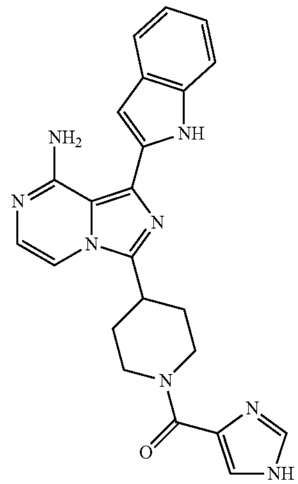 | 426.97 |
| 152 | 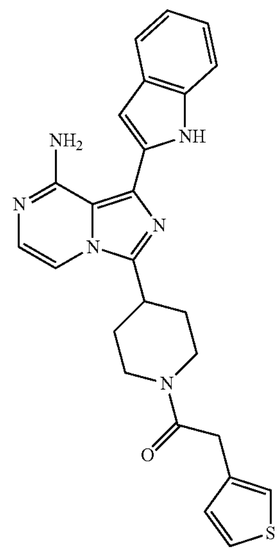 | 456.79 |
| 153 | 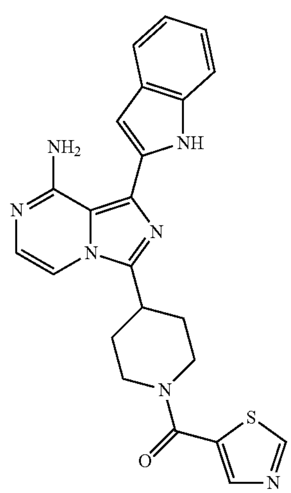 | 443.97 |

| Ex # | Structure | MH+ |
|---|---|---|
| 154 | 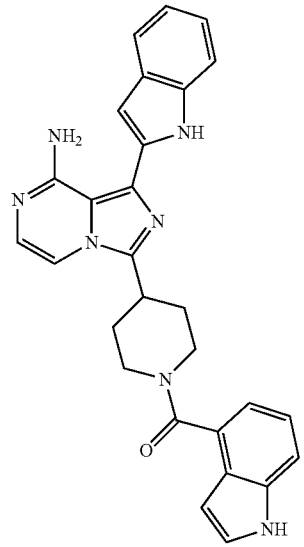 | 475.94 |
| 155 | 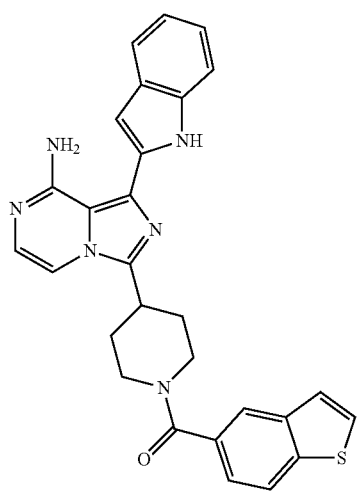 | 492.76 |
| 156 | 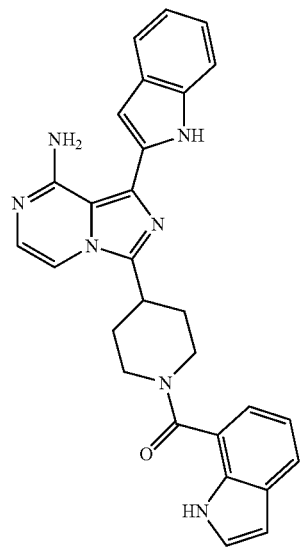 | 475.85 |

| Ex # | Structure | MH+ |
|---|---|---|
| 157 | 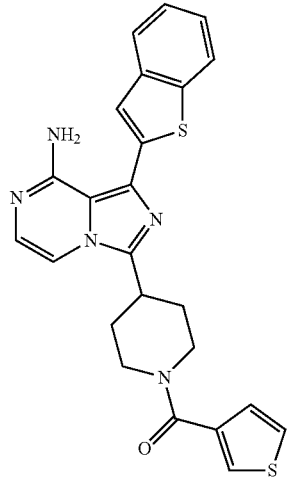 | 460.13 |
| 158 | 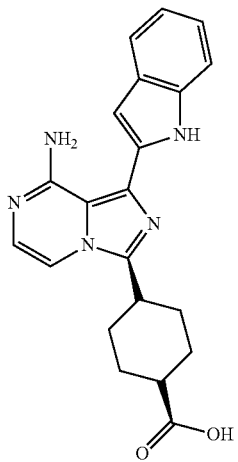 | 375.98 |
| 159 | 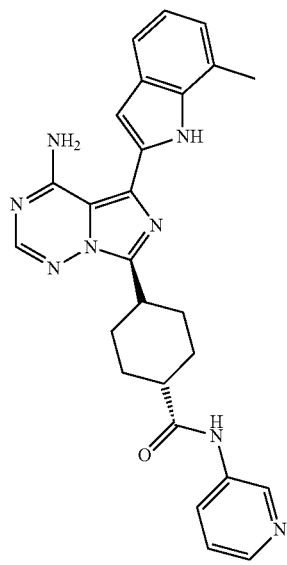 | 466.97 |

-continued
| Ex # | Structure | MH+ |
|---|---|---|
| 160 | 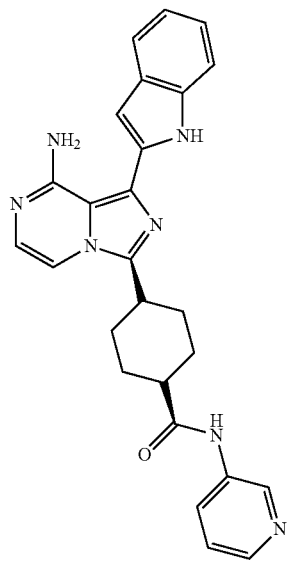 | 451.98 |
| 161 | 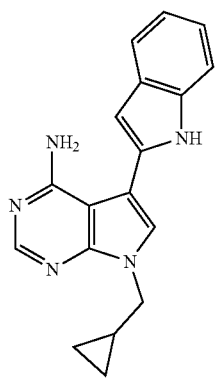 | 304.19 |
| 162 | 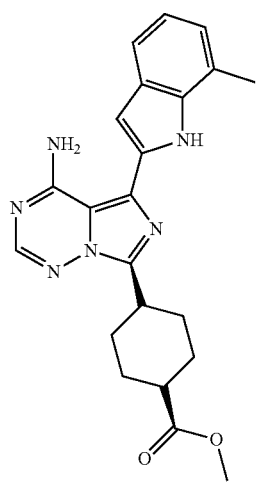 | 405.02 |

-continued

| Ex # | Structure | MH+ |
| --- | --- | --- |
| 163 | 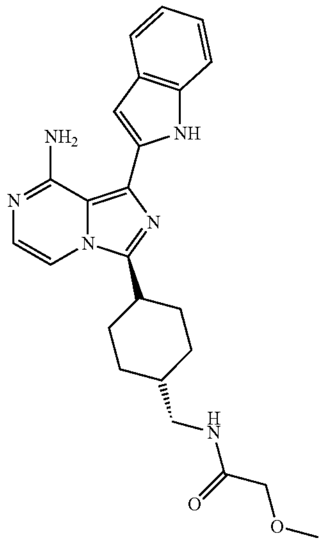 | 433.18 |
| 164 | 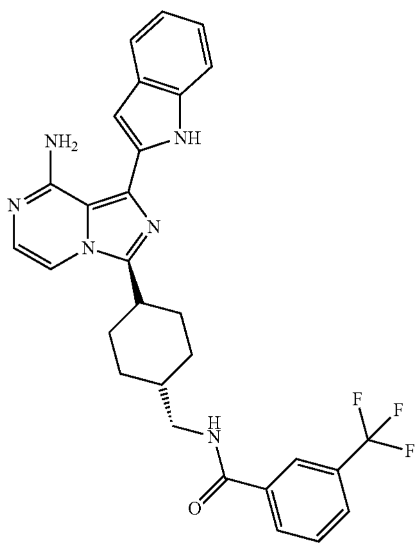 | 532.90 |
| 165 | 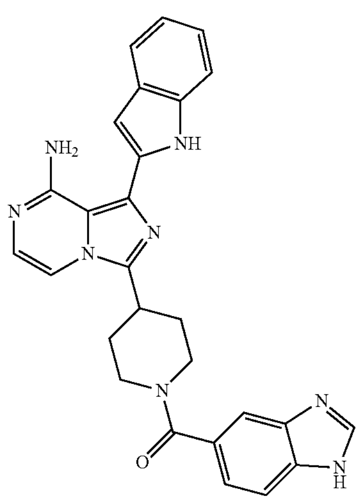 | 476.95 |

-continued
| Ex # | Structure | MH+ |
|---|---|---|
| 166 | 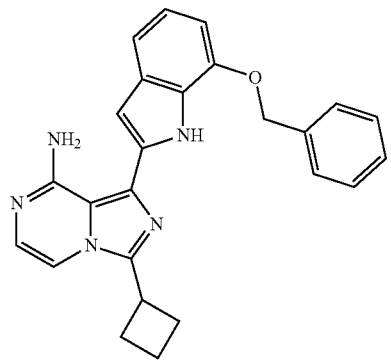 | 410.02 |
| 167 | 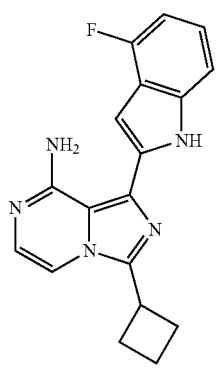 | 321.92 |
| 168 | 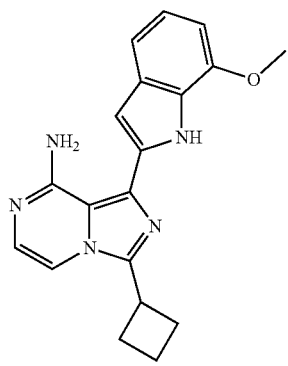 | 333.87 |
| 169 | 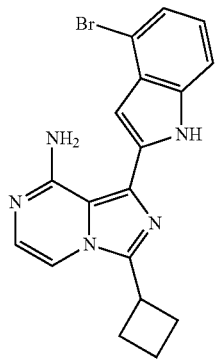 | 381.83<br>383.72 |

-continued
| Ex # | Structure | MH+ |
| --- | --- | --- |
| 170 | 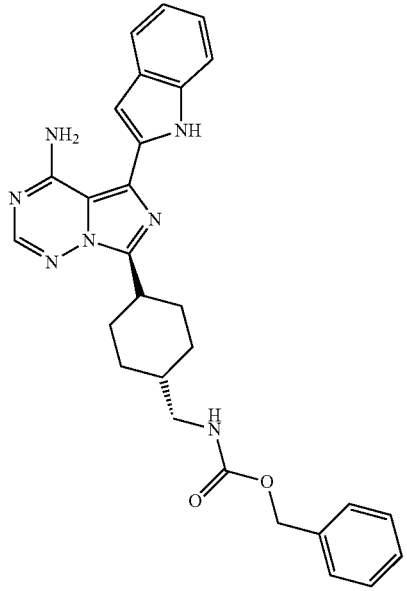 | 495.97 |
| 171 | 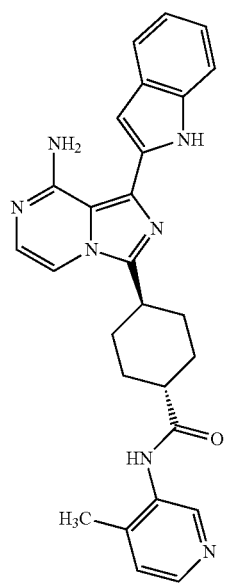 Chiral | 465.96 |

| Ex # | Structure | MH+ |
| --- | --- | --- |
| 172 | 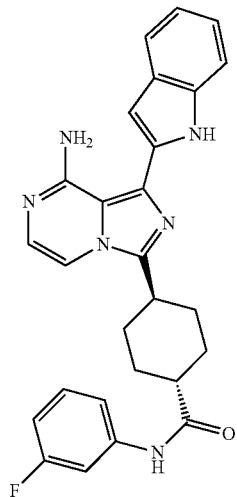 chiral | 468.84 470.50 |
| 173 | 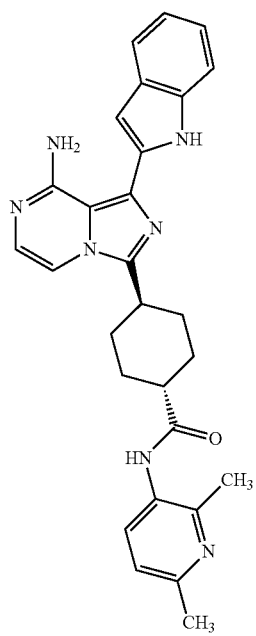 chiral | 480.20 |

| Ex # | Structure | MH+ |
|---|---|---|
| 174 | 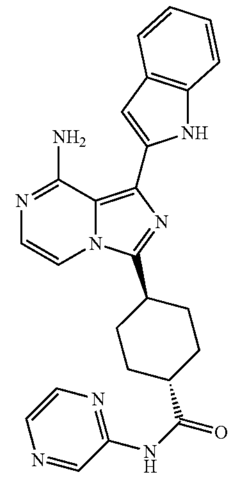 | 452.97 |
| 175 | 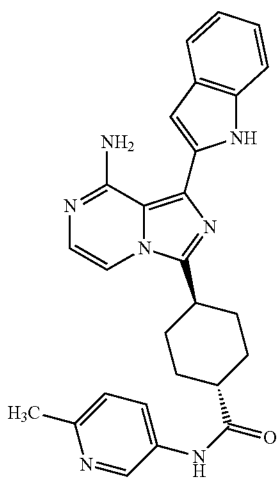 | 466.20 |
| 176 | 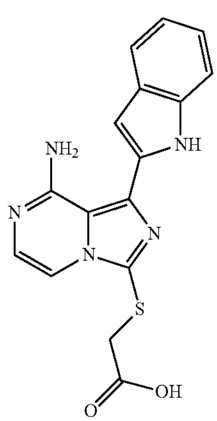 | 339.92 |

-continued

| Ex # | Structure | MH+ |
| --- | --- | --- |
| 177 | 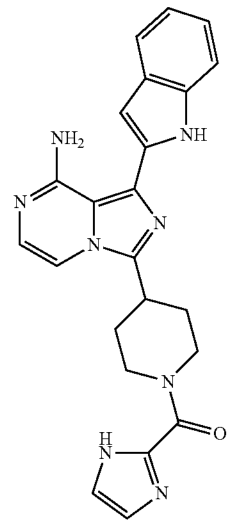 | 426.91 |
| 178 | 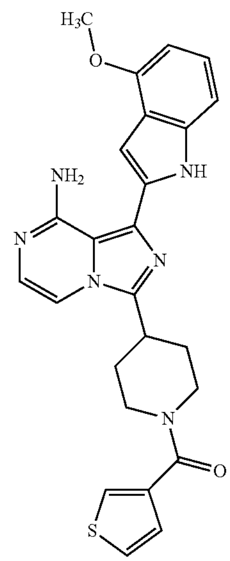 | 472.62 |
| 179 | 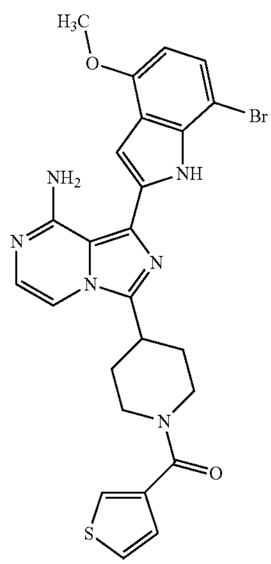 | 550.68<br>552.50 |

-continued
| Ex # | Structure | MH+ |
|---|---|---|
| 180 | 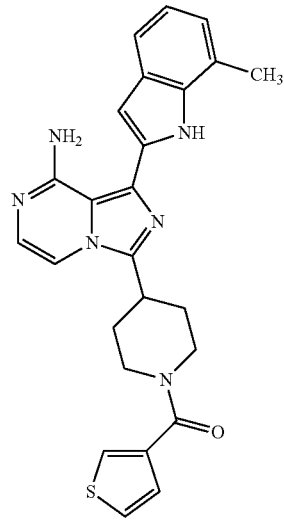 | 456.63 |
| 181 | 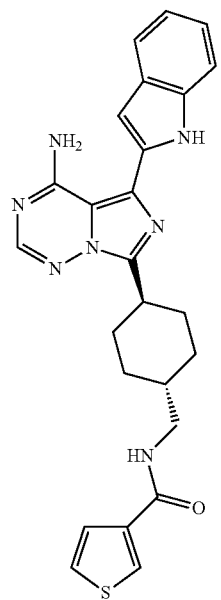
chiral | 471.98 |

-continued
| Ex # | Structure | MH+ |
|---|---|---|
| 182 | 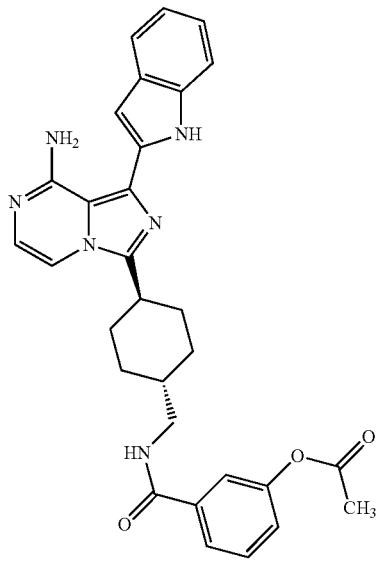 | 523.93 |
| 183 | 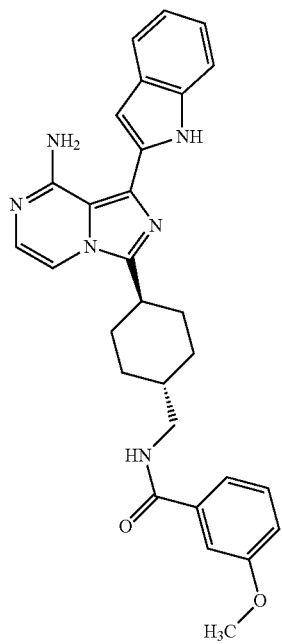 | 496.05 |

| Ex # | Structure | MH+ |
|---|---|---|
| 184 | 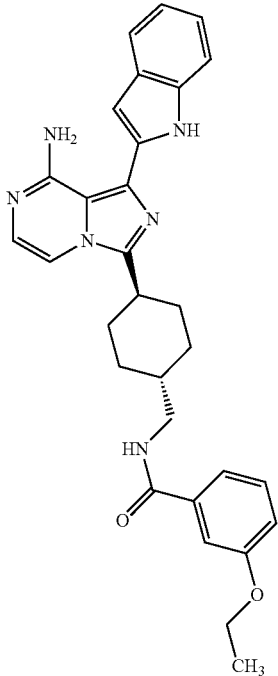 | 510.00 |
| 185 | 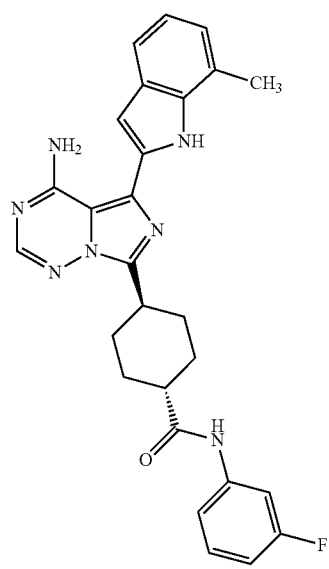 | 483.89 |

-continued
| Ex # | Structure | MH+ |
|---|---|---|
| 186 | 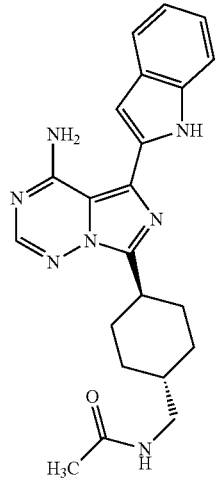 chiral | 404.18 |
| 187 | 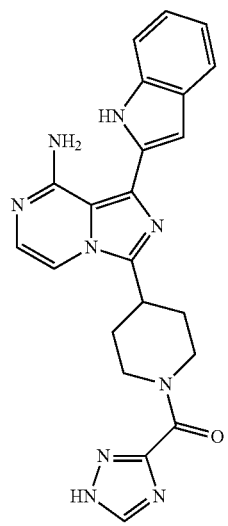 | 427.93 |
| 188 | 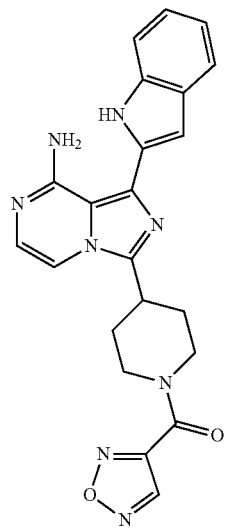 | 428.88 |

-continued
| Ex # | Structure | MH+ |
|---|---|---|
| 189 | 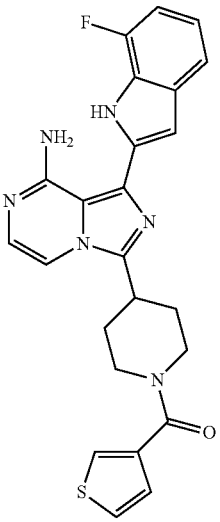 | 460.66 |
| 191 | 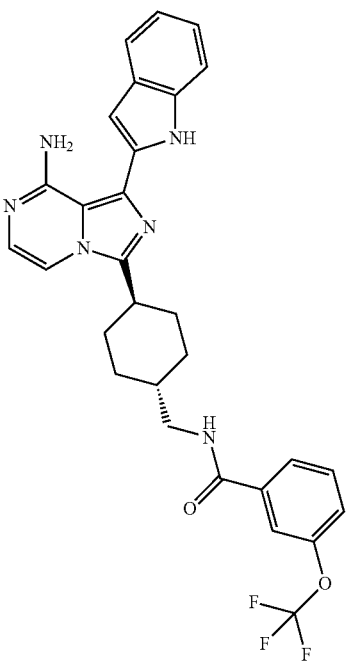 | 548.72 |
chiral

| Ex # | Structure | MH+ |
|---|---|---|
| 192 | 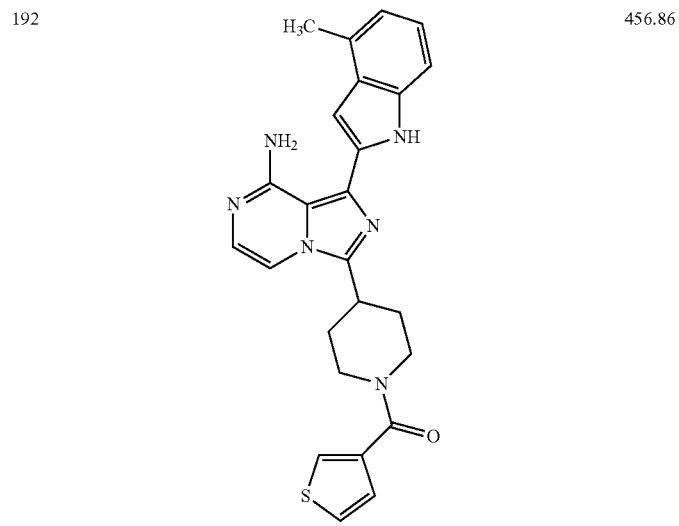 | 456.86 |
| 193 | 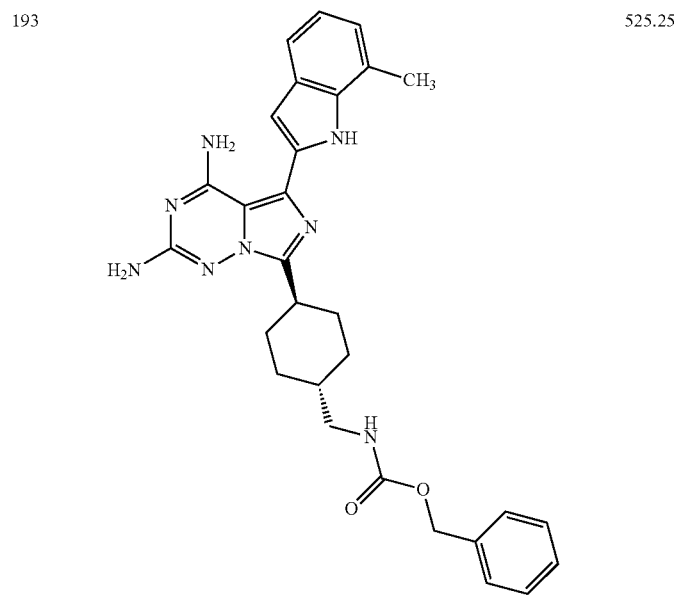 | 525.25 |

| Ex # | Structure | MH+ |
|---|---|---|
| 194 | 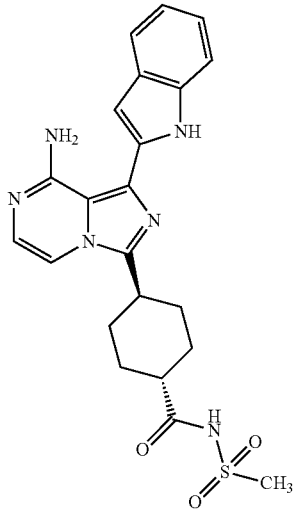 chiral | 467.21 |
| 195 | 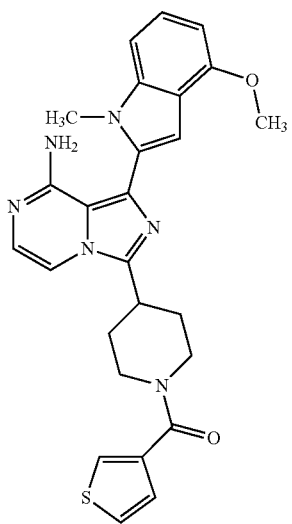 | 486.96 |
| 196 | 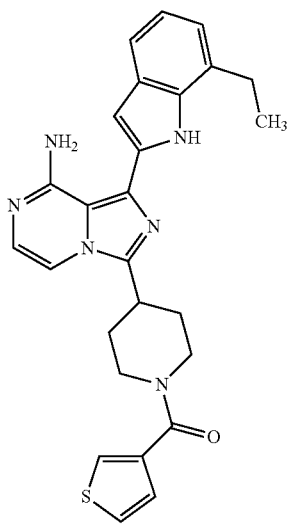 | 470.97 |

| Ex # | Structure | MH+ |
|---|---|---|
| 197 | 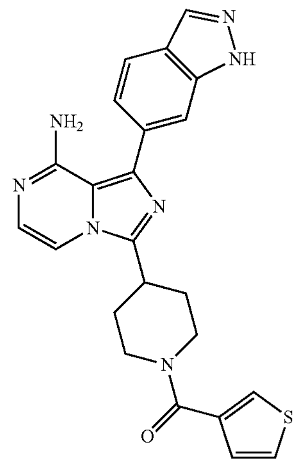 | 444.00 |
| 198 | 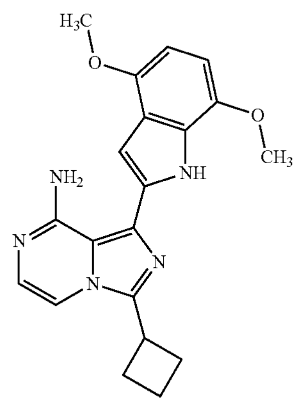 | 363.89 |
| 199 | (chiral) | 403.07 |

-continued

| Ex # | Structure | MH+ |
|---|---|---|
| 200 | 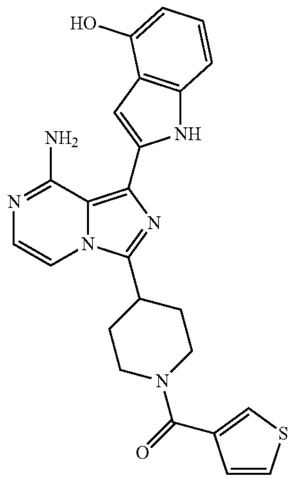 | 458.97 |
| 201 | 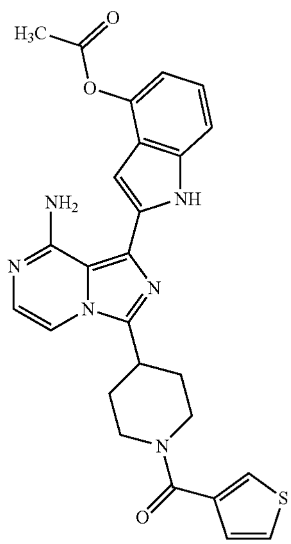 | 500.96 |
| 202 | 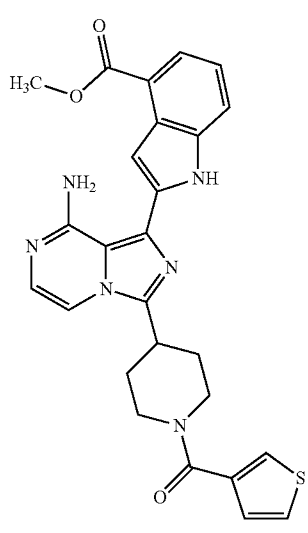 | 500.94 |

-continued

| Ex # | Structure | MH+ |
|---|---|---|
| 203 | 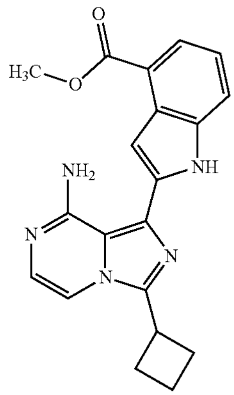 | 362.03 |
| 204 | 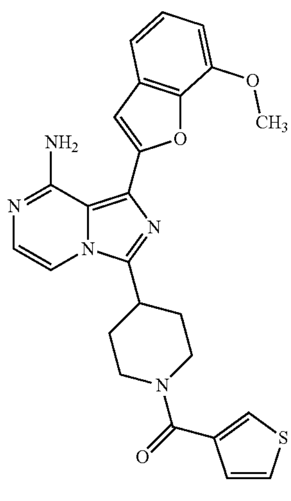 | 473.95 |
| 205 | 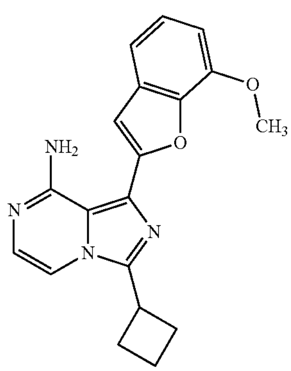 | 335.06 |

| Ex # | Structure | MH+ |
|---|---|---|
| 206 | 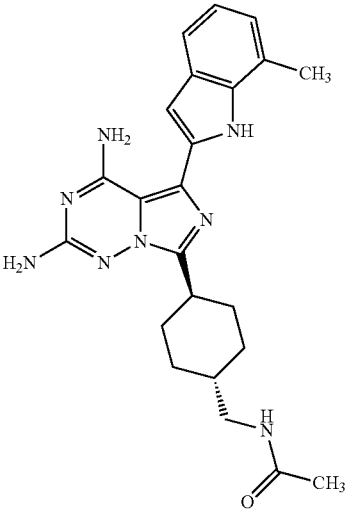 | 433.07 |
| 207 | 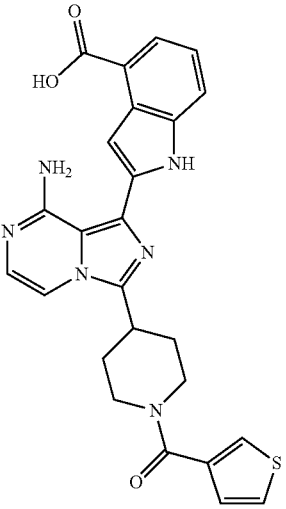 | 486.96 |
| 208 | 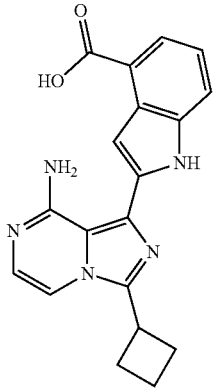 | 348.02 |

-continued

| Ex # | Structure | MH+ |
|---|---|---|
| 209 | 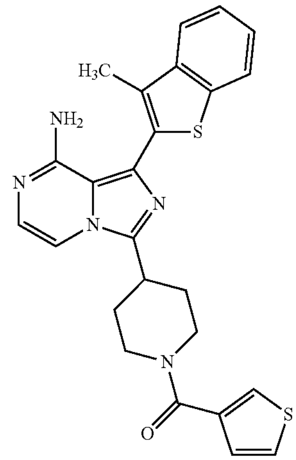 | 473.87 |
| 210 | 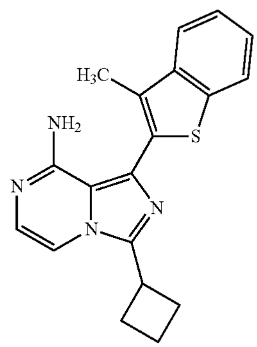 | 334.88 |
| 211 | 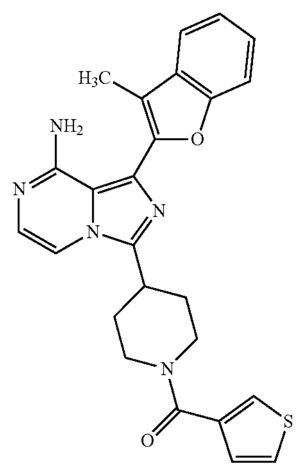 | 457.95 |
| 212 | 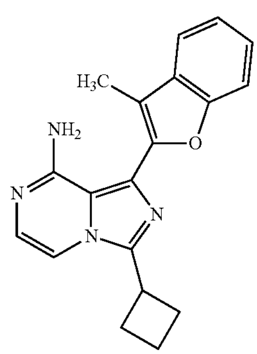 | 318.92 |

US 8,314,111 B2
287                                                                288
-continued
| Ex # | Structure | MH+ |
|------|-----------|-----|
| 213 | 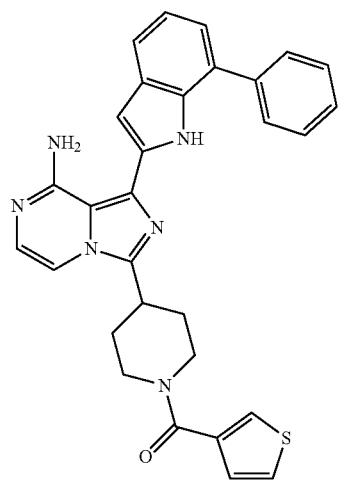 chiral | 475.02 |
| 214 | chiral | 425.17 427.06 |
| 215 | 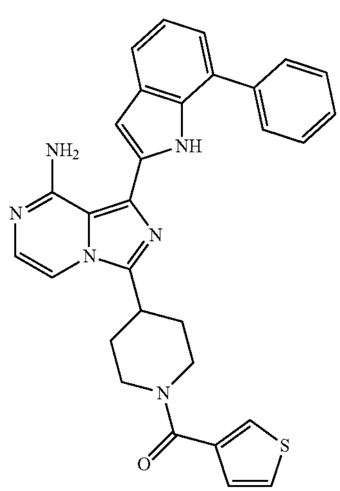 | 518.83 |

| Ex # | Structure | MH+ |
|---|---|---|
| 216 | 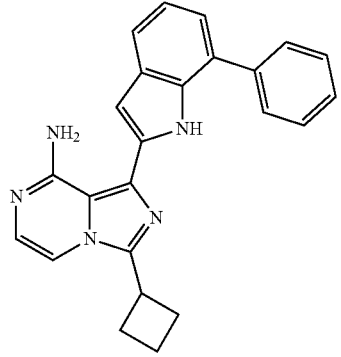 | 379.87 |
| 217 | 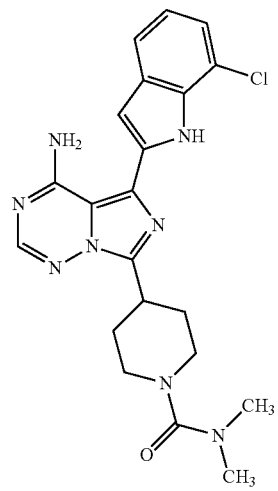 | 439.19 |
| 218 | 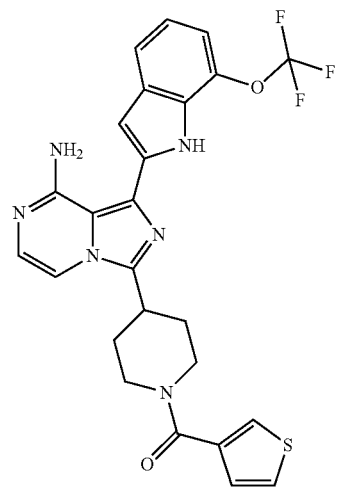 | 526.77 |

| Ex # | Structure | MH+ |
|---|---|---|
| 219 | 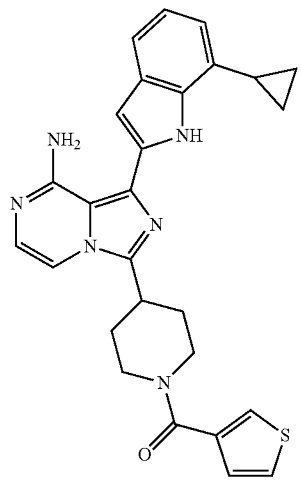 | 483.04 |
| 220 | 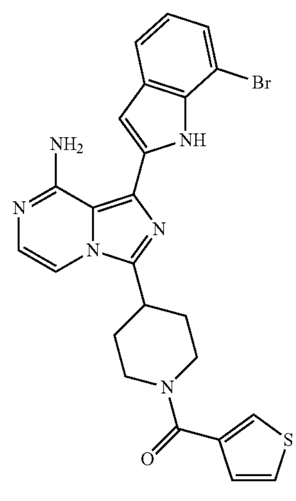 | 520.89 |
| 221 | 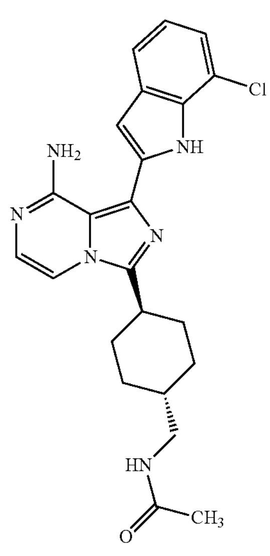 | 436.98<br>438.94 |

-continued

| Ex # | Structure | MH+ |
|---|---|---|
| 222 | 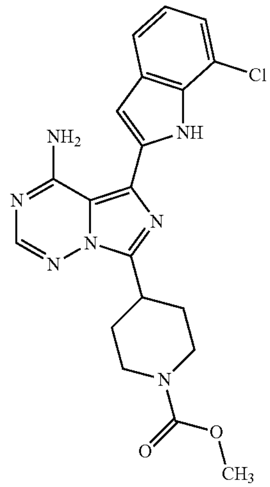 | 425.93 |
| 223 | chiral | 411.13<br>413.02 |
| 224 | 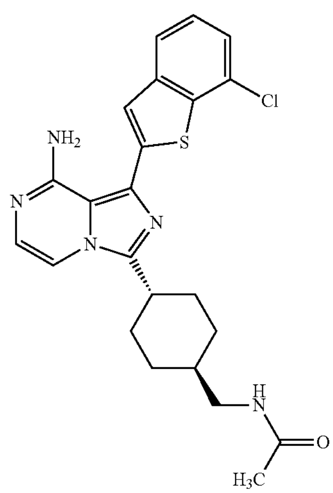 | 453.99 |

-continued

| Ex # | Structure | MH+ |
|---|---|---|
| 225 | 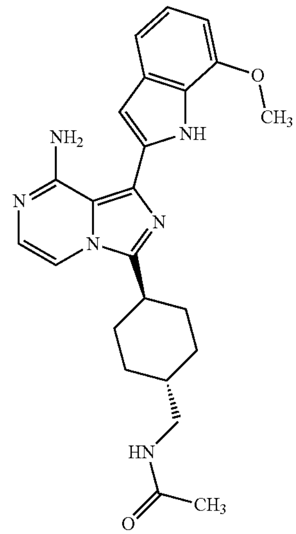 | 443.02 |
| 226 | 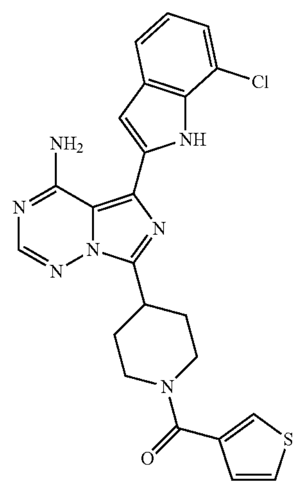 | 479.85 |
| 227 | 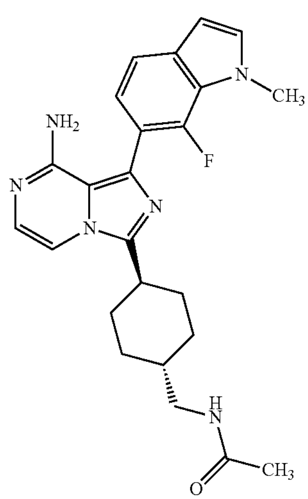 | 434.95 |

| Ex # | Structure | MH+ |
|---|---|---|
| 228 | 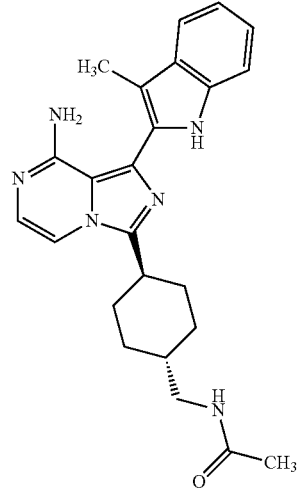 | 417.21 |
| 229 | 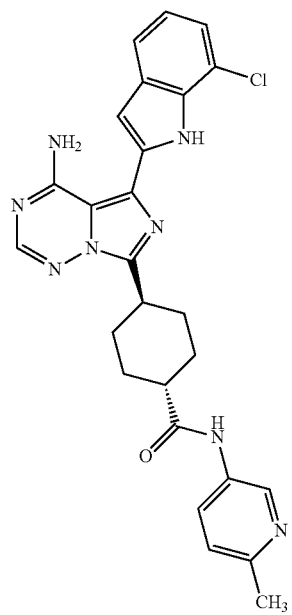<br>chiral | 500.99<br>502.98 |

| Ex # | Structure | MH+ |
|---|---|---|
| 230 | 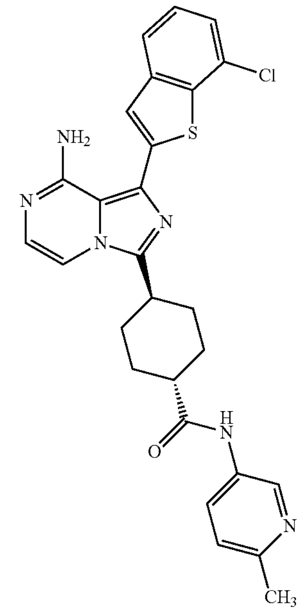 | 516.91<br>518.90 |
| 231 | 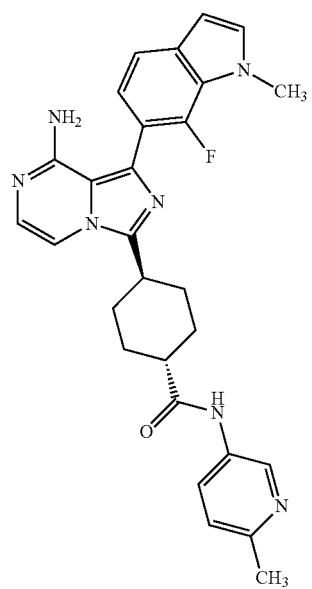 | 498.02 |

-continued

| Ex # | Structure | MH+ |
|---|---|---|
| 232 | 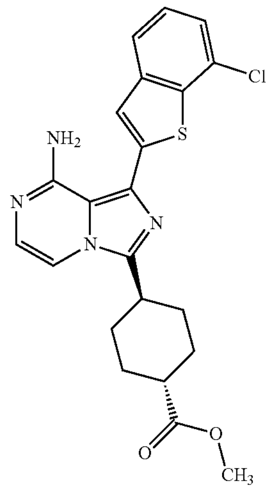 | 440.89 <br> 442.86 |
| 233 | 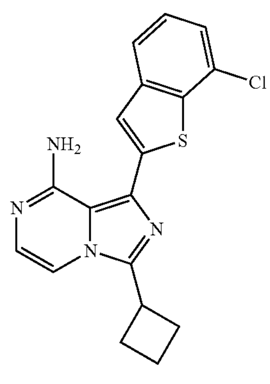 | 354.74 <br> 356.98 |
| 234 | 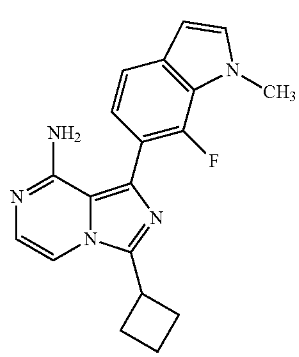 | 335.84 |

-continued

| Ex # | Structure | MH+ |
|---|---|---|
| 235 | 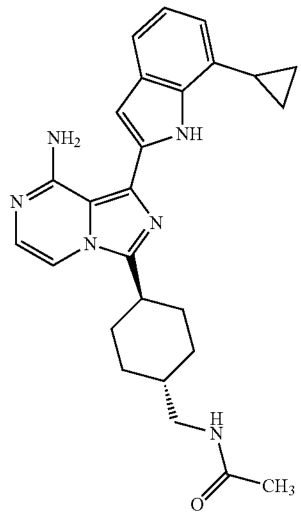 | 442.96 |
| 236 | 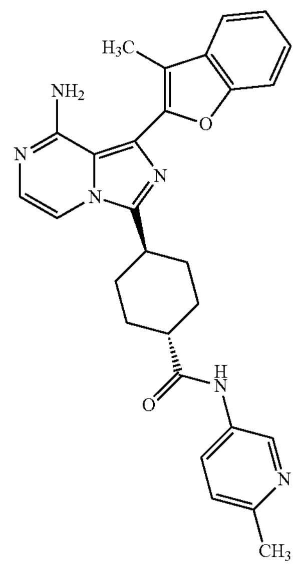 | 480.98 |
| 237 | 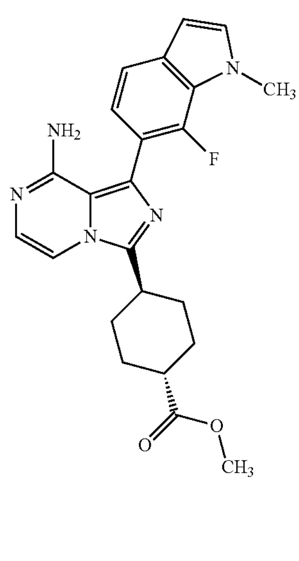 | 421.83 |

-continued
| Ex # | Structure | MH+ |
|---|---|---|
| 238 | 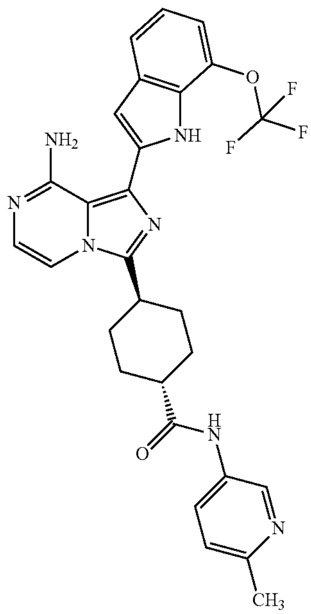 | 549.91 |
| 239 | 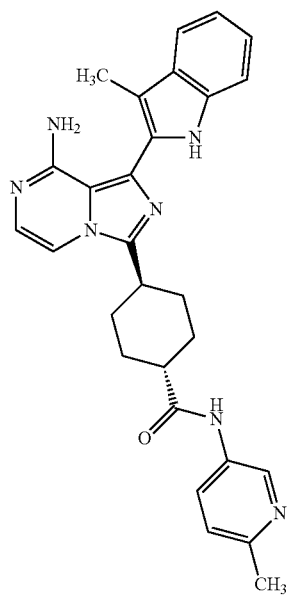 | 480.02 |

-continued

| Ex # | Structure | MH+ |
|---|---|---|
| 240 | 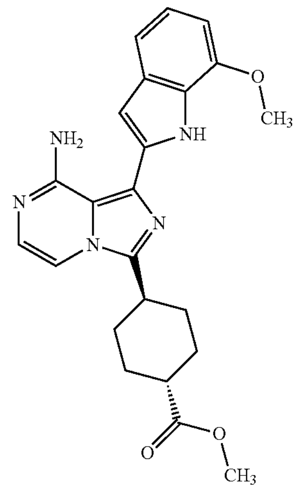 | 419.89 |
| 241 | 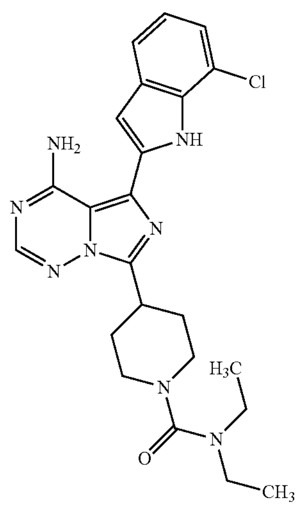 | 467.92 |
| 242 | 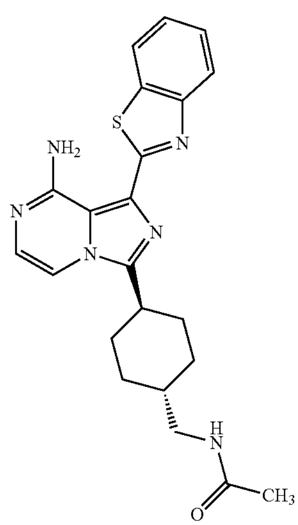 | 420.97 |

| Ex # | Structure | MH+ |
|---|---|---|
| 243 | 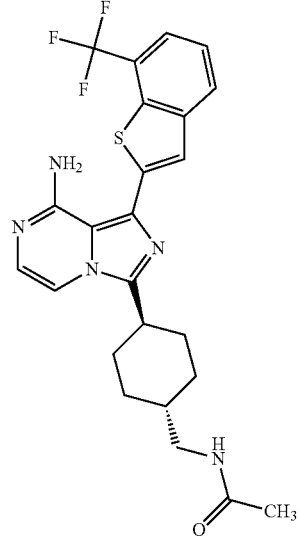 | 487.67 |
| 244 | 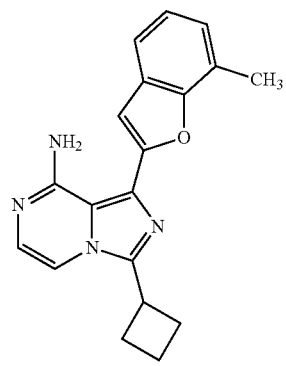 | 319.00 |
| 245 | 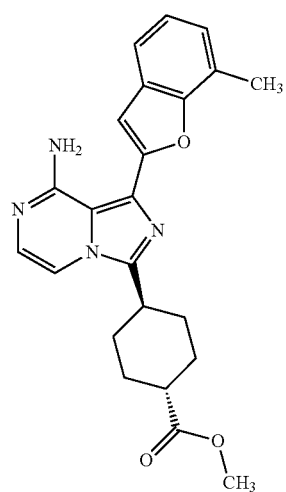 | 405.03 |

-continued

| Ex # | Structure | MH+ |
|---|---|---|
| 246 | 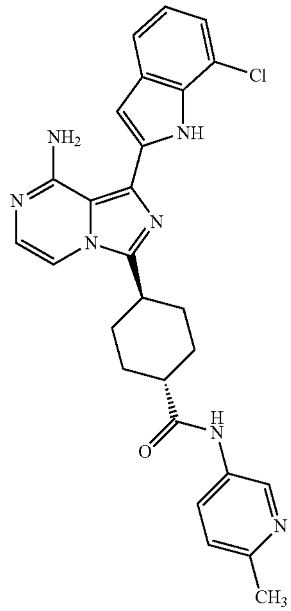 | 499.95<br>501.96 |
| 247 | 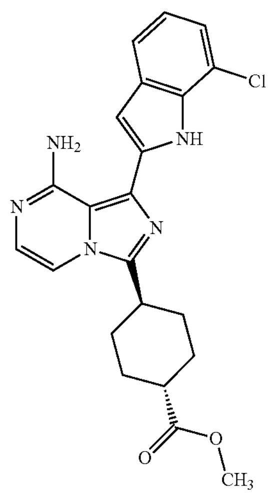 | 423.83<br>425.93 |
| 248 (chiral) | | 409.95<br>411.90 |

-continued

| Ex # | Structure | MH+ |
|---|---|---|
| 249 | 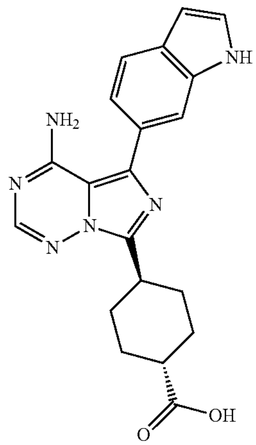 | 376.99 |
| 250 | 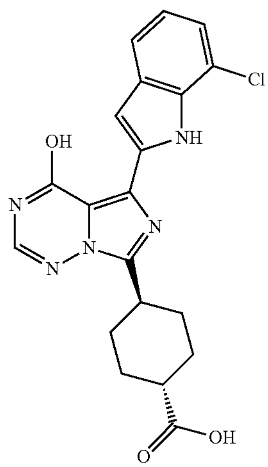 | 412.06<br>414.03 |
| 251 | 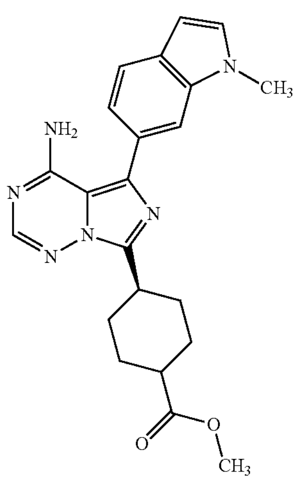 | 404.96 |

-continued
| Ex # | Structure | MH+ |
|---|---|---|
| 252 | 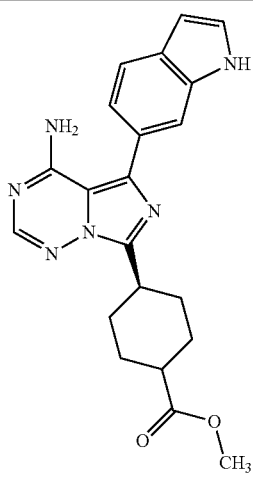 | 391.01 |
| 253 | 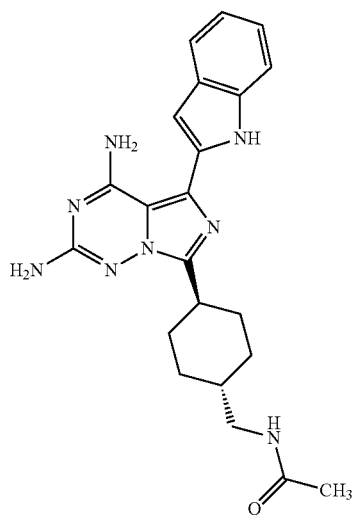 | 419.21 |
| 254 | 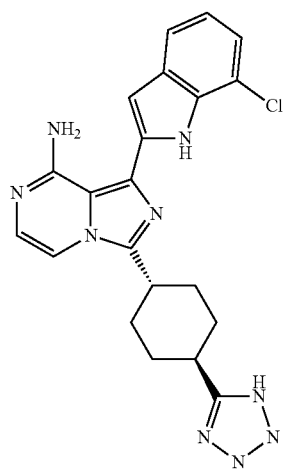 | 434.04 |

| Ex # | Structure | MH+ |
|---|---|---|
| 255 | 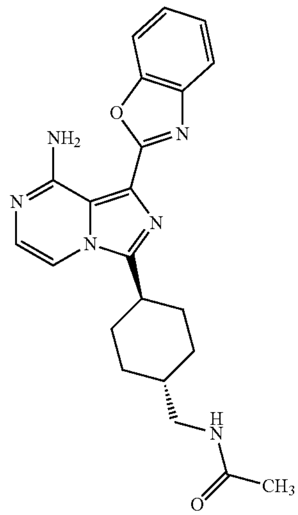 | 405.03 |
| 256 | 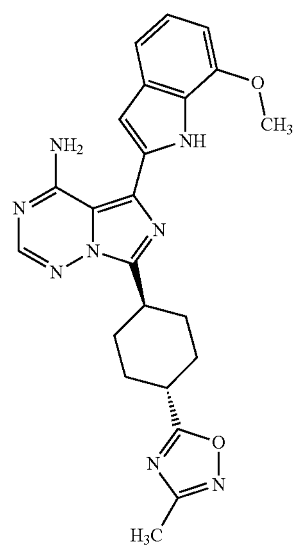 | 445.01 |
| 257 | 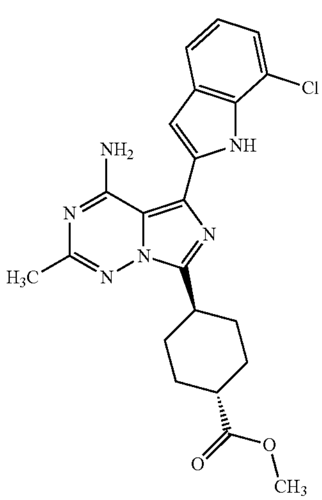 | 438.94<br>440.89 |

-continued

| Ex # | Structure | MH+ |
|---|---|---|
| 258 | 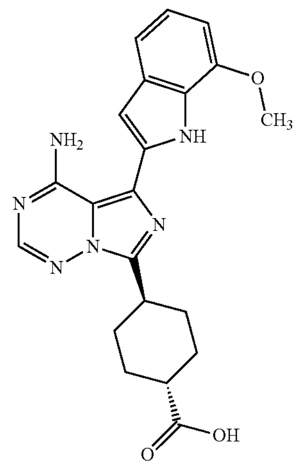 | 406.98<br>406.99 |
| 259 | 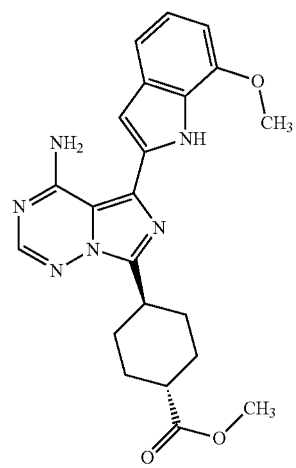 | 421.00 |
| 260 | 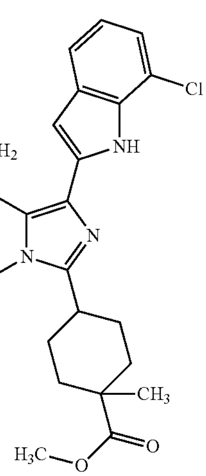 | 437.93<br>439.95 |

-continued
| Ex # | Structure | MH+ |
|---|---|---|
| 261 | 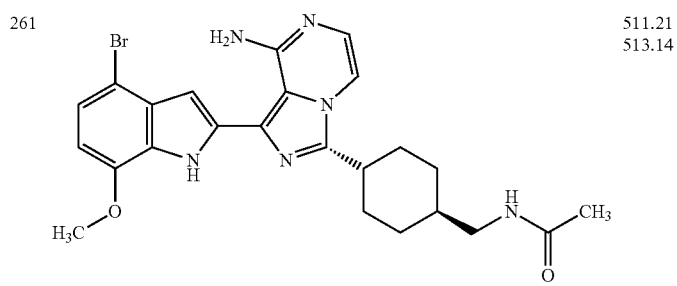 | 511.21<br>513.14 |
| 262 | 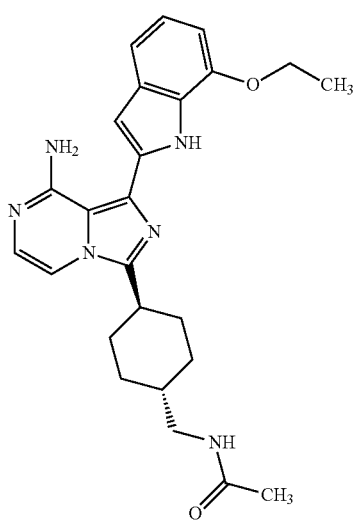<br>chiral | 447.03 |
| 263 | 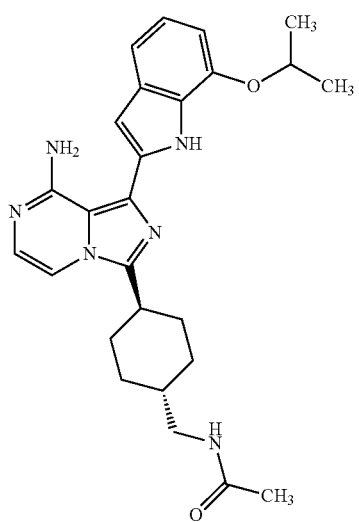<br>chiral | 461.05 |

| Ex # | Structure | MH+ |
|---|---|---|
| 264 | 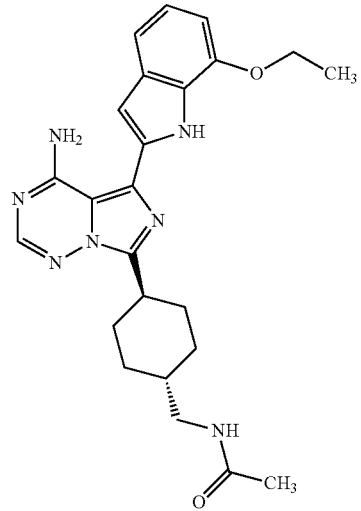<br>chiral | 447.99 |
| 265 | 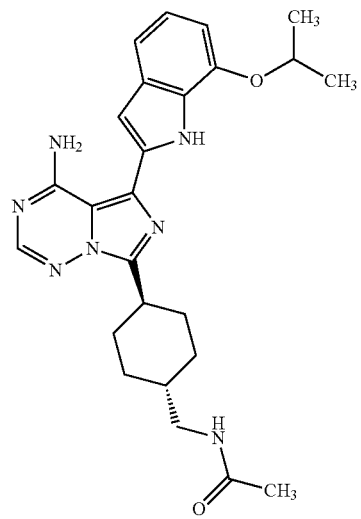<br>chiral | 462.00 |
| 266 | 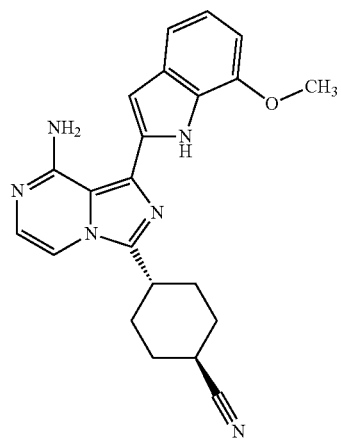 | 387.20 |

-continued

| Ex # | Structure | MH+ |
|---|---|---|
| 267 | 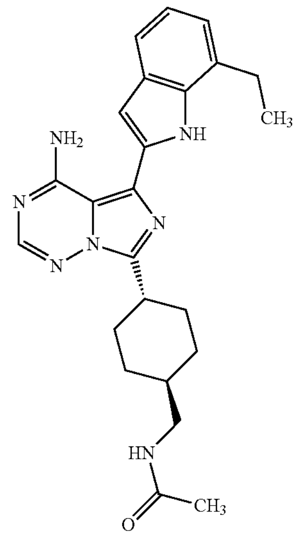 | 432.06 |
| 268 | 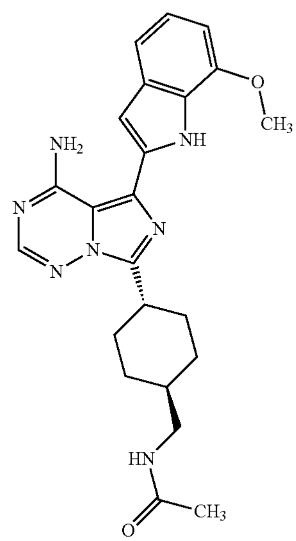 | 434.02<br>434.06 |
| 269 | 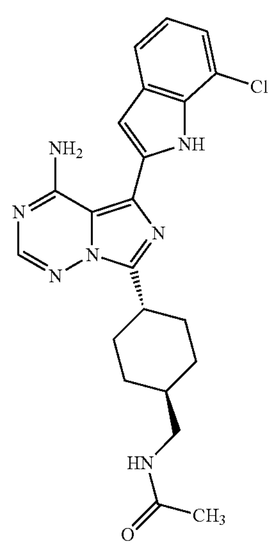 | 437.97<br>439.95 |

-continued

| Ex # | Structure | MH+ |
|---|---|---|
| 270 | 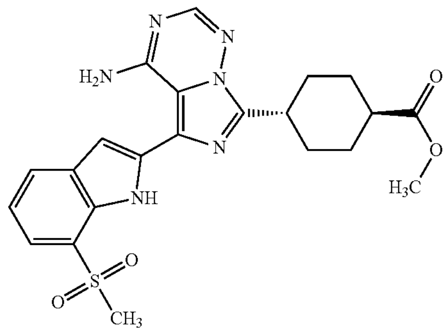 | 468.95 |
| 271 | 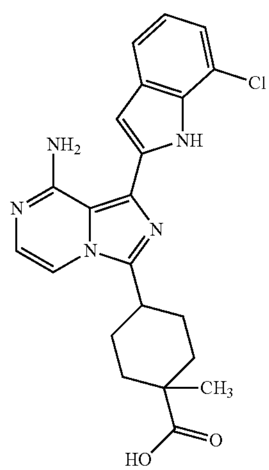 | 423.97<br>425.93 |
| 272 | 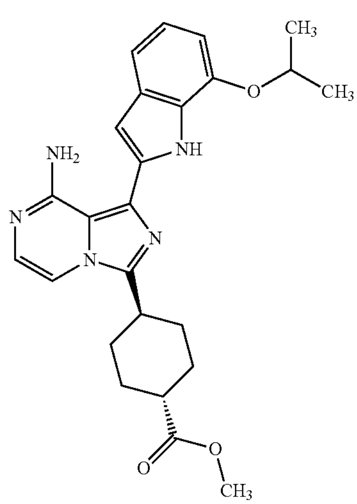 | 448.05 |

| Ex # | Structure | MH+ |
|---|---|---|
| 273 | 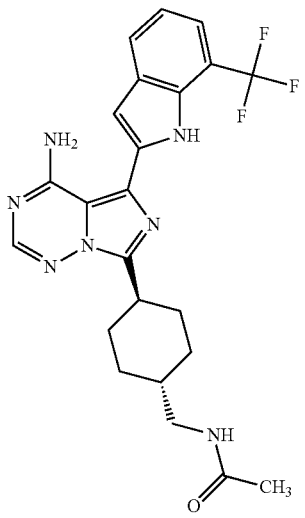 | 471.98 |
| 274 | 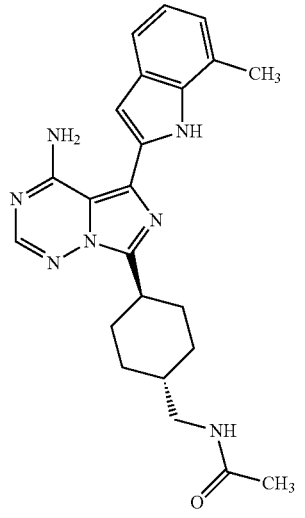 | 418.09 |
| 275 | 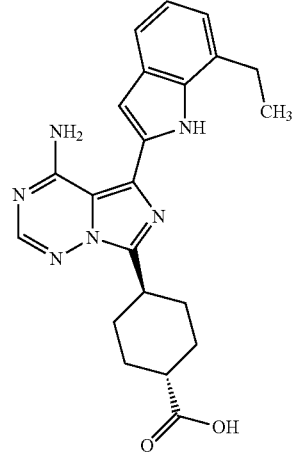 | 405.03 |

-continued
| Ex # | Structure | MH+ |
|---|---|---|
| 276 | 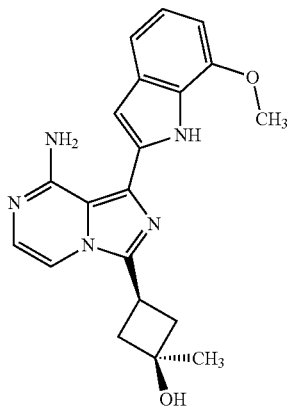<br>chiral | 363.98 |
| 277 | 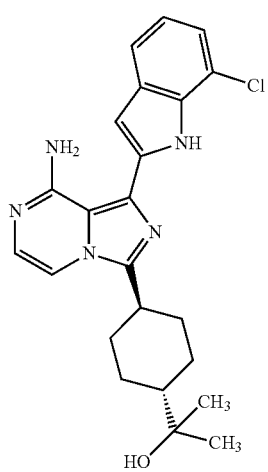<br>chiral | 423.97<br>425.99 |
| 278 | 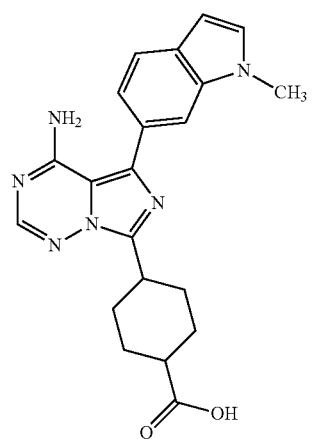 | 391.01 |

-continued

| Ex # | Structure | MH+ |
|---|---|---|
| 279 | 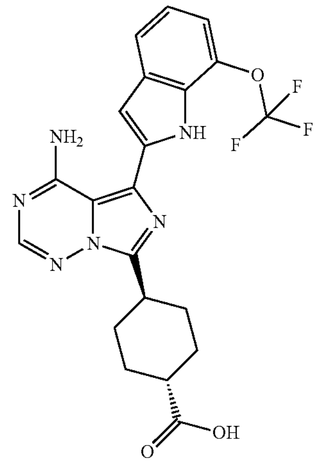 | 460.94 |
| 280 | 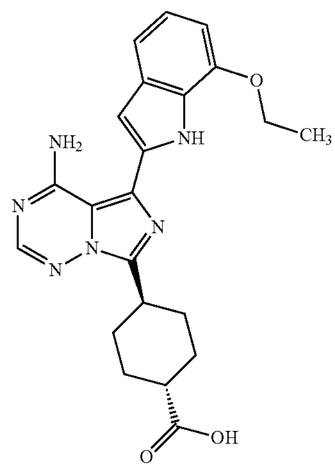 | 421.00 |
| 281 | 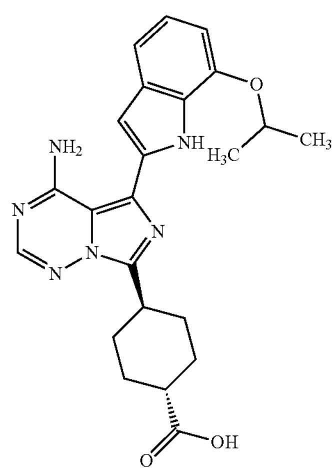 | 435.03 |

-continued
| Ex # | Structure | MH+ |
|---|---|---|
| 282 | 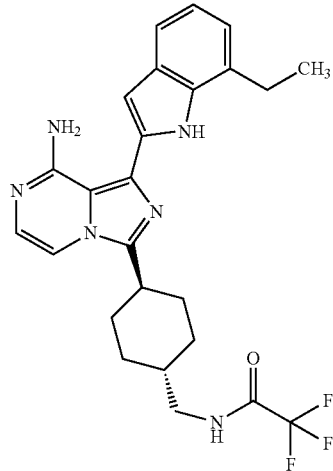 chiral | 485.32 |
| 283 | 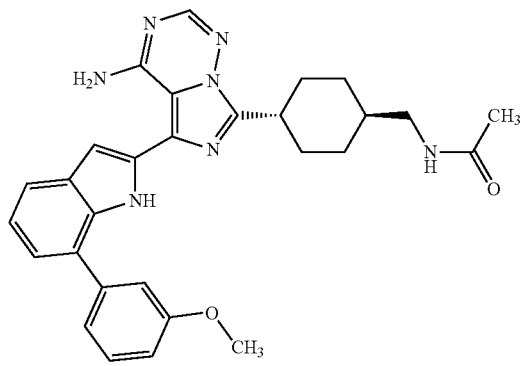 | 510.38 |
| 284 | 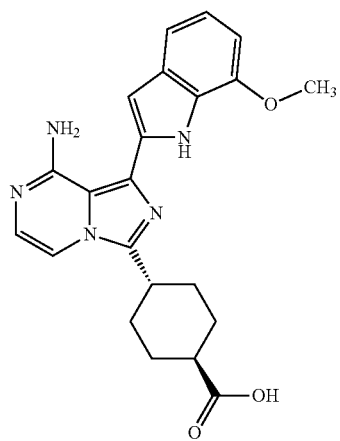 | 406.29 |

-continued
| Ex # | Structure | MH+ |
|---|---|---|
| 285 | 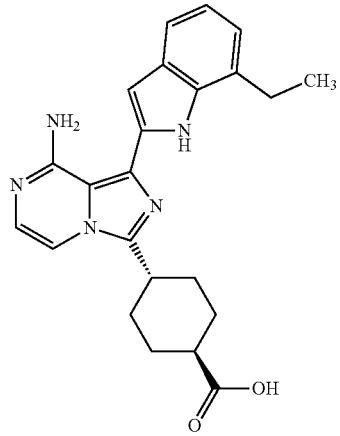 | 404.21 |
| 286 | 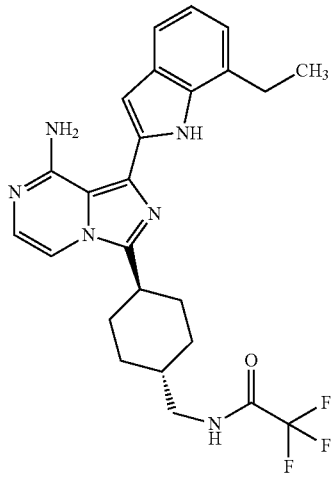
chiral | 420.53 |
| 287 | 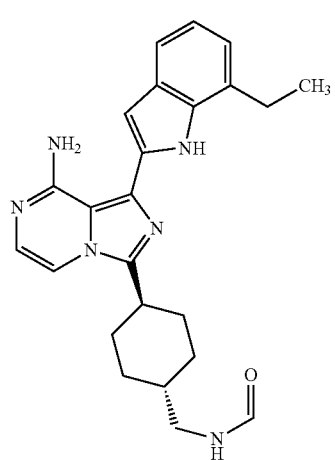 | 417.29 |

-continued
| Ex # | Structure | MH+ |
|---|---|---|
| 288 | 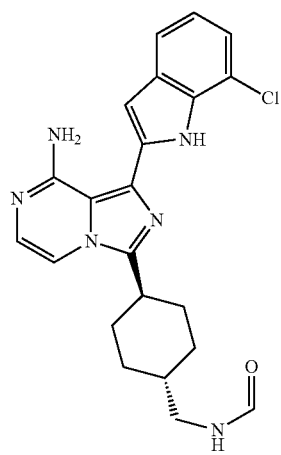 chiral | 423.29 |
| 289 | 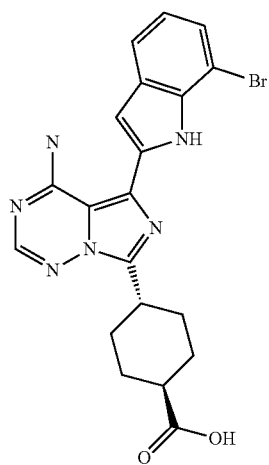 | 455.11 457.09 |
| 290 | 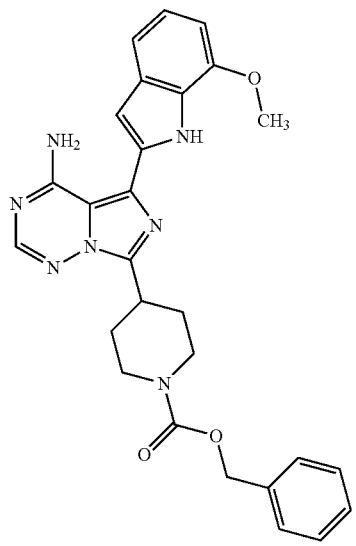 | 497.93 |

| Ex # | Structure | MH+ |
|---|---|---|
| 291 | 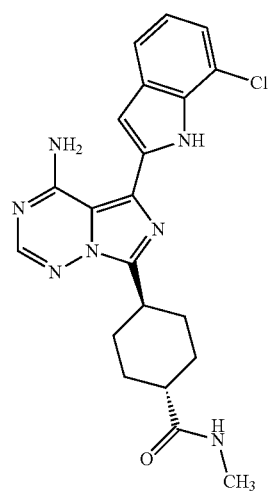<br>chiral | 424.04<br>425.99 |
| 292 | 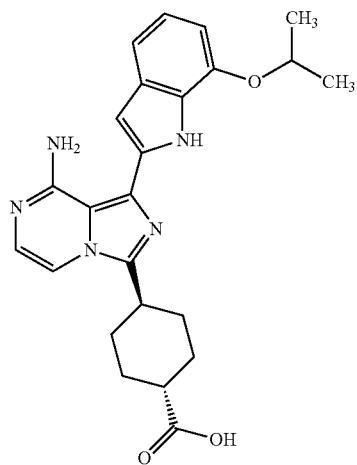<br>chiral | 434.08 |
| 293 | 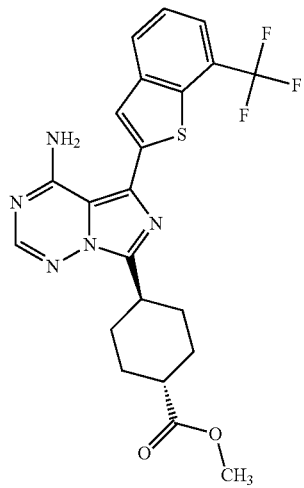<br>chiral | 475.89 |

| Ex # | Structure | MH+ |
|---|---|---|
| 294 | chiral | 461.94 |
| 295 | 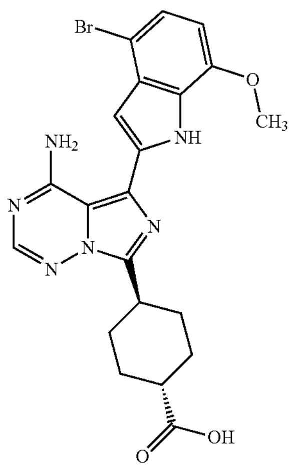 | 485.14<br>487.10 |
| 296 | Chiral | 491.18 |

| Ex # | Structure | MH+ |
|---|---|---|
| 297 | 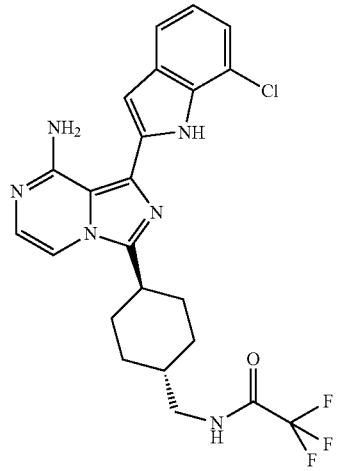<br>chiral | 488.63 |
| 298 | 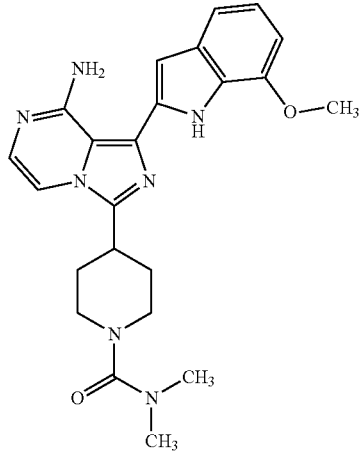 | 434.08 |
| 299 | 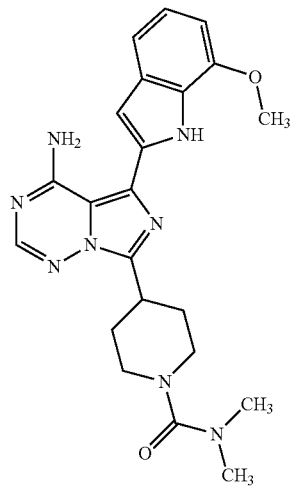 | 435.10 |

| Ex # | Structure | MH+ |
|---|---|---|
| 300 | 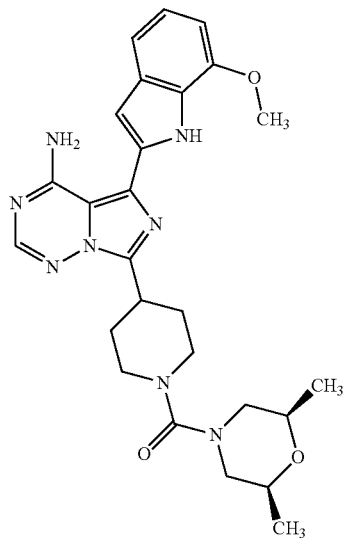<br>chiral | 505.10 |
| 301 | 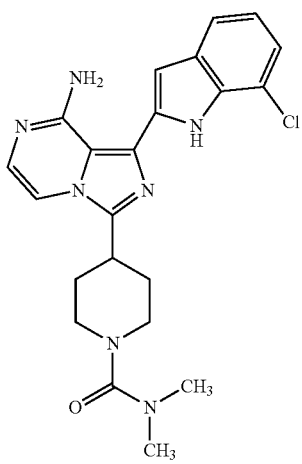 | 438.00 |
| 302 | 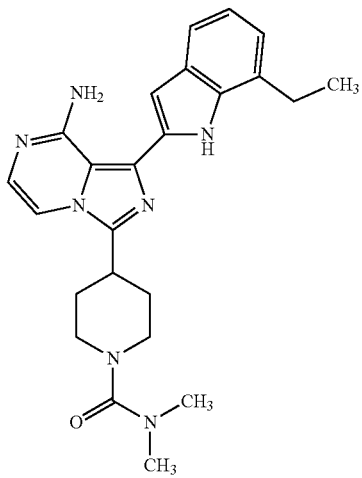 | 432.02 |

| Ex # | Structure | MH+ |
|---|---|---|
| 303 | 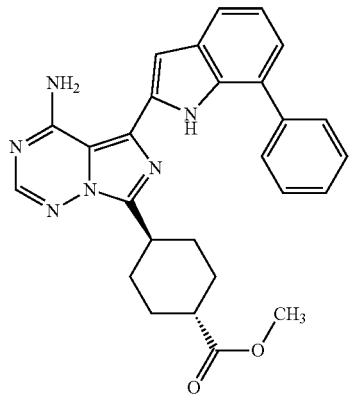 | 467.30 |
| 304 | 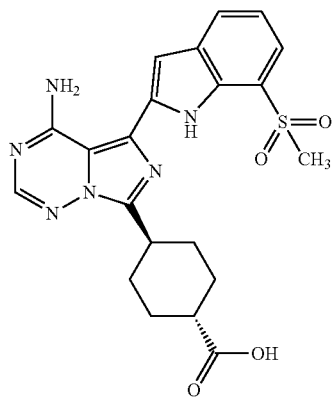 | 455.23 |
| 305 | 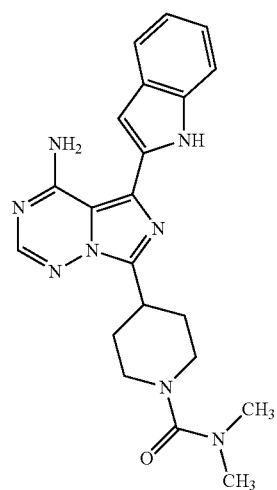 | 405.09 |

-continued
| Ex # | Structure | MH+ |
|---|---|---|
| 306 | 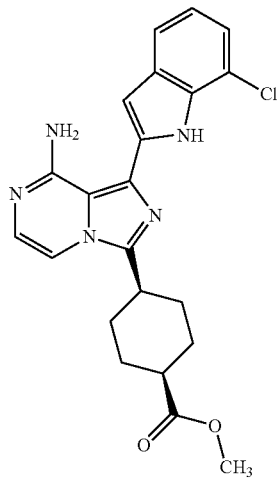<br>chiral | 424.13<br>426.23 |
| 307 | 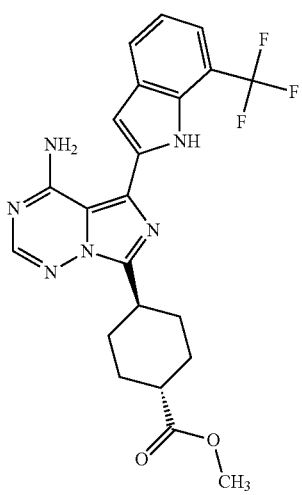<br>chiral | 458.99 |
| 308 | 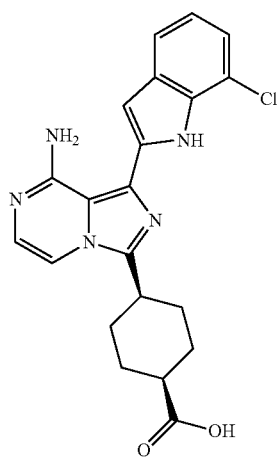<br>chiral | 409.97<br>411.96 |

-continued

| Ex # | Structure | MH+ |
|---|---|---|
| 309 | 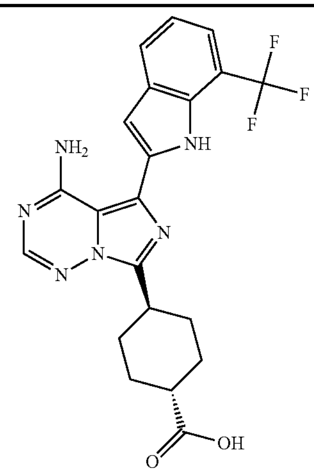 | 445<br>445.1 |
| | chiral | |
| 310 | 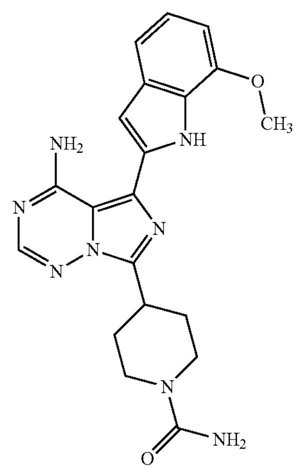 | 407.05 |
| 311 | 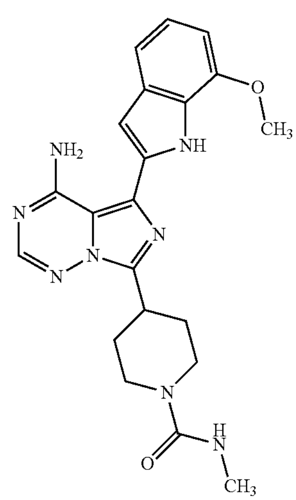 | 421.00 |

| Ex # | Structure | MH+ |
| --- | --- | --- |
| 312 | 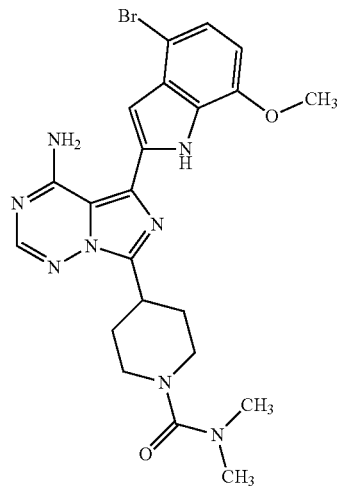 | 512.40 |
| 313 | 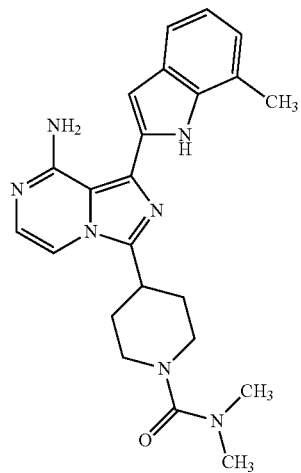 | 418.03 |
| 314 | 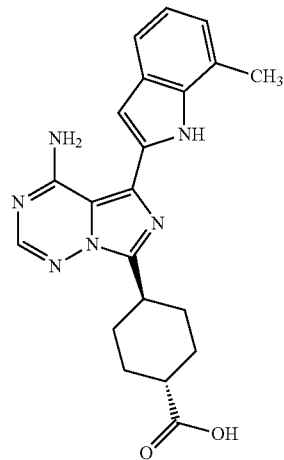 | 391.06 |

-continued
| Ex # | Structure | MH+ |
|---|---|---|
| 315 | 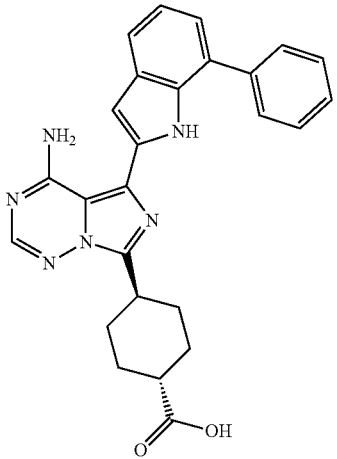 | 453.04<br>453.17<br>453.39 |
| 316 | 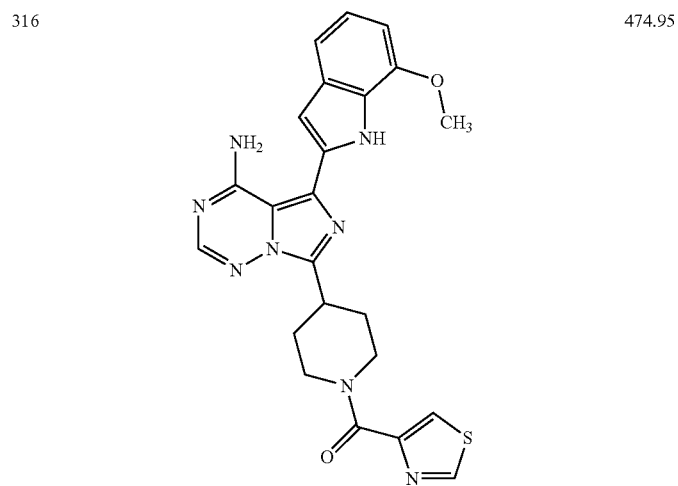 | 474.95 |
| 317 | 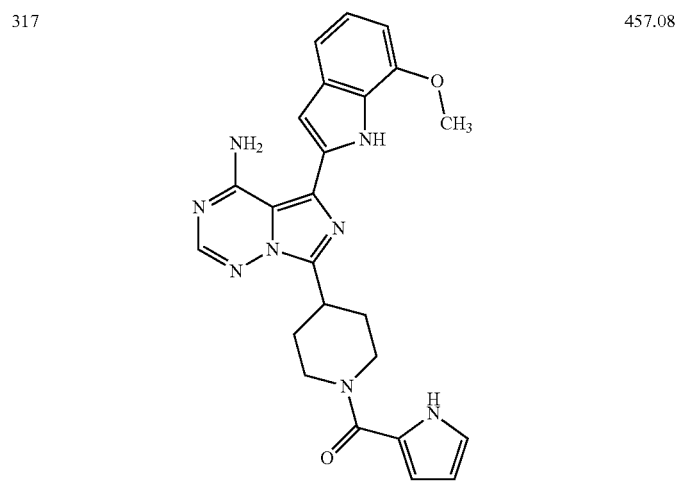 | 457.08 |

| Ex # | Structure | MH+ |
|---|---|---|
| 318 | 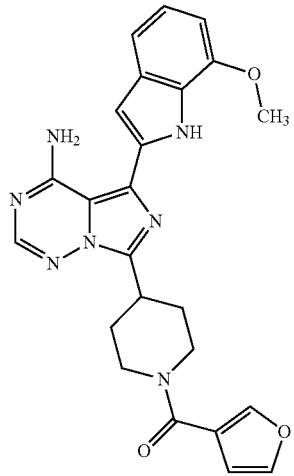 | 457.95 |
| 319 | 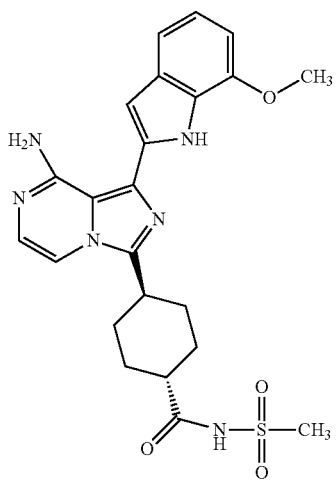 | 482.96 |
| 320 | 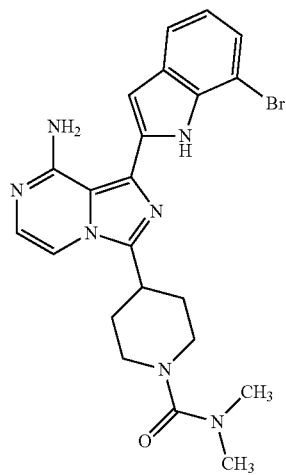 | 483.90 |

| Ex # | Structure | MH+ |
|---|---|---|
| 321 | 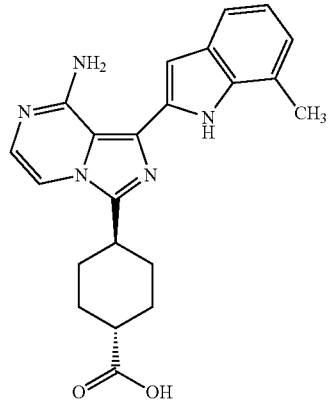 | 390.02 |
| 322 | 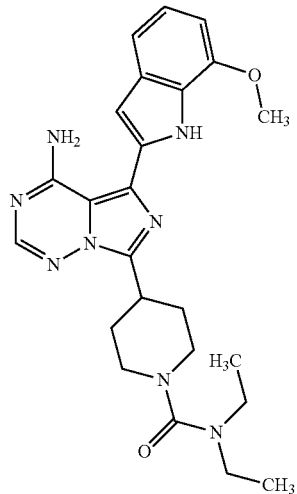 | 463.08 |
| 323 | 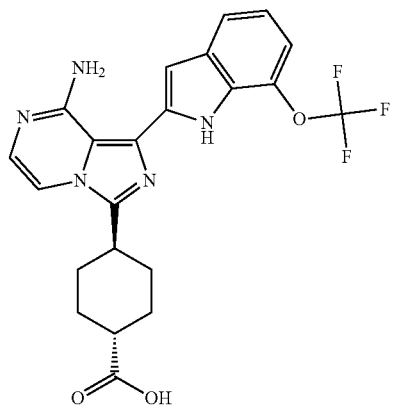 | 460.09 |

| Ex # | Structure | MH+ |
|---|---|---|
| 324 | 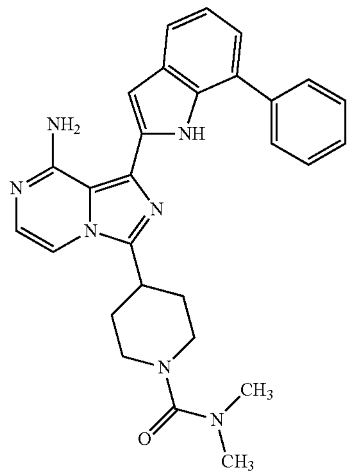 | 480.21 |
| 325 | 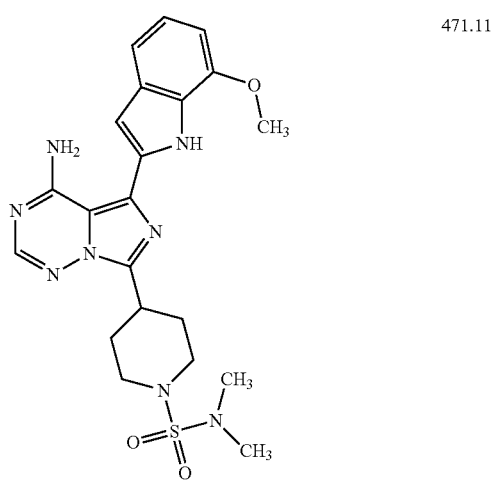 | 471.11 |
| 326 | 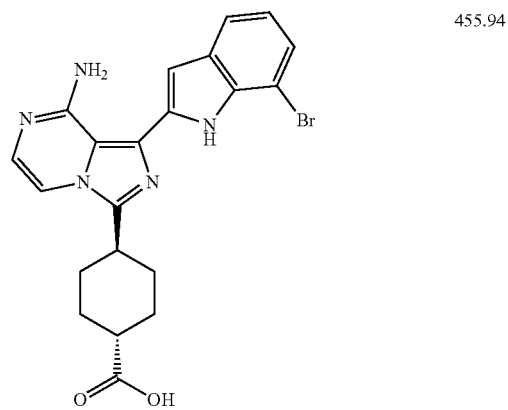 | 455.94 |

-continued
| Ex # | Structure | MH+ |
|---|---|---|
| 327 | 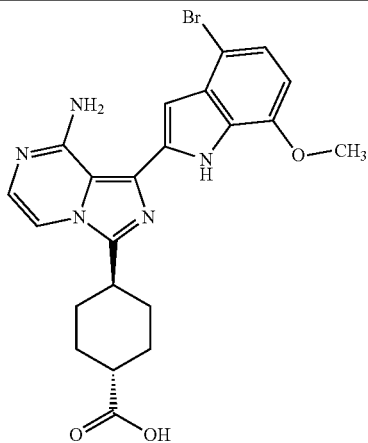 | 486.20 |
| 328 | 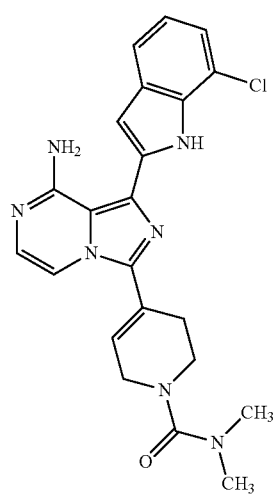 | 436.23<br>438.26 |
| 329 | 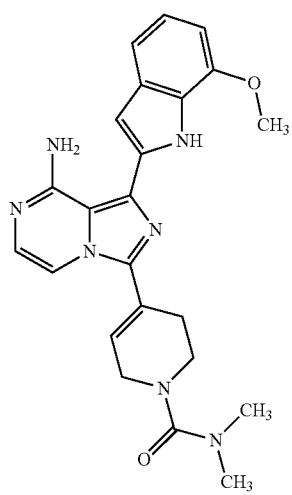 | 432.02 |

-continued

| Ex # | Structure | MH+ |
|---|---|---|
| 330 | 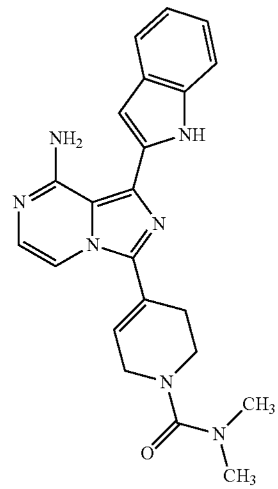 | 402.06 |
| 331 | 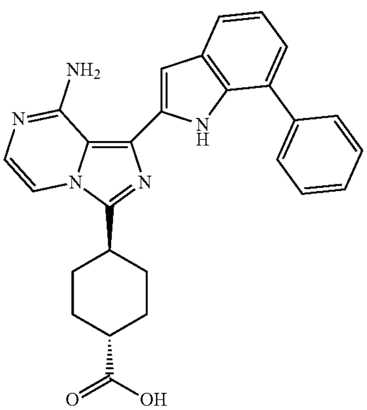 | 452.12 |
| 332 | | 434.25 | chiral

| Ex # | Structure | MH+ |
|---|---|---|
| 333 | 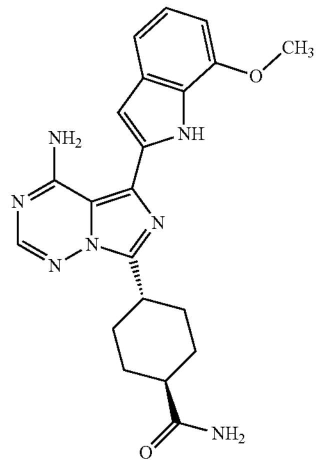 | 406.35<br>406.42 |
| 334 | 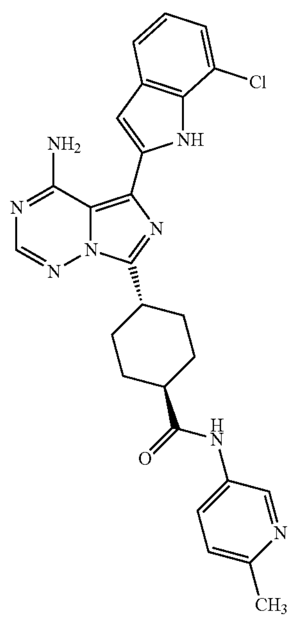 | 501.31 |
| 335 | 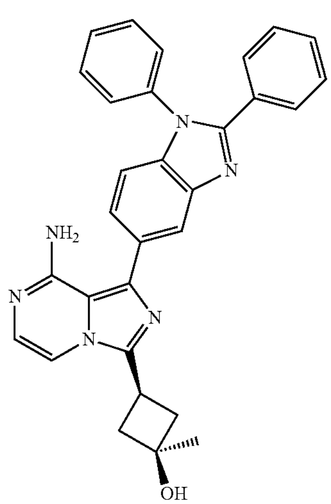 | 487.44 |

| Ex # | Structure | MH+ |
|---|---|---|
| 336 | 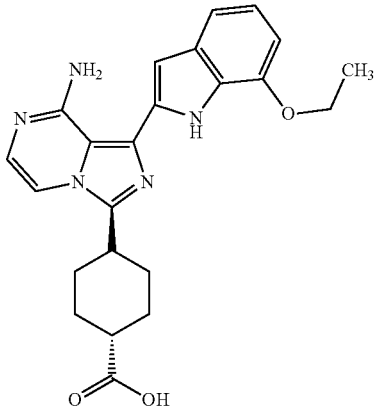 | 420.15<br>420.18 |
| 337 | 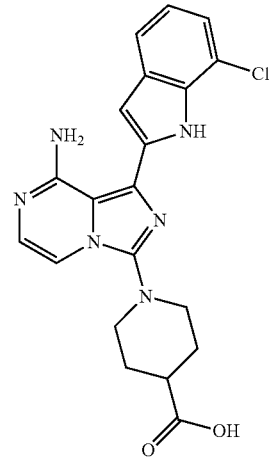 | 411.06<br>413.07 |
| 338 | 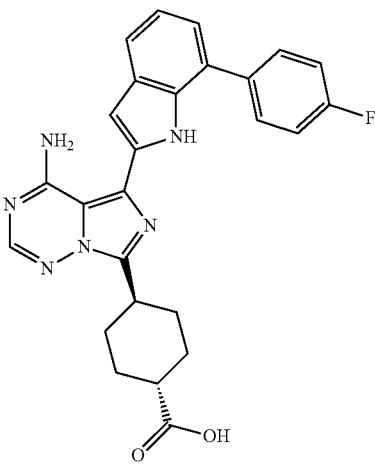<br>chiral | 471.35 |

-continued

| Ex # | Structure | MH+ |
|---|---|---|
| 339 | chiral | 454.07<br>456.03 |
| 340 | 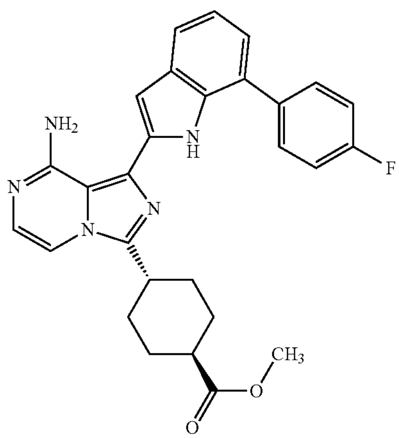 | 484.44 |
| 341 | 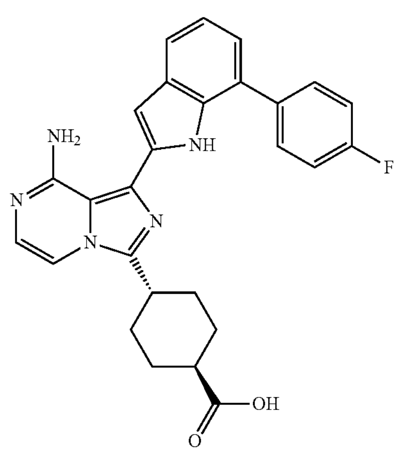 | 470.41 |

| Ex # | Structure | MH+ |
|---|---|---|
| 342 | 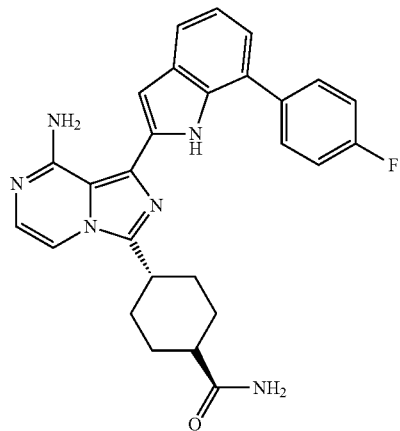 | 469.46 |
| 343 | 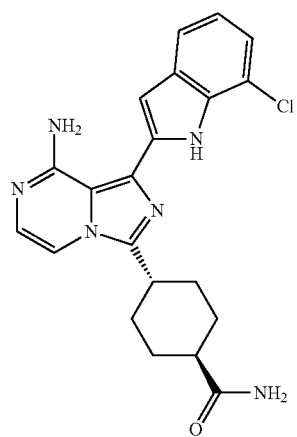 | 409.35 |
| 344 | 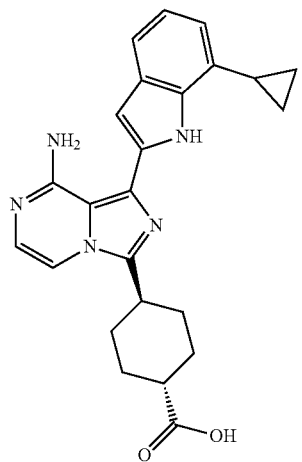 | 416.17 |

| Ex # | Structure | MH+ |
|---|---|---|
| 345 | 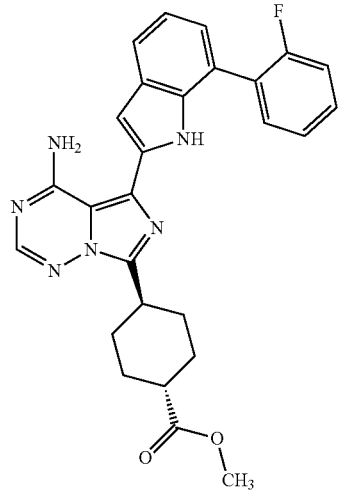<br>chiral | 485.39 |
| 346 | 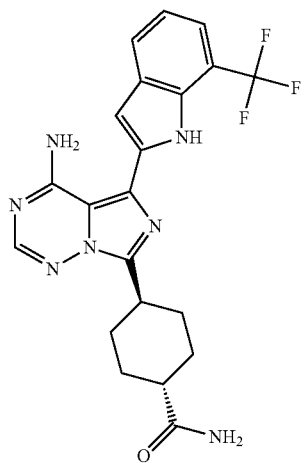<br>chiral | 444.10 |
| 347 | 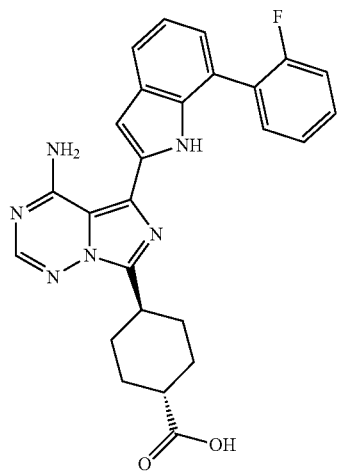 | 471.41 |

| Ex # | Structure | MH+ |
|---|---|---|
| 348 | 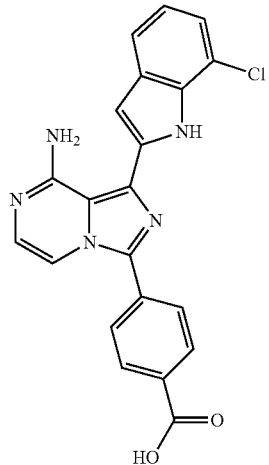 | 404.04<br>406.06 |
| 349 | 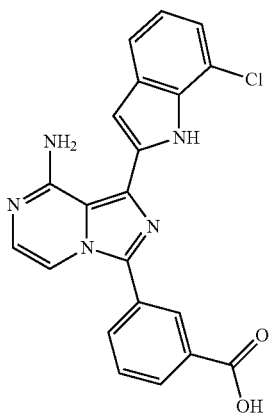 | 404.27<br>406.29 |
| 350 | 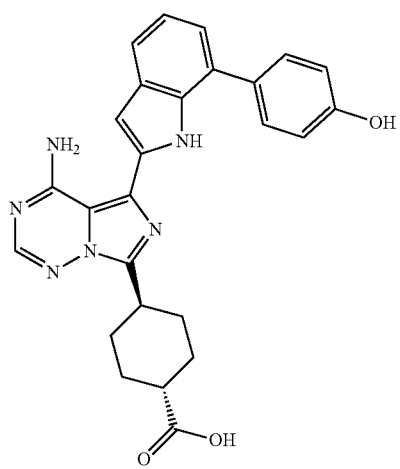<br>chiral | 469.39 |

-continued
| Ex # | Structure | MH+ |
| --- | --- | --- |
| 351 | 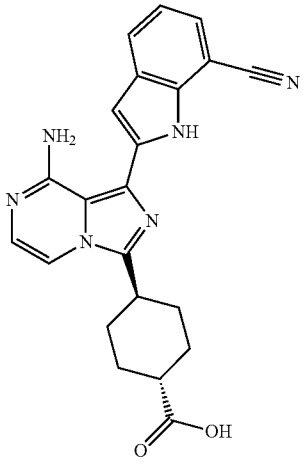 | 401.39 |
| 352 | 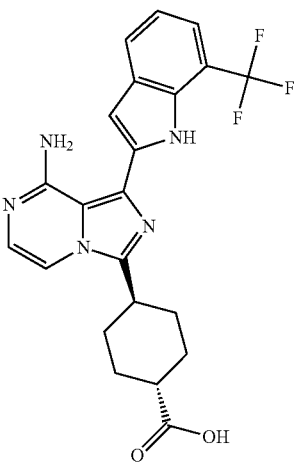 chiral | 444.16 |
| 353 | 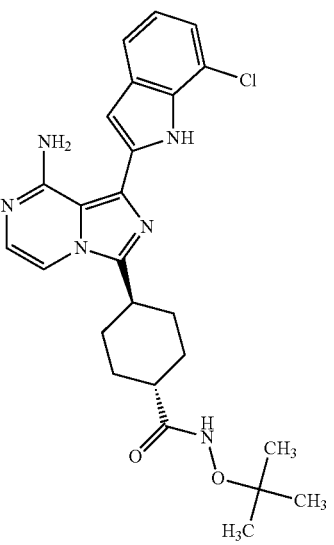 chiral | 481.12<br>483.14 |

-continued
| Ex # | Structure | MH+ |
|---|---|---|
| 354 | 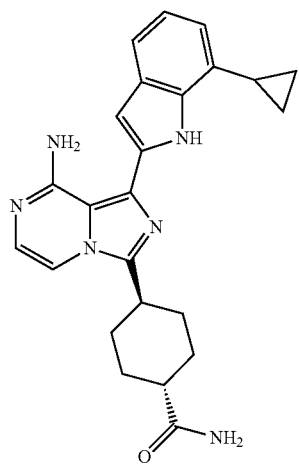 | 415.17 |
| 355 | 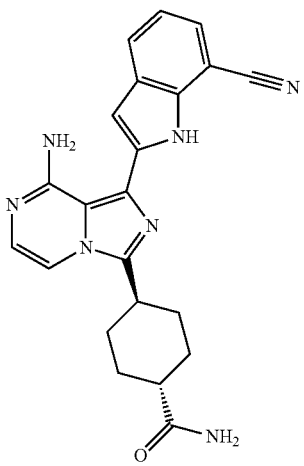 | 400.09 |
| 356 | 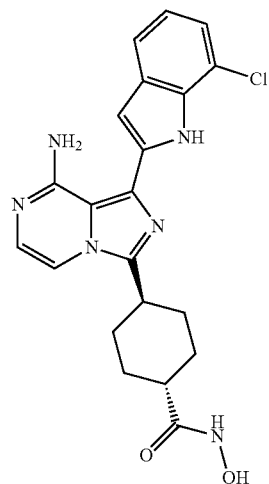 | 425.34<br>427.33 |

| Ex # | Structure | MH+ |
|---|---|---|
| 357 | chiral | 417.36 |
| 358 | chiral | 402.33 |
| 359 | 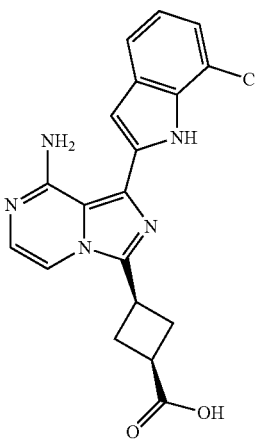 | 381.96<br>384.01 |

-continued

| Ex # | Structure | MH+ |
|------|-----------|-----|
| 360 | chiral | 487.01<br>489.03 |
| 361 | chiral | 495.03 |
| 362 | 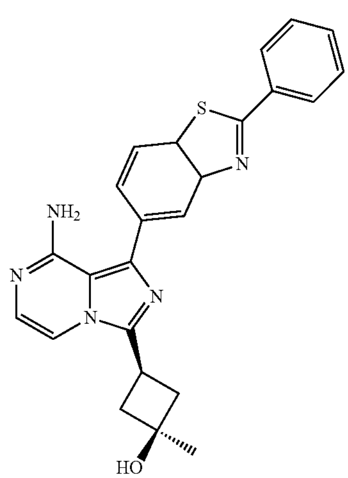 | 428.02 |

| Ex # | Structure | MH+ |
|---|---|---|
| 363 | 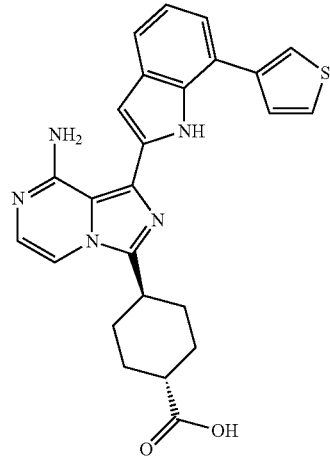<br>chiral | 458.32 |
| 364 | 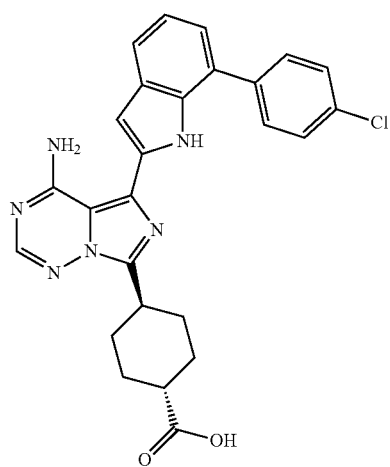<br>chiral | 487.01<br>488.90 |
| 365 | 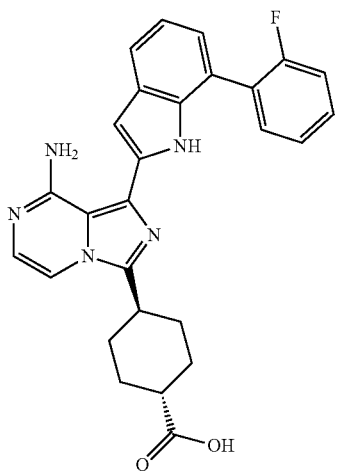<br>chiral | 470.37 |

-continued
| Ex # | Structure | MH+ |
|---|---|---|
| 366 | 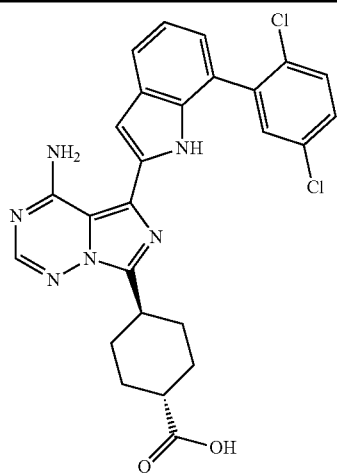 chiral | 521.27 523.27 |
| 367 | 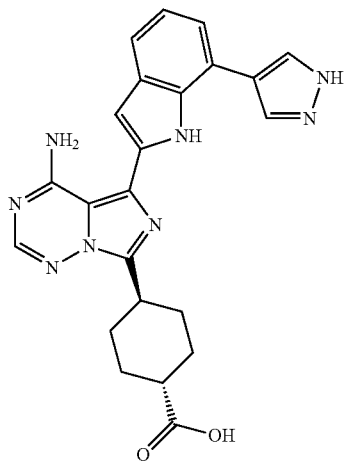 | 443.22 |
| 368 | 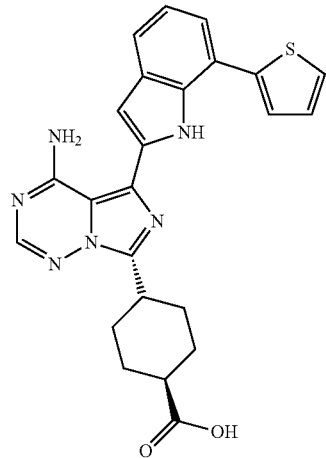 | 459.28 |

| Ex # | Structure | MH+ |
|---|---|---|
| 369 | 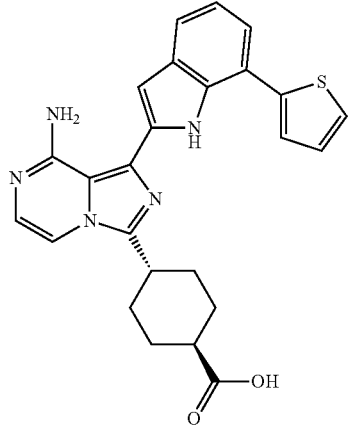 | 458.37 |
| 370 | 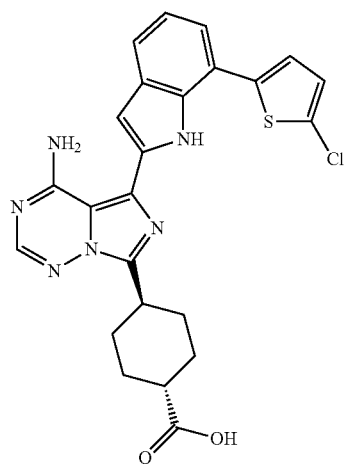 | 493.22<br>495.18 |
| 371 | 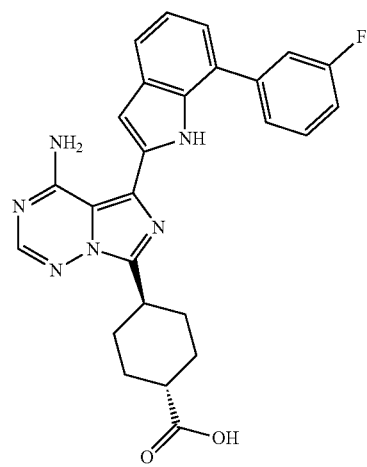 | 471.03 |
chiral -continued
| Ex # | Structure | MH+ |
|---|---|---|
| 372 | 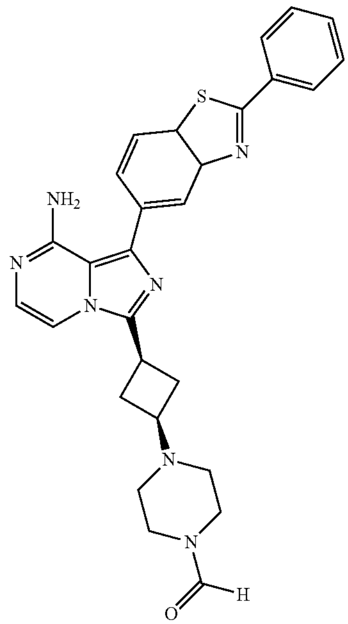 | 510.03 |
| 373 | 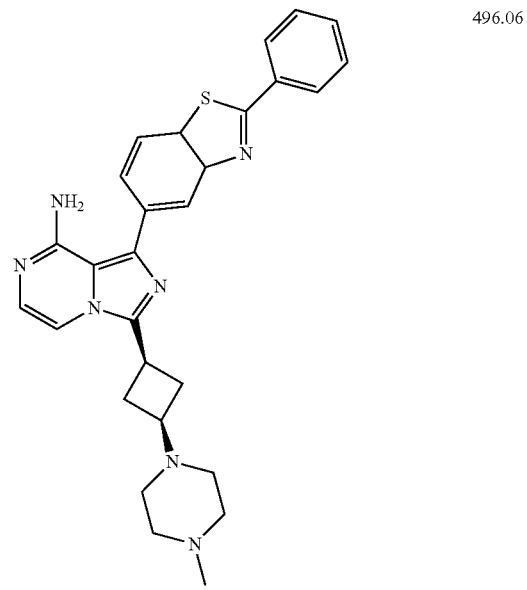 | 496.06 |

| Ex # | Structure | MH+ |
| --- | --- | --- |
| 374 | 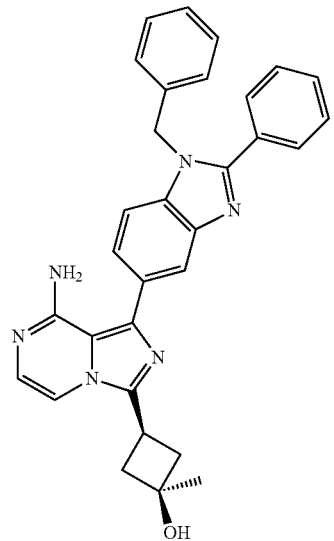 | 501.45 |
| 375 | 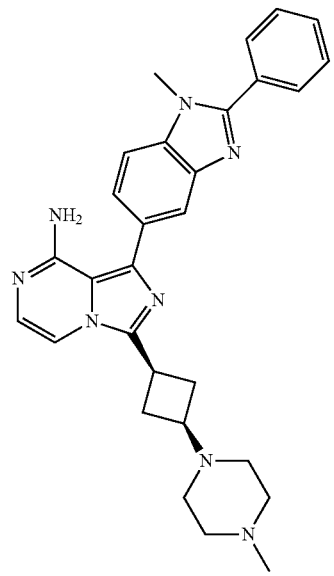 | 493.94 |

-continued
| Ex # | Structure | MH+ |
|---|---|---|
| 376 | 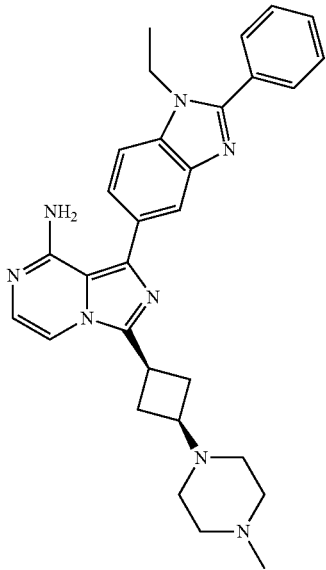 | 507.46 |
| 377 | 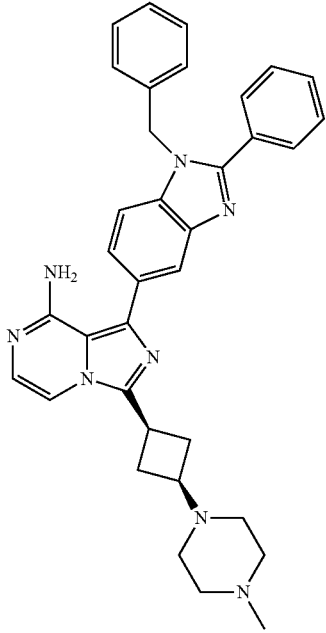 | 569.56 |

| Ex # | Structure | MH+ |
|---|---|---|
| 378 | 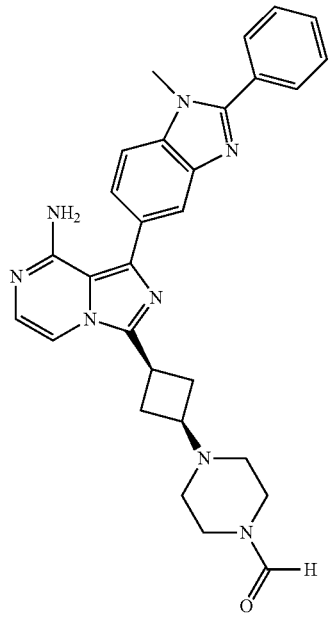 | 507.46 |
| 379 | 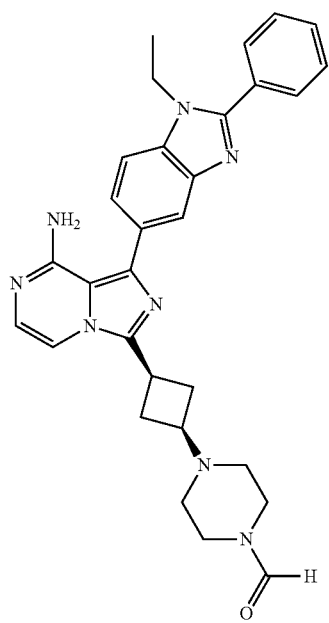 | 521.50 |

| Ex # | Structure | MH+ |
|---|---|---|
| 380 | 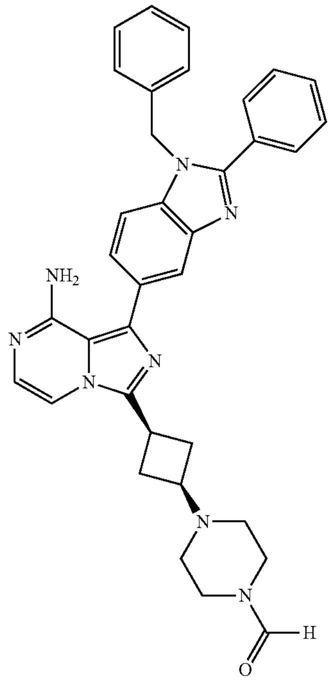 | 583.53 |
| 381 | 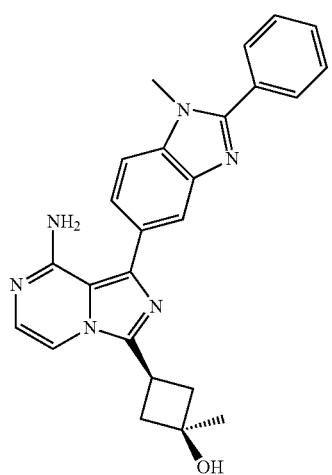 | 425.39 |
| 382 | 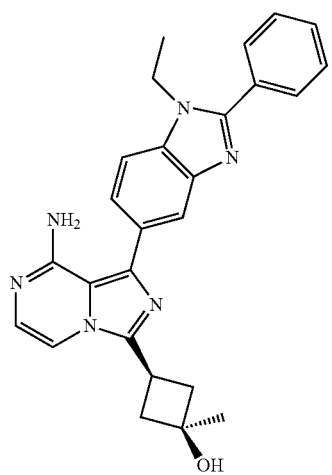 | 439.42 |

405
-continued
| Ex # | Structure | MH+ |
|---|---|---|
| 383 | 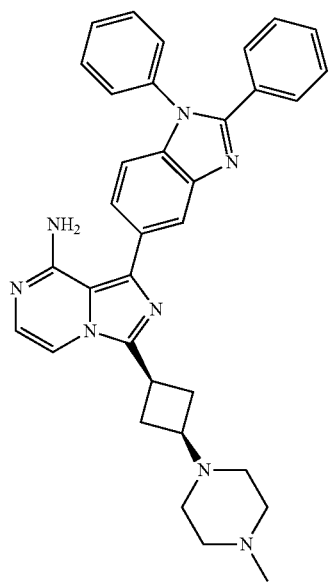 | 555.55 |
| 384 | 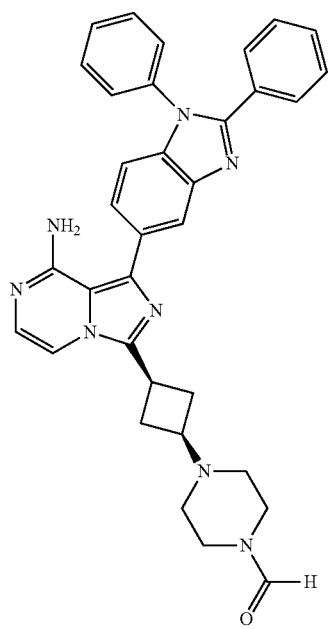 | 569.55 |

[1] The following compounds are expected to be active as inhibitors of mTOR. Where shown, X can be N or CH.
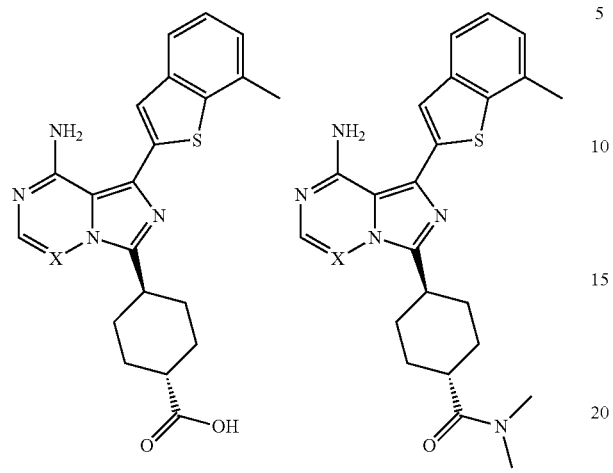
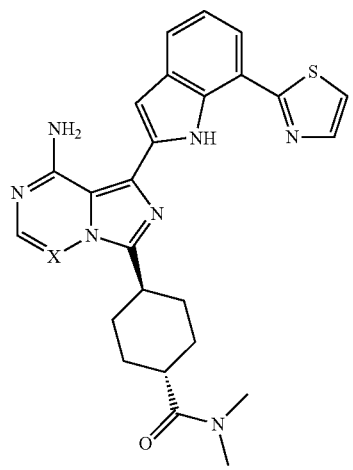
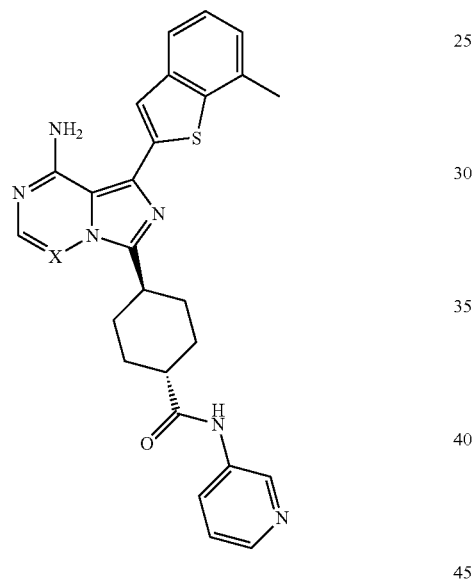
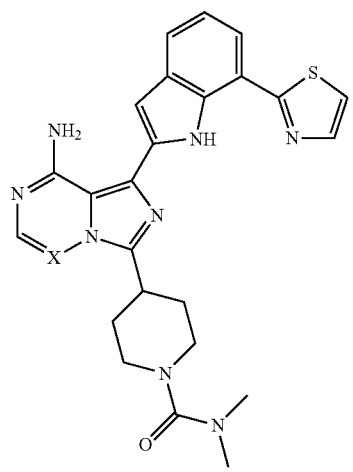
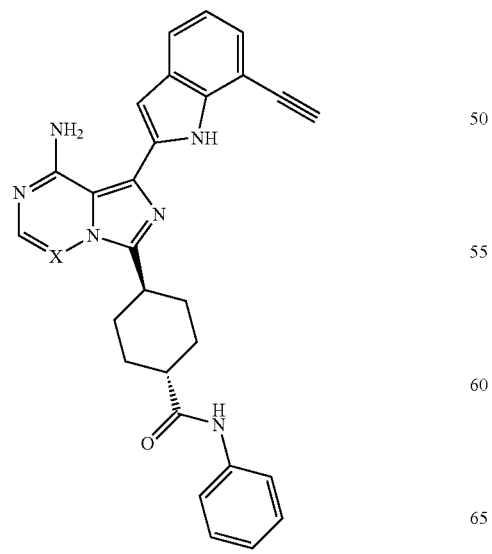
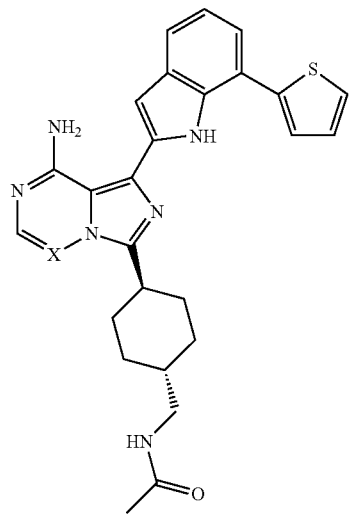

409
-continued
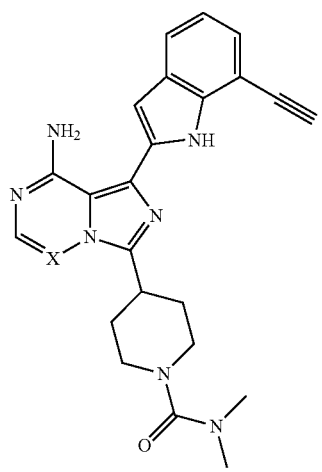
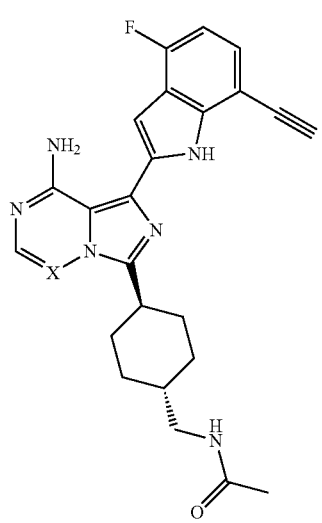
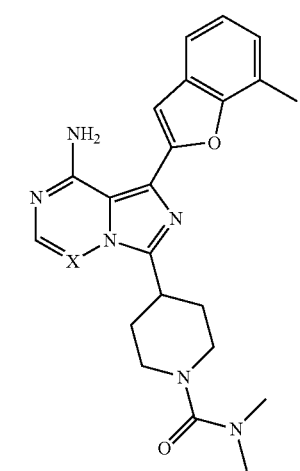
410
-continued
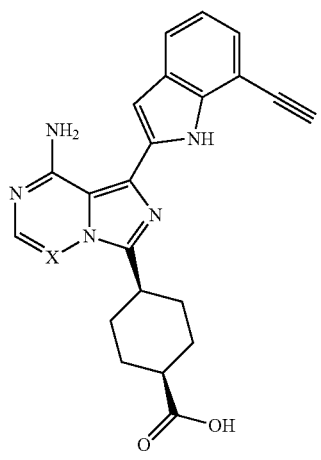
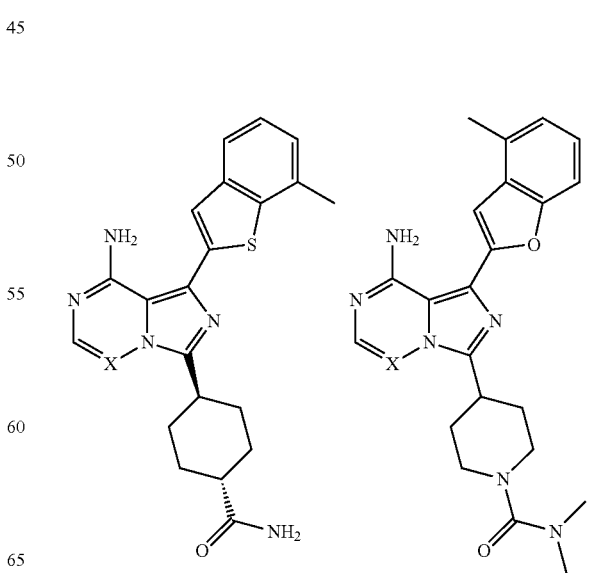

411
-continued
412
-continued
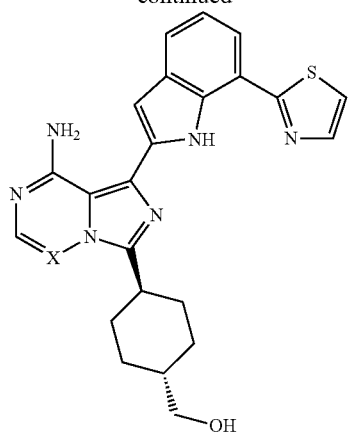
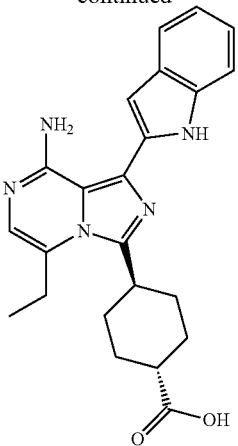
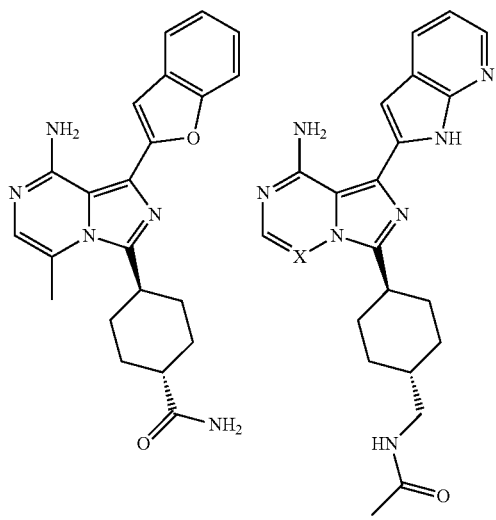
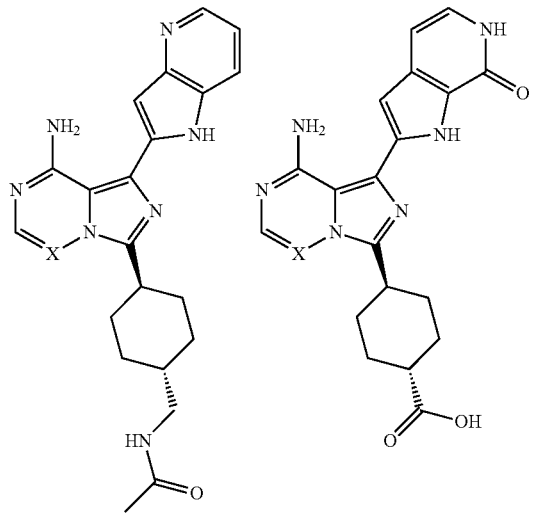
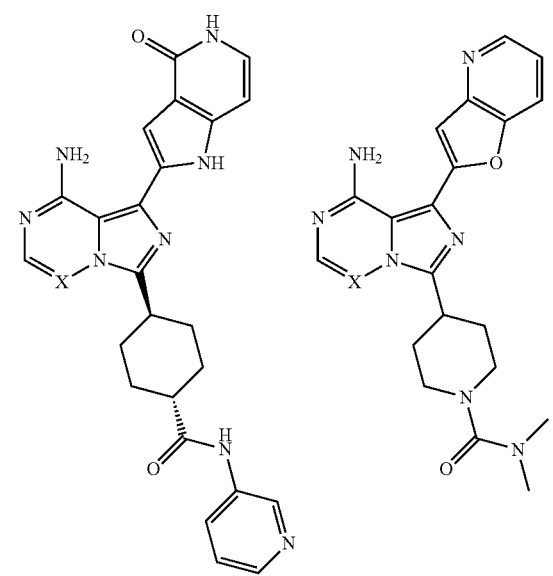

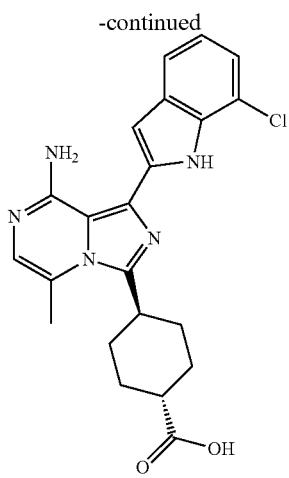

What is claimed is:
1. A compound represented by Formula (I)

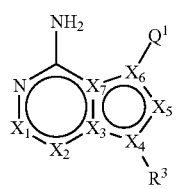

or a pharmaceutically acceptable salt thereof, wherein:
$X_1$ is CH; $X_2$, $X_4$, and $X_5$ are N; $X_3$, $X_6$, and $X_7$ are C;
$R^3$ is $C_{0-10}$alkyl, cyclo$C_{3-10}$alkyl, aminomethylcyclo$C_{3-10}$alkyl, bicyclo$C_{5-10}$alkyl, aryl, heteroaryl, aralkyl, heteroaralkyl, heterocyclyl or heterobicyclo$C_{5-10}$alkyl any of which is optionally substituted by one or more independent $G^{11}$ substituents;
$Q^1$ is -A($R^1$)$_m$B(W)$_n$ or —B($G^{11}$)$_n$A(Y)$_m$;
A and B are respectively, 5 and 6 membered aromatic or heteroaromatic rings, fused together to form a 9-membered heteroaromatic system selected from indolyl, benzimidazolyl, benzoxazolyl, benzofuranyl, and benzothienyl, and excluding 5-benzo[b]furyl and 3-indolyl;
$R^1$ is independently, hydrogen, —N($C_{0-8}$alkyl)($C_{0-8}$alkyl), hydroxyl, halogen, oxo, aryl(optionally substituted with 1 or more $R^{31}$ groups), hetaryl(optionally substituted with 1 or more $R^{31}$ groups), $C_{1-6}$alkyl, —$C_{0-8}$alkyl $C_{3-8}$cycloalkyl, —$C_{0-8}$alkyl-NR$^{311}$S(O)$_{0-2}$R$^{321}$, —$C_{0-8}$alkyl-NR$^{311}$S(O)$_{0-2}$NR$^{321}$R$^{331}$, —$C_{0-8}$alkyl-S(O)$_{0-2}$NR$^{311}$R$^{321}$, —$C_{0-8}$alkyl-NR$^{311}$COR$^{321}$, —$C_{0-8}$alkyl-NR$^{311}$CO$_2$R$^{321}$, —$C_{0-8}$alkyl-NR$^{311}$CONR$^{321}$R$^{331}$, —$C_{0-8}$alkyl-CONR$^{311}$R$^{321}$, —$C_{0-8}$alkyl-CON(R$^{311}$)S(O)$_{0-2}$R$^{321}$, —$C_{0-8}$alkyl-CO$_2$R$^{311}$, —$C_{0-8}$alkyl-S(O)$_{0-2}$R$^{311}$, —$C_{0-8}$alkyl-O—$C_{1-8}$alkyl, —$C_{0-8}$alkyl-O—$C_{0-8}$alkylC$_{3-8}$cycloalkyl, —$C_{0-8}$alkyl-O—$C_{0-8}$alkylheterocyclyl, —$C_{0-8}$alkyl-O—$C_{0-8}$alkylaryl, —$C_{0-8}$alkylaryl, —$C_{0-8}$alkylhetaryl, —$C_{0-8}$alkylheterocyclyl, —$C_{0-8}$alkyl-O—$C_{0-8}$alkylhetaryl, —$C_{0-8}$alkyl-S—$C_{0-8}$alkyl, —$C_{0-8}$alkyl-S—$C_{0-8}$alkylC$_{3-8}$cycloalkyl, —$C_{0-8}$alkyl-S—$C_{0-8}$alkylheterocyclyl, —$C_{0-8}$alkyl-S—$C_{0-8}$alkylaryl, —$C_{0-8}$alkyl-S—$C_{0-8}$alkylhetaryl, —$C_{0-8}$alkyl-N(R$^{311}$)—$C_{0-8}$alkyl, —$C_{0-8}$alkyl-N(R$^{311}$)—$C_{0-8}$alkylC$_{3-8}$cycloalkyl, —$C_{0-8}$alkyl-N(R$^{311}$)—$C_{0-8}$alkylheterocyclyl, —$C_{0-8}$alkyl-N(R$^{311}$)—$C_{0-8}$alkylaryl, —$C_{0-8}$alkyl-N(R$^{311}$)—$C_{0-8}$alkylhetaryl, —$C_{0-8}$alkyl-NR$^{311}$R$^{321}$, —$C_{2-8}$alkenyl, —$C_{2-8}$alkynyl, NO$_2$, CN, CF$_3$, OCF$_3$, OCHF$_2$;

W is independently, hydrogen, —N($C_{0-8}$alkyl)($C_{0-8}$alkyl), hydroxyl, halogen, oxo, aryl(optionally substituted with 1 or more $R^{31}$ groups), hetaryl(optionally substituted with 1 or more $R^{31}$ groups), $C_{1-6}$alkyl, —$C_{0-8}$alkyl $C_{3-8}$cycloalkyl, —$C_{0-8}$alkyl-NR$^{312}$S(O)$_{0-2}$R$^{322}$, —$C_{0-8}$alkyl-NR$^{311}$S(O)$_{0-2}$NR$^{321}$R$^{331}$, —$C_{0-8}$alkyl-NR$^{311}$CO$_2$R$^{321}$, —$C_{0-8}$alkyl-CON(R$^{311}$)S(O)$_{0-2}$R$^{321}$, —$C_{0-8}$alkyl-S(O)$_{0-2}$NR$^{312}$R$^{322}$, —$C_{0-8}$alkyl-NR$^{312}$COR$^{322}$, —$C_{0-8}$alkyl-NR$^{312}$CONR$^{322}$R$^{332}$, —$C_{0-8}$alkyl-CONR$^{312}$R$^{322}$, —$C_{0-8}$alkyl-CO$_2$R$^{312}$, —$C_{0-8}$alkylS(O)$_{0-2}$R$^{312}$, —$C_{0-8}$alkyl-O—$C_{1-8}$alkyl, —$C_{0-8}$alkyl-O—$C_{0-8}$alkylcyclyl, —$C_{0-8}$alkyl-O—$C_{0-8}$alkylheterocycloalkyl, —$C_{0-8}$alkyl-O—$C_{0-8}$alkylaryl, —$C_{0-8}$alkylaryl, —$C_{0-8}$alkylhetaryl, —$C_{0-8}$alkylheterocyclyl, -Oaryl, —$C_{0-8}$alkyl-O—$C_{0-8}$alkylhetaryl, —$C_{0-8}$alkyl-S—$C_{0-8}$alkyl, —$C_{0-8}$alkyl-S—$C_{0-8}$alkyl $C_{3-8}$cycloalkyl, —$C_{0-8}$alkyl-S—$C_{0-8}$alkylheterocycloalkyl, —$C_{0-8}$alkyl-S—$C_{0-8}$alkylaryl, —$C_{0-8}$alkyl-S—$C_{0-8}$alkylhetaryl, —$C_{0-8}$alkyl-N(R$^{312}$)—$C_{0-8}$alkyl, —$C_{0-8}$alkyl-N(R$^{312}$)—$C_{0-8}$alkylC$_{3-8}$cycloalkyl, —$C_{0-8}$alkyl-N(R$^{312}$)—$C_{0-8}$alkylheterocycloalkyl, —$C_{0-8}$alkyl-N(R$^{312}$)—$C_{0-8}$alkylaryl, —$C_{0-8}$alkyl-N(R$^{312}$)—$C_{0-8}$alkylhetaryl, $C_{0-8}$alkyl-NR$^{312}$R$^{322}$, —$C_{2-8}$alkenyl, -$C_{2-8}$alkynyl, NO$_2$, CN, CF$_3$, OCF$_3$, OCHF$_2$;

Y is independently, hydrogen, —N($C_{0-8}$alkyl)($C_{0-8}$alkyl), hydroxyl, halogen, oxo, aryl(optionally substituted with 1 or more $R^{31}$ groups), hetaryl(optionally substituted with 1 or more $R^{31}$ groups), $C_{0-6}$alkyl, —$C_{0-8}$alkyl $C_{3-8}$cycloalkyl, —$C_{0-8}$alkyl-NR$^{311}$S(O)$_{0-2}$R$^{321}$, —$C_{0-8}$alkyl-NR$^{311}$S(O)$_{0-2}$NR$^{321}$R$^{331}$, —$C_{0-8}$alkyl-NR$^{311}$CO$_2$R$^{321}$, —$C_{0-8}$alkyl-CON(R$^{311}$)S(O)$_{0-2}$R$^{321}$, —$C_{0-8}$alkyl-S(O)$_{0-2}$NR$^{311}$R$^{321}$, —$C_{0-8}$alkyl-NR$^{311}$COR$^{321}$, —$C_{0-8}$alkyl-NR$^{311}$CONR$^{321}$R$^{331}$, —$C_{0-8}$alkyl-CONR$^{311}$R$^{321}$, —$C_{0-8}$alkyl-CO$_2$R$^{311}$, —$C_{0-8}$alkyl S(O)$_{0-2}$R$^{311}$, —$C_{0-8}$alkyl-O—$C_{1-8}$alkyl, —$C_{0-8}$alkyl-O—$C_{0-8}$alkylC$_{3-8}$cycloalkyl, —$C_{0-8}$alkyl-O—$C_{0-8}$alkylheterocycloalkyl, —$C_{0-8}$alkyl-O—$C_{0-8}$alkylaryl, —$C_{0-8}$alkylaryl, —$C_{0-8}$alkylhetaryl, —$C_{0-8}$alkylheterocyclyl, —$C_{0-8}$alkyl-O—$C_{0-8}$alkylhetaryl, —$C_{0-8}$alkyl-S—$C_{0-8}$alkyl, —$C_{0-8}$alkyl-S—$C_{0-8}$alkylC$_{3-8}$cycloalkyl, —$C_{0-8}$alkyl-S—$C_{0-8}$alkylheterocycloalkyl, —$C_{0-8}$alkyl-S—$C_{0-8}$alkylaryl, —$C_{0-8}$alkyl-S—$C_{0-8}$alkylhetaryl, —$C_{0-8}$alkyl-N(R$^{311}$)—$C_{0-8}$alkyl, —$C_{0-8}$alkyl-N(R$^{311}$)—$C_{0-8}$alkylC$_{3-8}$cycloalkyl, —$C_{0-8}$alkyl-N(R$^{311}$)—$C_{0-8}$alkylheterocycloalkyl, —$C_{0-8}$alkyl-N(R$^{311}$)—$C_{0-8}$alkylaryl, —$C_{0-8}$alkyl-N(R$^{311}$)—$C_{0-8}$alkylhetaryl, —$C_{0-8}$alkyl-NR$^{311}$R$^{321}$, —$C_{2-8}$alkenyl, —$C_{2-8}$alkynyl, NO$_2$, CN, CF$_3$, OCF$_3$, OCHF$_2$ $G^{11}$ is halo, oxo, —CF$_3$, —OCF$_3$, —OR$^{312}$, —NR$^{312}$R$^{322}$, —(O)R$^{312}$, —C(O)C$_{3-8}$cycloalkyl, —CO$_2$C$_{3-8}$cycloalkyl, —CO$_2$R$^{312}$, —C(=O)NR$^{312}$R$^{322}$, —NO$_2$, —CN, —S(O)$_{0-2}$R$^{312}$, —SO$_2$NR$^{312}$R$^{322}$, NR$^{312}$(C=O)R$^{322}$, NR$^{312}$C(=O)OR$^{322}$, NR$^{312}$C(=O)NR$^{322}$R$^{332}$, NR$^{312}$S(O)$_{0-2}$R$^{322}$, —C(=S)OR$^{312}$, —C(=O)SR$^{312}$, —NR$^{312}$C(=NR$^{322}$)NR$^{332}$R$^{341}$, —NR$^{312}$C(=NR$^{322}$)OR$^{332}$, —NR$^{312}$C(=NR$^{322}$)SR$^{332}$, —OC(=O)OR$^{312}$, —OC(=O)NR$^{312}$R$^{322}$, —OC(=O)SR$^{312}$, —SC(=O)OR$^{312}$, —SC(=O)NR$^{312}$R$^{322}$, —P(O)OR$^{312}$OR$^{322}$, $C_{1-10}$alkylidene, $C_{0-10}$alkyl, $C_{2-10}$alkenyl, $C_{2-10}$alkynyl, —$C_{1-10}$alkoxy$C_{1-10}$alkyl, —$C_{1-10}$alkoxy$C_{2-10}$alkenyl, —$C_{1-10}$alkoxy$C_{2-10}$alkynyl, —$C_{1-10}$alkylthio$C_{1-10}$alkyl, $-C_{1-10}$alkylthio$C_{2-10}$alkenyl, $-C_{1-10}$alkylthio$C_{2-10}$alkynyl, cyclo$C_{3-8}$alkyl, cyclo$C_{3-8}$alkenyl, -cyclo$C_{3-8}$alkyl$C_{2-10}$alkyl, -cyclo$C_{3-8}$alkenyl$C_{1-10}$alkyl, -cyclo-$C_{3-8}$alkyl$C_{2-10}$alkenyl, -cyclo$C_{3-8}$alkenyl$C_{2-10}$alkenyl, -cyclo$C_{3-8}$alkyl$C_{2-10}$alkynyl, -cyclo$C_{3-8}$alkenyl$C_{2-10}$alkynyl, -heterocyclyl-$C_{0-10}$alkyl, -heterocyclyl-$C_{2-10}$alkenyl, or -heterocyclyl-$C_{2-10}$alkynyl, any of which is optionally substituted with one or more independent halo, oxo, $-CF_3$, $-OCF_3$, $-OR^{313}$, $-NR^{313}R^{323}$, $-C(O)R^{313}$, $-CO_2R^{313}$, $-C(=O)NR^{313}R^{323}$, $-NO_2$, $-CN$, $-S(O)_{0-2}R^{313}$, $-SO_2NR^{313}R^{323}$, $-NR^{313}C(=O)R^{323}$, $-NR^{313}C(=O)OR^{323}$, $-NR^{313}C(=O)NR^{323}R^{333}$, $-NR^{313}S(O)_{0-2}R^{323}$, $-C(=S)OR^{313}$, $-C(=O)SR^{313}$, $-NR^{313}C(=NR^{323})NR^{333}R^{342}$, $-NR^{313}C(=NR^{323})OR^{333}$, $-NR^{313}C(=NR^{323})SR^{333}$, $-OC(=O)OR^{333}$, $-OC(=O)NR^{313}R^{323}$, $-OC(=O)SR^{313}$, $-SC(=O)OR^{313}$, $-P(O)OR^{313}OR^{323}$, or $-SC(=O)NR^{313}R^{323}$ substituents;

or $G^{11}$ is aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, where the attachment point is from either the left or right as written, where any of which is optionally substituted with one or more independent halo, $-CF_3$, $-OCF_3$, $-OR^{313}$, $-NR^{313}R^{323}$, $-(O)R^{313}$, $-CO_2R^{313}$, $-C(=O)NR^{313}R^{323}$, $-NO_2$, $-CN$, $-S(O)_{0-2}R^{313}$, $-SO_2NR^{313}R^{323}$, $-NR^{313}C(=O)R^{323}$, $-NR^{313}C(=O)OR^{323}$, $-NR^{313}C(=O)NR^{323}R^{333}$, $-NR^{313}S(O)_{0-2}R^{323}$, $-C(=S)OR^{313}$, $-C(=O)SR^{313}$, $-NR^{323}C(=NR^{313})NR^{333}R^{342}$, $-NR^{313}C(=NR^{323})OR^{333}$, $-NR^{313}C(=NR^{323})SR^{333}$, $-OC(=O)OR^{313}$, $-OC(=O)NR^{313}R^{323}$, $-OC(=O)SR^{313}$, $-SC(=O)OR^{313}$, $-P(O)OR^{313}OR^{323}$, or $-SC(=O)NR^{313}R^{323}$ substituents; provided that $G^{11}$ is not $N-CH_2CO_2H$ when $R^3$ is 4-piperidinyl;

provided that $Q^1$ is not N-methyl-2-indolyl, N-(phenylsulfonyl)-2-indolyl, 4-benzyloxy-2-indolyl, or 2-carboxy-5-benzo [b]thienyl;

$R^{31}$, $R^{311}$, $R^{321}$, $R^{331}$, $R^{312}$, $R^{322}$, $R^{332}$, $R^{341}$, $R^{313}$, $R^{323}$, $R^{333}$, and $R^{342}$, in each instance, is independently $C_{1-8}$alkyl optionally substituted with an aryl, heterocyclyl or hetaryl substituent, or $C_{0-8}$alkyl optionally substituted with 1-6 independent halo, $-CON(C_{0-8}$alkyl)$(C_{0-8}$alkyl), $-CO(C_{0-8}$alkyl), $-OC_{0-8}$alkyl, -Oaryl, -Ohetaryl, -Oheterocyclyl, $-S(O)_{0-2}$aryl, $-S(O)_{0-2}$hetaryl, $-S(O)_{0-2}$heterocyclyl, $-S(O)_{0-2}C_{0-8}$alkyl, $-N(C_{0-8}$alkyl)$(C_{0-8}$alkyl), $-N(C_{0-8}$alkyl)CON$(C_{0-8}$alkyl)$(C_{0-8}$alkyl), $-N(C_{0-8}$ alkyl)CO$(C_{1-8}$alkyl), $-N(C_{0-8}$alkyl)CO$(C_{3-8}$cycloalkyl), $-N(C_{0-8}$alkyl)CO$_2(C_{1-8}$alkyl), $S(O)_{1-2}N(C_{0-8}$alkyl)$(C_{0-8}$alkyl), $-CON(C_{3-8}$cycloalkyl)$(C_{3-8}$cycloalkyl), $-CON(C_{0-8}$alkyl) $(C_{3-8}$cycloalkyl), $-N(C_{3-8}$cycloalkyl)CON$(C_{0-8}$alkyl)$(C_{0-8}$alkyl), $-N(C_{3-8}$cycloalkyl)CON$(C_{3-8}$cycloalkyl)$(C_{0-8}$alkyl), $-N(C_{0-8}$alkyl)CON$(C_{3-8}$cycloalkyl)$(C_{0-8}$alkyl), $-N(C_{0-8}$alkyl)CO$_2(C_{3-8}$cycloalkyl), $-N(C_{3-8}$cycloalkyl)CO$_2(C_{3-8}$cycloalkyl), $S(O)_{1-2}N(C_{0-8}$alkyl)$(C_{3-8}$cycloalkyl), $C_{2-8}$alkenyl, $C_{2-8}$alkynyl, CN, $CF_3$, OH, or optionally substituted aryl substituents; such that each of the above aryl, heterocyclyl, hetaryl, alkyl or cycloalkyl groups may be optionally, independently substituted with $-N(C_{0-8}$alkyl)$(C_{0-8}$alkyl), hydroxyl, halogen, oxo, aryl, hetaryl, $C_{0-6}$alkyl, $-C_{0-8}$alkylcyclyl, $-C_{0-8}$alkyl-N$(C_{0-8}$alkyl)$-S(O)_{0-2}-(C_{0-8}$alkyl), $-C_{0-8}$alkyl-S$(O)_{0-2}-N(C_{0-8}$alkyl)$(C_{0-8}$alkyl), $-C_{0-8}$alkyl-N$(C_{0-8}$alkyl)CO$(C_{0-8}$alkyl), $-C_{0-8}$alkyl-N$(C_{0-8}$alkyl)CO$-N(C_{0-8}$alkyl)$(C_{0-8}$alkyl), $-C_{0-8}$alkyl-CO$-N(C_{0-8}$alkyl)$(C_{0-8}$alkyl), $-C_{1-8}$alkyl-CO$_2-(C_{0-8}$alkyl), $-C_{0-8}$alkylS$(O)_{0-2}-(C_{0-8}$alkyl), $-C_{0-8}$alkyl-O-$C_{1-8}$alkyl, $-C_{0-8}$alkyl-O-$C_{0-8}$alkylcyclyl, $-C_{0-8}$alkyl-O-$C_{0-8}$alkylheterocyclyl, $-C_{0-8}$alkyl-O-$C_{0-8}$alkylaryl, $-C_{0-8}$alkyl-O-$C_{0-8}$alkylhetaryl, $-C_{0-8}$alkyl-S-$C_{0-8}$alkyl, $-C_{0-8}$alkyl-S-$C_{0-8}$alkylcyclyl, $-C_{0-8}$alkyl-S-$C_{0-8}$alkylheterocyclyl, $-C_{0-8}$alkyl-S-$C_{0-8}$alkylaryl, $-C_{0-8}$alkyl-S-$C_{0-8}$alkylhetaryl, $-C_{0-8}$alkyl-N$(C_{0-8}$alkyl)$-C_{0-8}$alkyl, $-C_{0-8}$alkyl-N$(C_{0-8}$alkyl)$-C_{0-8}$alkylcyclyl, $-C_{0-8}$alkyl-N$(C_{0-8}$alkyl)$-C_{0-8}$alkylheterocyclyl, $-C_{0-8}$alkyl-N$(C_{0-8}$alkyl)$-C_{0-8}$alkylaryl, $-C_{0-8}$alkyl-N$(C_{0-8}$alkyl)$-C_{0-8}$alkylhetaryl, $-C_{2-8}$alkenyl, $-C_{2-8}$alkynyl, $NO_2$, CN, $CF_3$, $OCF_3$, $OCHF_2$, $-C_{0-8}$alkyl-$C_{3-8}$cycloalkyl, $-C_{0-8}$alkyl-O-$C_{0-8}$alkyl, $-C_{0-8}$alkyl-N$(C_{0-8}$alkyl)$(C_{0-8}$alkyl), $-C_{0-8}$alkyl-S$(O)_{0-2}-C_{0-8}$alkyl, or heterocyclyl optionally substituted with 1-4 independent $C_{0-8}$alkyl, cyclyl, or substituted cyclyl substituents;

in the cases of $-NR^{311}R^{321}$, $-NR^{312}R^{322}$, $-NR^{332}R^{341}$, $-NR^{313}R^{323}$, and $-NR^{323}R^{333}$, the respective $R^{31}$ and $R^{32}$, $R^{311}$ and $R^{321}$, $R^{312}$ and $R^{322}$, $R^{331}$ and $R^{341}$, $R^{313}$ and $R^{323}$, and $R^{323}$ and $R^{333}$ are optionally taken together with the nitrogen atom to which they are attached to form a 3-10 membered saturated or unsaturated ring; wherein said ring in each instance independently is optionally substituted by one or more independent $-N(C_{0-8}$alkyl)$(C_{0-8}$alkyl), hydroxyl, halogen, oxo, aryl, hetaryl, $C_{0-6}$alkyl, $-C_{0-8}$alkyl$C_{3-8}$cycloalkyl, $-C_{0-8}$alkyl-N$(C_{0-8}$alkyl)S$(O)_{0-2}C_{0-8}$alkyl, $-C_{0-8}$alkyl-N$(C_{0-8}$alkyl)S$(O)_{0-2}N(C_{0-8}$alkyl)$(C_{0-8}$alkyl), $-C_{0-8}$alkyl-N$(C_{0-8}$alkyl)CO$_2(C_{0-8}$alkyl), $-C_{0-8}$alkyl-CON$((C_{0-8}$alkyl))S$(O)_{0-2}(C_{0-8}$alkyl), $-C_{0-8}$alkyl-S$(O)_{0-2}N(C_{0-8}$alkyl)$(C_{0-8}$alkyl), $-C_{0-8}$alkyl-N$(C_{0-8}$alkyl)CO$(C_{0-8}$alkyl), $-C_{0-8}$alkyl-N$(C_{0-8}$alkyl)CON$(C_{0-8}$alkyl)$(C_{0-8}$alkyl), $-C_{0-8}$alkyl-CON$(C_{0-8}$alkyl)$(C_{0-8}$alkyl), $-C_{0-8}$alkyl-CO$_2(C_{0-8}$alkyl), $-C_{0-8}$alkylS$(O)_{0-2}(C_{0-8}$alkyl), $-C_{0-8}$alkyl-O-$C_{0-8}$alkyl, $-C_{0-8}$alkyl-O-$C_{0-8}$alkylcyclyl, $-C_{0-8}$alkyl-O-$C_{0-8}$alkylheterocycloalkyl, $-C_{0-8}$alkyl-O-$C_{0-8}$alkylaryl, -O-aryl, $-C_{0-8}$alkyl-O-$C_{0-8}$alkylhetaryl, $-C_{0-8}$alkyl-S-$C_{0-8}$alkyl, $-C_{0-8}$alkyl-S-$C_{0-8}$alkyl$C_{3-8}$cycloalkyl, $-C_{0-8}$alkyl-S-$C_{0-8}$alkylheterocycloalkyl, $-C_{0-8}$alkyl-S-$C_{0-8}$alkylaryl, $-C_{0-8}$alkyl-S-$C_{0-8}$alkylhetaryl, $-C_{0-8}$alkyl-N$(C_{0-8}$alkyl)$-C_{0-8}$alkyl, $-C_{0-8}$alkyl-N$(C_{0-8}$alkyl)$-C_{0-8}$alkyl$C_{3-8}$cycloalkyl, $-C_{0-8}$alkyl-N$(C_{0-8}$alkyl)$-C_{0-8}$alkylheterocycloalkyl, $-C_{0-8}$alkyl-N$(C_{0-8}$alkyl)$C_{0-8}$alkylaryl, $-C_{0-8}$alkyl-N$(C_{0-8}$alkyl)$-C_{0-8}$alkylhetaryl, $-C_{0-8}$alkyl-N$(C_{0-8}$alkyl)$-(C_{0-8}$alkyl), $C_{2-8}$alkenyl, $C_{2-8}$alkynyl, $NO_2$, CN, $CF_3$, $OCF_3$, or $OCHF_2$ substituents; wherein said ring in each instance independently optionally includes one or more heteroatoms other than the nitrogen;

m is 0, 1, 2, or 3;

n is 0, 1, 2, 3, or 4.

2. A pharmaceutical composition comprising the compound or salt of claim 1 and a pharmaceutically acceptable carrier.

* * * * *

UNITED STATES PATENT AND TRADEMARK OFFICE
CERTIFICATE OF CORRECTION

PATENT NO.        : 8,314,111 B2
APPLICATION NO.   : 13/106954
DATED             : November 20, 2012
INVENTOR(S)       : Chen et al.

Page 1 of 1

It is certified that error appears in the above-identified patent and that said Letters Patent is hereby corrected as shown below:

On the title page,

In the title (54) and column 1,

"FUSED BICYCLIC MOTOR INHIBITORS" should read --FUSED BICYCLIC MTOR INHIBITORS--.

Signed and Sealed this
Nineteenth Day of March, 2013

Teresa Stanek Rea
*Acting Director of the United States Patent and Trademark Office*